(12) United States Patent
Harris et al.

(10) Patent No.: US 6,380,360 B1
(45) Date of Patent: Apr. 30, 2002

(54) POLYCYSTIC KIDNEY DISEASE 1 GENE AND USES THEREOF

(75) Inventors: Peter Charles Harris; Belen Peral; Christopher J. Ward; James Hughes, all of Oxford (GB); Martin Hendrik Breuning, Zaandam (NL); Dorothea Johanna Maria Peters; Jeroen Hendrik Roelfsema, both of Leiden (NL); Julian Sampson, Cardiff (GB); Dirkje Jorijntje Johanna Halley; Mark David Nellist, both of Rotterdam (NL); Lambertus Antonius Jacobus Janssen, Barendrecht (NL); Ajenne Lique Wilhelma Hesseling, Spijkenisse (NL)

(73) Assignee: Medical Research Council (GB)

( * ) Notice: Subject to any disclaimer, the term of this patent is extended or adjusted under 35 U.S.C. 154(b) by 0 days.

(21) Appl. No.: 09/052,469

(22) Filed: Mar. 31, 1998

Related U.S. Application Data

(62) Division of application No. 08/422,582, filed as application No. PCT/GB94/02822 on Dec. 23, 1994.

(30) Foreign Application Priority Data

Dec. 24, 1993 (GB) .............................................. 9326470
Jun. 14, 1994 (GB) .............................................. 9411900

(51) Int. Cl.[7] .......................... C07K 1/00; C07K 14/00; G01N 33/53
(52) U.S. Cl. ........................ 530/350; 435/7.1; 435/7.9; 435/69.1; 536/23.1
(58) Field of Search .......................... 530/350; 435/7.1, 435/7.9, 69.1; 536/23.1

(56) References Cited

U.S. PATENT DOCUMENTS 5,891,628 A  *  4/1999 Reeders et al. ................. 435/6

OTHER PUBLICATIONS

Ngo et al., in The Protein Folding Problem and Tertiary Stucture Prediction, 1994, Merz et al. (ed.), Birkhauser, Boston, MA, pp. 433 and 492–495, 1994.*
Engelman, et al., "Identifying nonpolar transbilayer helices in amino acid sequences of membrane proteins," Ann. Rev. Biophys. Chem., 15:321–53 (1986).
Aksentijevich, et al., Refined Mapping of the Gene Causing Familial Mediterranean Fever, by Linkage and Homozygosity Studies, Am. J. Hum. Genet., 53:451–461 (1993).
Altschul, et al., "Basic Local Alignment Search Tool", J. Mol. Biol., 215, 403–410 (1990).
Bevilacqua, et al., "Endothelial Leukocyte Adhesion Molecule 1: An Inducible Receptor for Neutrophils Related to Complement Regulatory Proteins and Lectins", Science, vol. 243, 1160–1187 (1989).

Breuning, et al., "Improved early diagnosis of adult polycystic kidney disease with flanking DNA markers", The Lancet, 1359–1361, Dec. 12, 1987.
Breuning, et al., "Genetic Heterogeneity of Polycystic Kidney Disease in Europe", Contrib. Nephrol., vol. 97, pp. 128–139 (1992).
Breuning, et al., Map of 16 polymorphic loci on the short arm of chromosome 16 close to the polycystic kidney disease gene(PKD1), F. Med Genet, vol. 27:603–613 (1990).
Brook–Carter, et al., "Deletion of the TSC2 and PKD1 genes associated with severe infantile polycystic kidney disease—a contiguous gene syndrome", Nature Genetics, vol. 8: 328–332, (1994).
Brown, et al., "X chromosome inactivation of the human TIMP gene," Nucleic Acids Research, vol. 18, No. 14 (1990).
Brümmendorf, et al., "Protein Profile", vol. 1, 1994, pp. 951–962.
Buckle, et al., "Fluorescent in situ hybridization", Human Genetic Disease, pp. 59–82.
Carone, et al., "Biology of Polycystic Kidney Disease", Laboratory Investigation, vol. 70, No. 4, p. 437 (1994).
Carone, et al., "Impaired tubulogenesis of cyst–derived cells from autosomal dominant polycystic kidneys," Kidney International; vol. 47 (1995) pp. 861–868.
Calvet, et al., "Polycystic kidney disease: Primary extracellular matrix abnornality or defective cellular differentiation?" , Kidney International, vol. 43 (1993) pp. 101–108.
Chapman, et al., "Intracranial aneurysms in autosomal dominant polycystic kidney disease", The New England Journal of Medicine, vol. 504, (1992).
Chao, "Neurotrophin Receptors: A Window into Neuronal Differentiation", Neuron, vol. 9, 583–593, Oct. (1992).
Chomczynski, et al., "Single–Step Method of RNA Isolation by Acid Guanidinium Thiocyanate–Phenol–Chloroform Extraction", Analytical Biochemistry, 162, 156–159 (1987).
Curtis, et al., "Sequence and expression of a membrane–associated C–type lectin that exhibits CD4–independent binding of human immunodeficiency virus envelope glycoprotein gp120", Proc. Natl. Acad. Sci. USA, vol. 89, pp. 8356–8360 (1992).
Dalgaard, "Bilateral Polycystic Disease of the Kidneys", Copenhagen (1957).

(List continued on next page.)

Primary Examiner—Karen Cochrane Carlson
Assistant Examiner—Holly Schmizer
(74) Attorney, Agent, or Firm—Palmer & Dodge, LLP; Kathleen M. Williams; Elizabeth N. Spar

(57) ABSTRACT

The present invention relates to the polycystic kidney disease 1 (PKD1) gene and its nucleic acid sequence, mutations thereof in patients having PKD1-associated disorders, the protein encoded by the PKD1 gene or its mutants, and their uses in disease diagnosis and therapy.

5 Claims, 88 Drawing Sheets

OTHER PUBLICATIONS

Daoust, et al., "Evidence for a Third Genetic Locus for Autosomal Dominant Polycystic Kidney Disease", Genomics 25, 733–736 (1995).

Davies et al., Polycystic Kidney Disease Re–evaluated: A Population–based Study, Quarterly Journal of Medicine, New Series 79, No. 290, pp. 477–85 (1991).

Deisseroth, et al., "Activation of phenotypic expression of human globin genes from nonerythroid cells by chromosome–dependent transfer to tetraploid mouse erythroleukemia cells", Proc. Natl. Acad. Sci. USA vol. 76, No. 5, pp. 2185–2189 (1979).

Dodé, et al., "Locus assignment of human a globin mutations by selective amplification and direct sequencing", British Journal of Haematology, vol. 76, 275–281 (1990).

Drickamer, et al., "Membrane receptors that mediate glycoprotein endocytosis: Structure and biosynthesis", Kidney International, vol. 32, Suppl. 23, pp. S–167–S–180, (1987).

Drickamer, "Two Distinct Classes of Carbohydrate–recognition Domains in Animal Lectins", The Journal of Biological Chemistry, Vol. 263, No. 20, pp. 9557–9560 (1988).

Ekblom, "Developmentally regulated conversion of mesenchyme to epithelium", The FASEB Journal, vol. 3, (1989).

European Polycystic Kidney Disease Consortium, "The Polycystic Kidney Disease 1 Gene Encodes a 14 kb Transcript and Lies within a Duplicated Region on Chromosome 16", Cell. vol. 77, 881–894, (1994).

The European Chromosome 16 Tuberous Sclerosis Consortium, "Identification and Characterization of the Tuberous Sclerosis Gene on Chromosome 16", Cell. vol. 75, 1305–1315 (1993).

Fick et al., "Characteristics of Very Early Onset Autosomal Dominant Polycystic Kidney Disease", Journal of the American Society of Nephrology, vol. 3 (1989).

Fick, et al., "Is there evidence for anticipation in autosomal–dominant polycystic kidney disease?", Kidney International, vol. 45, pp. 1153–1162 (1994).

Gabow, "Polycystic kidney disease: Clues to pathogenesis", Kidney International, vol. 40, pp. 989–996 (1991).

Gabow, "Autosomal Dominant Polycystic Kidney Disease", The New England Journal of Medicine, vol. 5, (1993).

Gabow, "Autosomal Dominant Polycystic Kidney Disease—More Than a Renal Disease", American Journal Kidney Diseases, vol. XVI, No. 5 (1990).

Germino, et al., "Identification of a Locus Which Shows No Genetic Recombination with the Autosomal Dominant Polycystic Kidney Disease Gene on Chromosome 16", Am. J. Hum. Genet. 46:925–933 (1990).

Germino, et al., "The Gene for Autosomal Dominant Polycystic Kidney Disease Lies in a 750–kb CpG–Rich Region", Genomics 13, 144–151 (1992).

Gower, et al., "Alternative Splicing Generates a Secreted Form of N–CAM in Muscle and Brain", Cell. vol. 55, 955–964 (1988).

Green, et al., "Loss of heterozygosity on chromosome 16p13.3 in hamartomas from tuberous sclerosis patients", Nature Genetics, vol. 6 (1994).

Harpaz, et al., "Many of the Immunoglobulin Superfamily Domains in Cell Adhesion Molecules and Surface Receptors Belong to a New Structural Set Which is Close to That Containing Variable Domains", J. Mol. Biol., vol. 238, 529–539 (1994).

Harris, et al., "A Long–Range Restriction Map between the α–Globin Complex and a Marker Closely Linked to the Polycystic Kidney Disease 1 (PKD1) Locus", Genomics, vol. 7, 195–206 (1990).

Harris, et al., "Rapid genetic analysis of families with polycystic kidney disease 1 by means of a microsatellite marker", vol. 338 (1991).

Hartmann, et al., "Predicting the orientation of eukaryotic membrane–spanning proteins", Proc. Natl. Acad. Sci. USA vol. 86, pp. 5786–5790 (1989).

Henikoff, "Unidirectional digestion with exonuclease III creates targeted breakpoints for DNA sequencing", Gene 28 351–359 (1984).

Heijne, "A new method for predicting signal sequence cleavage sites", Nucleic Acids Research, vol. 14 (1986).

Himmelbauer, et al., "Saturating the Region of the Polycystic Kidney Disease Gene with NotI Linking Clones", Am. J. Hum. Genet. 48:325–334 (1991).

Hossack et al., "Echocardiographic Findings In Autosomal Dominant Polycystic Kidney Disease", The New England Journal of Medicine, vol. 319, No. 14 (1988).

Huston, III, et al., "Value of Magnetic Resonance Angiography for the Detection of Intracranial Aneurysms in Autosomal Dominant Polycystic Kidney Disease", Journal of the American Society of Nephrology, vol. 3, No. 12 (1993).

Hyland, et al., "Probe, VK5B, is located in the same interval as the autosomal dominant adult polycystic kidney disease locus, PKD1", Hum. Genet 84:286–288 (1990).

Jia, et al., "The Proto–oncogene of v–eyk (v–ryk) Is a Novel Receptor–type Protein Tyrosine Kinase with Extracellular Ig/FN–III Domains", The Journal of Biological Chemistry, vol. 269, No. 3, pp. 1839–1844 (1994).

Jones, et al., "Crystal structure of an integrin–binding fragement fo vascular cell adhesion molecule–1 at 1.8 A resolution", Nature, vol. 373 (1995).

Keen, et al., "Rapid detection of single base mismatches as heteroduplexes on Hydrolink gels", TIG, vol. 7, No. 1, (1991).

Kimberling, et al., Autosomal Dominant Polycystic Kidney Disease: Localization of the Second Gene to Chromosome 4q13–q23, Genomics, vol. 18, 467–472(1993).

Kimberling et al., "Linkage Heterogeneity of Autosomal Dominant Polycystic Kidney Disease", The New England Journal of Medicine, vol. 319, No. 14 (1988).

Kobe, et al., "The leucine–rich repeat: a versatile binding motif," TIBS, vol. 19, (1994).

Kornblihtt, et al., "Primary structure of human fibronectin: differential splicing may generate at least 10 polypeptides from a single gene", The EMBO Journal, vol. 4, No. 7, pp. 1755–1759 (1985).

Kozak, An analysis of 5'–noncoding sequences from 699 vertebrate messenger RNAs, Nuclear Acids Research, vol. 15, No. 20 (1987).

Kuma, et al., Motifs of Cadherin–and Fibronectin Type III–related Sequences and Evolution of the Receptor––Type–Protein Tyrosine Kinases: Sequence Similarity between Proto–Oncogene ret and Cadherin Family, Mol. Biol. Evol., 10(3):539–551 (1993).

Kwon, et al., "A melanocyte–specific gene, Pmel 17, maps near the silver coat color locus on mouse chromosome 10 and is in a syntenic region of human chromosome12", Proc. Natl. Acad. Sci. USA vol. 88, pp. 9288–9232 (1991).

Lamballe, et al., trkC, a New Member of the trk Family of Tyrosine Proteins Kinases, Is a Receptor for Neurotropin–3, Cell, vol. 66, 967–979 (1991).

Legius, et al., "Somatic deletion of the neurofibromatosis type 1 gene in a neurofibrosarcoma supports a tumour suppressor gene hypothesis", Nature Genetics, vol. 3 (1993).

Love, et al, "An autosomal transcript in skeletal muscle with homology to dystrophin", Nature, vol. 339, No. 6219, pp. 55–58 (1989).

Mandel, "Questions of expansion", Nature Genetics, vol. 4 (1989).

Matsushita, et al., "Purification and Characterization of a Clostridium perfringens 120–Kilodalton Collagenase and Nucleotide Sequence of the Corresponding Gene", Journal of Bacteriology, pp. 149–156 (Jan. 1994).

McFarland, et al., "Lutropin–Choriogonadotropin Receptor: An Unusual Member of the G Protein–Coupled Receptor Family", Science, vol. 245.

Melton, et al., "Efficient in vitro synthesis of biologically active RNA and RNA hybridization Probes from plasmids containing a bacteriophage SP6 promoter", vol. 12, No. 18 (1984).

Milutinovic, et al., "Liver Cysts in Patients with Autosomal Dominant Polycystic Kidney Disease", The American Journal of Medicine, vol. 68 (1980).

Milutinovic, et al., "Autosomal Dominant Polycystic Kidney Disease—Early Diagnosis and Consideration of Pathogenesis", vol. 73, No. 6 (1980).

Nakashima, et al., "The amino acid composition is different between the cytoplasmic and extracellular sides in membrane proteins", vol. 303, No. 2, 3 , 141–146 (1992).

Oldberg, et al., "A collagen–binding 59–kd protein (fibromodulin) is structurally related to the small interstitial proteoglycans PG–S1 and PG–S2 (decorin)", The EMBO Journal, vol. 8, No. 9, pp. 2601–2604 (1989).

Oldberg, et al., "The partial amino acid sequence of bovine cartilage proteoglycan, deduced from a cDNA clone, contains numerous Ser–Gly sequences arranged in homologous repeats", Biochem. J., vol. 243, 255–259 (1987).

Parfrey, et al., "The Diagnosis And Prognosis of Autosomal Dominant Polycystic Kidney Disease", The New England Journal of Medicine, vol. 323, No. 16 (1990).

Pearson, et al., "Improved tools for biological sequence comparison", Proc. Natl. Acad. Sci. USA, vol. 85, pp. 2444–2448 (1988).

Peral, et al., "Evidence of Linkage Disequilibrium in the Spanish Polycystic Kidney Disease 1 Population", Am. J. Hum. Genet. 54:899–908 (1944).

Peral, et al., "Splicing mutations of the polycystic kidney disease 1 (PKD1) gene induced by intronic deletion", Human Molecular Genetics, vol. 4, No. 4 569–574 (1995).

Peters, et al., "Chromosome 4 localization of a second gene for autosomal dominant polycystic kidney disease", Nature Genetics, vol. 5, (1993).

Pound, et al., "Evidence of linkage disequilibrium between D16S94 and the adult onset polycystic kidney disease (PKD1) gene", Med. Genet, 29:247–248 (1992).

Ravine, et al., "Treatable complications in undiagnosed cases of autosomal dominant polycystic kidney disease", The Lancet, vol. 337, No. 8734 (1991).

Ravine, et al., "Phenotype and genotype heterogeneity in autosomal dominant polycystic kidney disease", The Lancet, vol. 340 (1992).

Reeders, "Multilocus polycystic disease", Nature Genetics, vol. 1 (1992).

Royle et al., "A hypervariable locus D16S309 located at the distal end of 16p", Nucleic Acids Research, vol. 20, No. 5.

Reeders, et al., "A highly polymorphic DNA marker linked to adult polycystic kidney disease on chromosome 16", Nature, vol. 317 (1985).

Reeders, et al., "Regional Localization of the Autosomal Dominant Polycystic Kidney Disease Locus", Genomics 3, 150–155 (1988).

Romeo, et al., "A Second Genetic Locus For Autosomal Dominant Polycystic Kidney Diseas", The Lancet (Jul. 2, 1988).

Roth, "Developing Relationships: Arterial Platelet Adhesion, Glycoprotein Ib, and Leucine–Rich Glycoproteins", Blood, vol. 77, No. 1 (1991).

Rothberg, et al., "slit: an extracellular–protein necessary for development of midline glia and commissural axon pathways contains both EGF and LRR domains", Genes & Development, 4:2169–2187 (1990).

Ryynanen, et al., "Localisation of a mutation producing autosomal dominant polycystic kidney disease without renal failure", Journal of Medical Genetics 24, 462–465 (1987).

Schafer, et al., "Characterization of the Han: SPRD rat model for hereditary polycystic kidney disease", Kidney International, vol. 46, pp. 134–152 (1994).

Scheff, et al., "Diverticular Disease in Patients with Chronic Renal Failure Due to Polycystic Kidney Disease", Annals of Internal Medicine, 92(Part 1):202–204 (1980).

Sipos, et al., "Predicting the topology of eukaryotic membrane proteins", Eur. J. Biochem. 213 1333–1340 (1993).

Snarey, et al., "Linkage Disequilibrium in the Regional of the Autosomal Dominant Polycystic Kidney Disease Gene (PKDI)", Am. J. Hum. Genet. 55:365–371 (1994).

Somlo, et al., "Fine Genetic Localization of the Gene for Autosomal Dominant Polycystic Kidney Disease (PKD1) with Respect to Physically Mapped Markers", Genomics 13, 152–158 (1992).

Somlo, et al., "A Kindred Exhibiting Cosegregation of an Overlap Connective Tissue Disorder and the Chromosome 16 Linked Form of Autosomal Dominant Polycystic Kidney Diseas", Journal of the American Society of Nephrology, vol. 4 (1993).

Streuli, et al., "A New Member Of The Immunoglobulin Superfamily That Has A Cytoplasmic Region Homologous To The Leukocyte Common Antigen", J. Exp. Med. vol. 168 (1988).

Takagi, et al., Primary Structure of the Target of Calcium Vector Protein of Amphioxus, Journal of Biological Chemistry, vol. 265, pp. 19721–19727 (1990).

Taylor, et al., Primary Structure of the Mannose Receptor Contains Multiple Motif Resembling Carbohydrate–recognition Domains, The Journal of Biological Chemistry, vol. 265, pp. 12156–12162 (1990).

Thompson, et al., "Isolation and Characterization of $(AC)_n$ Microsatellite Genetic Markers from Human Chromosome 16", Genomics 13, 402–406 (1992).

Volkmer, et al., "Structure of the Axonal Surface Recognition Molecule Neurofascin and Its Relationship to a Neural Subgroup of the Immunoglobulin Superfamily", The Journal of Cell Biology, vol. 118, 149–161 (1992).

Weis, et al., "Structure of a C–type mannose–binding protein complexed with an oligosaccharide", Nature, vol. 360 (1992).

Wieringa, et al., "A Minimal Intron Length but No Specific Internal Sequence is Required for Splicing the Large Rabbit B–Globin Intron", Cell, vol. 37, 915–925 (1984).

Williams, et al., "The Immunoglobulin Superfamily—Domains for Cell Surface Recognition", Ann. Rev. Immunol. 6:381–405 (1988).

Wilson, et al., "Tubulocystic epithelium", International Society of Nephrology, vol. 39, pp. 450–563 (1991).

Wright, et al., "Sample Preparation From Paraffin–Embedded Tissues", PCR Protocols: A Guide to Methods and Applications (1990).

Zerres, et al., "Childhood onset autosomal dominant polycystic kidney disease in sibs: clinical picture and recurrence risk", J Med Genet, 30:583–588 (1993).

Bork, et al., "Fibronectin type III modules in the receptor phosphatase CD45 and tapeworm antigens", Protein Science, 2: 1185–1187, (1993).

Frohman et al., "Rapid production of full–length cDNAs from rare transcripts: Amplification using a single gene–specific oligonucleotide primer", Proc. Natl. Acad. Sci. USA, vol. 85: 8998–9002, (Dec. 1988).

Adams et al., File Medicine Abstract No. 93364420, *Nature Genetics* 4:256–267 (1993).

Adams et al., File Medicine Abstract No. 94004965, *Nature Genetics* 4:373–380 (1993).

Burn et al., *Human Molecular Genetics* 4(4):575–582 (1995).

Germino et al., *Kidney International*, vol. 43, Supp. 39, S–20–S–25 (1993).

*An Introducution to Geneic Analysis*; W. H. Freeman and Company, Fifth Ed., pp. 427, 453–461 (1993).

Mulley et al., *Current Opinion in Genetics and Developement* 3: 425–431 (1993).

* cited by examiner

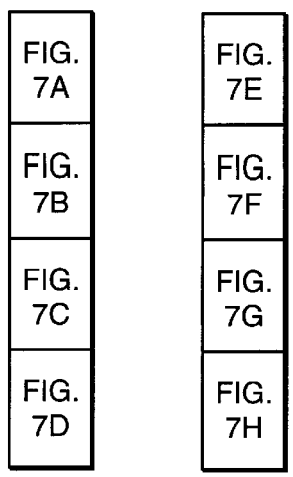

FIG. 7

| | | |
|---|---|---|
| 1 | CTCAACGAGGAGCCCCTGACGCTGGCGGGCGAGGAGATCGTGGCCCAGGGCAAGCGCTCG | 60 |
| 1 | L  N  E  E  P  L  T  L  A  G  E  E  I  V  A  Q  G  K  R  S | 20 |
| 61 | GACCCGCGGAGCCTGCTGTGCTATGGCGGCGCCCAGGGCCTGGCTGCCACTTCTCCATC | 120 |
| 21 | D  P  R  S  L  L  C  Y  G  G  A  P  G  P  G  C  H  F  S  I | 40 |
| 121 | CCCGAGGCTTTCAGCGGGGCCCTGGCCAACCTCAGTGACGTGGTGCAGCTCATCTTTCTG | 180 |
| 41 | P  E  A  F  S  G  A  L  A  N  L  S  D  V  V  Q  L  I  F  L | 60 |
| 181 | GTGGACTCCAATCCCTTTCCCTTTGGCTATATCAGCAACTACACCGTCTCCACCAAGGTG | 240 |
| 61 | V  D  S  N  P  F  P  F  G  Y  I  S  N  Y  T  V  S  T  K  V | 80 |
| 241 | GCCTCGATGGCATTCCAGACACAGGCCGCGCCCAGATCCCCATCGAGCGGCTGGCCTCA | 300 |
| 81 | A  S  M  A  F  Q  T  Q  A  G  A  Q  I  P  I  E  R  L  A  S | 100 |
| 301 | GAGCGCGCCATCACCGTGAAGGTGCCCAACAACTCGGACTGGGCTGCCCGGGGCCACCGC | 360 |
| 101 | E  R  A  I  T  V  K  V  P  N  N  S  D  W  A  A  R  G  H  R | 120 |
| 361 | AGCTCCGCCAACTCCGCCAACTCCGTTGTGGTCCAGCCCCAGGCCTCCGTCGGTGCTGTG | 420 |
| 121 | S  S  A  N  S  A  N  S  V  V  V  Q  P  Q  A  S  V  G  A  V | 140 |
| 421 | GTCACCCTGGACAGCAGCAACCCTGCGGCCGGGCTGCATCTGCAGCTCAACTATACGCTG | 480 |
| 141 | V  T  L  D  S  S  N  P  A  A  G  L  H  L  Q  L  N  Y  T  L | 160 |
| 481 | CTGGACGGCCACTACCTGTCTGAGGAACCTGAGCCCTACCTGGCAGTCTACCTACACTCG | 540 |
| 161 | L  D  G  H  Y  L  S  E  E  P  E  P  Y  L  A  V  Y  L  H  S | 180 |
| 541 | GAGCCCCGGCCCAATGAGCACAACTGCTCGGCTAGCAGGAGGATCCGCCCAGAGTCACTC | 600 |
| 181 | E  P  R  P  N  E  H  N  C  S  A  S  R  R  I  R  P  E  S  L | 200 |

FIG. 7A

```
601  CAGGGTGCTGACCACCGGCCCTACACCTTCTTCATTTCCCCGGGGAGCAGAGACCCAGCG  660
201    Q  G  A  D  H  R  P  Y  T  F  F  I  S  P  G  S  R  D  P  A   220

661  GGGAGTTACCATCTGAACCTCTCCAGCCACTTCCGCTGGTCGGCGCTGCAGGTGTCCGTG  720
221    G  S  Y  H  L  N  L  S  S  H  F  R  W  S  A  L  Q  V  S  W   240

721  GGCCTGTACACGTCCCTGTGCCAGTACTTCAGCGAGGAGGACATGGTGTGGCGGACAGAG  780
241    G  L  Y  T  S  L  C  Q  Y  F  S  E  E  D  M  V  W  R  T  E   260

781  GGGCTGCTGCCCCTGGAGGAGACCTCGCCCCGCCAGGCCGTCTGCCTCACCCGCCACCTC  840
261    G  L  L  P  L  E  E  T  S  P  R  Q  A  V  C  L  T  R  H  L   280

841  ACCGCCTTCGGCGCCAGCCTCTTCGTGCCCCCAAGCCATGTCCGCTTTGTGTTTCCTGAG  900
281    T  A  F  G  A  S  L  F  V  P  P  S  H  V  R  F  V  F  P  E   300

901  CCGACAGCGGATGTAAACTACATCGTCATGCTGACATGTGCTGTGTGCCTGGTGACCTAC  960
301    P  T  A  D  V  N  Y  I  V  M  L  T  C  A  V  C  L  V  T  Y   320

961  ATGGTCATGGCCGCCATCCTGCACAAGCTGGACCAGTTGGATGCCAGCCGGGGCCGCGCC  1020
321    M  V  M  A  A  I  L  H  K  L  D  Q  L  D  A  S  R  G  R  A   340

1021 ATCCCTTTCTGTGGGCAGCGGGGCCGCTTCAAGTACGAGATCCTCGTCAAGACAGGCTGG  1080
341    I  P  F  C  G  Q  R  G  R  F  K  Y  E  I  L  V  K  T  G  W   360

1081 GGCCGGGGCTCAGGTACCACGGCCCACGTGGGCATCATGCTGTATGGGGTGGACAGCCGG  1140
361    G  R  G  S  G  T  T  A  H  V  G  I  M  L  Y  G  V  D  S  R   380

1141 AGCGGCCACCGGCACCTGGACGGCGACAGAGCCTTCCACCGCAACAGCCTGGACATCTTC  1200
381    S  G  H  R  H  L  D  G  D  R  A  F  H  R  N  S  L  D  I  F   400

1201 CGGATCGCCACCCCGCACAGCCTGGGTAGCGTGTGGAAGATCCGAGTGTGGCACGACAAC  1260
401    R  I  A  T  P  H  S  L  G  S  V  W  K  I  R  V  W  H  D  N   420
```

FIG. 7B

| | | |
|---|---|---|
| 1261 | AAAGGGCTCAGCCCTGCCTGGTTCCTGCAGCACGTCATCGTCAGGGACCTGCAGACGGCA | 1320 |
| 421 | K G L S P A W F L Q H V I V R D L Q T A | 440 |
| 1321 | CGCAGCGCCTTCTTCCTGGTCAATGACTGGCTTTCGGTGGAGACGGAGGCCAACGGGGGC | 1380 |
| 441 | R S A F F L V N D W L S V E T E A N G G | 460 |
| 1381 | CTGGTGGAGAAGGAGGTGCTGGCCGCGAGCGACGCAGCCCTTTTGCGCTTCCGGCGCCTG | 140 |
| 461 | L V E K E V L A A S D A A L L R F R R L | 480 |
| 1441 | CTGGTGGCTGAGCTGCAGCGTGGCTTCTTTGACAAGCACATCTGGCTCTCCATATGGGAC | 1500 |
| 481 | L V A E L Q R G F F D K H I W L S I W D | 500 |
| 1501 | CGGCCGCCTCGTAGCCGTTTCACTCGCATCCAGAGGGCCACCTGCTGCGTTCTCCTCATC | 1560 |
| 501 | R P P R S R F T R I Q R A T C C V L L I | 520 |
| 1561 | TGCCTCTTCCTGGGCGCCAACGCCGTGTGGTACGGGCTGTTGGCGACTCTGCCTACAGC | 1620 |
| 521 | C L F L G A N A V W Y G A V G D S A Y S | 540 |
| 1621 | ACGGGGCATGTGTCCAGGCTGAGCCCGCTGAGCGTCGACACAGTCGCTGTTGGCCTCGTG | 1680 |
| 541 | T G H V S R L S P L S V D T V A V G L V | 560 |
| 1681 | TCCAGCGTGGTTGTCTATCCCGTCTACCTGGCCATCCTTTTTCTCTTCCGGATGTCCCGG | 1740 |
| 561 | S S V V V Y P V Y L A I L F L F R M S R | 580 |
| 1741 | AGCAAGGTGGCTGGGAGCCCGAGCCCCACACTGCCGGGCAGCAGGTGCTGGACATCGAC | 1800 |
| 581 | S K V A G S P S P T P A G Q Q V L D I D | 600 |
| 1801 | AGCTGCCTGGACTCGTCCGTGCTGGACAGCTCCTTCCTCACGTTCTCAGGCCTCCACGCT | 1860 |
| 601 | S C L D S S V L D S S F L T F S G L H A | 620 |
| 1861 | GAGGCCTTTGTTGGACAGATGAAGAGTGACTTGTTTCTGGATGATTCTAAGAGTCTGGTG | 1920 |
| 621 | E A F V G Q M K S D L F L D D S K S L V | 640 |

FIG. 7C

| | | |
|---|---|---|
| 1921 | TGCTGGCCCTCCGGCGAGGGAACGCTCAGTTGGCCGCACCTGCTCAGTGACCCGTCCATT | 1980 |
| 641 | C  W  P  S  G  E  G  T  L  S  W  P  D  L  L  S  D  P  S  I | 660 |
| 1981 | GTGGGTAGCAATCTGCGGCAGCTGGCACGGGGCCAGGCGGGCCATGGGCTGGGCCCAGAG | 2040 |
| 661 | V  G  S  N  L  R  Q  L  A  R  G  Q  A  G  H  G  L  G  P  E | 680 |
| 2041 | GAGGACGGCTTCTCCCTGGCCAGCCCCTCCTCGCCTGCCAAATCCTTCTCAGCATCAGAT | 2100 |
| 681 | E  D  G  F  S  L  A  S  P  Y  S  P  A  K  S  F  S  A  S  D | 700 |
| 2101 | GAAGACCTGATCCAGGAGGTCCTTGCCGAGGGGGTCAGCAGCCCAGCCCCTACCCAAGAC | 2160 |
| 701 | E  D  L  I  Q  Q  V  L  A  E  G  V  S  S  P  A  P  T  Q  D | 720 |
| 2161 | ACCCACATGGAAACGGACCTGCTCAGCAGCCTGTCCAGCACTCCTGGGGAGAAGACAGAG | 2220 |
| 721 | T  H  M  E  T  D  L  L  S  S  L  S  S  T  P  G  E  K  T  E | 740 |
| 2221 | ACGCTGGCGCTGCAGAGGCTGGGGGAGCTGGGGCCACCCAGCCCAGGCCTGAACTGGGAA | 2280 |
| 741 | T  L  A  L  Q  R  L  G  E  L  G  P  P  S  P  G  L  N  W  E | 760 |
| 2281 | CAGCCCCAGGCAGCGAGGCTGTCCAGGACAGGACTGGTGGAGGGTCTGCGGAAGCGCCTG | 2340 |
| 761 | Q  P  Q  A  A  R  L  S  R  T  G  L  V  E  G  L  R  K  R  L | 780 |
| 2341 | CTGCCGGCCTGGTGTGCCTCCCTGGCCCACGGGCTCAGCCTGCTCCTGGTGGCTGTGGCT | 2400 |
| 781 | L  P  A  W  C  A  S  L  A  H  G  L  S  L  L  L  V  A  V  A | 800 |
| 2401 | GTGGCTGTCTCAGGGTGGGTGGGTGCGAGCTTCCCCCCGGGCCTGAGTGTTGCGTGGCTC | 2460 |
| 801 | V  A  V  S  G  W  V  G  A  S  F  P  P  G  V  S  V  A  W  L | 820 |
| 2461 | CTGTCCAGCAGCGCCAGCTTCCTGGCCTCATTCCTCGGCTGGGAGCCACTGAAGGTCTTG | 2520 |
| 821 | L  S  S  S  A  S  F  L  A  S  F  L  G  W  E  P  L  K  V  L | 840 |

FIG. 7D

```
2521  CTGGAAGCCCTGTACTTCTCACTGGTGGCCAAGCGGCTGCACCCGGATGAAGATGACACC  2580
 841   L   E   A   L   Y   F   S   L   V   A   K   R   L   H   P   D   E   D   D   T    860

2581  CTGGTAGAGAGCCCGGCTGTGACGCCTGTGAGCGCACGTGTGCCCCGCGTACGGCCACCC  2640
 861   L   V   E   S   P   A   V   T   P   V   S   A   R   V   P   R   V   R   P   P    880

2641  CACGGCTTTGCACTCTTCCTGGCCAAGGAAGAAGCCCGCAAGGTCAAGAGGCTACATGGC  2700
 881   H   G   F   A   L   F   L   A   K   E   E   A   R   K   V   K   R   L   H   G    900

2701  ATGCTGCGGAGCCTCCTGGTGTACATGCTTTTTCTGCTGGTGACCCTGCTGGCCAGCTAT  2760
 901   M   L   R   S   L   L   V   Y   M   L   F   L   L   V   T   L   L   A   S   Y    920

2761  GGGGATGCCTCATGCCATGGGCACGCCTACCGTCTGCAAAGCGCCATCAAGCAGGAGCTG  2820
 921   G   D   A   S   C   H   G   H   A   Y   R   L   Q   S   A   I   K   Q   E   L    940

2821  CACAGCCGGGCCTTCCTGGCCATCACGCGGTCTGAGGAGCTCTGGCCATGGATGGCCCAC  2880
 941   H   S   R   A   F   L   A   I   T   R   S   E   E   L   W   P   W   M   A   H    960

2881  GTGCTGCTGCCCTACGTCCACGGGAACCAGTCCAGCCCAGAGCTGGGGCCCCCACGGCTG  2940
 961   V   L   L   P   Y   V   H   G   N   Q   S   S   P   E   L   G   P   P   R   L    980

2941  CGGCAGGTGCGGCTGCAGGAAGCACTCTACCCAGACCCTCCCGGCCCC`AGGGTCCACACG  3000
 981   R   Q   V   R   L   Q   E   A   L   Y   P   D   P   P   G   P   R   V   H   T   1000

3001  TGCTCGGCCGCAGGAGGCTTCAGCACCAGCGATTACGACGTTGGCTGGGAGAGTCCTCAC  3060
1001   C   S   A   A   G   G   F   S   T   S   D   Y   D   V   G   W   E   S   P   H   1020

3061  AATGGCTCGGGGACGTGGGCCTATTCAGCGCCGGATCTGCTGGGGGCATGGTCCTGGGGC  3120
1021   N   G   S   G   T   W   A   Y   S   A   P   D   L   L   G   A   W   S   W   G   1040
```

FIG. 7E

```
3121  TCCTGTGCCGTGTATGACAGCGGGGGCTACGTGCAGGAGCTGGGCCTGAGCCTGGAGGAG  3180
1041   S   C   A   V   Y   D   S   G   G   Y   V   Q   E   L   G   L   S   L   E   E   1060

3181  AGCCGCGACCGGCTGCGCTTCCTGCAGCTGCACAACTGGCTGGACAACAGGAGCCGCGCT  3240
1061   S   R   D   R   L   R   F   L   Q   L   H   N   W   L   D   N   R   S   R   A   1080

3241  GTGTTCCTGGAGCTCACGCGCTACAGCCCGGCCGTGGGGCTGCACGCCGCCGTCACGCTG  3300
1081   V   F   L   E   L   T   R   Y   S   P   A   V   G   L   H   A   A   V   T   L   1100

3301  CGCCTCGAGTTCCCGGCGGCCGGCCGCGCCCTGGCCGCCCTCAGCGTCCGCCCCTTTGCG  3360
1101   R   L   E   F   P   A   A   G   R   A   L   A   A   L   S   V   R   P   F   A   1120

3361  CTGCGCCGCCTCAGCGCGGGCCTCTCGCTGCCTCTGCTCACCTCGGTGTGCCTGCTGCTG  3420
1121   L   R   R   L   S   A   G   L   S   L   P   L   L   T   S   V   C   L   L   L   1140

3421  TTCGCCGTGCACTTCGCCGTGGCCGAGGCCCGTACTTGGCACAGGGAAGGGCGCTGGCGC  3480
1141   F   A   V   H   F   A   V   A   E   A   R   T   W   H   R   E   G   R   W   R   1160

3481  GTGCTGCGGCTCGGAGCCTGGGCGCGGTGGCTGCTGGTGGCGCTGACGGCGGCCACGGCA  3540
1161   V   L   R   L   G   A   W   A   R   W   L   L   V   A   L   T   A   A   T   A   1180

3541  CTGGTACGCCTCGCCCAGCTGGGTGCCGCTGACCGCCAGTGGACCCGTTTCGTGCGCGGC  3600
1181   L   V   R   L   A   Q   L   G   A   A   D   R   Q   W   T   R   F   V   R   G   1200

3601  CGCCCGCGCCGCTTCACTAGCTTCGACCAGGTGGCGCACGTGAGCTCCGCAGCCCGTGGC  3660
1201   R   P   R   R   F   T   S   F   D   Q   V   A   H   V   S   S   A   A   R   G   1220

3661  CTGGCGGCCTCGCTGCTCTTCCTGCTTTTGGTCAAGGCTGCCCAGCACGTACGCTTCGTG  3720
1221   L   A   A   S   L   L   F   L   L   L   V   K   A   A   Q   H   V   R   F   V   1240

3721  CGCCAGTGGTCCGTCTTTGGCAAGACATTATGCCGAGCTCTGCCAGAGCTCCTGGGGGTC  3780
1241   R   Q   W   S   V   F   G   K   T   L   C   R   A   L   P   E   L   L   G   V   1260
```

FIG. 7F

```
3781  ACCTTGGGCCTGGTGGTGCTCGGGGTAGCCTACGCCCAGCTGGCCATCCTGCTCGTGTCT  3840
1261   T  L  G  L  V  V  L  G  V  A  Y  A  Q  L  A  I  L  L  V  S   1280

3841  TCCTGTGTGGACTCCCTCTGGAGCGTGGCCCAGGCCCTGTTGGTGCTGTGCCCTGGGACT  3900
1281   S  C  V  D  S  L  W  S  V  A  Q  A  L  L  V  L  C  P  G  T   1300

3901  GGGCTCTCTACCCTGTGTCCTGCCGAGTCCTGGCACCTGTCACCCCTGCTGTGTGTGGGG  3960
1301   G  L  S  T  L  C  P  A  E  S  W  H  L  P  L  L  C  V  G      1320

3961  CTCTGGGCACTGCGGCTGTGGGGCGCCCTACGGCTGGGGGCTGTTATTCTCCGCTGGCGC  4020
1321   L  W  A  L  R  L  W  G  A  L  R  L  G  A  V  I  L  R  W  R   1340

4021  TACCACGCCTTGCGTGGAGAGCTGTACCGGCCGGCCTGGGAGCCCCAGGACTACGAGATG  4080
1341   Y  H  A  L  R  G  E  L  Y  R  P  A  W  E  P  Q  D  Y  E  M   1360

4081  GTGGAGTTGTTCCTGCGCAGGCTGCGCCTCTGGATGGGCCTCAGCAAGGTCAAGGAGTTC  4140
1361   V  E  L  F  L  R  R  L  R  L  W  M  G  L  S  K  V  K  E  F   1380

4141  CGCCACAAAGTCCGCTTTGAAGGGATGGAGCCGCTGCCCTCTCGCTCCTCCAGGGGCTCC  4200
1381   R  H  K  V  R  F  E  G  M  E  P  L  P  S  R  S  S  R  G  S   1400

4201  AAGGTATCCCCGGATGTGCCCCCACCCAGCGCTGGCTCCGATGCCTCGCACCCCTCCACC  4260
1401   K  V  S  P  D  V  P  P  P  S  A  G  S  D  A  S  H  P  S  T   1420

4261  TCCTCCAGCCAGCTGGATGGGCTGAGCGTGAGCCTGGGCCGGCTGGGGACAAGGTGTGAG  4320
1421   S  S  S  Q  L  D  G  L  S  V  S  L  G  R  L  G  T  R  C  E   1440

4321  CCTGAGCCCTCCCGCCTCCAAGCCGTGTTCGAGGCCCTGCTCACCCAGTTTGACCGACTC  4380
1441   P  E  P  S  R  L  Q  A  V  F  E  A  L  L  T  Q  F  D  R  L   1460
```

FIG. 7G

| | | |
|---|---|---|
| 4381 | AACCAGGCCACAGAGGACGTCTACCAGCTGGAGCAGCAGCTGCACAGCCTGCAAGGCCGC | 4440 |
| 1461 | N  Q  A  T  E  D  V  Y  Q  L  E  Q  Q  L  H  S  L  Q  G  R | 1480 |
| 4441 | AGGAGCAGCCGGGCGCCCGCCGGATCTTCCCGTGGCCCATCCCCGGGCCTGCGGCCAGCA | 4500 |
| 1481 | R  S  S  R  A  P  A  G  S  S  R  G  P  S  P  G  L  R  P  A | 1500 |
| 4501 | CTGCCCAGCCGCCTTGCCCGGGCCAGTCGGGGTGTGGACCTGGCCACTGGCCCCAGCAGG | 4560 |
| 1501 | L  P  S  R  L  A  R  A  S  R  G  V  D  L  A  T  G  P  S  R | 1520 |
| 4561 | ACACCTTCGGGCCAAGAACAAGGTCCACCCCAGCAGCACTTAGTCCTCCTTCCTGGCGGG | 4620 |
| 1521 | T  P  S  G  Q  E  Q  G  P  P  Q  Q  H  L  V  L  L  P  G  G | 1540 |
| 4621 | GGTGGGCCGTGGAGTCGGAGTGGACACCGCTCAGTATTACTTTCTGCCGCTGTCAAGGCC | 4689 0 |
| 1541 | G  G  P  W  S  R  S  G  H  R  S  V  L  L  S  A  A  V  K  A | 1560 |
| 4681 | GAGGGCCAGGCAGAATGGCTGCACGTAGGTTCCCCAGAGAGCAGGCAGGGGCATCTGTCT | 4740 |
| 1561 | E  G  Q  A  E  W  L  H  V  G  S  P  E  S  R  Q  G  H  L  S | 1580 |
| 4741 | GTCTGTGGGCTTCAGCACTTTAAAGAGGCTGTGTGGCCAACCAGGACCCAGGGTCCCCTC | 4800 |
| 1581 | V  C  G  L  Q  H  F  K  E  A  V  W  P  T  R  T  Q  G  P  L | 1600 |
| 4801 | CCCAGCTCCCTTGGAAGGACACAGCAGTATTGGACGGTTTCTAGCCTCTGAGATGCTAA | 4860 |
| 1601 | P  S  S  L  G  K  D  T  A  V  L  D  G  F | 1620 |
| 4861 | TTTATTTCCCCGAGTCCTCAGGTACAGCGGGCTGTGCCCGGCCCCACCCCCTGGGCAGAT | 4920 |
| 4921 | GTCCCCCACTGCTAAGGCTGCTGGCTTCAGGGAGGGTTAGCCTGCACCGCCGCCACCCTG | 4980 |
| 4981 | CCCCTAAGTTATTACCTCTCCAGTTCCTACCGTACTCCCTGCACCGTCTCACTGTGTGTC | 5040 |
| 5041 | TCGTCTCAGTAATTTATATGGTGTTAAAATGTGTATATTTTTGTATGTCACTATTTTCAC | 5100 |
| 5101 | TAGGGCTGAGGGGCCTGCGCCCAGAGCTGGCCTCCCCCAACACCTGCTGCGCTTGGTAGG | 5160 |
| 5161 | TGTGGTGGCGTTATGGCAGCCCGGCTGCTGCTTGGATGCGAGCTTGGCCTTGGGCCGGTG | 5220 |
| 5221 | CTGGGGGCACAGCTGTCTGCCAGGCACTCTCATCACCCCAGAGGCCTTGTCATCCTCCCT | 5280 |
| 5281 | TGCCCCAGGCCAGGTAGCAAGAGAGCAGCGCCCAGGCCTGCTGGCATCAGGTCTGGGCAA | 5340 |
| 5341 | CTAGCAGGACTAGGCATGTCAGAGGACCCCAGGGTGGTTAGAGGAAAAGACTCCTCCTGG | 5400 |
| 5401 | GGGCTGGCTCCCAGGGTGGAGGAAGGTGACTGTGTGTGTGTGTGTGTGCGCGCGCGACGC | 5460 |
| 5461 | GCGACTGTGCTGTATGGCCCAGGCACGCTCAAGGCCCTCGGAGCTGGCTGTGCCTGCTTC | 5520 |
| 5521 | TGTGTACCACTTCTGTGGGCATGGCCGCTTCTAGAGCCTCGACACCCCCCAACCCCCGC | 5580 |
| 5581 | ACCAAGCAGACAAAGTCAATAAAAGAGCTGTCTGACTGCAAAAAAAAAAAAA 5631 | |

FIG. 7H

```
AGCTTGGCAC CATCAAGGGC CAGTTCAACT TTGTCCACGT GATCGTCACC CCGCTGGACT    60
ACGAGTGCAA CCTGGTGTCC CTGCAGTGCA GGAAAGACAT GGAGGGCCTT GTGGACACCA   120
GCGTGGCCAA GATCGTGTCT GACCGCAACC TGCCCTTCGT GGCCCGCCAG ATGGCCCTGC   180
ACGCAAATAT GGCCTCACAG GTGCATCATA GCCGCTCCAA CCCCACCGAT ATCTACCCCT   240
CCAAGTGGAT TGCCCGGCTC CGCCACATCA AGCGGCTCCG CCAGCCGATC TGCGAGGAAG   300
CCGCCTACTC CAACCCCAGC CTACCTCTGG TGCACCCTCC GTCCCATAGC AAAGCCCCTG   360
CACAGACTCC AGCCGAGCCC ACACCTGGCT ATGAGGTGGG CCAGCGGAAG CGCCTCATCT   420
CCTGGTGGA GGACTTCACC GAGTTTGTGT GAGGCCGGGG CCCTCCCTCC TGCACTGGCC   480
TTGGACGGTA TTGCCTGTCA GTGAAATAAA TAAAGTCCTG ACCCCAGTGC ACAGACATAG   540
AGGCACAGAT TGC                                                      553
                      (1A1HO.6)
```

FIG. 8

```
CTGGTGTGTG TGAGACGTGC GGGGCTGGGA AGTGTTGGCA GAGCCGCGAG TACCGTCCTC    60
ACTCCTTTTG TTCTTTTGAC GTAAGCTGGC GAGTGGCACT GCCTGAGTTC CGCTCAGTGC   120
CGCCCTGAT GTGCGGACCC CGCTGCATTC TTGCTGTTAG GTGGTGGCGG TGTGCGCTGT   180
CGCTGGTGGG CACCGAGAGT CTTTGGGAGC TTTGGGGAGG TTGTGCCAAG CCTGAGCCTC   240
GACGTCCCCC TTCCCGGCTT TCTGTTGGCT CTTCTGAGGC CAGGGCATCT CTATGAGGGC   300
CTCCTGCTGG AGCCGTCTCT GTGGATCTCC TCTGCCATCC TGGCCCATGA GTGGGTGATG   360
CGCTGGCCAC CATCTGGTGA CAGTGGCCGG GCACCGCTGC CAAATGTGGG TCCCGCATCT   420
GCAAGCCCCT CCCTGGGTCC CCTAGGGTAT GGGGTGGTTC TGCCACTGCC CTCGCTCCCC   480
CACCTTGGGG TGCCTCTCCC CCTGCTCGTG GGGAGA                             517
                      (CW10L)
```

FIG. 9A

```
1  AGGCAGGTCT CCCCCACGAG CAGGGGAGAG GCACCCAAGG T
                      (CW10R)
```

FIG. 9B

```
C GGC GCC GCC TGC CGC GTC AAC TGC TCG GGC CGC GGG CTG CGG ACG        46
  Gly Ala Ala Cys Arg Val Asn Cys Ser Gly Arg Gly Leu Arg Thr
   1               5                  10                  15

CTC GGT CCC GCG CTG CGC ATC CCC GCG GAC GCC ACA GCG CTA GAC GTC      94
Leu Gly Pro Ala Leu Arg Ile Pro Ala Asp Ala Thr Ala Leu Asp Val
                 20                  25                  30

TCC CAC AAC CTG CTC CGG GCG CTG GAC GTT GGG CTC CTG GCG AAC CTC     142
Ser His Asn Leu Leu Arg Ala Leu Asp Val Gly Leu Leu Ala Asn Leu
             35                  40                  45

TCG GCG CTG GCA GAG CTG GAT ATA AGC AAC AAC AAG ATT TCT ACG TTA     190
Ser Ala Leu Ala Glu Leu Asp Ile Ser Asn Asn Lys Ile Ser Thr Leu
         50                  55                  60

GAA GAA GGA ATA TTT GCT AAT TTA TTT AAT TTA AGT GAA ATA AAC CTG     238
Glu Glu Gly Ile Phe Ala Asn Leu Phe Asn Leu Ser Glu Ile Asn Leu
     65                  70                  75

AGT GGG AAC CCG TTT GAG TGT GAC TGT GGC CTG GCG TGG CTG CCG CGA     286
Ser Gly Asn Pro Phe Glu Cys Asp Cys Gly Leu Ala Trp Leu Pro Arg
 80                  85                  90                  95

TGG GCG GAG GAG CAG CAG GTG CGG GTG GTG CAG CCC GAG GCA GCC ACG     334
Trp Ala Glu Glu Gln Gln Val Arg Val Val Gln Pro Glu Ala Ala Thr
                100                 105                 110

TGT GCT GGG CCT GGC TCC CTG GCT GGC CAG CCT CTG CTT GGC ATC CCC     382
Cys Ala Gly Pro Gly Ser Leu Ala Gly Gln Pro Leu Leu Gly Ile Pro
            115                 120                 125
```

FIG. 10A

```
TTG CTG GAC AGT GGC TGT GGT GAG GAG TAT GTC GCC TGC CTC CCT GAC      430
Leu Leu Asp Ser Gly Cys Gly Glu Glu Tyr Val Ala Cys Leu Pro Asp
        130                 135                 140

AAC AGC TCA GGC ACC GTG GCA GCA GTG TCC TTT TCA GCT GCC CAC GAA      478
Asn Ser Ser Gly Thr Val Ala Ala Val Ser Phe Ser Ala Ala His Glu
    145                 150                 155

GGC CTG CTT CAG CCA GAG GCC TGC AGC GCC TTC TGC TTC TCC ACC GGC      526
Gly Leu Leu Gln Pro Glu Ala Cys Ser Ala Phe Cys Phe Ser Thr Gly
160                 165                 170                 175

CAG GGC CTC GCA GCC CTC TCG GAG CAG GGC TGG TGC CTG TGT GGG GCG      574
Gln Gly Leu Ala Ala Leu Ser Glu Gln Gly Trp Cys Leu Cys Gly Ala
                180                 185                 190

GCC CAG CCC TCC AGT GCC TCC TTT GCC TGC CTG TCC CTC TGC TCC GGC      622
Ala Gln Pro Ser Ser Ala Ser Phe Ala Cys Leu Ser Leu Cys Ser Gly
            195                 200                 205

CCC CCG CCA CCT CCT GCC CCC ACC TGT AGG GGC CCC ACC CTC CTC CAG      670
Pro Pro Pro Pro Pro Ala Pro Thr Cys Arg Gly Pro Thr Leu Leu Gln
        210                 215                 220

CAC GTC TTC CCT GCC TCC CCA GGG GCC ACC CTG GTG GGG CCC CAC GGA      718
His Val Phe Pro Ala Ser Pro Gly Ala Thr Leu Val Gly Pro His Gly
    225                 230                 235
```

FIG. 10A-1

```
CCT CTG GCC TCT GGC CAG CTA GCA GCC TTC CAC ATC GCT GCC CCG CTC      766
Pro Leu Ala Ser Gly Gln Leu Ala Ala Phe His Ile Ala Ala Pro Leu
240             245             250             255

CCT GTC ACT GCC ACA CGC TGG GAC TTC GGA GAC GGC TCC GCC GAG GTG      814
Pro Val Thr Ala Thr Arg Trp Asp Phe Gly Asp Gly Ser Ala Glu Val
                260             265             270

GAT GCC GCT GGG CCG GCT GCC TCG CAT CGC TAT GTG CTG CCT GGG CGC      862
Asp Ala Ala Gly Pro Ala Ala Ser His Arg Tyr Val Leu Pro Gly Arg
            275             280             285

TAT CAC GTG ACG GCC GTG CTG GCC CTG GGG GCC GGC TCA GCC CTG CTG      910
Tyr His Val Thr Ala Val Leu Ala Leu Gly Ala Gly Ser Ala Leu Leu
        290             295             300

GGG ACA GAC GTG CAG GTG GAA GCG GCA CCT GCC GCC CTG GAG CTC GTG      958
Gly Thr Asp Val Gln Val Glu Ala Ala Pro Ala Ala Leu Glu Leu Val
    305             310             315

TGC CCG TCC TCG GTG CAG AGT GAC GAG AGC CTT GAC CTC AGC ATC CAG     1006
Cys Pro Ser Ser Val Gln Ser Asp Glu Ser Leu Asp Leu Ser Ile Gln
320             325             330             335

AAC CGC GGT GGT TCA GGC CTG GAG GCC GCC TAC AGC ATC GTG GCC CTG     1054
Asn Arg Gly Gly Ser Gly Leu Glu Ala Ala Tyr Ser Ile Val Ala Leu
            340             345             350

GGC GAG GAG CCG GCC CGA GCG GTG CAC CCG CTC TGC CCC TCG GAC ACG     1102
Gly Glu Glu Pro Ala Arg Ala Val His Pro Leu Cys Pro Ser Asp Thr
        355             360             365
```

FIG. 10A-2

```
GAG ATC TTC CCT GGC AAC GGG CAC TGC TAC CGC CTG GTG GTG GAG AAG       1150
Glu Ile Phe Pro Gly Asn Gly His Cys Tyr Arg Leu Val Val Glu Lys
        370             375             380

GCG GCC TGG CTG CAG GCG CAG GAG CAG TGT CAG GCC TGG GCC GGG GCC       1198
Ala Ala Trp Leu Gln Ala Gln Glu Gln Cys Gln Ala Trp Ala Gly Ala
    385             390             395

GCC CTG GCA ATG GTG GAC AGT CCC GCC GTG CAG CGC TTC CTG GTC TCC       1246
Ala Leu Ala Met Val Asp Ser Pro Ala Val Gln Arg Phe Leu Val Ser
400             405             410             415

CGG GTC ACC AGG AGC CTA GAC GTG TGG ATC GGC TTC TCG ACT GTG CAG       1294
Arg Val Thr Arg Ser Leu Asp Val Trp Ile Gly Phe Ser Thr Val Gln
            420             425             430

GGG GTG GAG GTG GGC CCA GCG CCG CAG GGC GAG GCC TTC AGC CTG GAG       1342
Gly Val Glu Val Gly Pro Ala Pro Gln Gly Glu Ala Phe Ser Leu Glu
        435             440             445

AGC TGC CAG AAC TGG CTG CCC GGG GAG CCA CAC CCA GCC ACA GCC GAG       1390
Ser Cys Gln Asn Trp Leu Pro Gly Glu Pro His Pro Ala Thr Ala Glu
    450             455             460

CAC TGC GTC CGG CTC GGG CCC ACC GGG TGG TGT AAC ACC GAC CTG TGC       1438
His Cys Val Arg Leu Gly Pro Thr Gly Trp Cys Asn Thr Asp Leu Cys
465             470             475
```

FIG. 10A-3

```
TCA GCG CCG CAC AGC TAC GTC TGC GAG CTG CAG CCC GGA GGC CCA GTG        1486
Ser Ala Pro His Ser Tyr Val Cys Glu Leu Gln Pro Gly Gly Pro Val
480             485             490             495

CAG GAT GCC GAG AAC CTC CTC GTG GGA GCG CCC AGT GGG GAC CTG CAG        1534
Gln Asp Ala Glu Asn Leu Leu Val Gly Ala Pro Ser Gly Asp Leu Gln
            500             505             510

GGA CCC CTG ACG CCT CTG GCA CAG CAG GAC GGC CTC TCA GCC CCG CAC        1582
Gly Pro Leu Thr Pro Leu Ala Gln Gln Asp Gly Leu Ser Ala Pro His
                515             520             525

GAG CCC GTG GAG GTC ATG GTA TTC CCG GGC CTG CGT CTG AGC CGT GAA        1630
Glu Pro Val Glu Val Met Val Phe Pro Gly Leu Arg Leu Ser Arg Glu
            530             535             540

GCC TTC CTC ACC ACG GCC GAA TTT GGG ACC CAG GAG CTC CGG CGG CCC        1678
Ala Phe Leu Thr Thr Ala Glu Phe Gly Thr Gln Glu Leu Arg Arg Pro
            545             550             555

GCC CAG CTG CGG CTG CAG GTG TAC CGG CTC CTC AGC ACA GCA GGG ACC        1726
Ala Gln Leu Arg Leu Gln Val Tyr Arg Leu Leu Ser Thr Ala Gly Thr
560             565             570             575

CCG GAG AAC GGC AGC GAG CCT GAG AGC AGG TCC CCG GAC AAC AGG ACC        1774
Pro Glu Asn Gly Ser Glu Pro Glu Ser Arg Ser Pro Asp Asn Arg Thr
                580             585             590

CAG CTG GCC CCC GCG TGC ATG CCA GGG GGA CGC TGG TGC CCT GGA GCC        1822
Gln Leu Ala Pro Ala Cys Met Pro Gly Gly Arg Trp Cys Pro Gly Ala
            595             600             605
```

FIG. 10A-4

```
AAC ATC TGC TTG CCG CTG GAC GCC TCT TGC CAC CCC CAG GCC TGC GCC        1870
Asn Ile Cys Leu Pro Leu Asp Ala Ser Cys His Pro Gln Ala Cys Ala
        610                 615                 620

AAT GGC TGC ACG TCA GGG CCA GGG CTA CCC GGG GCC CCC TAT GCG CTA        1918
Asn Gly Cys Thr Ser Gly Pro Gly Leu Pro Gly Ala Pro Tyr Ala Leu
        625                 630                 635

TGG AGA GAG TTC CTC TTC TCC GTT GCC GCG GGG CCC CCC GCG CAG TAC        1966
Trp Arg Glu Phe Leu Phe Ser Val Ala Ala Gly Pro Pro Ala Gln Tyr
640                 645                 650                 655

TCG GTC ACC CTC CAC GGC CAG GAT GTC CTC ATG CTC CCT GGT GAC CTC        2014
Ser Val Thr Leu His Gly Gln Asp Val Leu Met Leu Pro Gly Asp Leu
                    660                 665                 670

GTT GGC TTG CAG CAC GAC GCT GGC CCT GGC GCC CTC CTG CAC TGC TCG        2062
Val Gly Leu Gln His Asp Ala Gly Pro Gly Ala Leu Leu His Cys Ser
                675                 680                 685

CCG GCT CCC GGC CAC CCT GGT CCC CAG GCC CCG TAC CTC TCC GCC AAC        2110
Pro Ala Pro Gly His Pro Gly Pro Gln Ala Pro Tyr Leu Ser Ala Asn
        690                 695                 700

GCC TCG TCA TGG CTG CCC CAC TTG CCA GCC CAG CTG GAG GGC ACT TGG        2158
Ala Ser Ser Trp Leu Pro His Leu Pro Ala Gln Leu Glu Gly Thr Trp
        705                 710                 715
```

FIG. 10A-5

```
GCC TGC CCT GCC TGT GCC CTG CGG CTG CTT GCA GCC ACG GAA CAG CTC        2206
Ala Cys Pro Ala Cys Ala Leu Arg Leu Leu Ala Ala Thr Glu Gln Leu
720             725                 730                 735

ACC GTG CTG CTG GGC TTG AGG CCC AAC CCT GGA CTG CGG ATG CCT GGG        2254
Thr Val Leu Leu Gly Leu Arg Pro Asn Pro Gly Leu Arg Met Pro Gly
                740                 745                 750

CGC TAT GAG GTC CGG GCA GAG GTG GGC AAT GGC GTG TCC AGG CAC AAC        2302
Arg Tyr Glu Val Arg Ala Glu Val Gly Asn Gly Val Ser Arg His Asn
            755                 760                 765

CTC TCC TGC AGC TTT GAC GTG GTC TCC CCA GTG GCT GGG CTG CGG GTC        2350
Leu Ser Cys Ser Phe Asp Val Val Ser Pro Val Ala Gly Leu Arg Val
        770                 775                 780

ATC TAC CCT GCC CCC CGC GAC GGC CGC CTC TAC GTG CCC ACC AAC GGC        2398
Ile Tyr Pro Ala Pro Arg Asp Gly Arg Leu Tyr Val Pro Thr Asn Gly
785                 790                 795

TCA GCC TTG GTG CTC CAG GTG GAC TCT GGT GCC AAC GCC ACG GCC ACG        2446
Ser Ala Leu Val Leu Gln Val Asp Ser Gly Ala Asn Ala Thr Ala Thr
800                 805                 810                 815

GCT CGC TGG CCT GGG GGC AGT GTC AGC GCC CGC TTT GAG AAT GTC TGC        2494
Ala Arg Trp Pro Gly Gly Ser Val Ser Ala Arg Phe Glu Asn Val Cys
                820                 825                 830

CCT GCC CTG GTG GCC ACC TTC GTG CCC GGC TGC CCC TGG GAG ACC AAC        2542
Pro Ala Leu Val Ala Thr Phe Val Pro Gly Cys Pro Trp Glu Thr Asn
            835                 840                 845
```

FIG. 10A-6

```
GAT ACC CTG TTC TCA GTG GTA GCA CTG CCG TGG CTC AGT GAG GGG GAG        2590
Asp Thr Leu Phe Ser Val Val Ala Leu Pro Trp Leu Ser Glu Gly Glu
        850                 855                 860

CAC GTG GTG GAC GTG GTG GTG GAA AAC AGC GCC AGC CGG GCC AAC CTC        2638
His Val Val Asp Val Val Val Glu Asn Ser Ala Ser Arg Ala Asn Leu
        865                 870                 875

AGC CTG CGG GTG ACG GCG GAG GAG CCC ATC TGT GGC CTC CGC GCC ACG        2686
Ser Leu Arg Val Thr Ala Glu Glu Pro Ile Cys Gly Leu Arg Ala Thr
880                 885                 890                 895

CCC AGC CCC GAG GCC CGT GTA CTG CAG GGA GTC CTA GTG AGG TAC AGC        2734
Pro Ser Pro Glu Ala Arg Val Leu Gln Gly Val Leu Val Arg Tyr Ser
        900                 905                 910

CCC GTG GTG GAG GCC GGC TCG GAC ATG GTC TTC CGG TGG ACC ATC AAC        2782
Pro Val Val Glu Ala Gly Ser Asp Met Val Phe Arg Trp Thr Ile Asn
        915                 920                 925

GAC AAG CAG TCC CTG ACC TTC CAG AAC GTG GTC TTC AAT GTC ATT TAT        2830
Asp Lys Gln Ser Leu Thr Phe Gln Asn Val Val Phe Asn Val Ile Tyr
        930                 935                 940

CAG AGC GCG GCG GTC TTC AAG CTC TCA CTG ACG GCC TCC AAC CAC GTG        2878
Gln Ser Ala Ala Val Phe Lys Leu Ser Leu Thr Ala Ser Asn His Val
        945                 950                 955
```

FIG. 10A-7

```
AGC AAC GTC ACC GTG AAC TAC AAC GTA ACC GTG GAG CGG ATG AAC AGG      2926
Ser Asn Val Thr Val Asn Tyr Asn Val Thr Val Glu Arg Met Asn Arg
960             965             970             975

ATG CAG GGT CTG CAG GTC TCC ACA GTG CCG GCC GTG CTG TCC CCC AAT      2974
Met Gln Gly Leu Gln Val Ser Thr Val Pro Ala Val Leu Ser Pro Asn
        980             985             990

GCC ACA CTG GTA CTG ACG GGT GGT GTG CTG GTG GAC TCA GCT GTG GAG      3022
Ala Thr Leu Val Leu Thr Gly Gly Val Leu Val Asp Ser Ala Val Glu
            995             1000            1005

GTG GCC TTC CTG TGG AAC TTT GGG GAT GGG GAG CAG GCC CTC CAC CAG      3070
Val Ala Phe Leu Trp Asn Phe Gly Asp Gly Glu Gln Ala Leu His Gln
        1010            1015            1020

TTC CAG CCT CCG TAC AAC GAG TCC TTC CCG GTT CCA GAC CCC TCG GTG      3118
Phe Gln Pro Pro Tyr Asn Glu Ser Phe Pro Val Pro Asp Pro Ser Val
            1025            1030            1035

GCC CAG GTG CTG GTG GAG CAC AAT GTC ATG CAC ACC TAC GCT GCC CCA      3166
Ala Gln Val Leu Val Glu His Asn Val Met His Thr Tyr Ala Ala Pro
1040            1045            1050            1055

GGT GAG TAC CTC CTG ACC GTG CTG GCA TCT AAT GCC TTC GAG AAC CTG      3214
Gly Glu Tyr Leu Leu Thr Val Leu Ala Ser Asn Ala Phe Glu Asn Leu
            1060            1065            1070

ACG CAG CAG GTG CCT GTG AGC GTG CGC GCC TCC CTG CCC TCC GTG GCT      3262
Thr Gln Gln Val Pro Val Ser Val Arg Ala Ser Leu Pro Ser Val Ala
        1075            1080            1085
```

FIG. 10A-8

```
GTG GGT GTG AGT GAC GGC GTC CTG GTG GCC GGC CGG CCC GTC ACC TTC        3310
Val Gly Val Ser Asp Gly Val Leu Val Ala Gly Arg Pro Val Thr Phe
        1090            1095                1100

TAC CCG CAC CCG CTG CCC TCG CCT GGG GGT GTT CTT TAC ACG TGG GAC        3358
Tyr Pro His Pro Leu Pro Ser Pro Gly Gly Val Leu Tyr Thr Trp Asp
        1105            1110                1115

TTC GGG GAC GGC TCC CCT GTC CTG ACC CAG AGC CAG CCG GCT GCC AAC        3406
Phe Gly Asp Gly Ser Pro Val Leu Thr Gln Ser Gln Pro Ala Ala Asn
1120            1125                1130            1135

CAC ACC TAT GCC TCG AGG GGC ACC TAC CAC GTG CGC CTG GAG GTC AAC        3454
His Thr Tyr Ala Ser Arg Gly Thr Tyr His Val Arg Leu Glu Val Asn
        1140                1145                1150

AAC ACG GTG AGC GGT GCG GCG GCC CAG GCG GAT GTG CGC GTC TTT GAG        3502
Asn Thr Val Ser Gly Ala Ala Ala Gln Ala Asp Val Arg Val Phe Glu
        1155                1160                1165

GAG CTC CGC GGA CTC AGC GTG GAC ATG AGC CTG GCC GTG GAG CAG GGC        3550
Glu Leu Arg Gly Leu Ser Val Asp Met Ser Leu Ala Val Glu Gln Gly
        1170            1175                1180

GCC CCC GTG GTG GTC AGC GCC GCG GTG CAG ACG GGC GAC AAC ATC ACG        3598
Ala Pro Val Val Val Ser Ala Ala Val Gln Thr Gly Asp Asn Ile Thr
        1185            1190                1195
```

FIG. 10A-9

```
TGG ACC TTC GAC ATG GGG GAC GGC ACC GTG CTG TCG GGC CCG GAG GCA        3646
Trp Thr Phe Asp Met Gly Asp Gly Thr Val Leu Ser Gly Pro Glu Ala
1200             1205             1210             1215

ACA GTG GAG CAT GTG TAC CTG CGG GCA CAG AAC TGC ACA GTG ACC GTG        3694
Thr Val Glu His Val Tyr Leu Arg Ala Gln Asn Cys Thr Val Thr Val
             1220             1225             1230

GGT GCG GCC AGC CCC GCC GGC CAC CTG GCC CGG AGC CTG CAC GTG CTG        3742
Gly Ala Ala Ser Pro Ala Gly His Leu Ala Arg Ser Leu His Val Leu
         1235             1240             1245

GTC TTC GTC CTG GAG GTG CTG CGC GTT GAA CCC GCC GCC TGC ATC CCC        3790
Val Phe Val Leu Glu Val Leu Arg Val Glu Pro Ala Ala Cys Ile Pro
     1250             1255             1260

ACG CAG CCT GAC GCG CGG CTC ACG GCC TAC GTC ACC GGG AAC CCG GCC        3838
Thr Gln Pro Asp Ala Arg Leu Thr Ala Tyr Val Thr Gly Asn Pro Ala
 1265             1270             1275

CAC TAC CTC TTC GAC TGG ACC TTC GGG GAT GGC TCC TCC AAC ACG ACC        3886
His Tyr Leu Phe Asp Trp Thr Phe Gly Asp Gly Ser Ser Asn Thr Thr
1280             1285             1290             1295

GTG CGG GGG TGC CCG ACG GTG ACA CAC AAC TTC ACG CGG AGC GGC ACG        3934
Val Arg Gly Cys Pro Thr Val Thr His Asn Phe Thr Arg Ser Gly Thr
             1300             1305             1310

TTC CCC CTG GCG CTG GTG CTG TCC AGC CGC GTG AAC AGG GCG CAT TAC        3982
Phe Pro Leu Ala Leu Val Leu Ser Ser Arg Val Asn Arg Ala His Tyr
         1315             1320             1325

TTC ACC AGC ATC TGC GTG GAG CCA GAG GTG GGC AAC GTC ACC CTG CAG        4030
Phe Thr Ser Ile Cys Val Glu Pro Glu Val Gly Asn Val Thr Leu Gln
     1330             1335             1340
```

FIG. 10A-10

```
TTC ACC AGC ATC TGC GTG GAG CCA GAG GTG GGC AAC GTC ACC CTG CAG      4030
Phe Thr Ser Ile Cys Val Glu Pro Glu Val Gly Asn Val Thr Leu Gln
        1330            1335            1340

CCA GAG AGG CAG TTT GTG CAG CTC GGG GAC GAG GCC TGG CTG GTG GCA      4078
Pro Glu Arg Gln Phe Val Gln Leu Gly Asp Glu Ala Trp Leu Val Ala
        1345            1350            1355

TGT GCC TGG CCC CCG TTC CCC TAC CGC TAC ACC TGG GAC TTT GGC ACC      4126
Cys Ala Trp Pro Pro Phe Pro Tyr Arg Tyr Thr Trp Asp Phe Gly Thr
1360            1365            1370            1375

GAG GAA GCC GCC CCC ACC CGT GCC AGG GGC CCT GAG GTG ACG TTC ATC      4174
Glu Glu Ala Ala Pro Thr Arg Ala Arg Gly Pro Glu Val Thr Phe Ile
        1380            1385            1390

TAC CGA GAC CCA GGC TCC TAT CTT GTG ACA GTC ACC GCG TCC AAC AAC      4222
Tyr Arg Asp Pro Gly Ser Tyr Leu Val Thr Val Thr Ala Ser Asn Asn
        1395            1400            1405

ATC TCT GCT GCC AAT GAC TCA GCC CTG GTG GAG GTG CAG GAG CCC GTG      4270
Ile Ser Ala Ala Asn Asp Ser Ala Leu Val Glu Val Gln Glu Pro Val
        1410            1415            1420

CTG GTC ACC AGC ATC AAG GTC AAT GGC TCC CTT GGG CTG GAG CTG CAG      4318
Leu Val Thr Ser Ile Lys Val Asn Gly Ser Leu Gly Leu Glu Leu Gln
        1425            1430            1435
```

FIG. 10A-11

```
CAG CCG TAC CTG TTC TCT GCT GTG GGC CGT GGG CGC CCC GCC AGC TAC    4366
Gln Pro Tyr Leu Phe Ser Ala Val Gly Arg Gly Arg Pro Ala Ser Tyr
1440            1445            1450            1455

CTG TGG GAT CTG GGG GAC GGT GGG TGG CTC GAG GGT CCG GAG GTC ACC    4414
Leu Trp Asp Leu Gly Asp Gly Gly Trp Leu Glu Gly Pro Glu Val Thr
            1460            1465            1470

CAC GCT TAC AAC AGC ACA GGT GAC TTC ACC GTT AGG GTG GCC GGC TGG    4462
His Ala Tyr Asn Ser Thr Gly Asp Phe Thr Val Arg Val Ala Gly Trp
        1475            1480            1485

AAT GAG GTG AGC CGC AGC GAG GCC TGG CTC AAT GTG ACG GTG AAG CGG    4510
Asn Glu Val Ser Arg Ser Glu Ala Trp Leu Asn Val Thr Val Lys Arg
    1490            1495            1500

CGC GTG CGG GGG CTC GTC GTC AAT GCA AGC CGC ACG GTG GTG CCC CTG    4558
Arg Val Arg Gly Leu Val Val Asn Ala Ser Arg Thr Val Val Pro Leu
1505            1510            1515

AAT GGG AGC GTG AGC TTC AGC ACG TCG CTG GAG GCC GGC AGT GAT GTG    4606
Asn Gly Ser Val Ser Phe Ser Thr Ser Leu Glu Ala Gly Ser Asp Val
1520            1525            1530            1535

CGC TAT TCC TGG GTG CTC TGT GAC CGC TGC ACG CCC ATC CCT GGG GGT    4654
Arg Tyr Ser Trp Val Leu Cys Asp Arg Cys Thr Pro Ile Pro Gly Gly
            1540            1545            1550

CCT ACC ATC TCT TAC ACC TTC CGC TCC GTG GGC ACC TTC AAT ATC ATC    4702
Pro Thr Ile Ser Tyr Thr Phe Arg Ser Val Gly Thr Phe Asn Ile Ile
        1555            1560            1565
```

FIG. 10A-12

```
GTC ACG GCT GAG AAC GAG GTG GGC TCC GCC CAG GAC AGC ATC TTC GTC    4750
Val Thr Ala Glu Asn Glu Val Gly Ser Ala Gln Asp Ser Ile Phe Val
        1570            1575            1580

TAT GTC CTG CAG CTC ATA GAG GGG CTG CAG GTG GTG GGC GGT GGC CGC    4798
Tyr Val Leu Gln Leu Ile Glu Gly Leu Gln Val Val Gly Gly Gly Arg
        1585            1590            1595

TAC TTC CCC ACC AAC CAC ACG GTA CAG CTG CAG GCC GTG GTT AGG GAT    4846
Tyr Phe Pro Thr Asn His Thr Val Gln Leu Gln Ala Val Val Arg Asp
1600            1605            1610            1615

GGC ACC AAC GTC TCC TAC AGC TGG ACT GCC TGG AGG GAC AGG GGC CCG    4894
Gly Thr Asn Val Ser Tyr Ser Trp Thr Ala Trp Arg Asp Arg Gly Pro
        1620            1625            1630

GCC CTG GCC GGC AGC GGC AAA GGC TTC TCG CTC ACC GTG CTC GAG GCC    4942
Ala Leu Ala Gly Ser Gly Lys Gly Phe Ser Leu Thr Val Leu Glu Ala
        1635            1640            1645

GGC ACC TAC CAT GTG CAG CTG CGG GCC ACC AAC ATG CTG GGC AGC GCC    4990
Gly Thr Tyr His Val Gln Leu Arg Ala Thr Asn Met Leu Gly Ser Ala
        1650            1655            1660

TGG GCC GAC TGC ACC ATG GAC TTC GTG GAG CCT GTG GGG TGG CTG ATG    5038
Trp Ala Asp Cys Thr Met Asp Phe Val Glu Pro Val Gly Trp Leu Met
        1665            1670            1675
```

FIG. 10A-13

```
GTG ACC GCC TCC CCG AAC CCA GCT GCC GTC AAC ACA AGC GTC ACC CTC      5086
Val Thr Ala Ser Pro Asn Pro Ala Ala Val Asn Thr Ser Val Thr Leu
1680            1685            1690            1695

AGT GCC GAG CTG GCT GGT GGC AGT GGT GTC GTA TAC ACT TGG TCC TTG      5134
Ser Ala Glu Leu Ala Gly Gly Ser Gly Val Val Tyr Thr Trp Ser Leu
        1700            1705            1710

GAG GAG GGG CTG AGC TGG GAG ACC TCC GAG CCA TTT ACC ACC CAT AGC      5182
Glu Glu Gly Leu Ser Trp Glu Thr Ser Glu Pro Phe Thr Thr His Ser
        1715            1720            1725

TTC CCC ACA CCC GGC CTG CAC TTG GTC ACC ATG ACG GCA GGG AAC CCG      5230
Phe Pro Thr Pro Gly Leu His Leu Val Thr Met Thr Ala Gly Asn Pro
        1730            1735            1740

CTG GGC TCA GCC AAC GCC ACC GTG GAA GTG GAT GTG CAG GTG CCT GTG      5278
Leu Gly Ser Ala Asn Ala Thr Val Glu Val Asp Val Gln Val Pro Val
        1745            1750            1755

AGT GGC CTC AGC ATC AGG GCC AGC GAG CCC GGA GGC AGC TTC GTG GCG      5326
Ser Gly Leu Ser Ile Arg Ala Ser Glu Pro Gly Gly Ser Phe Val Ala
1760            1765            1770            1775

GCC GGG TCC TCT GTG CCC TTT TGG GGG CAG CTG GCC ACG GGC ACC AAT      5374
Ala Gly Ser Ser Val Pro Phe Trp Gly Gln Leu Ala Thr Gly Thr Asn
                1780            1785            1790

GTG AGC TGG TGC TGG GCT GTG CCC GGC GGC AGC AGC AAG CGT GGC CCT      5422
Val Ser Trp Cys Trp Ala Val Pro Gly Gly Ser Ser Lys Arg Gly Pro
        1795            1800            1805
```

FIG. 10A-14

```
CAT GTC ACC ATG GTC TTC CCG GAT GCT GGC ACC TTC TCC ATC CGG CTC      5470
His Val Thr Met Val Phe Pro Asp Ala Gly Thr Phe Ser Ile Arg Leu
        1810            1815            1820

AAT GCC TCC AAC GCA GTC AGC TGG GTC TCA GCC ACG TAC AAC CTC ACG      5518
Asn Ala Ser Asn Ala Val Ser Trp Val Ser Ala Thr Tyr Asn Leu Thr
        1825            1830            1835

GCG GAG GAG CCC ATC GTG GGC CTG GTG CTG TGG GCC AGC AGC AAG GTG      5566
Ala Glu Glu Pro Ile Val Gly Leu Val Leu Trp Ala Ser Ser Lys Val
1840            1845            1850            1855

GTG GCG CCC GGG CAG CTG GTC CAT TTT CAG ATC CTG CTG GCT GCC GGC      5614
Val Ala Pro Gly Gln Leu Val His Phe Gln Ile Leu Leu Ala Ala Gly
                1860            1865            1870

TCA GCT GTC ACC TTC CGC CTG CAG GTC GGC GGG GCC AAC CCC GAG GTG      5662
Ser Ala Val Thr Phe Arg Leu Gln Val Gly Gly Ala Asn Pro Glu Val
            1875            1880            1885

CTC CCC GGG CCC CGT TTC TCC CAC AGC TTC CCC CGC GTC GGA GAC CAC      5710
Leu Pro Gly Pro Arg Phe Ser His Ser Phe Pro Arg Val Gly Asp His
        1890            1895            1900

GTG GTG AGC GTG CGG GGC AAA AAC CAC GTG AGC TGG GCC CAG GCG CAG      5758
Val Val Ser Val Arg Gly Lys Asn His Val Ser Trp Ala Gln Ala Gln
        1905            1910            1915
```

FIG. 10A-15

```
GTG CGC ATC GTG GTG CTG GAG GCC GTG AGT GGG CTG CAG ATG CCC AAC      5806
Val Arg Ile Val Val Leu Glu Ala Val Ser Gly Leu Gln Met Pro Asn
1920            1925            1930            1935

TGC TGC GAG CCT GGC ATC GCC ACG GGC ACT GAG AGG AAC TTC ACA GCC      5854
Cys Cys Glu Pro Gly Ile Ala Thr Gly Thr Glu Arg Asn Phe Thr Ala
                1940            1945            1950

CGC GTG CAG CGC GGC TCT CGG GTC GCC TAC GCC TGG TAC TTC TCG CTG      5902
Arg Val Gln Arg Gly Ser Arg Val Ala Tyr Ala Trp Tyr Phe Ser Leu
            1955            1960            1965

CAG AAG GTC CAG GGC GAC TCG CTG GTC ATC CTG TCG GGC CGC GAC GTC      5950
Gln Lys Val Gln Gly Asp Ser Leu Val Ile Leu Ser Gly Arg Asp Val
        1970            1975            1980

ACC TAC ACG CCC GTG GCC GCG GGG CTG TTG GAG ATC CAG GTG CGC GCC      5998
Thr Tyr Thr Pro Val Ala Ala Gly Leu Leu Glu Ile Gln Val Arg Ala
    1985            1990            1995

TTC AAC GCC CTG GGC AGT GAG AAC CGC ACG CTG GTG CTG GAG GTT CAG      6046
Phe Asn Ala Leu Gly Ser Glu Asn Arg Thr Leu Val Leu Glu Val Gln
2000            2005            2010            2015

GAC GCC GTC CAG TAT GTG GCC CTG CAG AGC GGC CCC TGC TTC ACC AAC      6094
Asp Ala Val Gln Tyr Val Ala Leu Gln Ser Gly Pro Cys Phe Thr Asn
            2020            2025            2030

CGC TCG GCG CAG TTT GAG GCC GCC ACC AGC CCC AGC CCC CGG CGT GTG      6142
Arg Ser Ala Gln Phe Glu Ala Ala Thr Ser Pro Ser Pro Arg Arg Val
        2035            2040            2045
```

FIG. 10A-16

```
GCC TAC CAC TGG GAC TTT GGG GAT GGG TCG CCA GGG CAG GAC ACA GAT      6190
Ala Tyr His Trp Asp Phe Gly Asp Gly Ser Pro Gly Gln Asp Thr Asp
        2050            2055            2060

GAG CCC AGG GCC GAG CAC TCC TAC CTG AGG CCT GGG GAC TAC CGC GTG      6238
Glu Pro Arg Ala Glu His Ser Tyr Leu Arg Pro Gly Asp Tyr Arg Val
        2065            2070            2075

CAG GTG AAC GCC TCC AAC CTG GTG AGC TTC TTC GTG GCG CAG GCC ACG      6286
Gln Val Asn Ala Ser Asn Leu Val Ser Phe Phe Val Ala Gln Ala Thr
    2080            2085            2090            2095

GTG ACC GTC CAG GTG CTG GCC TGC CGG GAG CCG GAG GTG GAC GTG GTC      6334
Val Thr Val Gln Val Leu Ala Cys Arg Glu Pro Glu Val Asp Val Val
            2100            2105            2110

CTG CCC CTG CAG GTG CTG ATG CGG CGA TCA CAG CGC AAC TAC TTG GAG      6382
Leu Pro Leu Gln Val Leu Met Arg Arg Ser Gln Arg Asn Tyr Leu Glu
        2115            2120            2125

GCC CAC GTT GAC CTG CGC GAC TGC GTC ACC TAC CAG ACT GAG TAC CGC      6430
Ala His Val Asp Leu Arg Asp Cys Val Thr Tyr Gln Thr Glu Tyr Arg
        2130            2135            2140

TGG GAG GTG TAT CGC ACC GCC AGC TGC CAG CGG CCG GGG CGC CCA GCG      6478
Trp Glu Val Tyr Arg Thr Ala Ser Cys Gln Arg Pro Gly Arg Pro Ala
        2145            2150            2155
```

FIG. 10A-17

```
CGT GTG GCC CTG CCC GGC GTG GAC GTG AGC CGG CCT CGG CTG GTG CTG         6526
Arg Val Ala Leu Pro Gly Val Asp Val Ser Arg Pro Arg Leu Val Leu
2160            2165            2170            2175

CCG CGG CTG GCG CTG CCT GTG GGG CAC TAC TGC TTT GTG TTT GTC GTG         6574
Pro Arg Leu Ala Leu Pro Val Gly His Tyr Cys Phe Val Phe Val Val
                2180            2185            2190

TCA TTT GGG GAC ACG CCA CTG ACA CAG AGC ATC CAG GCC AAT GTG ACG         6622
Ser Phe Gly Asp Thr Pro Leu Thr Gln Ser Ile Gln Ala Asn Val Thr
            2195            2200            2205

GTG GCC CCC GAG CGC CTG GTG CCC ATC ATT GAG GGT GGC TCA TAC CGC         6670
Val Ala Pro Glu Arg Leu Val Pro Ile Ile Glu Gly Gly Ser Tyr Arg
        2210            2215            2220

GTG TGG TCA GAC ACA CGG GAC CTG GTG CTG GAT GGG AGC GAG TCC TAC         6718
Val Trp Ser Asp Thr Arg Asp Leu Val Leu Asp Gly Ser Glu Ser Tyr
    2225            2230            2235

GAC CCC AAC CTG GAG GAC GGC GAC CAG ACG CCG CTC AGT TTC CAC TGG         6766
Asp Pro Asn Leu Glu Asp Gly Asp Gln Thr Pro Leu Ser Phe His Trp
2240            2245            2250            2255

GCC TGT GTG GCT TCG ACA CAG AGG GAG GCT GGC GGG TGT GCG CTG AAC         6814
Ala Cys Val Ala Ser Thr Gln Arg Glu Ala Gly Gly Cys Ala Leu Asn
                2260            2265            2270

TTT GGG CCC CGC GGG AGC AGC ACG GTC ACC ATT CCA CGG GAG CGG CTG         6862
Phe Gly Pro Arg Gly Ser Ser Thr Val Thr Ile Pro Arg Glu Arg Leu
            2275            2280            2285
```

FIG. 10A-18

```
GCG GCT GGC GTG GAG TAC ACC TTC AGC CTG ACC GTG TGG AAG GCC GGC        6910
Ala Ala Gly Val Glu Tyr Thr Phe Ser Leu Thr Val Trp Lys Ala Gly
        2290            2295                2300

CGC AAG GAG GAG GCC ACC AAC CAG ACG GTG CTG ATC CGG AGT GGC CGG        6958
Arg Lys Glu Glu Ala Thr Asn Gln Thr Val Leu Ile Arg Ser Gly Arg
    2305            2310                2315

GTG CCC ATT GTG TCC TTG GAG TGT GTG TCC TGC AAG GCA CAG GCC GTG        7006
Val Pro Ile Val Ser Leu Glu Cys Val Ser Cys Lys Ala Gln Ala Val
2320            2325            2330            2335

TAC GAA GTG AGC CGC AGC TCC TAC GTG TAC TTG GAG GGC CGC TGC CTC        7054
Tyr Glu Val Ser Arg Ser Ser Tyr Val Tyr Leu Glu Gly Arg Cys Leu
            2340            2345                2350

AAT TGC AGC AGC GGC TCC AAG CGA GGG CGG TGG GCT GCA CGT ACG TTC        7102
Asn Cys Ser Ser Gly Ser Lys Arg Gly Arg Trp Ala Ala Arg Thr Phe
            2355            2360                2365

AGC AAC AAG ACG CTG GTG CTG GAT GAG ACC ACC ACA TCC ACG GGC AGT        7150
Ser Asn Lys Thr Leu Val Leu Asp Glu Thr Thr Thr Ser Thr Gly Ser
            2370            2375                2380

GCA GGC ATG CGA CTG GTG CTG CGG CGG GGC GTG CTG CGG GAC GGC GAG        7198
Ala Gly Met Arg Leu Val Leu Arg Arg Gly Val Leu Arg Asp Gly Glu
        2385            2390                2395
```

FIG. 10A-19

```
GGA TAC ACC TTC ACG CTC ACG GTG CTG GGC CGC TCT GGC GAG GAG GAG      7246
Gly Tyr Thr Phe Thr Leu Thr Val Leu Gly Arg Ser Gly Glu Glu Glu
2400            2405            2410            2415

GGC TGC GCC TCC ATC CGC CTG TCC CCC AAC CGC CCG CCG CTG GGG GGC      7294
Gly Cys Ala Ser Ile Arg Leu Ser Pro Asn Arg Pro Pro Leu Gly Gly
            2420            2425            2430

TCT TGC CGC CTC TTC CCA CTG GGC GCT GTG CAC GCC CTC ACC ACC AAG      7342
Ser Cys Arg Leu Phe Pro Leu Gly Ala Val His Ala Leu Thr Thr Lys
        2435            2440            2445

GTG CAC TTC GAA TGC ACG GGC TGG CAT GAC GCG GAG GAT GCT GGC GCC      7390
Val His Phe Glu Cys Thr Gly Trp His Asp Ala Glu Asp Ala Gly Ala
            2450            2455            2460

CCG CTG GTG TAC GCC CTG CTG CGG CGC TGT CGC CAG GGC CAC TGC          7438
Pro Leu Val Tyr Ala Leu Leu Leu Arg Arg Cys Arg Gln Gly His Cys
        2465            2470            2475

GAG GAG TTC TGT GTC TAC AAG GGC AGC CTC TCC AGC TAC GGA GCC GTG      7486
Glu Glu Phe Cys Val Tyr Lys Gly Ser Leu Ser Ser Tyr Gly Ala Val
2480            2485            2490            2495

CTG CCC CCG GGT TTC AGG CCA CAC TTC GAG GTG GGC CTG GCC GTG GTG      7534
Leu Pro Pro Gly Phe Arg Pro His Phe Glu Val Gly Leu Ala Val Val
            2500            2505            2510

GTG CAG GAC CAG CTG GGA GCC GCT GTG GTC GCC CTC AAC AGG TCT TTG      7582
Val Gln Asp Gln Leu Gly Ala Ala Val Val Ala Leu Asn Arg Ser Leu
        2515            2520            2525
```

FIG. 10A-20

```
GCC ATC ACC CTC CCA GAG CCC AAC GGC AGC GCA ACG GGG CTC ACA GTC      7630
Ala Ile Thr Leu Pro Glu Pro Asn Gly Ser Ala Thr Gly Leu Thr Val
        2530            2535            2540

TGG CTG CAC GGG CTC ACC GCT AGT GTG CTC CCA GGG CTG CTG CGG CAG      7678
Trp Leu His Gly Leu Thr Ala Ser Val Leu Pro Gly Leu Leu Arg Gln
        2545            2550            2555

GCC GAT CCC CAG CAC GTC ATC GAG TAC TCG TTG GCC CTG GTC ACC GTG      7726
Ala Asp Pro Gln His Val Ile Glu Tyr Ser Leu Ala Leu Val Thr Val
2560            2565            2570            2575

CTG AAC GAG TAC GAG CGG GCC CTG GAC GTG GCG GCA GAG CCC AAG CAC      7774
Leu Asn Glu Tyr Glu Arg Ala Leu Asp Val Ala Ala Glu Pro Lys His
        2580            2585            2590

GAG CGG CAG CAC CGA GCC CAG ATA CGC AAG AAC ATC ACG GAG ACT CTG      7822
Glu Arg Gln His Arg Ala Gln Ile Arg Lys Asn Ile Thr Glu Thr Leu
        2595            2600            2605

GTG TCC CTG AGG GTC CAC ACT GTG GAT GAC ATC CAG CAG ATC GCT GCT      7870
Val Ser Leu Arg Val His Thr Val Asp Asp Ile Gln Gln Ile Ala Ala
        2610            2615            2620

GCG CTG GCC CAG TGC ATG GGG CCC AGC AGG GAG CTC GTA TGC CGC TCG      7918
Ala Leu Ala Gln Cys Met Gly Pro Ser Arg Glu Leu Val Cys Arg Ser
        2625            2630            2635
```

FIG. 10A-21

```
TGC CTG AAG CAG ACG CTG CAC AAG CTG GAG GCC ATG ATG CTC ATC CTG         7966
Cys Leu Lys Gln Thr Leu His Lys Leu Glu Ala Met Met Leu Ile Leu
2640            2645            2650            2655

CAG GCA GAG ACC ACC GCG GGC ACC GTG ACG CCC ACC GCC ATC GGA GAC         8014
Gln Ala Glu Thr Thr Ala Gly Thr Val Thr Pro Thr Ala Ile Gly Asp
        2660            2665            2670

AGC ATC CTC AAC ATC ACA GGA GAC CTC ATC CAC CTG GCC AGC TCG GAC         8062
Ser Ile Leu Asn Ile Thr Gly Asp Leu Ile His Leu Ala Ser Ser Asp
            2675            2680            2685

GTG CGG GCA CCA CAG CCC TCA GAG CTG GGA GCC GAG TCA CCA TCT CGG         8110
Val Arg Ala Pro Gln Pro Ser Glu Leu Gly Ala Glu Ser Pro Ser Arg
        2690            2695            2700

ATG GTG GCG TCC CAG GCC TAC AAC CTG ACC TCT GCC CTC ATG CGC ATC         8158
Met Val Ala Ser Gln Ala Tyr Asn Leu Thr Ser Ala Leu Met Arg Ile
        2705            2710            2715

CTC ATG CGC TCC CGC GTG CTC AAC GAG GAG CCC CTG ACG CTG GCG GGC         8206
Leu Met Arg Ser Arg Val Leu Asn Glu Glu Pro Leu Thr Leu Ala Gly
2720            2725            2730            2735

GAG GAG ATC GTG GCC CAG GGC AAG CGC TCG GAC CCG CGG AGC CTG CTG         8254
Glu Glu Ile Val Ala Gln Gly Lys Arg Ser Asp Pro Arg Ser Leu Leu
            2740            2745            2750

TGC TAT GGC GGC GCC CCA GGG CCT GGC TGC CAC TTC TCC ATC CCC GAG         8302
Cys Tyr Gly Gly Ala Pro Gly Pro Gly Cys His Phe Ser Ile Pro Glu
        2755            2760            2765
```

FIG. 10A-22

```
GCT TTC AGC GGG GCC CTG GCC AAC CTC AGT GAC GTG GTG CAG CTC ATC         8350
Ala Phe Ser Gly Ala Leu Ala Asn Leu Ser Asp Val Val Gln Leu Ile
        2770            2775            2780

TTT CTG GTG GAC TCC AAT CCC TTT CCC TTT GGC TAT ATC AGC AAC TAC         8398
Phe Leu Val Asp Ser Asn Pro Phe Pro Phe Gly Tyr Ile Ser Asn Tyr
        2785            2790            2795

ACC GTC TCC ACC AAG GTG GCC TCG ATG GCA TTC CAG ACA CAG GCC GGC         8446
Thr Val Ser Thr Lys Val Ala Ser Met Ala Phe Gln Thr Gln Ala Gly
2800            2805            2810            2815

GCC CAG ATC CCC ATC GAG CGG CTG GCC TCA GAG CGC GCC ATC ACC GTG         8494
Ala Gln Ile Pro Ile Glu Arg Leu Ala Ser Glu Arg Ala Ile Thr Val
        2820            2825            2830

AAG GTG CCC AAC AAC TCG GAC TGG GCT GCC CGG GGC CAC CGC AGC TCC         8542
Lys Val Pro Asn Asn Ser Asp Trp Ala Ala Arg Gly His Arg Ser Ser
        2835            2840            2845

GCC AAC TCC GCC AAC TCC GTT GTG GTC CAG CCC CAG GCC TCC GTC GGT         8590
Ala Asn Ser Ala Asn Ser Val Val Val Gln Pro Gln Ala Ser Val Gly
        2850            2855            2860

GCT GTG GTC ACC CTG GAC AGC AGC AAC CCT GCG GCC GGG CTG CAT CTG         8638
Ala Val Val Thr Leu Asp Ser Ser Asn Pro Ala Ala Gly Leu His Leu
        2865            2870            2875
```

FIG. 10A-23

```
CAG CTC AAC TAT ACG CTG CTG GAC GGC CAC TAC CTG TCT GAG GAA CCT        8686
Gln Leu Asn Tyr Thr Leu Leu Asp Gly His Tyr Leu Ser Glu Glu Pro
2880            2885            2890            2895

GAG CCC TAC CTG GCA GTC TAC CTA CAC TCG GAG CCC CGG CCC AAT GAG        8734
Glu Pro Tyr Leu Ala Val Tyr Leu His Ser Glu Pro Arg Pro Asn Glu
            2900            2905            2910

CAC AAC TGC TCG GCT AGC AGG AGG ATC CGC CCA GAG TCA CTC CAG GGT        8782
His Asn Cys Ser Ala Ser Arg Arg Ile Arg Pro Glu Ser Leu Gln Gly
            2915            2920            2925

GCT GAC CAC CGG CCC TAC ACC TTC TTC ATT TCC CCG GGG AGC AGA GAC        8830
Ala Asp His Arg Pro Tyr Thr Phe Phe Ile Ser Pro Gly Ser Arg Asp
            2930            2935            2940

CCA GCG GGG AGT TAC CAT CTG AAC CTC TCC AGC CAC TTC CGC TGG TCG        8878
Pro Ala Gly Ser Tyr His Leu Asn Leu Ser Ser His Phe Arg Trp Ser
2945            2950            2955

GCG CTG CAG GTG TCC GTG GGC CTG TAC ACG TCC CTG TGC CAG TAC TTC        8926
Ala Leu Gln Val Ser Val Gly Leu Tyr Thr Ser Leu Cys Gln Tyr Phe
2960            2965            2970            2975

AGC GAG GAG GAC ATG GTG TGG CGG ACA GAG GGG CTG CTG CCC CTG GAG        8974
Ser Glu Glu Asp Met Val Trp Arg Thr Glu Gly Leu Leu Pro Leu Glu
            2980            2985            2990

GAG ACC TCG CCC CGC CAG GCC GTC TGC CTC ACC CGC CAC CTC ACC GCC        9022
Glu Thr Ser Pro Arg Gln Ala Val Cys Leu Thr Arg His Leu Thr Ala
            2995            3000            3005
```

FIG. 10A-24

```
TTC GGC GCC AGC CTC TTC GTG CCC CCA AGC CAT GTC CGC TTT GTG TTT      9070
Phe Gly Ala Ser Leu Phe Val Pro Pro Ser His Val Arg Phe Val Phe
    3010            3015            3020

CCT GAG CCG ACA GCG GAT GTA AAC TAC ATC GTC ATG CTG ACA TGT GCT      9118
Pro Glu Pro Thr Ala Asp Val Asn Tyr Ile Val Met Leu Thr Cys Ala
    3025            3030            3035

GTG TGC CTG GTG ACC TAC ATG GTC ATG GCC GCC ATC CTG CAC AAG CTG      9166
Val Cys Leu Val Thr Tyr Met Val Met Ala Ala Ile Leu His Lys Leu
3040            3045            3050            3055

GAC CAG TTG GAT GCC AGC CGG GGC CGC GCC ATC CCT TTC TGT GGG CAG      9214
Asp Gln Leu Asp Ala Ser Arg Gly Arg Ala Ile Pro Phe Cys Gly Gln
            3060            3065            3070

CGG GGC CGC TTC AAG TAC GAG ATC CTC GTC AAG ACA GGC TGG GGC CGG      9262
Arg Gly Arg Phe Lys Tyr Glu Ile Leu Val Lys Thr Gly Trp Gly Arg
        3075            3080            3085

GGC TCA GGT ACC ACG GCC CAC GTG GGC ATC ATG CTG TAT GGG GTG GAC      9310
Gly Ser Gly Thr Thr Ala His Val Gly Ile Met Leu Tyr Gly Val Asp
        3090            3095            3100

AGC CGG AGC GGC CAC CGG CAC CTG GAC GGC GAC AGA GCC TTC CAC CGC      9358
Ser Arg Ser Gly His Arg His Leu Asp Gly Asp Arg Ala Phe His Arg
    3105            3110            3115
```

FIG. 10A-25

```
AAC AGC CTG GAC ATC TTC CGG ATC GCC ACC CCG CAC AGC CTG GGT AGC       9406
Asn Ser Leu Asp Ile Phe Arg Ile Ala Thr Pro His Ser Leu Gly Ser
3120            3125            3130            3135

GTG TGG AAG ATC CGA GTG TGG CAC GAC AAC AAA GGG CTC AGC CCT GCC       9454
Val Trp Lys Ile Arg Val Trp His Asp Asn Lys Gly Leu Ser Pro Ala
        3140            3145            3150

TGG TTC CTG CAG CAC GTC ATC GTC AGG GAC CTG CAG ACG GCA CGC AGC       9502
Trp Phe Leu Gln His Val Ile Val Arg Asp Leu Gln Thr Ala Arg Ser
            3155            3160            3165

GCC TTC TTC CTG GTC AAT GAC TGG CTT TCG GTG GAG ACG GAG GCC AAC       9550
Ala Phe Phe Leu Val Asn Asp Trp Leu Ser Val Glu Thr Glu Ala Asn
        3170            3175            3180

GGG GGC CTG GTG GAG AAG GAG GTG CTG GCC GCG AGC GAC GCA GCC CTT       9598
Gly Gly Leu Val Glu Lys Glu Val Leu Ala Ala Ser Asp Ala Ala Leu
        3185            3190            3195

TTG CGC TTC CGG CGC CTG CTG GTG GCT GAG CTG CAG CGT GGC TTC TTT       9646
Leu Arg Phe Arg Arg Leu Leu Val Ala Glu Leu Gln Arg Gly Phe Phe
3200            3205            3210            3215

GAC AAG CAC ATC TGG CTC TCC ATA TGG GAC CGG CCG CCT CGT AGC CGT       9694
Asp Lys His Ile Trp Leu Ser Ile Trp Asp Arg Pro Pro Arg Ser Arg
            3220            3225            3230

TTC ACT CGC ATC CAG AGG GCC ACC TGC TGC GTT CTC CTC ATC TGC CTC       9742
Phe Thr Arg Ile Gln Arg Ala Thr Cys Cys Val Leu Leu Ile Cys Leu
            3235            3240            3245
```

FIG. 10A-26

```
TTC CTG GGC GCC AAC GCC GTG TGG TAC GGG GCT GTT GGC GAC TCT GCC    9790
Phe Leu Gly Ala Asn Ala Val Trp Tyr Gly Ala Val Gly Asp Ser Ala
        3250            3255            3260

TAC AGC ACG GGG CAT GTG TCC AGG CTG AGC CCG CTG AGC GTC GAC ACA    9838
Tyr Ser Thr Gly His Val Ser Arg Leu Ser Pro Leu Ser Val Asp Thr
        3265            3270            3275

GTC GCT GTT GGC CTG GTG TCC AGC GTG GTT GTC TAT CCC GTC TAC CTG    9886
Val Ala Val Gly Leu Val Ser Ser Val Val Val Tyr Pro Val Tyr Leu
3280            3285            3290            3295

GCC ATC CTT TTT CTC TTC CGG ATG TCC CGG AGC AAG GTG GCT GGG AGC    9934
Ala Ile Leu Phe Leu Phe Arg Met Ser Arg Ser Lys Val Ala Gly Ser
            3300            3305            3310

CCG AGC CCC ACA CCT GCC GGG CAG CAG GTG CTG GAC ATC GAC AGC TGC    9982
Pro Ser Pro Thr Pro Ala Gly Gln Gln Val Leu Asp Ile Asp Ser Cys
        3315            3320            3325

CTG GAC TCG TCC GTG CTG GAC AGC TCC TTC CTC ACG TTC TCA GGC CTC    10030
Leu Asp Ser Ser Val Leu Asp Ser Ser Phe Leu Thr Phe Ser Gly Leu
        3330            3335            3340

CAC GCT GAG GCC TTT GTT GGA CAG ATG AAG AGT GAC TTG TTT CTG GAT    10078
His Ala Glu Ala Phe Val Gly Gln Met Lys Ser Asp Leu Phe Leu Asp
        3345            3350            3355
```

FIG. 10A-27

```
GAT TCT AAG AGT CTG GTG TGC TGG CCC TCC GGC GAG GGA ACG CTC AGT          10126
Asp Ser Lys Ser Leu Val Cys Trp Pro Ser Gly Glu Gly Thr Leu Ser
3360            3365            3370            3375

TGG CCG GAC CTG CTC AGT GAC CCG TCC ATT GTG GGT AGC AAT CTG CGG          10174
Trp Pro Asp Leu Leu Ser Asp Pro Ser Ile Val Gly Ser Asn Leu Arg
        3380            3385            3390

CAG CTG GCA CGG GGC CAG GCG GGC CAT GGG CTG GGC CCA GAG GAG GAC          10222
Gln Leu Ala Arg Gly Gln Ala Gly His Gly Leu Gly Pro Glu Glu Asp
        3395            3400            3405

GGC TTC TCC CTG GCC AGC CCC TAC TCG CCT GCC AAA TCC TTC TCA GCA          10270
Gly Phe Ser Leu Ala Ser Pro Tyr Ser Pro Ala Lys Ser Phe Ser Ala
        3410            3415            3420

TCA GAT GAA GAC CTG ATC CAG CAG GTC CTT GCC GAG GGG GTC AGC AGC          10318
Ser Asp Glu Asp Leu Ile Gln Gln Val Leu Ala Glu Gly Val Ser Ser
        3425            3430            3435

CCA GCC CCT ACC CAA GAC ACC CAC ATG GAA ACG GAC CTG CTC AGC AGC          10366
Pro Ala Pro Thr Gln Asp Thr His Met Glu Thr Asp Leu Leu Ser Ser
3440            3445            3450            3455

CTG TCC AGC ACT CCT GGG GAG AAG ACA GAG ACG CTG GCG CTG CAG AGG          10414
Leu Ser Ser Thr Pro Gly Glu Lys Thr Glu Thr Leu Ala Leu Gln Arg
        3460            3465            3470

CTG GGG GAG CTG GGG CCA CCC AGC CCA GGC CTG AAC TGG GAA CAG CCC          10462
Leu Gly Glu Leu Gly Pro Pro Ser Pro Gly Leu Asn Trp Glu Gln Pro
        3475            3480            3485
```

FIG. 10A-28

```
CAG GCA GCG AGG CTG TCC AGG ACA GGA CTG GTG GAG GGT CTG CGG AAG      10510
Gln Ala Ala Arg Leu Ser Arg Thr Gly Leu Val Glu Gly Leu Arg Lys
    3490            3495            3500

CGC CTG CTG CCG GCC TGG TGT GCC TCC CTG GCC CAC GGG CTC AGC CTG      10558
Arg Leu Leu Pro Ala Trp Cys Ala Ser Leu Ala His Gly Leu Ser Leu
    3505            3510            3515

CTC CTG GTG GCT GTG GCT GTG GCT GTC TCA GGG TGG GTG GGT GCG AGC      10606
Leu Leu Val Ala Val Ala Val Ala Val Ser Gly Trp Val Gly Ala Ser
3520            3525            3530            3535

TTC CCC CCG GGC GTG AGT GTT GCG TGG CTC CTG TCC AGC AGC GCC AGC      10654
Phe Pro Pro Gly Val Ser Val Ala Trp Leu Leu Ser Ser Ser Ala Ser
            3540            3545            3550

TTC CTG GCC TCA TTC CTC GGC TGG GAG CCA CTG AAG GTC TTG CTG GAA      10702
Phe Leu Ala Ser Phe Leu Gly Trp Glu Pro Leu Lys Val Leu Leu Glu
            3555            3560            3565

GCC CTG TAC TTC TCA CTG GTG GCC AAG CGG CTG CAC CCG GAT GAA GAT      10750
Ala Leu Tyr Phe Ser Leu Val Ala Lys Arg Leu His Pro Asp Glu Asp
            3570            3575            3580

GAC ACC CTG GTA GAG AGC CCG GCT GTG ACG CCT GTG AGC GCA CGT GTG      10798
Asp Thr Leu Val Glu Ser Pro Ala Val Thr Pro Val Ser Ala Arg Val
            3585            3590            3595
```

FIG. 10A-29

```
CCC CGC GTA CGG CCA CCC CAC GGC TTT GCA CTC TTC CTG GCC AAG GAA    10846
Pro Arg Val Arg Pro Pro His Gly Phe Ala Leu Phe Leu Ala Lys Glu
3600            3605            3610            3615

GAA GCC CGC AAG GTC AAG AGG CTA CAT GGC ATG CTG CGG AGC CTC CTG    10894
Glu Ala Arg Lys Val Lys Arg Leu His Gly Met Leu Arg Ser Leu Leu
        3620            3625            3630

GTG TAC ATG CTT TTT CTG CTG GTG ACC CTG CTG GCC AGC TAT GGG GAT    10942
Val Tyr Met Leu Phe Leu Leu Val Thr Leu Leu Ala Ser Tyr Gly Asp
            3635            3640            3645

GCC TCA TGC CAT GGG CAC GCC TAC CGT CTG CAA AGC GCC ATC AAG CAG    10990
Ala Ser Cys His Gly His Ala Tyr Arg Leu Gln Ser Ala Ile Lys Gln
                3650            3655            3660

GAG CTG CAC AGC CGG GCC TTC CTG GCC ATC ACG CGG TCT GAG GAG CTC    11038
Glu Leu His Ser Arg Ala Phe Leu Ala Ile Thr Arg Ser Glu Glu Leu
3665            3670            3675

TGG CCA TGG ATG GCC CAC GTG CTG CTG CCC TAC GTC CAC GGG AAC CAG    11086
Trp Pro Trp Met Ala His Val Leu Leu Pro Tyr Val His Gly Asn Gln
3680            3685            3690            3695

TCC AGC CCA GAG CTG GGG CCC CCA CGG CTG CGG CAG GTG CGG CTG CAG    11134
Ser Ser Pro Glu Leu Gly Pro Pro Arg Leu Arg Gln Val Arg Leu Gln
                3700            3705            3710

GAA GCA CTC TAC CCA GAC CCT CCC GGC CCC AGG GTC CAC ACG TGC TCG    11182
Glu Ala Leu Tyr Pro Asp Pro Pro Gly Pro Arg Val His Thr Cys Ser
            3715            3720            3725
```

FIG. 10A-30

```
GCC GCA GGA GGC TTC AGC ACC AGC GAT TAC GAC GTT GGC TGG GAG AGT        11230
Ala Ala Gly Gly Phe Ser Thr Ser Asp Tyr Asp Val Gly Trp Glu Ser
        3730            3735            3740

CCT CAC AAT GGC TCG GGG ACG TGG GCC TAT TCA GCG CCG GAT CTG CTG        11278
Pro His Asn Gly Ser Gly Thr Trp Ala Tyr Ser Ala Pro Asp Leu Leu
        3745            3750            3755

GGG GCA TGG TCC TGG GGC TCC TGT GCC GTG TAT GAC AGC GGG GGC TAC        11326
Gly Ala Trp Ser Trp Gly Ser Cys Ala Val Tyr Asp Ser Gly Gly Tyr
3760            3765            3770            3775

GTG CAG GAG CTG GGC CTG AGC CTG GAG GAG AGC CGC GAC CGG CTG CGC        11374
Val Gln Glu Leu Gly Leu Ser Leu Glu Glu Ser Arg Asp Arg Leu Arg
        3780            3785            3790

TTC CTG CAG CTG CAC AAC TGG CTG GAC AAC AGG AGC CGC GCT GTG TTC        11422
Phe Leu Gln Leu His Asn Trp Leu Asp Asn Arg Ser Arg Ala Val Phe
        3795            3800            3805

CTG GAG CTC ACG CGC TAC AGC CCG GCC GTG GGG CTG CAC GCC GCC GTC        11470
Leu Glu Leu Thr Arg Tyr Ser Pro Ala Val Gly Leu His Ala Ala Val
        3810            3815            3820

ACG CTG CGC CTC GAG TTC CCG GCG GCC GGC CGC GCC CTG GCC GCC CTC        11518
Thr Leu Arg Leu Glu Phe Pro Ala Ala Gly Arg Ala Leu Ala Ala Leu
        3825            3830            3835
```

FIG. 10A-31

```
AGC GTC CGC CCC TTT GCG CTG CGC CGC CTC AGC GCG GGC CTC TCG CTG       11566
Ser Val Arg Pro Phe Ala Leu Arg Arg Leu Ser Ala Gly Leu Ser Leu
3840            3845            3850            3855

CCT CTG CTC ACC TCG GTG TGC CTG CTG CTG TTC GCC GTG CAC TTC GCC       11614
Pro Leu Leu Thr Ser Val Cys Leu Leu Leu Phe Ala Val His Phe Ala
                3860            3865            3870

GTG GCC GAG GCC CGT ACT TGG CAC AGG GAA GGG CGC TGG CGC GTG CTG       11662
Val Ala Glu Ala Arg Thr Trp His Arg Glu Gly Arg Trp Arg Val Leu
            3875            3880            3885

CGG CTC GGA GCC TGG GCG CGG TGG CTG CTG GTG GCG CTG ACG GCG GCC       11710
Arg Leu Gly Ala Trp Ala Arg Trp Leu Leu Val Ala Leu Thr Ala Ala
        3890            3895            3900

ACG GCA CTG GTA CGC CTC GCC CAG CTG GGT GCC GCT GAC CGC CAG TGG       11758
Thr Ala Leu Val Arg Leu Ala Gln Leu Gly Ala Ala Asp Arg Gln Trp
    3905            3910            3915

ACC CGT TTC GTG CGC GGC CGC CCG CGC CGC TTC ACT AGC TTC GAC CAG       11806
Thr Arg Phe Val Arg Gly Arg Pro Arg Arg Phe Thr Ser Phe Asp Gln
3920            3925            3930            3935

GTG GCG CAC GTG AGC TCC GCA GCC CGT GGC CTG GCG GCC TCG CTG CTC       11854
Val Ala His Val Ser Ser Ala Ala Arg Gly Leu Ala Ala Ser Leu Leu
                3940            3945            3950

TTC CTG CTT TTG GTC AAG GCT GCC CAG CAC GTA CGC TTC GTG CGC CAG       11902
Phe Leu Leu Leu Val Lys Ala Ala Gln His Val Arg Phe Val Arg Gln
                3955            3960            3965
```

FIG. 10A-32

```
TGG TCC GTC TTT GGC AAG ACA TTA TGC CGA GCT CTG CCA GAG CTC CTG          11950
Trp Ser Val Phe Gly Lys Thr Leu Cys Arg Ala Leu Pro Glu Leu Leu
        3970            3975            3980

GGG GTC ACC TTG GGC CTG GTG GTG CTC GGG GTA GCC TAC GCC CAG CTG          11998
Gly Val Thr Leu Gly Leu Val Val Leu Gly Val Ala Tyr Ala Gln Leu
        3985            3990            3995

GCC ATC CTG CTC GTG TCT TCC TGT GTG GAC TCC CTC TGG AGC GTG GCC          12046
Ala Ile Leu Leu Val Ser Ser Cys Val Asp Ser Leu Trp Ser Val Ala
4000            4005            4010            4015

CAG GCC CTG TTG GTG CTG TGC CCT GGG ACT GGG CTC TCT ACC CTG TGT          12094
Gln Ala Leu Leu Val Leu Cys Pro Gly Thr Gly Leu Ser Thr Leu Cys
        4020            4025            4030

CCT GCC GAG TCC TGG CAC CTG TCA CCC CTG CTG TGT GTG GGG CTC TGG          12142
Pro Ala Glu Ser Trp His Leu Ser Pro Leu Leu Cys Val Gly Leu Trp
        4035            4040            4045

GCA CTG CGG CTG TGG GGC GCC CTA CGG CTG GGG GCT GTT ATT CTC CGC          12190
Ala Leu Arg Leu Trp Gly Ala Leu Arg Leu Gly Ala Val Ile Leu Arg
        4050            4055            4060

TGG CGC TAC CAC GCC TTG CGT GGA GAG CTG TAC CGG CCG GCC TGG GAG          12238
Trp Arg Tyr His Ala Leu Arg Gly Glu Leu Tyr Arg Pro Ala Trp Glu
        4065            4070            4075
```

FIG. 10A-33

```
CCC CAG GAC TAC GAG ATG GTG GAG TTG TTC CTG CGC AGG CTG CGC CTC    12286
Pro Gln Asp Tyr Glu Met Val Glu Leu Phe Leu Arg Arg Leu Arg Leu
4080            4085            4090            4095

TGG ATG GGC CTC AGC AAG GTC AAG GAG TTC CGC CAC AAA GTC CGC TTT    12334
Trp Met Gly Leu Ser Lys Val Lys Glu Phe Arg His Lys Val Arg Phe
        4100            4105            4110

GAA GGG ATG GAG CCG CTG CCC TCT CGC TCC TCC AGG GGC TCC AAG GTA    12382
Glu Gly Met Glu Pro Leu Pro Ser Arg Ser Ser Arg Gly Ser Lys Val
            4115            4120            4125

TCC CCG GAT GTG CCC CCA CCC AGC GCT GGC TCC GAT GCC TCG CAC CCC    12430
Ser Pro Asp Val Pro Pro Pro Ser Ala Gly Ser Asp Ala Ser His Pro
    4130            4135            4140

TCC ACC TCC TCC AGC CAG CTG GAT GGG CTG AGC GTG AGC CTG GGC CGG    12478
Ser Thr Ser Ser Ser Gln Leu Asp Gly Leu Ser Val Ser Leu Gly Arg
        4145            4150            4155

CTG GGG ACA AGG TGT GAG CCT GAG CCC TCC CGC CTC CAA GCC GTG TTC    12526
Leu Gly Thr Arg Cys Glu Pro Glu Pro Ser Arg Leu Gln Ala Val Phe
4160            4165            4170            4175

GAG GCC CTG CTC ACC CAG TTT GAC CGA CTC AAC CAG GCC ACA GAG GAC    12574
Glu Ala Leu Leu Thr Gln Phe Asp Arg Leu Asn Gln Ala Thr Glu Asp
            4180            4185            4190

GTC TAC CAG CTG GAG CAG CAG CTG CAC AGC CTG CAA GGC CGC AGG AGC    12622
Val Tyr Gln Leu Glu Gln Gln Leu His Ser Leu Gln Gly Arg Arg Ser
        4195            4200            4205
```

FIG. 10A-34

```
AGC CGG GCG CCC GCC GGA TCT TCC CGT GGC CCA TCC CCG GGC CTG CGG         12670
Ser Arg Ala Pro Ala Gly Ser Ser Arg Gly Pro Ser Pro Gly Leu Arg
        4210            4215            4220

CCA GCA CTG CCC AGC CGC CTT GCC CGG GCC AGT CGG GGT GTG GAC CTG         12718
Pro Ala Leu Pro Ser Arg Leu Ala Arg Ala Ser Arg Gly Val Asp Leu
    4225            4230            4235

GCC ACT GGC CCC AGC AGG ACA CCT TCG GGC CAA GAA CAA GGT CCA CCC         12766
Ala Thr Gly Pro Ser Arg Thr Pro Ser Gly Gln Glu Gln Gly Pro Pro
    4240            4245            4250            4255

CAG CAG CAC TTA GTC CTC CTT CCT GGC GGG GGT GGG CCG TGG AGT CGG         12814
Gln Gln His Leu Val Leu Leu Pro Gly Gly Gly Gly Pro Trp Ser Arg
            4260            4265            4270

AGT GGA CAC CGC TCA GTA TTA CTT TCT GCC GCT GTC AAG GCC GAG GGC         12862
Ser Gly His Arg Ser Val Leu Leu Ser Ala Ala Val Lys Ala Glu Gly
            4275            4280            4285

CAG GCA GAA TGG CTG CAC GTA GGT TCC CCA GAG AGC AGG CAG GGG CAT         12910
Gln Ala Glu Trp Leu His Val Gly Ser Pro Glu Ser Arg Gln Gly His
            4290            4295            4300

CTG TCT GTC TGT GGG CTT CAG CAC TTT AAA GAG GCT GTG TGG CCA ACC         12958
Leu Ser Val Cys Gly Leu Gln His Phe Lys Glu Ala Val Trp Pro Thr
    4305            4310            4315
```

FIG. 10A-35

```
AGG ACC CAG GGT CCC CTC CCC AGC TCC CTT GGG AAG GAC ACA GCA GTA     13006
Arg Thr Gln Gly Pro Leu Pro Ser Ser Leu Gly Lys Asp Thr Ala Val
4320            4325            4330            4335

TTG GAC GGT TTC TAGCCTCTGA GATGCTAATT TATTTCCCCG AGTCCTCAGG         13058
Leu Asp Gly Phe

TACAGCGGGC TGTGCCCGGC CCCACCCCCT GGGCAGATGT CCCCCACTGC TAAGGCTGCT   13118

GGCTTCAGGG AGGGTTAGCC TGCACCGCCG CCACCCTGCC CCTAAGTTAT TACCTCTCCA   13178

GTTCCTACCG TACTCCCTGC ACCGTCTCAC TGTGTGTCTC GTGTCAGTAA TTTATATGGT   13238

GTTAAAATGT GTATATTTTT GTATGTCACT ATTTTCACTA GGGCTGAGGG GCCTGCGCCC   13298

AGAGCTGGCC TCCCCCAACA CCTGCTGCGC TTGGTAGGTG TGGTGGCGTT ATGGCAGCCC   13358

GGCTGCTGCT TGGATGCGAG CTTGGCCTTG GCCCGGTGCT GGGGCACAG CTGTCTGCCA    13418

GGCACTCTCA TCACCCCAGA GGCCTTGTCA TCCTCCCTTG CCCCAGGCCA GGTAGCAAGA   13478

GAGCAGCGCC CAGGCCTGCT GGCATCAGGT CTGGGCAAGT AGCAGGACTA GGCATGTCAG   13538

AGGACCCCAG GGTGGTTAGA GGAAAAGACT CCTCCTGGGG GCTGGCTCCC AGGGTGGAGG   13598

AAGGTGACTG TGTGTGTGTG TGTGTGCGCG CGCGACGCGC GAGTGTGCTG TATGGCCCAG   13658

GCAGCCTCAA GGCCCTGGA GCTGGCTGTG CCTGCTTCTG TGTACCACTT CTGTGGGCAT    13718

GCCCGCTTCT AGAGCCTCGA CACCCCCCCA ACCCCCGCAC CAAGCAGACA AAGTCAATAA   13778

AAGAGCTGTC TGACTGCAAA AAAAAAAA                                      13807
```

FIG. 10A-36

```
  1  GCACTGCAGCGCCAGCGTCCGAGCGGGCGGCCGAGCTCCCGGAGCGGCCTGGCCCCGAGC   60

61  CCCGAGCGGGCGTCGCTCAGCAGCAGGTCGCGGCCGCGCAGCCCCATCCAGCCCCGCGCC  120

121  CGCCATGCCGTCCGCGGGCCCCGCCTGAGCTGCGGTCTCCGCGCGCGGGCGGGCCTGGGG  180

181  ACGGCGGGGCCATGCGCGCGCTGCCCTAACGATGCCGCCCGCCGCGCCCGCCCGCCTGGC  240
  1                                    M  P  P  A  A  P  A  R  L  A   10

241  GCTGGCCCTGGGCCTGGGCCTGTGGCTCGGGGCGCTGGCGGGGGGCCCCGGGCGCGGCTG  300
 11   L  A  L  G  L  G  L  W  L  G  A  L  A  G  G  P  G  R  G  C   30
                                         ▲
301  CGGGCCCTGCGAGCCCCCCTGCCTCTGCGGCCCAGCGCCCGGCGCCGCCTGCCGCGTCAA  360
 31   G  P  C  E  P  P  C  L  C  G  P  A  P  G  A  A  C  R  V  N   50
                                                                *
361  CTGCTCGGGCCGCGGGCTGCGGACGCTCGGTCCCGCGCTGCGCATCCCCGCGGACGCCAC  420
 51   C  S  G  R  G  L  R  T  L  G  P  A  L  R  I  P  A  D  A  T   70

421  AGCGCTAGACGTCTCCCACAACCTGCTCCGGGCGCTGGACGTTGGGCTCCTGGCGAACCT  480
 71   A  L  D  V  S  H  N  L  L  R  A  L  D  V  G  L  L  A  N  L   90
                                                                *
481  CTCGGCGCTGGCAGAGCTGGATATAAGCAACAACAAGATTTCTACGTTAGAAGAAGGAAT  540
 91   S  A  L  A  E  L  D  I  S  N  N  K  I  S  T  L  E  E  G  I  110

541  ATTTGCTAATTTATTTAATTTAAGTGAAATAAACCTGAGTGGGAACCCGTTTGAGTGTGA  600
111   F  A  N  L  F  N  L  S  E  I  N  L  S  G  N  P  F  E  C  D  130
                *                 *
```

FIG. 15A

```
601  CTGTGGCCTGGCGTGGCTGCCGCGATGGGCGGAGGAGCAGCAGGTGCGGGTGGTGCAGCC  660
131   C  G  L  A  W  L  P  R  W  A  E  E  Q  Q  V  R  V  V  Q  P   150

661  CGAGGCAGCCACGTGTGCTGGGCCTGGCTCCCTGGCTGGCCAGCCTCTGCTTGGCATCCC  720
151   E  A  A  T  C  A  G  P  G  S  L  A  G  Q  P  L  L  G  I  P   170

721  CTTGCTGGACAGTGGCTGTGGTGAGGAGTATGTCGCCTGCCTCCCTGACAACAGCTCAGG  780
171   L  L  D  S  G  C  G  E  E  Y  V  A  C  L  P  D  N  S  S  G   190
                                                          *
781  CACCGTGGCAGCAGTGTCCTTTTCAGCTGCCCACGAAGGCCTGCTTCAGCCAGAGGCCTG  840
191   T  V  A  A  V  S  F  S  A  A  H  E  G  L  L  Q  P  E  A  C   210

841  CAGCGCCTTCTGCTTCTCCACCGGCCAGGGCCTCGCAGCCCTCTCGGAGCAGGGCTGGTG  900
211   S  A  F  C  F  S  T  G  Q  G  L  A  A  L  S  E  Q  G  W  C   230

901  CCTGTGTGGGGCGGCCCAGCCCTCCAGTGCCTCCTTTGCCTGCCTGTCCCTCTGCTCCGG  960
231   L  C  G  A  A  Q  P  S  S  A  S  F  A  C  L  S  L  C  S  G   250

961  CCCCCCGCCACCTCCTGCCCCCACCTGTAGGGGCCCCACCCTCCTCCAGCACGTCTTCCC  1020
251   P  P  P  P  A  P  T  C  R  G  P  T  L  L  Q  H  V  F  P     270

1021 TGCCTCCCCAGGGGCCACCCTGGTGGGGCCCCACGGACCTCTGGCCTCTGGCCAGCTAGC  1080
271   A  S  P  G  A  T  L  V  G  P  H  G  P  L  A  S  G  Q  L  A   290

1081 AGCCTTCCACATCGCTGCCCCGCTCCCTGTCACTGCCACACGCTGGGACTTCGGAGACGG  1140
291   A  F  H  I  A  A  P  L  P  V  T  A  T  R  W  D  F  G  D  G   310

1141 CTCCGCCGAGGTGGATGCCGCTGGGCCGGCTGCCTCGCATCGCTATGTGCTGCCTGGGCG  1200
311   S  A  E  V  D  A  A  G  P  A  A  S  H  R  Y  V  L  P  G  R   330
```

FIG. 15B

```
1201 CTATCACGTGACGGCCGTGCTGGCCCTGGGGGCCGGCTCAGCCCTGCTGGGGACAGACGT 1260
331  Y  H  V  T  A  V  L  A  L  G  A  G  S  A  L  L  G  T  D  V   350

1261 GCAGGTGGAAGCGGCACCTGCCGCCCTGGAGCTCGTGTGCCCGTCCTCGGTGCAGAGTGA 1320
351  Q  V  E  A  A  P  A  A  L  E  L  V  C  P  S  S  V  Q  S  D   370

1321 CGAGAGCCTTGACCTCAGCATCCAGAACCGCGGTGGTTCAGGCCTGGAGGCCGCCTACAG 1380
371  E  S  L  D  L  S  I  Q  N  R  G  G  S  G  L  E  A  A  Y  S   390

1381 CATCGTGGCCCTGGGCGAGGAGCCGGCCCGAGCGGTGCACCCGCTCTGCCCCTCGGACAC 1440
391  I  V  A  L  G  E  E  P  A  R  A  V  H  P  L  C  P  S  D  T   410

1441 GGAGATCTTCCCTGGCAACGGGCACTGCTACCGCCTGGTGGTGGAGAAGGCGGCCTGGCT 1500
411  E  I  F  P  G  N  G  H  C  Y  R  L  V  V  E  K  A  A  W  L   430

1501 GCAGGCGCAGGAGCAGTGTCAGGCCTGGGCCGGGGCCGCCCTGGCAATGGTGGACAGTCC 1560
431  Q  A  Q  E  Q  C  Q  A  W  A  G  A  A  L  A  M  V  D  S  P   450

1561 CGCCGTGCAGCGCTTCCTGGTCTCCCGGGTCACCAGGAGCCTAGACGTGTGGATCGGCTT 1620
451  A  V  Q  R  F  L  V  S  R  V  T  R  S  L  D  V  W  I  G  F   470

1621 CTCGACTGTGCAGGGGGTGGAGGTGGGCCCAGCGCCGCAGGGCGAGGCCTTCAGCCTGGA 1680
471  S  T  V  Q  G  V  E  V  G  P  A  P  Q  G  E  A  F  S  L  E   490

1681 GAGCTGCCAGAACTGGCTGCCCGGGGAGCCACACCCAGCCACAGCCGAGCACTGCGTCCG 1740
491  S  C  Q  N  W  L  P  G  E  P  H  P  A  T  A  E  H  C  V  R   510

1741 GCTCGGGCCCACCGGGTGGTGTAACACCGACCTGTGCTCAGCGCCGCACAGCTACGTCTG 1800
511  L  G  P  T  G  W  C  N  T  D  L  C  S  A  P  H  S  Y  V  C   530
```

FIG. 15C

```
1801  CGAGCTGCAGCCCGGAGGCCCAGTGCAGGATGCCGAGAACCTCCTCGTGGGAGCGCCCAG  1860
531    E  L  Q  P  G  G  P  V  Q  D  A  E  N  L  L  V  G  A  P  S   550

1861  TGGGGACCTGCAGGGACCCCTGACGCCTCTGGCACAGCAGGACGGCCTCTCAGCCCCGCA  1920
551    G  D  L  Q  G  P  L  T  P  L  A  Q  Q  D  G  L  S  A  P  H   570

1921  CGAGCCCGTGGAGGTCATGGTATTCCCGGGCCTGCGTCTGAGCCGTGAAGCCTTCCTCAC  1980
571    E  P  V  E  V  M  V  F  P  G  L  R  L  S  R  E  A  F  L  T   590

1981  CACGGCCGAATTTGGGACCCAGGAGCTCCGGCGGCCCGCCCAGCTGCGGCTGCAGGTGTA  2040
591    T  A  E  F  G  T  Q  E  L  R  R  P  A  Q  L  R  L  Q  V  Y   610

2041  CCGGCTCCTCAGCACAGCAGGGACCCCGGAGAACGGCAGCGAGCCTGAGAGCAGGTCCCC  2100
611    R  L  L  S  T  A  G  T  P  E  N  G  S  E  P  E  S  R  S  P   630
                                         *

2101  GGACAACAGGACCCAGCTGGCCCCCGCGTGCATGCCAGGGGGACGCTGGTGCCCTGGAGC  2160
631    D  N  R  T  Q  L  A  P  A  C  M  P  G  G  R  W  C  P  G  A   650
        *

2161  CAACATCTGCTTGCCGCTGGACGCCTCTTGCCACCCCAGGCCTGCGCCAATGGCTGCAC   2220
651    N  I  C  L  P  L  D  A  S  C  H  P  Q  A  C  A  N  G  C  T   670

2221  GTCAGGGCCAGGGCTACCCGGGGCCCCCTATGCGCTATGGAGAGAGTTCCTCTTCTCCGT  2280
671    S  G  P  G  L  P  G  A  P  Y  A  L  W  R  E  F  L  F  S  V   690

2281  TGCCGCGGGGCCCCCCGCGCAGTACTCGGTCACCCTCCACGGCCAGGATGTCCTCATGCT  2340
691    A  A  G  P  P  A  Q  Y  S  V  T  L  H  G  Q  D  V  L  M  L   710

2341  CCCTGGTGACCTCGTTGGCTTGCAGCACGACGCTGGCCCTGGCGCCCTCCTGCACTGCTC  2400
711    P  G  D  L  V  G  L  Q  H  D  A  G  P  G  A  L  L  H  C  S   730
```

FIG. 15D

```
2401 GCCGGCTCCCGGCCACCCTGGTCCCCAGGCCCCGTACCTCTCCGCCAACGCCTCGTCATG 2460
731   P  A  P  G  H  P  G  P  Q  A  P  Y  L  S  A  N  A  S  S  W  750
                                                         *
2461 GCTGCCCCACTTGCCAGCCCAGCTGGAGGGCACTTGGGCCTGCCCTGCCTGTGCCCTGCG 2520
751   L  P  H  L  P  A  Q  L  E  G  T  W  A  C  P  A  C  A  L  R  770

2521 GCTGCTTGCAGCCACGGAACAGCTCACCGTGCTGCTGGGCTTGAGGCCCAACCCTGGACT 2580
771   L  L  A  A  T  E  Q  L  T  V  L  L  G  L  R  P  N  P  G  L  790

2581 GCGGATGCCTGGGCGCTATGAGGTCCGGGCAGAGGTGGGCAATGGCGTGTCCAGGCACAA 2640
791   R  M  P  G  R  Y  E  V  R  A  E  V  G  N  G  V  S  R  H  N  810
                                                               *
2641 CCTCTCCTGCAGCTTTGACGTGGTCTCCCCAGTGGCTGGGCTGCGGGTCATCTACCCTGC 2700
811   L  S  C  S  F  D  V  V  S  P  V  A  G  L  R  V  I  Y  P  A  830

2701 CCCCCGCGACGGCCGCCTCTACGTGCCCACCAACGGCTCAGCCTTGGTGCTCCAGGTGGA 2760
831   P  R  D  G  R  L  Y  V  P  T  N  G  S  A  L  V  L  Q  V  D  850
                                    *
2761 CTCTGGTGCCAACGCCACGGCCACGGCTCGCTGGCCTGGGGGCAGTGTCAGCGCCCGCTT 2820
851   S  G  A  N  A  T  A  T  A  R  W  P  G  G  S  V  S  A  R  F  870
            *
2821 TGAGAATGTCTGCCCTGCCCTGGTGGCCACCTTCGTGCCCGGCTGCCCCTGGGAGACCAA 2880
871   E  N  V  C  P  A  L  V  A  T  F  V  P  G  C  P  W  E  T  N  890
                                                               *
2881 CGATACCCTGTTCTCAGTGGTAGCACTGCCGTGGCTCAGTGAGGGGGAGCACGTGGTGGA 2940
891   D  T  L  F  S  V  V  A  L  P  W  L  S  E  G  E  H  V  V  D  910

2941 CGTGGTGGTGGAAAACAGCGCCAGCCGGGCCAACCTCAGCCTGCGGGTGACGGCGGAGGA 3000
911   V  V  V  E  N  S  A  S  R  A  N  L  S  L  R  V  T  A  E  E  930
                        *
3001 GCCCATCTGTGGCCTCCGCGCCACGCCCAGCCCCGAGGCCCGTGTACTGCAGGGAGTCCT 3060
931   P  I  C  G  L  R  A  T  P  S  P  E  A  R  V  L  Q  G  V  L  950
```

FIG. 15E

```
3061  AGTGAGGTACAGCCCCGTGGTGGAGGCCGGCTCGGACATGGTCTTCCGGTGGACCATCAA  3120
951    V  R  Y  S  P  V  V  E  A  G  S  D  M  V  F  R  W  T  I  N   970

3121  CGACAAGCAGTCCCTGACCTTCCAGAACGTGGTCTTCAATGTCATTTATCAGAGCGCGGC  3180
971    D  K  Q  S  L  T  F  Q  N  V  V  F  N  V  I  Y  Q  S  A  A   990

3181  GGTCTTCAAGCTCTCACTGACGGCCTCCAACCACGTGAGCAACGTCACCGTGAACTACAA  3240
991    V  F  K  L  S  L  T  A  S  N  H  V  S  N  V  T  V  N  Y  N  1010
                                                *
3241  CGTAACCGTGGAGCGGATGAACAGGATGCAGGGTCTGCAGGTCTCCACAGTGCCGGCCGT  3300
1011   V  T  V  E  R  M  N  R  M  Q  G  L  Q  V  S  T  V  P  A  V  1030

3301  GCTGTCCCCCAATGCCACACTGGTACTGACGGGTGGTGTGCTGGTGGACTCAGCTGTGGA  3360
1031   L  S  P  N  A  T  L  V  L  T  G  G  V  L  V  D  S  A  V  E  1050
             *
3361  GGTGGCCTTCCTGTGGAACTTTGGGGATGGGGAGCAGGCCCTCCACCAGTTCCAGCCTCC  3420
1051   V  A  F  L  W  N  F  G  D  G  E  Q  A  L  H  Q  F  Q  P  P  1070

3421  GTACAACGAGTCCTTCCCGGTTCCAGACCCCTCGGTGGCCCAGGTGCTGGTGGAGCACAA  3480
1071   Y  N  E  S  F  P  V  P  D  P  S  V  A  Q  V  L  V  E  H  N  1090
          *
3481  TGTCATGCACACCTACGCTGCCCCAGGTGAGTACCTCCTGACCGTGCTGGCATCTAATGC  3540
1091   V  M  H  T  Y  A  A  P  G  E  Y  L  L  T  V  L  A  S  N  A  1110

3541  CTTCGAGAACCTGACGCAGCAGGTGCCTGTGAGCGTGCGCGCCTCCCTGCCCTCCGTGGC  3600
1111   F  E  N  L  T  Q  Q  V  P  V  S  V  R  A  S  L  P  S  V  A  1130
             *
```

FIG. 15F

```
3601  TGTGGGTGTGAGTGACGGCGTCCTGGTGGCCGGCCGGCCCGTCACCTTCTACCCGCACCC  3660
1131   V  G  V  S  D  G  V  L  V  A  G  R  P  V  T  F  Y  P  H  P   1150

3661  GCTGCCCTCGCCTGGGGGTGTTCTTTACACGTGGGACTTCGGGGACGGCTCCCCTGTCCT  3720
1151   L  P  S  P  G  G  V  L  Y  T  W  D  F  G  D  G  S  P  V  L   1170

3721  GACCCAGAGCCAGCCGGCTGCCAACCACACCTATGCCTCGAGGGGCACCTACCACGTGCG  3780
1171   T  Q  S  Q  P  A  A  N  H  T  Y  A  S  R  G  T  Y  H  V  R   1190
                            *

3781  CCTGGAGGTCAACAACACGGTGAGCGGTGCGGCGGCCCAGGCGGATGTGCGCGTCTTTGA  3840
1191   L  E  V  N  N  T  V  S  G  A  A  A  Q  A  D  V  R  V  F  E   1210
              *

3841  GGAGCTCCGCGGACTCAGCGTGGACATGAGCCTGGCCGTGGAGCAGGGCGCCCCCGTGGT  3900
1211   E  L  R  G  L  S  V  D  M  S  L  A  V  E  Q  G  A  P  V  V   1230

3901  GGTCAGCGCCGCGGTGCAGACGGGCGACAACATCACGTGGACCTTCGACATGGGGGACGG  3960
1231   V  S  A  A  V  Q  T  G  D  N  I  T  W  T  F  D  M  G  D  G   1250
                                     *

3961  CACCGTGCTGTCGGGCCCGGAGGCAACAGTGGAGCATGTGTACCTGCGGGCACAGAACTG  4020
1251   T  V  L  S  G  P  E  A  T  V  E  H  V  Y  L  R  A  Q  N  C   1270
                                                              *

4021  CACAGTGACCGTGGGTGCGGCCAGCCCCGCCGGCCACCTGGCCCGGAGCCTGCACGTGCT  4080
1271   T  V  T  V  G  A  A  S  P  A  G  H  L  A  R  S  L  H  V  L   1290

4081  GGTCTTCGTCCTGGAGGTGCTGCGCGTTGAACCCGCCGCCTGCATCCCCACGCAGCCTGA  4140
1291   V  F  V  L  E  V  L  R  V  E  P  A  A  C  I  P  T  Q  P  D   1310

4141  CGCGCGGCTCACGGCCTACGTCACCGGGAACCCGGCCCACTACCTCTTCGACTGGACCTT  4200
1311   A  R  L  T  A  Y  V  T  G  N  P  A  H  Y  L  F  D  W  T  F   1330
```

FIG. 15G

```
4201 CGGGGATGGCTCCTCCAACACGACCGTGCGGGGGTGCCCGACGGTGACACACAACTTCAC 4260
1331  G  D  G  S  S  N  T  T  V  R  G  C  P  T  V  T  H  N  F  T  1350
                   *                                   *
4261 GCGGAGCGGCACGTTCCCCCTGGCGCTGGTGCTGTCCAGCCGCGTGAACAGGGCGCATTA 4320
1351  R  S  G  T  F  P  L  A  L  V  L  S  S  R  V  N  R  A  H  Y  1370

4321 CTTCACCAGCATCTGCGTGGAGCCAGAGGTGGGCAACGTCACCCTGCAGCCAGAGAGGCA 4380
1371  F  T  S  I  C  V  E  P  E  V  G  N  V  T  L  Q  P  E  R  Q  1390
                                        *
4381 GTTTGTGCAGCTCGGGGACGAGGCCTGGCTGGTGGCATGTGCCTGGCCCCCGTTCCCCTA 4440
1391  F  V  Q  L  G  D  E  A  W  L  V  A  C  A  W  P  P  F  P  Y  1410

4441 CCGCTACACCTGGGACTTTGGCACCGAGGAAGCCGCCCCCACCCGTGCCAGGGGCCCTGA 4500
1411  R  Y  T  W  D  F  G  T  E  E  A  A  P  T  R  A  R  G  P  E  1430

4501 GGTGACGTTCATCTACCGAGACCCAGGCTCCTATCTTGTGACAGTCACCGCGTCCAACAA 4560
1431  V  T  F  I  Y  R  D  P  G  S  Y  L  V  T  V  T  A  S  N  N  1450
                                                              *
4561 CATCTCTGCTGCCAATGACTCAGCCCTGGTGGAGGTGCAGGAGCCCGTGCTGGTCACCAG 4620
1451  I  S  A  A  N  D  S  A  L  V  E  V  Q  E  P  V  L  V  T  S  1470
               *
4621 CATCAAGGTCAATGGCTCCCTTGGGCTGGAGCTGCAGCAGCCGTACCTGTTCTCTGCTGT 4680
1471  I  K  V  N  G  S  L  G  L  E  L  Q  Q  P  Y  L  F  S  A  V  1490
            *
4681 GGGCCCGTGGGCGCCCCGCCAGCTACCTGTGGGATCTGGGGGACGGTGGGTGGCTCGAGGG 4740
1491  G  R  G  R  P  A  S  Y  L  W  D  L  G  D  G  G  W  L  E  G  1510

4741 TCCGGAGGTCACCCACGCTTACAACAGCACAGGTGACTTCACCGTTAGGGTGGCCGGCTG 4800
1511  P  E  V  T  H  A  Y  N  S  T  G  D  F  T  V  R  V  A  G  W  1530
                         *
```

FIG. 15H

```
4801 GAATGAGGTGAGCCGCAGCGAGGCCTGGCTCAATGTGACGGTGAAGCGGCGCGTGCGGGG 4860
1531   N  E  V  S  R  S  E  A  W  L  N  V  T  V  K  R  R  V  R  G  1550
                                      *
4861 GCTCGTCGTCAATGCAAGCCGCACGGTGGTGCCCCTGAATGGGAGCGTGAGCTTCAGCAC 4920
1551   L  V  V  N  A  S  R  T  V  V  P  L  N  G  S  V  S  F  S  T  1570
               *                          *
4921 GTCGCTGGAGGCCGGCAGTGATGTGCGCTATTCCTGGGTGCTCTGTGACCGCTGCACGCC 4980
1571   S  L  E  A  G  S  D  V  R  Y  S  W  V  L  C  D  R  C  T  P  1590

4981 CATCCCTGGGGGTCCTACCATCTCTTACACCTTCCGCTCCGTGGGCACCTTCAATATCAT 5040
1591   I  P  G  G  P  T  I  S  Y  T  F  R  S  V  G  T  F  N  I  I  1610

5041 CGTCACGGCTGAGAACGAGGTGGGCTCCGCCCAGGACAGCATCTTCGTCTATGTCCTGCA 5100
1611   V  T  A  E  N  E  V  G  S  A  Q  D  S  I  F  V  Y  V  L  Q  1630

5101 GCTCATAGAGGGGCTGCAGGTGGTGGGCGGTGGCCGCTACTTCCCCACCAACCACACGGT 5160
1631   L  I  E  G  L  Q  V  V  G  G  G  R  Y  F  P  T  N  H  T  V  1650
                                                          *
5161 ACAGCTGCAGGCCGTGGTTAGGGATGGCACCAACGTCTCCTACAGCTGGACTGCCTGGAG 5220
1651   Q  L  Q  A  V  V  R  D  G  T  N  V  S  Y  S  W  T  A  W  R  1670
                                *
5221 GGACAGGGGCCCGGCCCTGGCCGGCAGCGGCAAAGGCTTCTCGCTCACCGTGCTCGAGGC 5280
1671   D  R  G  P  A  L  A  G  S  G  K  G  F  S  L  T  V  L  E  A  1690

5281 CGGCACCTACCATGTGCAGCTGCGGGCCACCAACATGCTGGGCAGCGCCTGGGCCGACTG 5340
1691   G  T  Y  H  V  Q  L  R  A  T  N  M  L  G  S  A  W  A  D  C  1710

5341 CACCATGGACTTCGTGGAGCCTGTGGGGGTGGCTGATGGTGACCGCCTCCCCGAACCCAGC 5400
1711   T  M  D  F  V  E  P  V  G  W  L  M  V  T  A  S  P  N  P  A  1730
```

FIG. 15I

```
5341  CACCATGGACTTCGTGGAGCCTGTGGGGTGGCTGATGGTGACCGCCTCCCCGAACCCAGC  5400
1711   T  M  D  F  V  E  P  V  G  W  L  M  V  T  A  S  P  N  P  A   1730

5401  TGCCGTCAACACAAGCGTCACCCTCAGTGCCGAGCTGGCTGGTGGCAGTGGTGTCGTATA  5460
1731   A  V  N  T  S  V  T  L  S  A  E  L  A  G  G  S  G  V  V  Y   1750
          *
5461  CACTTGGTCCTTGGAGGAGGGGCTGAGCTGGGAGACCTCCGAGCCATTTACCACCCATAG  5520
1751   T  W  S  L  E  E  G  L  S  W  E  T  S  E  P  F  T  T  H  S   1770

5521  CTTCCCCACACCCGGCCTGCACTTGGTCACCATGACGGCAGGGAACCCGCTGGGCTCAGC  5580
1771   F  P  T  P  G  L  H  L  V  T  M  T  A  G  N  P  L  G  S  A   1790

5581  CAACGCCACCGTGGAAGTGGATGTGCAGGTGCCTGTGAGTGGCCTCAGCATCAGGGCCAG  5640
1791   N  A  T  V  E  V  D  V  Q  V  P  V  S  G  L  S  I  R  A  S   1810
       *
5641  CGAGCCCGGAGGCAGCTTCGTGGCGGCCGGGTCCTCTGTGCCCTTTTGGGGGCAGCTGGC  5700
1811   E  P  G  G  S  F  V  A  A  G  S  S  V  P  F  W  G  Q  L  A   1830

5701  CACGGGCACCAATGTGAGCTGGTGCTGGGCTGTGCCCGGCGGCAGCAGCAAGCGTGGCCC  5760
1831   T  G  T  N  V  S  W  C  W  A  V  P  G  G  S  S  K  R  G  P   1850
                *
5761  TCATGTCACCATGGTCTTCCCGGATGCTGGCACCTTCTCCATCCGGCTCAATGCCTCCAA  5820
1851   H  V  T  M  V  F  P  D  A  G  T  F  S  I  R  L  N  A  S  N   1870
                                                             *
5821  CGCAGTCAGCTGGGTCTCAGCCACGTACAACCTCACGGCGGAGGAGCCCATCGTGGGCCT  5880
1871   A  V  S  W  V  S  A  T  Y  N  L  T  A  E  E  P  I  V  G  L   1890
                            *
5881  GGTGCTGTGGGCCAGCAGCAAGGTGGTGGCGCCCGGGCAGCTGGTCCATTTTCAGATCCT  5940
1891   V  L  W  A  S  S  K  V  V  A  P  G  Q  L  V  H  F  Q  I  L   1910

5941  GCTGGCTGCCGGCTCAGCTGTCACCTTCCGCCTGCAGGTCGGCGGGGCCAACCCCGAGGT  6000
1911   L  A  A  G  S  A  V  T  F  R  L  Q  V  G  G  A  N  P  E  V   1930
```

FIG. 15J

```
6001  GCTCCCCGGGCCCCGTTTCTCCCACAGCTTCCCCCGCGTCGGAGACCACGTGGTGAGCGT  6060
1931   L  P  G  P  R  F  S  H  S  F  P  R  V  G  D  H  V  V  S  V    1950

6061  GCGGGGCAAAAACCACGTGAGCTGGGCCCAGGCGCAGGTGCGCATCGTGGTGCTGGAGGC  6120
1951   R  G  K  N  H  V  S  W  A  Q  A  Q  V  R  I  V  V  L  E  A    1970

6121  CGTGAGTGGGCTGCAGATGCCCAACTGCTGCGAGCCTGGCATCGCCACGGGCACTGAGAG  6180
1971   V  S  G  L  Q  M  P  N  C  C  E  P  G  I  A  T  G  T  E  R    1990

6181  GAACTTCACAGCCCGCGTGCAGCGCGGCTCTCGGGTCGCCTACGCCTGGTACTTCTCGCT  6240
1991   N  F  T  A  R  V  Q  R  G  S  R  V  A  Y  A  W  Y  F  S  L    2010
       *

6241  GCAGAAGGTCCAGGGCGACTCGCTGGTCATCCTGTCGGGCCGCGACGTCACCTACACGCC  6300
2011   Q  K  V  Q  G  D  S  L  V  I  L  S  G  R  D  V  T  Y  T  P    2030

6301  CGTGGCCGCGGGGCTGTTGGAGATCCAGGTGCGCGCCTTCAACGCCCTGGGCAGTGAGAA  6360
2031   V  A  A  G  L  L  E  I  Q  V  R  A  F  N  A  L  G  S  E  N    2050
                                                                *

6361  CCGCACGCTGGTGCTGGAGGTTCAGGACGCCGTCCAGTATGTGGCCCTGCAGAGCGGCCC  6420
2051   R  T  L  V  L  E  V  Q  D  A  V  Q  Y  V  A  L  Q  S  G  P    2070

6421  CTGCTTCACCAACCGCTCGGCGCAGTTTGAGGCCGCCACCAGCCCCAGCCCCCGGCGTGT  6480
2071   C  F  T  N  R  S  A  Q  F  E  A  A  T  S  P  S  P  R  R  V    2090
                *

6481  GGCCTACCACTGGGACTTTGGGGATGGGTCGCCAGGGCAGGACACAGATGAGCCCAGGGC  6540
2091   A  Y  H  W  D  F  G  D  G  S  P  G  Q  D  T  D  E  P  R  A    2110

6541  CGAGCACTCCTACCTGAGGCCTGGGGACTACCGCGTGCAGGTGAACGCCTCCAACCTGGT  6600
2111   E  H  S  Y  L  R  P  G  D  Y  R  V  Q  V  N  A  S  N  L  V    2130
                                                   *
```

FIG. 15K

```
6601  GAGCTTCTTCGTGGCGCAGGCCACGGTGACCGTCCAGGTGCTGGCCTGCCGGGAGCCGGA  6660
2131   S   F   F   V   A   Q   A   T   V   T   V   Q   V   L   A   C   R   E   P   E    2150

6661  GGTGGACGTGGTCCTGCCCCTGCAGGTGCTGATGCGGCGATCACAGCGCAACTACTTGGA  6720
2151   V   D   V   V   L   P   L   Q   V   L   M   R   R   S   Q   R   N   Y   L   E    2170

6721  GGCCCACGTTGACCTGCGCGACTGCGTCACCTACCAGACTGAGTACCGCTGGGAGGTGTA  6780
2171   A   H   V   D   L   R   D   C   V   T   Y   Q   T   E   Y   R   W   E   V   Y    2190

6781  TCGCACCGCCAGCTGCCAGCGGCCGGGGCGCCCAGCGCGTGTGGCCCTGCCCGGCGTGGA  6840
2191   R   T   A   S   C   Q   R   P   G   R   P   A   R   V   A   L   P   G   V   D    2210

6841  CGTGAGCCGGCCTCGGCTGGTGCTGCCGCGGCTGGCGCTGCCTGTGGGGCACTACTGCTT  6900
2211   V   S   R   P   R   L   V   L   P   R   L   A   L   P   V   G   H   Y   C   F    2230

6901  TGTGTTTGTCGTGTCATTTGGGGACACGCCACTGACACAGAGCATCCAGGCCAATGTGAC  6960
2231   V   F   V   V   S   F   G   D   T   P   L   T   Q   S   I   Q   A   N   V   T    2250
                                                                           *
6961  GGTGGCCCCCGAGCGCCTGGTGCCCATCATTGAGGGTGGCTCATACCGCGTGTGGTCAGA  7020
2251   V   A   P   E   R   L   V   P   I   I   E   G   G   S   Y   R   V   W   S   D    2270

7021  CACACGGGACCTGGTGCTGGATGGGAGCGAGTCCTACGACCCCAACCTGGAGGACGGCGA  7080
2271   T   R   D   L   V   L   D   G   S   E   S   Y   D   P   N   L   E   D   G   D    2290

7081  CCAGACGCCGCTCAGTTTCCACTGGGCCTGTGTGGCTTCGACACAGAGGGAGGCTGGCGG  7140
2291   Q   T   P   L   S   F   H   W   A   C   V   A   S   T   Q   R   E   A   G   G    2310

7141  GTGTGCGCTGAACTTTGGGCCCCGCGGGAGCAGCACGGTCACCATTCCACGGGAGCGGCT  7200
2311   C   A   L   N   F   G   P   R   G   S   S   T   V   T   I   P   R   E   R   L    2330
```

FIG. 15L

```
7201 GGCGGCTGGCGTGGAGTACACCTTCAGCCTGACCGTGTGGAAGGCCGGCCGCAAGGAGGA 7260
2331    A  A  G  V  E  Y  T  F  S  L  T  V  W  K  A  G  R  K  E  E   2350

7261 GGCCACCAACCAGACGGTGCTGATCCGGAGTGGCCGGGTGCCCATTGTGTCCTTGGAGTG 7320
2351    A  T  N  Q  T  V  L  I  R  S  G  R  V  P  I  V  S  L  E  C   2370
              *

7321 TGTGTCCTGCAAGGCACAGGCCGTGTACGAAGTGAGCCGCAGCTCCTACGTGTACTTGGA 7380
2371    V  S  C  K  A  Q  A  V  Y  E  V  S  R  S  S  Y  V  Y  L  E   2390

7381 GGGCCGCTGCCTCAATTGCAGCAGCGGCTCCAAGCGAGGGCGGTGGGCTGCACGTACGTT 7440
2391    G  R  C  L  N  C  S  S  G  S  K  R  G  R  W  A  A  R  T  F   2410
                    *

7441 CAGCAACAAGACGCTGGTGCTGGATGAGACCACCACATCCACGGGCAGTGCAGGCATGCG 7500
2411    S  N  K  T  L  V  L  D  E  T  T  T  S  T  G  S  A  G  M  R   2430
           *

7501 ACTGGTGCTGCGGCGGGGCGTGCTGCGGGACGGCGAGGGATACACCTTCACGCTCACGGT 7560
2431    L  V  L  R  R  G  V  L  R  D  G  E  G  Y  T  F  T  L  T  V   2450

7561 GCTGGGCCGCTCTGGCGAGGAGGAGGGCTGCGCCTCCATCCGCCTGTCCCCCAACCGCCC 7620
2451    L  G  R  S  G  E  E  E  G  C  A  S  I  R  L  S  P  N  R  P   2470

7621 GCCGCTGGGGGGCTCTTGCCGCCTCTTCCCACTGGGCGCTGTGCACGCCCTCACCACCAA 7680
2471    P  L  G  G  S  C  R  L  F  P  L  G  A  V  H  A  L  T  T  K   2490

7681 GGTGCACTTCGAATGCACGGGCTGGCATGACGCGGAGGATGCTGGCGCCCCGCTGGTGTA 7740
2491    V  H  F  E  C  T  G  W  H  D  A  E  D  A  G  A  P  L  V  Y   2510

7741 CGCCCTGCTGCTGCGGCGCTGTCGCCAGGGCCACTGCGAGGAGTTCTGTGTCTACAAGGG 7800
2511    A  L  L  L  R  R  C  R  Q  G  H  C  E  E  F  C  V  Y  K  G   2530
```

FIG. 15M

```
7801  CAGCCTCTCCAGCTACGGAGCCGTGCTGCCCCCGGGTTTCAGGCCACACTTCGAGGTGGG    7860
2531   S   L   S   S   Y   G   A   V   L   P   P   G   F   R   P   H   F   E   V   G    2550

7861  CCTGGCCGTGGTGGTGCAGGACCAGCTGGGAGCCGCTGTGGTCGCCCTCAACAGGTCTTT    7920
2551   L   A   V   V   V   Q   D   Q   L   G   A   A   V   V   A   L   N   R   S   L    2570
                                                                       *

7921  GGCCATCACCCTCCCAGAGCCCAACGGCAGCGCAACGGGGCTCACAGTCTGGCTGCACGG    7980
2571   A   I   T   L   P   E   P   N   G   S   A   T   G   L   T   V   W   L   H   G    2590
                               *                      TM1

7981  GCTCACCGCTAGTGTGCTCCCAGGGCTGCTGCGGCAGGCCGATCCCCAGCACGTCATCGA    8040
2591   L   T   A   S   V   L   P   G   L   L   R   Q   A   D   P   Q   H   V   I   E    2610

8041  GTACTCGTTGGCCCTGGTCACCGTGCTGAACGAGTACGAGCGGGCCCTGGACGTGGCGGC    8100
2611   Y   S   L   A   L   V   T   V   L   N   E   Y   E   R   A   L   D   V   A   A    2630

8101  AGAGCCCAAGCACGAGCGGCAGCACCGAGCCCAGATACGCAAGAACATCACGGAGACTCT    8160
2631   E   P   K   H   E   R   Q   H   R   A   Q   I   R   K   N   I   T   E   T   L    2650
                                                           *

8161  GGTGTCCCTGAGGGTCCACACTGTGGATGACATCCAGCAGATCGCTGCTGCGCTGGCCCA    8220
2651   V   S   L   R   V   H   T   V   D   D   I   Q   Q   I   A   A   A   L   A   Q    2670

8221  GTGCATGGGGCCCAGCAGGGAGCTCGTATGCCGCTCGTGCCTGAAGCAGACGCTGCACAA    8280
2671   C   M   G   P   S   R   E   L   V   C   R   S   C   L   K   Q   T   L   H   K    2690

8281  GCTGGAGGCCATGATGCTCATCCTGCAGGCAGAGACCACCGCGGGCACCGTGACGCCCAC    8340
2691   L   E   A   M   M   L   I   L   Q   A   E   T   T   A   G   T   V   T   P   T    2710
                                              TM2
```

FIG. 15N

```
8341 CGCCATCGGAGACAGCATCCTCAACATCACAGGAGACCTCATCCACCTGGCCAGCTCGGA 8400
2711  A  I  G  D  S  I  L  N  I  T  G  D  L  I  H  L  A  S  S  D  2730
                           *

8401 CGTGCGGGCACCACAGCCCTCAGAGCTGGGAGCCGAGTCACCATCTCGGATGGTGGCGTC 8460
2731  V  R  A  P  Q  P  S  E  L  G  A  E  S  P  S  R  M  V  A  S  2750

8461 CCAGGCCTACAACCTGACCTCTGCCCTCATGCGCATCCTCATGCGCTCCCGCGTGCTCAA 8520
2751  Q  A  Y  N  L  T  S  A  L  M  R  I  L  M  R  S  R  V  L  N  2770
            *

8521 CGAGGAGCCCCTGACGCTGGCGGGCGAGGAGATCGTGGCCCAGGGCAAGCGCTCGGACCC 8580
2771  E  E  P  L  T  L  A  G  E  E  I  V  A  Q  G  K  R  S  D  P  2790

8581 GCGGAGCCTGCTGTGCTATGGCGGCGCCCCAGGGCCTGGCTGCCACTTCTCCATCCCCGA 8640
2791  R  S  L  L  C  Y  G  G  A  P  G  P  G  C  H  F  S  I  P  E  2810

8641 GGCTTTCAGCGGGGCCCTGGCCAACCTCAGTGACGTGGTGCAGCTCATCTTTCTGGTGGA 8700
2811  A  F  S  G  A  L  A  N  L  S  D  V  V  Q  L  I  F  L  V  D  2830
                           *

8701 CTCCAATCCCTTTCCCTTTGGCTATATCAGCAACTACACCGTCTCCACCAAGGTGGCCTC 8760
2831  S  N  P  F  P  F  G  Y  I  S  N  Y  T  V  S  T  K  V  A  S  2850
                                 *

8761 GATGGCATTCCAGACACAGGCCGGCGCCCAGATCCCCATCGAGCGGCTGGCCTCAGAGCG 8820
2851  M  A  F  Q  T  Q  A  G  A  Q  I  P  I  E  R  L  A  S  E  R  2870

8821 CGCCATCACCGTGAAGGTGCCCAACAACTCGGACTGGGCTGCCCGGGGCCACCGCAGCTC 8880
2871  A  I  T  V  K  V  P  N  N  S  D  W  A  A  R  G  H  R  S  S  2890
                           *

8881 CGCCAACTCCGCCAACTCCGTTGTGGTCCAGCCCCAGGCCTCCGTCGGTGCTGTGGTCAC 8940
2891  A  N  S  A  N  S  V  V  V  Q  P  Q  A  S  V  G  A  V  V  T  2910
```

FIG. 15O

| | | |
|---|---|---|
| 8941 | CCTGGACAGCAGCAACCCTGCGGCCGGGCTGCATCTGCAGCTCAACTATACGCTGCTGGA | 9000 |
| 2911 | L  D  S  S  N  P  A  A  G  L  H  L  Q  L  N  Y  T  L  L  D | 2930 |
| |                                           * | |
| 9001 | CGGCCACTACCTGTCTGAGGAACCTGAGCCCTACCTGGCAGTCTACCTACACTCGGAGCC | 9060 |
| 2931 | G  H  Y  L  S  E  E  P  E  P  Y  L  A  V  Y  L  H  S  E  P | 2950 |
| 9061 | CCGGCCCAATGAGCACAACTGCTCGGCTAGCAGGAGGATCCGCCCAGAGTCACTCCAGGG | 9120 |
| 2951 | R  P  N  E  H  N  C  S  A  S  R  R  I  R  P  E  S  L  Q  G | 2970 |
| |                 * | |
| 9121 | TGCTGACCACCGGCCCTACACCTTCTTCATTTCCCCGGGGAGCAGAGACCCAGCGGGGAG | 9180 |
| 2971 | A  D  H  R  P  Y  T  F  F  I  S  P  G  S  R  D  P  A  G  S | 2990 |
| 9181 | TTACCATCTGAACCTCTCCAGCCACTTCCGCTGGTCGGCGCTGCAGGTGTCCGTGGGCCT | 9240 |
| 2991 | Y  H  L  N  L  S  S  H  F  R  W  S  A  L  Q  V  S  V  G  L | 3010 |
| |        * | |
| 9241 | GTACACGTCCCTGTGCCAGTACTTCAGCGAGGAGGACATGGTGTGGCGGACAGAGGGGCT | 9300 |
| 3011 | Y  T  S  L  C  Q  Y  F  S  E  E  D  M  V  W  R  T  E  G  L | 3030 |
| 9301 | GCTGCCCCTGGAGGAGACCTCGCCCCGCCAGGCCGTCTGCCTCACCCGCCACCTCACCGC | 9360 |
| 3031 | L  P  L  E  E  T  S  P  R  Q  A  V  C  L  T  R  H  L  T  A | 3050 |
| 9361 | CTTCGGCGCCAGCCTCTTCGTGCCCCCAAGCCATGTCCGCTTTGTGTTTCCTGAGCCGAC | 9420 |
| 3051 | F  G  A  S  L  F  V  P  P  S  H  V  R  F  V  F  P  E  P  T | 3070 |
| 9421 | AGCGGATGTAAACTACATCGTCATGCTGACATGTGCTGTGTGCCTGGTGACCTACATGGT | 9480 |
| 3071 | A  D  V  N  <u>Y  I  V  M  L  T  C  A  V  C  L  V  T  Y  M  V</u> | 3090 |
| |                                    TM3 | |
| 9481 | CATGGCCGCCATCCTGCACAAGCTGGACCAGTTGGATGCCAGCCGGGGCCGCGCCATCCC | 9540 |
| 3091 | <u>M  A  A  I  L</u>  H  K  L  D  Q  L  D  A  S  R  G  R  A  I  P | 3110 |

FIG. 15P

```
9541  TTTCTGTGGGCAGCGGGGCCGCTTCAAGTACGAGATCCTCGTCAAGACAGGCTGGGGCCG  9600
3111   F  C  G  Q  R  G  R  F  K  Y  E  I  L  V  K  T  G  W  G  R  3130

9601  GGGCTCAGGTACCACGGCCCACGTGGGCATCATGCTGTATGGGGTGGACAGCCGGAGCGG  9660
3131   G  S  G  T  T  A  H  V  G  I  M  L  Y  G  V  D  S  R  S  G  3150

9661  CCACCGGCACCTGGACGGCGACAGAGCCTTCCACCGCAACAGCCTGGACATCTTCCGGAT  9720
3151   H  R  H  L  D  G  D  R  A  F  H  R  N  S  L  D  I  F  R  I  3170

9721  CGCCACCCCGCACAGCCTGGGTAGCGTGTGGAAGATCCGAGTGTGGCACGACAACAAAGG  9780
3171   A  T  P  H  S  L  G  S  V  W  K  I  R  V  W  H  D  N  K  G  3190

9781  GCTCAGCCCTGCCTGGTTCCTGCAGCACGTCATCGTCAGGGACCTGCAGACGGCACGCAG  9840
3191   L  S  P  A  W  F  L  Q  H  V  I  V  R  D  L  Q  T  A  R  S  3210

9841  CGCCTTCTTCCTGGTCAATGACTGGCTTTCGGTGGAGACGGAGGCCAACGGGGGCCTGGT  9900
3211   A  F  F  L  V  N  D  W  L  S  V  E  T  E  A  N  G  G  L  V  3230

9901  GGAGAAGGAGGTGCTGGCCGCGAGCGACGCAGCCCTTTTGCGCTTCCGGCGCCTGCTGGT  9960
3231   E  K  E  V  L  A  A  S  D  A  A  L  L  R  F  R  R  L  L  V  3250

9961  GGCTGAGCTGCAGCGTGGCTTCTTTGACAAGCACATCTGGCTCTCCATATGGGACCGGCC  10020
3251   A  E  L  Q  R  G  F  F  D  K  H  I  W  L  S  I  W  D  R  P  3270

10021 GCCTCGTAGCCGTTTCACTCGCATCCAGAGGGCCACCTGCTGCGTTCTCCTCATCTGCCT  10080
3271   P  R  S  R  F  T  R  I  Q  R  A  T  C  C  V  L  L  I  C  L  3290
                                          ‾  ‾  ‾  ‾  ‾  ‾  ‾  ‾  ‾  ‾
10081 CTTCCTGGGCGCCAACGCCGTGTGGTACGGGGCTGTTGGCGACTCTGCCTACAGCACGGG  10140
3291   F  L  G  A  N  A  V  W  Y  G  A  V  G  D  S  A  Y  S  T  G  3310
       ‾  ‾  ‾  ‾  ‾  ‾  ‾  ‾  ‾  ‾
       TM4
```

FIG. 15Q

```
10141  GCATGTGTCCAGGCTGAGCCCGCTGAGCGTCGACACAGTCGCTGTTGGCCTGGTGTCCAG  10200
3311    H  V  S  R  L  S  P  L  S  V  D  T  V  A  V  G  L  V  S  S   3330

10201  CGTGGTTGTCTATCCCGTCTACCTGGCCATCCTTTTTCTCTTCCGGATGTCCCGGAGCAA  10260
3331    V  V  V  Y  P  V  Y  L  A  I  L  F  L  F  R  M  S  R  S  K   3350
                         TM5
10261  GGTGGCTGGGAGCCCGAGCCCCACACCTGCCGGGCAGCAGGTGCTGGACATCGACAGCTG  10320
3351    V  A  G  S  P  S  P  T  P  A  G  Q  Q  V  L  D  I  D  S  C   3370

10321  CCTGGACTCGTCCGTGCTGGACAGCTCCTTCCTCACGTTCTCAGGCCTCCACGCTGAGGC  10380
3371    L  D  S  S  V  L  D  S  S  F  L  T  F  S  G  L  H  A  E  A   3390

10381  CTTTGTTGGACAGATGAAGAGTGACTTGTTTCTGGATGATTCTAAGAGTCTGGTGTGCTG  10440
3391    F  V  G  Q  M  K  S  D  L  F  L  D  D  S  K  S  L  V  C  W   3410

10441  GCCCTCCGGCGAGGGAACGCTCAGTTGGCCGGACCTGCTCAGTGACCCGTCCATTGTGGG  10500
3411    P  S  G  E  G  T  L  S  W  P  D  L  L  S  D  P  S  I  V  G   3430

10501  TAGCAATCTGCGGCAGCTGGCACGGGGCCAGGCGGGCCATGGGCTGGGCCCAGAGGAGGA  10560
3431    S  N  L  R  Q  L  A  R  G  Q  A  G  H  G  L  G  P  E  E  D   3450

10561  CGGCTTCTCCCTGGCCAGCCCCTACTCGCCTGCCAAATCCTTCTCAGCATCAGATGAAGA  10620
3451    G  F  S  L  A  S  P  Y  S  P  A  K  S  F  S  A  S  D  E  D   3470

10621  CCTGATCCAGCAGGTCCTTGCCGAGGGGGTCAGCAGCCCAGCCCCTACCCAAGACACCCA  10680
3471    L  I  Q  Q  V  L  A  E  G  V  S  S  P  A  P  T  Q  D  T  H   3490

10681  CATGGAAACGGACCTGCTCAGCAGCCTGTCCAGCACTCCTGGGGAGAAGACAGAGACGCT  10740
3491    M  E  T  D  L  L  S  S  L  S  S  T  P  G  E  K  T  E  T  L   3510
```

FIG. 15R

| | | |
|---|---|---|
| 10741 | GGCGCTGCAGAGGCTGGGGGAGCTGGGGCCACCCAGCCCAGGCCTGAACTGGGAACAGCC | 10800 |
| 3511 | A L Q R L G E L G P P S P G L N W E Q P | 3530 |

| | | |
|---|---|---|
| 10801 | CCAGGCAGCGAGGCTGTCCAGGACAGGACTGGTGGAGGGTCTGCGGAAGCGCCTGCTGCC | 10860 |
| 3531 | Q A A R L S R T G L V E G L R K R L L P | 3550 |

| | | |
|---|---|---|
| 10861 | GGCCTGGTGTGCCTCCCTGGCCCACGGGCTCAGCCTGCTCCTGGTGGCTGTGGCTGTGGC | 10920 |
| 3551 | A W C A S L A H G L S L L L V A V A V A | 3570 |

TM6

| | | |
|---|---|---|
| 10921 | TGTCTCAGGGTGGGTGGGTGCGAGCTTCCCCCCGGGCGTGAGTGTTGCGTGGCTCCTGTC | 10980 |
| 3571 | V S G W V G A S F P P G V S V A W L L S | 3590 |

| | | |
|---|---|---|
| 10981 | CAGCAGCGCCAGCTTCCTGGCCTCATTCCTCGGCTGGGAGCCACTGAAGGTCTTGCTGGA | 11040 |
| 3591 | S S A S F L A S F L G W E P L K V L L E | 3610 |

TM7

| | | |
|---|---|---|
| 11041 | AGCCCTGTACTTCTCACTGGTGGCCAAGCGGCTGCACCCGGATGAAGATGACACCCTGGT | 11100 |
| 3611 | A L Y F S L V A K R L H P D E D D T L V | 3630 |

| | | |
|---|---|---|
| 11101 | AGAGAGCCCGGCTGTGACGCCTGTGAGCGCACGTGTGCCCCGCGTACGGCCACCCCACGG | 11160 |
| 3631 | E S P A V T P V S A R V P R V R P P H G | 3650 |

| | | |
|---|---|---|
| 11161 | CTTTGCACTCTTCCTGGCCAAGGAAGAAGCCCGCAAGGTCAAGAGGCTACATGGCATGCT | 11220 |
| 3651 | F A L F L A K E E A R K V K R L H G M L | 3670 |

| | | |
|---|---|---|
| 11221 | GCGGAGCCTCCTGGTGTACATGCTTTTTCTGCTGGTGACCCTGCTGGCCAGCTATGGGGA | 11280 |
| 3671 | R S L L V Y M L F L L V T L L A S Y G D | 3690 |

```
11281  TGCCTCATGCCATGGGCACGCCTACCGTCTGCAAAGCGCCATCAAGCAGGAGCTGCACAG  11340
 3691   A   S   C   H   G   H   A   Y   R   L   Q   S   A   I   K   Q   E   L   H   S    3710

11341  CCGGGCCTTCCTGGCCATCACGCGGTCTGAGGAGCTCTGGCCATGGATGGCCCACGTGCT  11400
 3711   R   A   F   L   A   I   T   R   S   E   E   L   W   P   W   M   A   H   V   L    3730

11401  GCTGCCCTACGTCCACGGGAACCAGTCCAGCCCAGAGCTGGGGCCCCCACGGCTGCGGCA  11460
 3731   L   P   Y   V   H   G   N   Q   S   S   P   E   L   G   P   P   R   L   R   Q    3750
                                *

11461  GGTGCGGCTGCAGGAAGCACTCTACCCAGACCCTCCCGGCCCCAGGGTCCACACGTGCTC  11520
 3751   V   R   L   Q   E   A   L   Y   P   D   P   P   G   P   R   V   H   T   C   S    3770

11521  GGCCGCAGGAGGCTTCAGCACCAGCGATTACGACGTTGGCTGGGAGAGTCCTCACAATGG  11580
 3771   A   A   G   G   F   S   T   S   D   Y   D   V   G   W   E   S   P   H   N   G    3790
                                                                            *

11581  CTCGGGGACGTGGGCCTATTCAGCGCCGGATCTGCTGGGGGCATGGTCCTGGGGCTCCTG  11640
 3791   S   G   T   W   A   Y   S   A   P   D   L   L   G   A   W   S   W   G   S   C    3810

11641  TGCCGTGTATGACAGCGGGGGCTACGTGCAGGAGCTGGGCCTGAGCCTGGAGGAGAGCCG  11700
 3811   A   V   Y   D   S   G   G   Y   V   Q   E   L   G   L   S   L   E   E   S   R    3830

11701  CGACCGGCTGCGCTTCCTGCAGCTGCACAACTGGCTGGACAACAGGAGCCGCGCTGTGTT  11760
 3831   D   R   L   R   F   L   Q   L   H   N   W   L   D   N   R   S   R   A   V   F    3850
                                                *

11761  CCTGGAGCTCACGCGCTACAGCCCGGCCGTGGGGCTGCACGCCGCCGTCACGCTGCGCCT  11820
 3851   L   E   L   T   R   Y   S   P   A   V   G   L   H   A   A   V   T   L   R   L    3870

11821  CGAGTTCCCGGCGGCCGGCCGCGCCCTGGCCGCCCTCAGCGTCCGCCCCTTTGCGCTGCG  11880
 3871   E   F   P   A   A   G   R   A   L   A   A   L   S   V   R   P   F   A   L   R    3890
```

FIG. 15T

```
11881  CCGCCTCAGCGCGGGCCTCTCGCTGCCTCTGCTCACCTCGGTGTGCCTGCTGCTGTTCGC  11940
 3891    R   L   S   A   G   L   S   L   P   L   L   T   S   V   C   L   L   L   F   A    3910
                         ─────────────────────────────────────────────────────────
                                                TM9

11941  CGTGCACTTCGCCGTGGCCGAGGCCCGTACTTGGCACAGGGAAGGGCGCTGGCGCGTGCT  12000
 3911    V   H   F   A   V   A   E   A   R   T   W   H   R   E   G   R   W   R   V   L    3930
         ─────────────────

12001  GCGGCTCGGAGCCTGGGCGCGGTGGCTGCTGGTGGCGCTGACGGCGGCCACGGCACTGGT  12060
 3931    R   L   G   A   W   A   R   W   L   L   V   A   L   T   A   A   T   A   L   V    3950

12061  ACGCCTCGCCCAGCTGGGTGCCGCTGACCGCCAGTGGACCCGTTTCGTGCGCGGCCGCCC  12120
 3951    R   L   A   Q   L   G   A   A   D   R   Q   W   T   R   F   V   R   G   R   P    3970

12121  GCGCCGCTTCACTAGCTTCGACCAGGTGGCGCACGTGAGCTCCGCAGCCCGTGGCCTGGC  12180
 3971    R   R   F   T   S   F   D   Q   V   A   H   V   S   S   A   A   R   G   L   A    3990

12181  GGCCTCGCTGCTCTTCCTGCTTTTGGTCAAGGCTGCCCAGCACGTACGCTTCGTGCGCCA  12240
 3991    A   S   L   L   F   L   L   L   V   K   A   A   Q   H   V   R   F   V   R   Q    4010

12241  GTGGTCCGTCTTTGGCAAGACATTATGCCGAGCTCTGCCAGAGCTCCTGGGGGTCACCTT  12300
 4011    W   S   V   F   G   K   T   L   C   R   A   L   P   E   L   L   G   V   T   L    4030
                                                                         ─────────

12301  GGGCCTGGTGGTGCTCGGGGTAGCCTACGCCCAGCTGGCCATCCTGCTCGTGTCTTCCTG  12360
 4031    G   L   V   V   L   G   V   A   Y   A   Q   L   A   I   L   L   V   S   S   C    4050
         ─────────────────────────────────────────────────────
                            TM10

12361  TGTGGACTCCCTCTGGAGCGTGGCCCAGGCCCTGTTGGTGCTGTGCCCTGGGACTGGGCT  12420
 4051    V   D   S   L   W   S   V   A   Q   A   L   L   V   L   C   P   G   T   G   L    4070
                         ─────────────────────────────────────────
                                        TM11

12421  CTCTACCCTGTGTCCTGCCGAGTCCTGGCACCTGTCACCCCTGCTGTGTGTGGGGCTCTG  12480
 4071    S   T   L   C   P   A   E   S   W   H   L   S   P   L   L   C   V   G   L   W    4090
         ─────────────────
```

FIG. 15U

```
12481 GGCACTGCGGCTGTGGGGCGCCCTACGGCTGGGGGCTGTTATTCTCCGCTGGCGCTACCA 12540
 4091  A  L  R  L  W  G  A  L  R  L  G  A  V  I  L  R  W  R  Y  H   4110

12541 CGCCTTGCGTGGAGAGCTGTACCGGCCGGCCTGGGAGCCCCAGGACTACGAGATGGTGGA 12600
 4111  A  L  R  G  E  L  Y  R  P  A  W  E  P  Q  D  Y  E  M  V  E   4130

12601 GTTGTTCCTGCGCAGGCTGCGCCTCTGGATGGGCCTCAGCAAGGTCAAGGAGTTCCGCCA 12660
 4131  L  F  L  R  R  L  R  L  W  M  G  L  S  K  V  K  E  F  R  H   4150

12661 CAAAGTCCGCTTTGAAGGGATGGAGCCGCTGCCCTCTCGCTCCTCCAGGGGCTCCAAGGT 12720
 4151  K  V  R  F  E  G  M  E  P  L  P  S  R  S  S  R  G  S  K  V   4170

12721 ATCCCCGGATGTGCCCCCACCCAGCGCTGGCTCCGATGCCTCGCACCCCTCCACCTCCTC 12780
 4171  S  P  D  V  P  P  P  S  A  G  S  D  A  S  H  P  S  T  S  S   4190

12781 CAGCCAGCTGGATGGGCTGAGCGTGAGCCTGGGCCGGCTGGGGACAAGGTGTGAGCCTGA 12840
 4191  S  Q  L  D  G  L  S  V  S  L  G  R  L  G  T  R  C  E  P  E   4210

12841 GCCCTCCCGCCTCCAAGCCGTGTTCGAGGCCCTGCTCACCCAGTTTGACCGACTCAACCA 12900
 4211  P  S  R  L  Q  A  V  F  E  A  L  L  T  Q  F  D  R  L  N  Q   4230

12901 GGCCACAGAGGACGTCTACCAGCTGGAGCAGCAGCTGCACAGCCTGCAAGGCCGCAGGAG 12960
 4231  A  T  E  D  V  Y  Q  L  E  Q  Q  L  H  S  L  Q  G  R  R  S   4250

12961 CAGCCGGGCGCCCGCCGGATCTTCCCGTGGCCCATCCCCGGGCCTGCGGCCAGCACTGCC 13020
 4251  S  R  A  P  A  G  S  S  R  G  P  S  P  G  L  R  P  A  L  P   4270

13021 CAGCCGCCTTGCCCGGGCCAGTCGGGGTGTGGACCTGGCCACTGGCCCCAGCAGGACACC 13080
 4271  S  R  L  A  R  A  S  R  G  V  D  L  A  T  G  P  S  R  T  P   4290
```

FIG. 15V

| | | |
|---|---|---|
| 13081 | CCTTCGGGCCAAGAACAAGGTCCACCCCAGCAGCACTTAGTCCTCCTTCCTGGCGGGGGT | 13140 |
| 4291 | L  R  A  K  N  K  V  H  P  S  S  T | 4310 |
| 13141 | GGGCCGTGGAGTCGGAGTGGACACCGCTCAGTATTACTTTCTGCCGCTGTCAAGGCCGAG | 13200 |
| 13201 | GGCCAGGCAGAATGGCTGCACGTAGGTTCCCCAGAGAGCAGGCAGGGGCATCTGTCTGTC | 13260 |
| 13261 | TGTGGGCTTCAGCACTTTAAAGAGGCTGTGTGGCCAACCAGGACCCAGGGTCCCCTCCCC | 13320 |
| 13321 | AGCTCCCTTGGGAAGGACACAGCAGTATTGGACGGTTTCTAGCCTCTGAGATGCTAATTT | 13380 |
| 13381 | ATTTCCCCGAGTCCTCAGGTACAGCGGGCTGTGCCCGGCCCCACCCCCTGGGCAGATGTC | 13440 |
| 13441 | CCCCACTGCTAAGGCTGCTGGCTTCAGGGAGGGTTAGCCTGCACCGCCGCCACCCTGCCC | 13500 |
| 13501 | CTAAGTTATTACCTCTCCAGTTCCTACCGTACTCCCTGCACCGTCTCACTGTGTGTCTCG | 13560 |
| 13561 | TGTCAGTAATTTATATGGTGTTAAAATGTGTATATTTTTGTATGTCACTATTTTCACTAG | 13620 |
| 13621 | GGCTGAGGGGCCTGCGCCCAGAGCTGGCCTCCCCCAACACCTGCTGCGCTTGGTAGGTGT | 13680 |
| 13681 | GGTGGCGTTATGGCAGCCCGGCTGCTGCTTGGATGCGAGCTTGGCCTTGGGCCGGTGCTG | 13740 |
| 13741 | GGGGCACAGCTGTCTGCCAGGCACTCTCATCACCCCAGAGGCCTTGTCATCCTCCCTTGC | 13800 |
| 13801 | CCCAGGCCAGGTAGCAAGAGAGCAGCGCCCAGGCCTGCTGGCATCAGGTCTGGGCAAGTA | 13860 |
| 13861 | GCAGGACTAGGCATGTCAGAGGACCCCAGGGTGGTTAGAGGAAAAGACTCCTCCTGGGGG | 13920 |
| 13921 | CTGGCTCCCAGGGTGGAGGAAGGTGACTGTGTGTGTGTGTGTGCGCGCGCGACGCGCG | 13980 |
| 13981 | AGTGTGCTGTATGGCCCAGGCAGCCTCAAGGCCCTCGGAGCTGGCTGTGCCTGCTTCTGT | 14040 |
| 14041 | GTACCACTTCTGTGGGCATGGCCGCTTCTAGAGCCTCGACACCCCCCCAACCCCCGCACC | 14100 |
| 14101 | AAGCAGACAAAGTCAATAAAAGAGCTGTCTGACTGCAAAAAAAAAAAA | 14148 |

```
PKD1           HPLCPSDTEIFPGNGHCYRLVVEKAAWLQAQEQCQA WAGAAIAWDSPAVQRFIVSRVTRSLD VWIGLSTV
BRA3           ECTCPGNLDWQEYDGHCYWASTYQVRMNDAQLACQTVHPGAYLATOSQLENAFISETVSNNR IWIGLNDI
Kupffer        LQLIM  QDWKYFNGKEYYFSRDKKSWHFAENFCVS QGAHIASVTSQEEQAFIVQITNAVDH  WIGLTDQ
C.S.P          QKICE  EGWTKFQGHCYRHFPDRATWVDAESQCRK QQSHLSSLVTPEEQEFVNNNAQDYQ   WIGLNDK
RTCCP          VNMVEHQSCYWFSHSGKAWAEAEKYQL        ENAHIVVINSWEEQKEIVQHTNPFNT WIGLTDS
ASIAL.         LLAGESTAWYMNASSELMTYDEASAYCQR      DYTHIVAIQNKEEINYINSNLKHSPSYWIGERKV
E_Selectin     WEMTFFQGNCYFMSNSQRNWHDSITACKE      GAQLMVIKSAEEQNFLQLQSSRSRNFTWMGLSDL
GP120 binding  CHPCP

CONC

```
PKD1A       LEAHVDLRDCVTY        QEEIRMEVYRTASCQRGRPARVAIPGVDVSRP
     B      ESYDENLEDGDQI        PLSIHMACV
     C      RSSYVYLECRQLNCSSGSKRCRMAAR   ASTQREAGGCAINFGPRGSS
     D      CRLFFLGAVHALTTKVHFECTGMHDA   TFSNKTLVLDTTTSTGSAGM
NEUROGLIAN  DNRSPILHYTLQI NTSFIPASMDAA   EDAGAPLVYALLLRRCRQGHCEEFCVYKGSLSS
L1          DHNAPIEKYDIEYEDKEMAPEKMYSL   YEKYPNTD
F11         DNHSPISKYTLQSK  TFLSEEMKDA   GKVPGNQ
TAG1        DNHSPIAKYTLQAR  TPPAGKMKQV   KTEPSDYEGNME
F3          PSEAPTEVGVKVLS  SSELSVHMKHV  RTNPANLEGNAE
NCAM        TGGVPILKYKAEW   KSLGEEAMHSK  WYDAKEANMEGHDKEAAAHRVQVTSQEY
DOC         LSWRPPAEAKGNI   QTFIVFFSR    WTDAKEANMEG
LAR         PSAPPQKVMCVSM  GSTTVRVSMVPP  EGDNRERALNTTQPGSL
HPTP        TVPSPWKDIGISI  KANSLLISMSHG  PADSRNGVITQYSVAHEAVDGEDRGRHVDGISREHS
RN          VSDVP RDLEWVAATPTSLLISMDAP   SGNVERYRLMLMDKGILVHGGVVDKHAT
                                         AVTVRYMBITYGETGGNSPVQEFTVPGSKS

B strands           A           B              C                    D

CONSENSUS       P    h  h  h    W            hph
                                   h   h   r
```

FIG. 19A

| FIG. 19A |
| FIG. 19B |

FIG. 19

POLYCYSTIC KIDNEY DISEASE 1 GENE AND USES THEREOF

This application is a divisional of U.S. application Ser. No. 8/422,582 filed Apr. 14, 1995 which claims priority to International Application PCTGB94/02822 filed Dec. 23, 1994.

BACKGROUND TO THE INVENTION

In humans, one of the commonest of all genetic disorders is autosomal dominant polycystic kidney disease (ADPKD) also termed adult polycystic kidney disease (APKD), affecting approximately 1/1000 individuals (Dalgaard, 1957). ADPKD is a progressive disease of cyst formation and enlargement typically leading to end stage renal disease (ESRD) in late middle age. The major cause of morbidity in ADPKD is progressive renal disease characterized by the formation and enlargement of fluid filled cysts, resulting in grossly enlarged kidneys. Renal function deteriorates as normal tissue is compromised by cystic growth, resulting in end stage renal disease (ESRD) in more than 50% of patients by the age of 60 years (Gabow, et al., 1992). ADPKD accounts for 8–10% of all renal transplantation and dialysis patients in Europe and the USA (Gabow, 1993).

ADPKD also causes cystic growth in other organs (reviewed in Gabow, 1990) and occasionally presents in childhood (Fink, et al., 1993; Zerres, et al., 1993). Extrarenal manifestations include liver cysts (Milutinovic, et al., 1980), and more rarely cysts of the pancreas (Gabow, 1993) and other organs. Intracranial aneurysms occur in approximately 5% of patients and are a significant cause of morbidity and mortality due to subarachnoid haemorrhage (Chapman, et al., 1992). ADPKD is associated with a higher prevalence of various connective tissue disorders. An increased prevalence of heart valve defects (Hossack, et al., 1988), hernia (Gabow, 1990) and colonic diverticulae (Scheff, et al., 1980) have been reported.

Considerable progress has been made in the last few years in understanding the pathophysiology of ADPKD (and other animal models of cystic disease). Cysts in ADPKD are known to develop from outpouchings of descending or ascending kidney tubules and the early stages are characterized by a thickening and disorganization of the basement membrane, accompanied by a de-differentiation of tubular epithelial cells. Several of the characteristics of ADPKD epithelia: altered growth responses, abnormal expression of various proteins and reversal of polarity, may be a sign of this de-differentiation and important in cyst expansion. The nature of the primary defect which triggers these changes is, however, unknown and consequently much effort has been devoted to identifying the causative agent by genetic means.

The first step towards positional cloning of an ADPKD gene was the demonstration of linkage of one locus now designated the polycystic kidney disease 1 (PKD1) locus to the α globin cluster on the short arm of chromosome 16 (Reeders, et al., 1985). Subsequently, families with ADPKD unlinked to markers on 16p were described (Kimberling, et al., 1988; Romeo, et al., 1988) and a second ADPKD locus (PKD2) has recently been assigned to chromosome region 4q13–q23 (Kimberling, et al., 1993; Peter, et al., 1993). It is estimated that approximately 85% of ADPKD is due to PKD1 (Peters and Sankuijl, 1992) with PKD2 accounting for most of the remainder. PKD2 appears to be milder condition with a later age of onset and ESRD (Parfrey, et al., 1990; Gabow, et al., 1992; Ravine, et al., 1992).

The position of the PKD1 locus was refined to chromosome band 16p13.3 and many markers were isolated from that region (Breuning, et al., 1987; Reeders, et al., 1988; Breuning, et al., 1990; Germino, et al., 1990; Hyland, et al., 1990; Himmelbauer, et al., 1991). Their order, and the position of the PKD1 locus, has been determined by extensive linkage analysis in normal and PKD1 families and by the use of a panel of somatic cell hybrids (Reeders et al., 1988; Breuning, et al., 1990; Germino, et al., 1990). ADPKD is genetically heterogenous with loci mapped not only to 16p13.3 (PKD1), but also to chromosome 4 (PKD2). Although the phenotype of PKD1 and PKD2 are clearly similar, it is now well documented that PKD1 (which accounts for about 85% of ADPKD; (Peters, 1992) is a more severe disease with an average age at ESRD of about 56 years compared to about 71.5 years for PKD2 (Ravine, 1992). An accurate long range restriction map of the 16p13.3 region (Harris, et al., 1990; Germino, et al., 1992) has located the PKD1 locus in an interval of approximately 600 kb between the markers GGG1 and SM7 (Harris, et al., 1991; Somlo, et al., 1992) (see FIG. 1a). The density of CpG islands and identification of many mRNA transcripts indicated that this area is rich in gene sequences. Germino et al. (1992) estimated that the candidate region contains approximately 20 genes.

Identification of the PKD1 gene from within this area has thus proved difficult and other means to pinpoint the disease gene have been sought. Linkage disequilibrium has been demonstrated between PKD1 and the proximal marker VK5, in a Scottish population (Pound, et al., 1992) and between PKD1 and BLu24 (see FIG. 1a), in a Spanish population (Peval, et al., 1994). Studies with additional markers have shown evidence of a common ancestor in a proportion of each population (Peval, et al., 1994; Snarey, et al., 1994), but the association has not precisely positioned the PKD1 locus.

Disease associated genomic rearrangements, detected by cytogenetics or pulsed field gel electrophoresis (PFGE) have been instrumental in the identification of various genes associated with various genetic disorders. Hitherto, no such abnormalities related to PKD1 have been described. This situation contrasts with that for the tuberous sclerosis locus, which lies within 16p13.3 (TSC2) In that case, TSC associated deletions were detected by PFGE within the interval thought to contain the PKD1 gene and their characterisation was a significant step toward the rapid identification of the TSC2 gene (European Chromosome 16 Tuberous Sclerosis Consortium, 1993). The TSC2 gene therefore maps within the candidate region for the hitherto unidentified PKD1 gene; as polycystic kidneys are a feature common to TSC and ADPKD1 (Bernstein and Robbins, 1991) the possibility of an etiological link, as proposed by Kandt et al. (1992), was considered. A contiguous gene syndrome resulting from the disruption of PKD1 and the adjacent tuberous sclerosis 2 (TSC2) gene, which is associated with TSC and severe childhood onset polycystic kidney disease, has also been defined (Brook-Carter et al., 1994).

We have now identified a pedigree in which the two distinct phenotypes, typical ADPKD or TSC, are seen in different members. In this family, the two individuals with ADPKD are carriers of a balanced chromosome translocation with a breakpoint within 16p1.3.3. We have located the chromosome 16 translocation breakpoint and a gene disrupted by this rearrangement has been defined; the discovery of additional mutations of that gene in other PKD1 patients shows that we have identified the PKD1 gene. Full characterisation of the PKD1 transcript has been significantly complicated because of the unusual genomic region containing most of the gene. All but 3.5 kb at the 3' end of the transcript (which is about 14 kb in total) is encoded by a region which is reiterated several times elsewhere on the same chromosome (in 16p1.3.1 and termed the HG area). The structure of the duplication is complex, with some regions copied more times than others, and the HG region encoding three large transcripts. The transcripts from the HG area are: HG-A (21 kb), HG-B (17 kb) and HG-C (8.5 kb) and although these have 3' ends which differ from PKD1, over most of their length they share substantial homology to the PKD1 transcript. Consequently, cloning and characterizing a bona fide PKD1 cDNA has proven difficult. To overcome the problem caused by duplication we have cloned cDNAs covering the entire transcript from a cell line which contains the PKD1 but not the HG loci. Characterisation of these cDNAs has enabled the PKD1 protein sequence to be predicted and led to the identification of several homologies with described motifs.

SUMMARY OF THE INVENTION

Accordingly, in one aspect, this invention provides an isolated, purified or recombinant nucleic acid sequence comprising:

(a) a PKD1-encoding nucleic acid or its complementary strand, (b) a sequence substantially homologous to, or capable of hybridizing to, a substantial portion of a molecule defined in (a) above, or (c) a fragment of a molecule defined in (a) or (b) above.

In particular, there is provided a sequence wherein the PKD1 gene has the nucleic acid sequence according to FIG. 15 (SEQ. I.D. NO. 7), or the partial sequence of FIGS. 7 (SEQ. I.D. NO. 1) or 10 (SEQ. I.D. NO. 5). The invention therefore includes a DNA molecule coding for a polypeptide having the amino acid sequence of FIG. 15 (SEQ. I.D. NO. 8), or a polypeptide fragment thereof; and genomic DNA corresponding to a molecule as in (a)–(c) above.

As used herein, "substantially homologous" refers to a nucleic acid strand that is sufficiently duplicative of the PKD1 sequence presented in FIG. 15 (SEQ. I.D. NO. 7) such that it is capable of hybridizing to that sequence under moderately stringent, and preferably stringent conditions, as defined herein below. Preferably, "substantially homologous" refers to a homology of between 97 and 100%. Further, such a strand will encode or be complementary to a strand that encodes PKD1 protein having the biological activity described below. As used herein, a "substantial portion of a molecule" refers to at least 60%, preferably 80% and most preferably 90% of the molecule in terms of its linear residue length or its molecular weight. "Nucleic acid" refers to both DNA and RNA.

The PKD1 gene described herein is a gene found on human chromosome 16, and the results of studies described herein form the basis for concluding that this PKD1 gene encodes a protein called PKD1 protein which has a role in the prevention or suppression of ADPKD. The PKD1 gene therefore includes the DNA sequences shown in FIG. 15 (SEQ. I.D. NO. 7) and all functional equivalents. By "functional equivalents", we mean nucleic acid sequences that are substantially homologous to the PKD1 nucleic acid sequence, as presented in FIG. 15 (SEQ. I.D. NO. 7), and encoding a protein that possesses one or more of the biological functions or activities of PKD1; i.e., that is involved in cell/cell adhesion, cell/cell recognition or cell/cell communication, for example to effect adhesion of cells to other cells or components of the extracellular matrix; effect communication and/or interaction between epithelial cells and the basal membrane (whether in kidneys or otherwise); assist in development of connective tissue such as assembly and/or maintenance of the basal membrane; in signal transduction between cells or cells and components of the extracellular matrix; and/or to promote binding of cells carrying proteins such as integrins or carbohydrates to target cells. The biological function of PKD1 of course includes maintaining a healthy physiological state; that is, the native protein's aberrations or absence results in ADPKD or an associated disorder.

The PKD1 gene may furthermore include regulatory regions which control the expression of the PKD1 coding sequence, including promoter, enhancer and terminator regions. Other DNA sequences such as introns spliced from the end-product PKD1 RNA transcript are also encompassed. Although work has been carried out in relation to the human gene, the corresponding genetic and functional sequences present in lower animals are also encompassed.

The present invention therefore further provides a PKD1 gene or its complementary strand having the sequence according to FIG. 15 (SEQ. I.D. NO. 7) which gene or strand is mutated in some ADPKD patients (more specifically, PKD1 patients). Therefore, the invention further provides a nucleic acid sequence comprising a mutant PKD1 gene as described herein, including wherein Intron 43 as defined hereinbelow has a deletion of 18 or 20bp resulting in an intron of 55 or 57bp.

As used herein, "PKD1 mutant" or "mutation" encompasses alterations of the native PKD1 nucleotide (SEQ. I.D. NO. 7) or amino acid sequence (SEQ. I.D. NO. 8] as defined by FIG. 15, i.e., substitutions, deletions or additions, and also encompasses deletion of DNA containing the entire PKD1 gene.

The invention further provides a nucleic acid sequence comprising a mutant PKD1 gene, especially one selected from a sequence comprising a partial sequence according to FIGS. 7 (SEQ. I.D. NO. 19 and/or 10 (SEQ. I.D. NO. 5), or the corresponding sequences disclosed in FIG. 15 (SEQ. I.D. NO. 7) when:

(a) [OX114] base pairs 1746-2192 as defined in FIG. 7 (SEQ. I.D. NO. 1) deleted (446bp);

(b) [OX32] base pairs 3696-3831 as defined in FIG. 7 (SEQ. I.D. NO. 1) are deleted by a splicing defect;

(c) [OX875] about 5.5kb flanked by the two XbaI sites shown in FIG. 3a are deleted and the EcoR1 site separating the CW10

(41kb) and JH1 (18kb) sites is thereby absent (d) [WS531 about 100kb extending between the JH1 and CW21 and the SM6 and JH17 sites shown in FIG. 6 and the PKD1 gene is thereby absent, the deletion lying proximally between SM6 and JH17;

(e) [461] 18bp are the 75bp intron amplified by the primer pair 3A3C (SEQ. I.D. NOS. 11 and 12) insert at position 3696 of the 3' sequence (SEQ. I.D. NO. 18) shown in FIG. 11 (SEQ. I.D. NO. 18];

(f) [OX1054] 20 bp are deleted in the 75bp intron amplified by the primer pair 3A3C (SEQ. I.D. NOS. 11 and 12] insert at position 3696 of the 3' sequence (SEQ. I.D. NO. 1) as shown in FIG. 11 (SEQ. I.D. NO. 18];

(g) [WS212) about 75 kb are deleted between SM9-CW9 distally and the PKD1 3'UTR proximally as shown in FIG. 12;

(h) [WS-215) about 160 kb are deleted between CW20 and SM6-JH17 as shown in FIG. 12;

(i) [WS-227) about 50kb are deleted between CW20 and JH11 as shown in FIG. 12;

(j) [WS-219) about 27kb are deleted between JH1 and JH6 as shown in FIG. 12;

(k) [WS-250) about 160kb are deleted between CW20 and Blu24 as shown in FIG. 12;

(l) [WS-194) about 65kb is deleted between CW20 and CW10.

The invention therefore extends to RNA molecules comprising an RNA sequence corresponding to any of the DNA sequences set out above. Such molecule may be the transcript reference PBP and identifiable with respect to the restriction map of FIG. 3a and having a length of about 14 KB.

In another aspect, the invention provides a nucleic acid probe having a sequence as set out above; in particular, this invention extends to a purified nucleic acid probe which hybridizes to at least a portion of the DNA or RNA molecule of any of the preceding sequences. Preferably, the probe includes a label such as a radiolabel, for example, a $^{32}$P label.

In another aspect, this invention provides a purified DNA or RNA coding for a protein comprising the amino acid sequence of FIG. 15 (SEQ. I.D. NO. 8), or a protein polypeptide having homologous properties with said protein, or having at least one functional domain or active site in common with said protein.

The DNA molecule defined above may be incorporated in a recombinant cloning vector for expressing a protein having the amino acid sequence of FIG. 15 [Seq. I.D. NO. 8), or a protein or a polypeptide having at least one functional domain or active site in common with said protein. Such a vector may include any vector for expression in bacteria, e.g., *E. coli;* yeast, insect, or mammalian cells.

The invention also features a nucleic acid probe for detecting PKD1 nucleic acid comprising 10 consecutive nucleotides as presented in FIG. 15 (SEQ. I.D. NO. 7). Preferably, the probe may comprise 15, 20, 50, 100, 200, or 300, etc., consecutive nucleotides (nt) presented in FIG. 13, and may fall within the size range 15nt-13kb, 100nt-5kb, 150nt-4kb, 300nt-2kb, and 500nt-1kb.

Probes are used according to the invention in hybridization reactions to identify PKD1 sequences, whether they be native or mutated PKD1 DNA or RNA, as disclosed herein. Such probes are useful for identifying the PKD1 gene or a mutation thereof, as defined herein.

The invention also features a synthetic polypeptide corresponding in amino acid residue sequence to at least a portion of the sequence of naturally occurring PKD1, and having a molecular weight equal to less than that of the native protein. A synthetic polypeptide of the invention is useful for inducing the production of antibodies specific for the synthetic polypeptide and that bind to naturally occurring PKD1.

Preferred embodiments of this aspect of the invention include a group of synthetic polypeptides whose members correspond to a fragment of the PKD1 protein comprising a stretch of amino acids of at least 8, and preferably 15, 30, 50, or 100 residues in length from the sequence disclosed in FIG. 15 (SEQ. I.D. NO. 8].

In another aspect, the invention provides a polypeptide encoded by a sequence as set out above, or having the amino acid sequence according to the amino acid sequence of FIG. 15 (SEQ. I.D. NO. 8), or a protein or polypeptide having homologous properties with said protein, or having at least one functional domain or active site in common with said protein. In particular, there is provided an isolated, purified or recombinant polypeptide comprising a PKD1 protein or a mutant or variant thereof or encoded by a sequence set out above or a variant thereof having substantially the same activity as the PKD1 protein. The present invention may further comprise a polypeptide having 9 or 13 transmembrane pairs instead of 11 transmembrane domains as described hereinbelow. Further comprising this invention is a molecule which interacts with a polypeptide as herein described which molecule synergises, causes, enhances or is necessary for the functioning of the PKD1 protein as herein described.

The invention also encompasses recombinant expression vectors comprising a nucleic acid or isolated DNA encoding PKD1 and a process for preparing PKD1 polypeptide, comprising culturing a suitable host cell comprising the vector under conditions suitable for promoting expression of PKD1, and recovering said PKD1.

This invention also provides an in vitro method of determining whether an individual is likely to be affected with tuberous sclerosis, comprising assaying a biological sample from the individual to determine the presence and/or amount of PKD1 protein or polypeptide having the amino acid sequence of FIG. 15 (SEQ. I.D. NO. 8].

As used herein, "biological sample" includes any fluid or tissue sample from a mammal, preferably a human, including but not limited to blood, urine, saliva, any body organ tissue, cells from any body tissue, including blood cells.

Additionally or alternatively, a sample may be assayed to determine the presence and/or amount of mRNA coding for the protein or polypeptide having the amino acid sequence of FIG. 15 (SEQ. I.D. NO. 8), or to determine the fragment lengths of fragments of nucleotide sequences coding for the protein or polypeptide of FIG. 15 (SEQ. I.D. NO. 8), or to detect inactivating mutations in DNA coding for a protein having the amino acid sequence of FIG. 15 (SEQ. I.D. NO. 8) or a protein having homologous properties. The screening preferably includes applying a nucleic acid amplification process, as described herein in detail, to said sample to amplify a fragment of the DNA sequence. The nucleic acid amplification process advantageously utilizes at least one of the following sets of primers as identified herein: AH3 F9 (SEQ. I.D. NO. 9): AH3 B7 (SEQ. I.D. NO. 10); 3A3 C1 (SEQ. I.D. NO. 11]: 3A3 C2(SEQ. I.D. NO. 12) and AH4 F2 (SEQ. I.D. NO. 13: JH14 B3 (SEQ. I.D. NO. 14].

Alternatively, the screening method may comprise digesting the sample DNA to provide EcoRI fragments and hybridizing with a DNA probe which hybridizes to the EcoRI fragment identified (A) in FIG. 3(*a*), and the DNA probe may comprise the DNA probe CW10(SEQ. I.D. NO. 4) identified herein.

Another screening method may comprise digesting the sample to provide BamHI fragments and hybridizing with a DNA probe which hybridizes to the BamHI fragment identified (B) in FIG. 3(*a*), and the DNA probe may comprise the DNA probe 1A1H.6 identified herein.

A method according to the present invention may comprise detecting a PKD1-associated disorder in a patient suspected of having or having predisposition to the disorder (i.e., a carrier), the method comprising detecting the presence of and/or evaluating the characteristics of PKD1 DNA, PKD1 mRNA and or PKD1 protein in a sample taken from the patient. Such method may comprise detecting and/or evaluating whether the PKD1 DNA is deleted, missing, mutated, aberrant or not expressing normal PKD1 protein. One way of carrying out such a method comprises: A. taking a biological, tissue or biopsy sample from the patient; B. detecting the presence of and/or evaluating the characteristics of PKD1 DNA, PKD1 mRNA and/or PKD1 protein in the sample to obtain a first set of results; C. comparing the first set of results with a second set of results obtained using the same or similar methodology for an individual that is not suspected of having the disorder; and if the first and second sets of results differ in that the PKD1 DNA is deleted, missing, aberrant, mutated or not expressing PKD1 protein then that is indicative of the presence, predisposition or tendency of the patient to develop the disorder. As used herein, a "PKD1 -associated disorder" refers to adult polycystic kidney disease, as described herein, and also refers to tuberous sclerosis, as well as other disorders having symptoms such as cyst formation in common with these diseases.

A specific method according to the invention comprises extracting from a patient a sample of PKD1 DNA or DNA from the PKD1 locus purporting to be PKD1 DNA, cultivating the sample in vitro and analyzing the resulting protein, and comparing the resulting protein with normal PKD1 protein according to the well-established Protein Truncation Test. Less sensitive tests include analysis of RNA using RT PCR (reverse transcriptase polymerase chain reaction), and examination of genomic DNA.

Step C of the above method may be replaced by: comparing the first set of results with a second set of results obtained using the same or similar methodology in an individual that is known to have the or at least one of the disorder (s) ; and if the first and second sets of results are substantially identical, this indicates that the PKD1 DNA in the patient is deleted, mutated or not expressing normal PKD1 protein.

The invention further provides a method of characterizing a mutation in a subject suspected of having a mutation in the PKD1 gene, which method comprises: A. amplifying each of the exons in the PKD1 gene of the subject; B. denaturing the complementary strands of the amplified exons; C. diluting the denatured separate, complementary strands to allow each single-stranded DNA molecule to assume a secondary structural confirmation; D. subjecting the DNA molecule to electrophoresis under non-denaturing conditions; E. comparing the electrophoresis pattern of the single-stranded molecule with the electrophoresis pattern of a single-stranded molecule containing the same amplified exon from a control individual which has either a normal or PKD1 heterozygous genotype; and, F. sequencing any amplification product which has an electrophoretic pattern different from the pattern obtained from the DNA of the control individual.

The invention also extends to a diagnostic kit for carrying out a method as set out above, comprising nucleic acid primers for amplifying a fragment of the DNA or RNA sequences defined above, and packaging means therefore. The kit may optionally include written instructions stating that the primers are to be used for detection of disorders associated with the PKD1 gene. The nucleic acid primers may comprise at least one of the following sets: AH3 F9 (SEQ. I.D. NO. 9): AH3 B7 (SEQ. I.D. NO. 10]: 3A3 C1 (SEQ. I.D. NO. 11]: 3A3 C2 (SEQ. I.D. NO. 12); and AH4 F2 (SEQ. I.D. NO. 13): JH14 B3 (SEQ. I.D. NO. 14].

Another embodiment of kit mat combine one or more substances for digesting a sample to provide EcoRI fragments and a DNA probe as previously defined. A further embodiment of kit may comprise one or more substances for digesting a sample to provide BamHI fragments and a DNA probe as previously defined.

A vector (such as Bluescript (available from Stratagene)) comprising a nucleic acid sequence set out above; and a host cell (such as *E. coli* strain SL-1 Blue (available from Stratagene) transfected or transformed with the vector are also provided, together with the use of such a vector or a nucleic acid sequence set out above in gene therapy and/or in the preparation of an agent for treating or preventing a PKD1-associated disorder.

Therefore, there is further provided a method of treating or preventing a PKD1-associated disorder which method comprises administering to a patient in need thereof a functional PKD1 gene to affected cells in a manner that permits expression of PKD1 protein therein and/or a transcript produced from a mutated chromosome (such as the deleted WS-212 chromosome) which is capable of expressing functional-PKD1 protein therein.

As used herein, the term "hybridization" refers to conventional DNA/DNA or DNA/RNA hybridization conditions. For example, for a DNA or RNA probe of about 10–50 nucleotides, moderately stringent hybridization conditions are preferred and include 10×SSC, 5× Denhardts, 0.1% SDS, at 35–50 degrees for 15 hours; for a probe of about 50–300 nucleotides, "stringent" hybridization conditions are preferred and refer to hybridization in 6×SSC, 5×Denhardts, 0.1% SDS at 65 degrees for 15 hours.

The present invention further provides the use of PKD1 protein or polycystin or a mutant or variant thereof having substantially the same biological activity there as in therapy. In particular, to effect cell adhesion, recognition or communication for example to effect adhesion of cells to other cells or components of the G extracellular matrix; effect communication and/or interaction between epithelial cells and the basal membrane (whether in kidneys or otherwise); assisting in development of connective tissue such as assembly and/or maintenance of the basal membrane; in signal transduction between cells or cells and components of the extracellular matrix; and/or to promote binding of cells carrying proteins such as integrins or carbohydrates to target cells.

Accordingly, where it is preferred to administer the polypeptide directly to a patient in need thereof, the invention further provides the use of a PKD1 protein or polycystin in the preparation of a medicament. Therefore, there is also provided a pharmaceutical formulation comprising a PKD1 protein, functional PKD1 gene and/or a transcript produced from a mutated chromosome which is capable of expressing functional PKD1 protein, in association with a pharmaceutically acceptable carrier therefor.

The invention also features an immunoglobin, i.e., a polyclonal or monoclonal antibody specific for an epitope of PKD1, which epitope is found in the amino acid sequence presented in FIG. 15 (SEQ. I.D. NO. 8].

The invention also features a method of assaying for the presence of PKD1 in a sample of mammalian, preferably human cells, comprising the steps of: (a) providing an antibody specific for said PKD1; and (b) assaying for the presence of PKD1 by admixing an aliquot from a sample of mammalian cells with antibody under conditions sufficient to allow for formation and detection of an immune complex of PKD1 and the antibody. Such method is useful for detecting disorders involving aberrant expression of the PKD1 gene or processing of the protein, as described herein.

Preferably, this method includes providing a monoclonal antibody specific for an epitope that is antigenically the same, as determined by Western blot assay, ELISA or immunocytochemical staining, and substantially corresponds in amino acid sequence to the amino acid sequence of a portion of PKD1 and having a molecular weight equal to less than that of PKD1.

The invention thus also features a kit for detecting PKD1, the kit including at least one package containing an antibody or idiotype-containing polyamide portion of an antibody raised to a synthetic polypeptide of this invention or to a conjugate of that polypeptide bound to a carrier. An indicating group or label is utilized to indicate the formation of an immune reaction between the antibody and PKD1 when the antibody is admixed with tissue or cells.

Further features will become more fully apparent in the following description of the embodiments of this invention and from the appended claims.

BRIEF DESCRIPTION OF THE DRAWINGS

Before describing preferred embodiments of the invention in detail, the drawings will briefly be described.

(bottom): A detailed map of the distal part of the PKD1 candidate region showing: the area of 16p13.3 duplicated in 16p1.3.1 (hatched); C, Cla I restriction sites; the breakpoints in the somatic cell hybrids, N-OH1 and P-MWH2A; DNA probes and the TSC2 gene. The limits of the position of the translocation breakpoint found in family 77 (see b), determined by evidence of heterozygosity (in 77-4) and PFGE (see c and text) is also indicated. The contig covering the 77 breakpoint region consists of the cosmids: 1, CW9D; 2, ZDS5; 3, JH2A; 4, REP59; 5, JC10.2B; 6, CW10III; 7, SM25A; 8, SMII; 9, NM17.

Figure 1A:
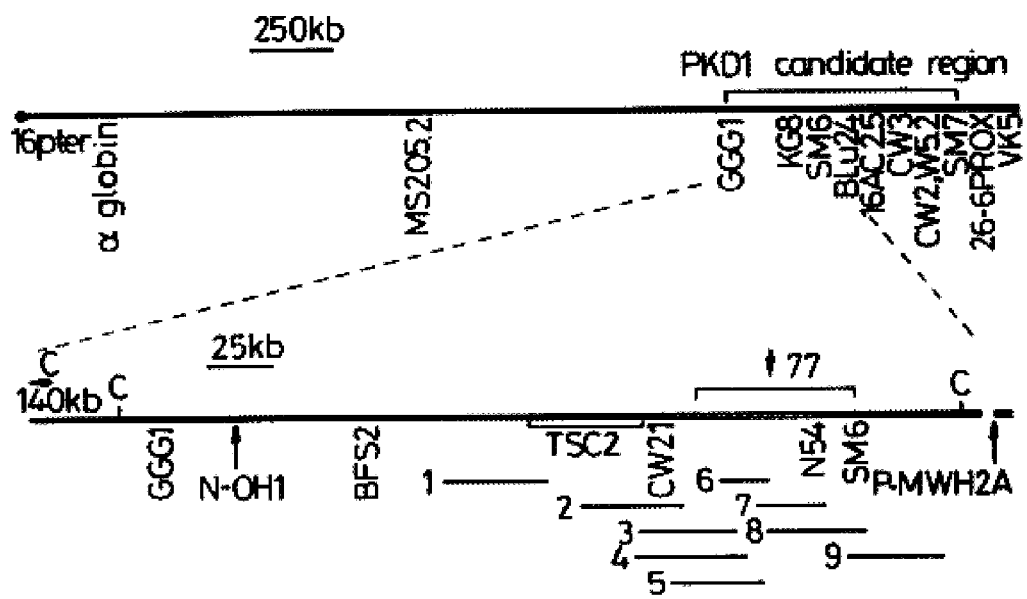
FIG. 1a (top): A long range map of the terminal region of the short arm of chromosome 16 showing the PKD1 candidate region defined by genetic linkage analysis. The positions of selected DNA probes and microsatellites used for haplotype, linkage or heterozygosity analyses are indicated. Markers previously described in linkage disequilibrium studies are shown in bold (from: Harris, et al., 1990; Harris, et al., 1991; Germino, et al., 1992; Somlo, et al., 1992; Peral, et al., 1994; Snarey, et al., 1994).
Figure 1B:
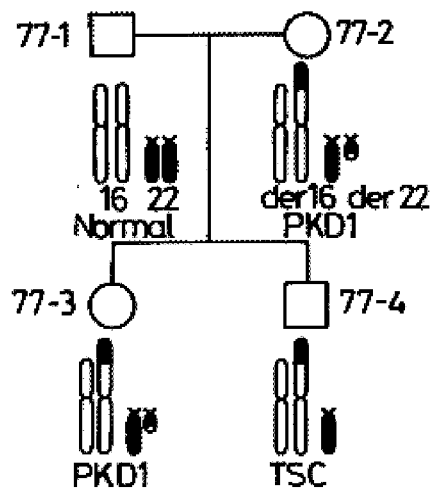

FIG. 1b: Pedigree of family 77 which segregates a 16;22 translocation; showing the chromosomal composition of each subject. Individuals 77-2 and 77-3 have the balanced products of the exchange—and have PKD1; 77-4 is monosomic for 16p1.3.3→16pter and 22q11.21→>pter—and has TSC.

Figure 1C:
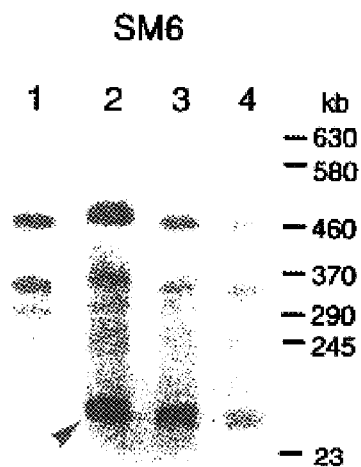

FIG. 1c: PFGE of DNA from members of the 77 family: 77-1 (1); 77-2 (2); 77-3 (3); 77-4 (4); digested with Cla I and hybridised with SM6. In addition to the normal fragments of 340 and partially digested fragment of 480 kb a proximal breakpoint fragment of approximately 100 kb (arrowed) is seen in individuals, 77-2, 77-3 and 77-4; concordant with segregation of the der(16) chromosome.

Figure 2:
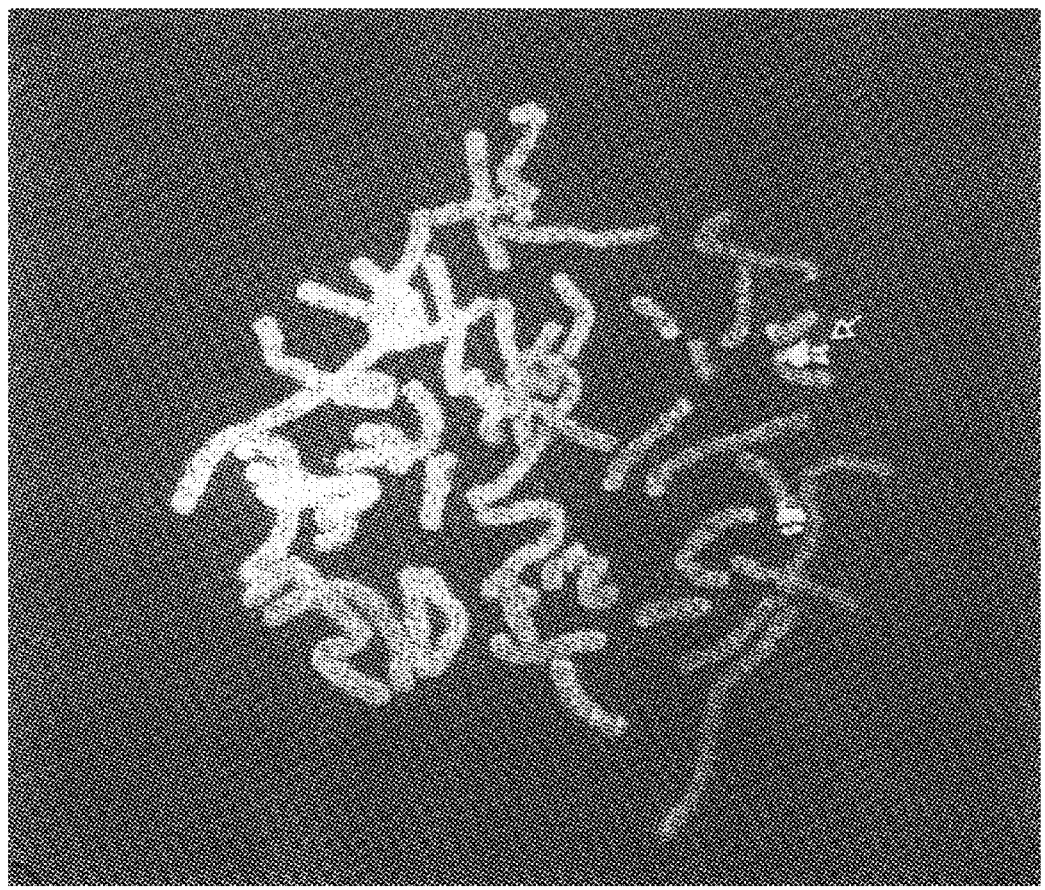

FIG. 2: FISH of the cosmid CW10III (cosmid 6; FIG. 1a) to a normal male metaphase. Duplication of this locus is illustrated with two sites of hybridisation on 16p; the distal site (the PKD1 region) is arrowed. The signal from the proximal site (16p13.1) is stronger than that from the distal, indicating that sequences homologous to CW10III are reiterated in 16p1.3.1.

Figure 3A:
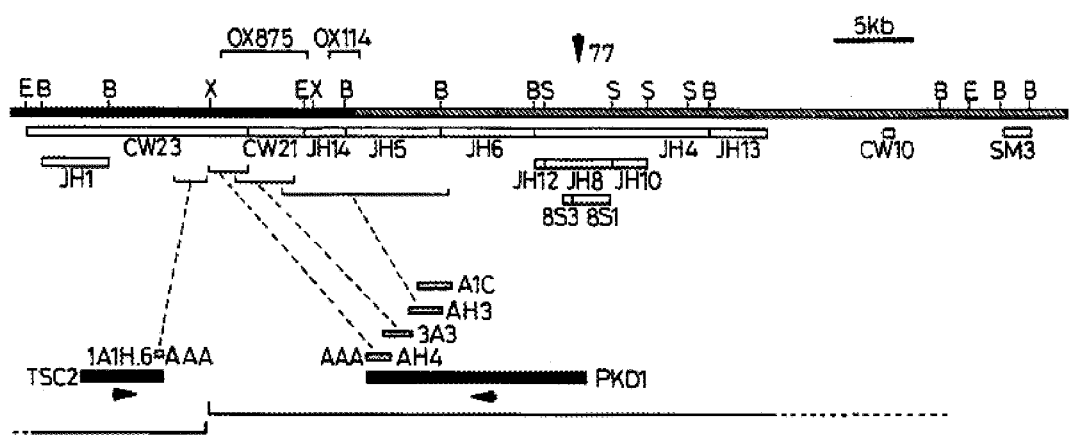

FIG. 3a: A detailed map of the 77 translocation region showing the precise localisation of the 77 breakpoint and the region that is duplicated in 16p1.3.1 (hatched). DNA probes (open boxes); the transcripts, PKD1 and TSC2 (filled boxes; with direction of transcription indicated by an arrow) and cDNAs (grey boxes) are shown below the genomic map. The known genomic extent of each gene is indicated at the bottom of the diagram and the approximate genomic locations of each cDNA is indicated under the genomic map. The positions of genomic deletions found in PKD1 patients, OX875 and OX114, are also indicated. Restriction sites for EcoR I (E) and incomplete maps for BamH I (B); Sac I (S) and Xba I (X) are shown. SM3 is a 2kb BamH1 fragment shown at the 5' end of the gene.

Figure 3B:
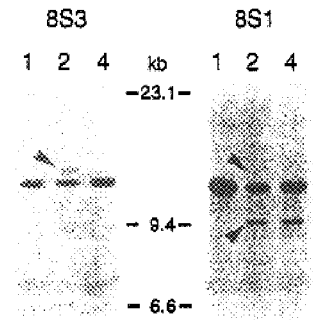

FIG. 3b: Southern blots of BamH I digested DNA from individuals: 77-1 (1); 77-2 (2); and 77-4 (4) hybridised with: left panel, 8S3 and right panel, 8S1 (see a). 8S3 detects a novel fragment on the telomeric side of the breakpoint (12 kb: arrowed) associated with the der(22) chromosome in 77-2, but not 77-4; 8S1 identifies a novel fragment on the centromeric side of the breakpoint (9 kb: arrowed)—associated with the der(16) chromosome—in 77-2 and 77-4. The telomeric breakpoint fragment is also seen weakly with 8S1 (arrowed) indicating that the breakpoint lies in the distal part of 8S1. The 8S3 and 8S1 loci are both duplicated; the normal BamH I fragment detected at the 16p13.3 site by these probes is 11 kb (see a), but a similar sized fragment is also detected at the 16p1.3.1 site. Consequently, the breakpoint fragments are much fainter than the normal (16p1.3.1 plus 16p1.3.3) band.

Figure 4A:
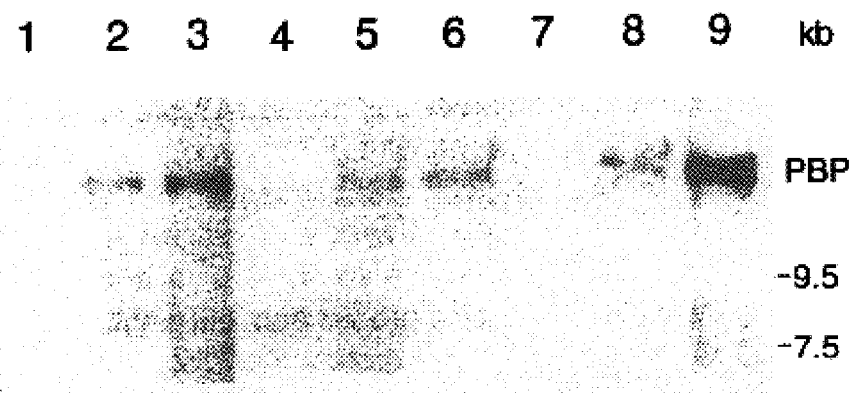

FIG. 4a: PBP cDNA, 3A3, hybridised to a Northern blot containing about 1 μg polyA selected mRNA per lane of the tissue specific cell lines: lane 1, MJ, EBV-transformed lymphocytes; lane 2, K562, erythroleukemia; lane 3, FS1, normal fibroblasts; lane 4, HeLa, cervical carcinoma; lane 5, G401, renal Wilm's tumour; lane 6, Hep3B, hepatoma; lane 7, RT29, colonic adenocarcinoma; lane 8, SW13, adrenal carcinoma; lane 9, G-CCM, astrocytoma. A single transcript of approximately 14 kb is seen; the highest level of expression is in fibroblasts and in the astrocytoma cell line, G-CCM. Although in this comparative experiment little expression is seen in lanes 1, 4 and 7, we have demonstrated at least a low level of expression in these cell lines on other Northern blots and by RT-PCR (see later).

Figure 4B:
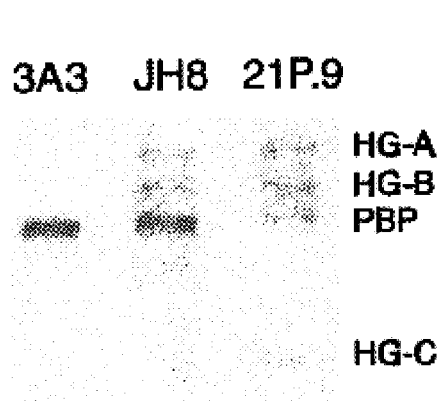

FIG. 4b: A Northern blot containing about 20 μg of total RNA from the cell line G-CCM hybridised with cDNAs or a genomic probe which identify various parts of the PBP gene. Left panel, a single about 14 kb transcript is seen with a cDNA from the single copy area, 3A3. Right panel, a cDNA, 21P.9, that is homologous to parts of the region that is duplicated (JH12, JH8 and JH10; see FIG. 3a) hybridises to the PBP transcript and three novel transcripts; HG-A (about 21 kb), HG-B (about 17kb) and HG-C (8.5 kb). A similar pattern of transcripts is seen with cDNAs and genomic fragments that hybridise to the area between JH5 and JH13, with the exception of the JH8 area. Middle panel, JH8 hybridises to the transcripts PBP, HG-A and HG-B but not to HG-C.

Figure 4C:
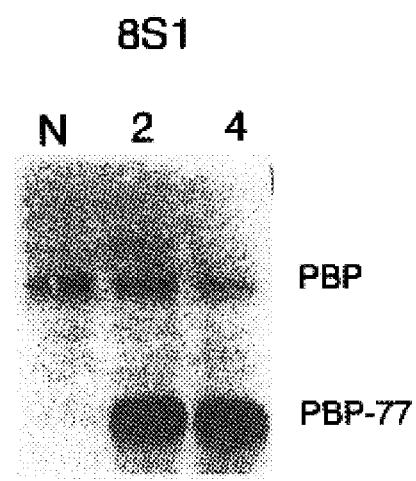

FIG. 4c: A Northern blot of 20 μg total fibroblast RNA from: normal control (N); 77-2 (2); 77-4 (4) hybridised with 8S1, which contains the 16;22 translocation breakpoint (see FIG. 3). A transcript of about 9 kb (PBP-77) is identified in the two patients with this translocation but not in the normal control. PBP-77 is a chimeric PBP transcript formed due to the translocation and is not seen in 77-2 or 77-4 RNA with probes which map distal to the breakpoint.

Figure 5A:
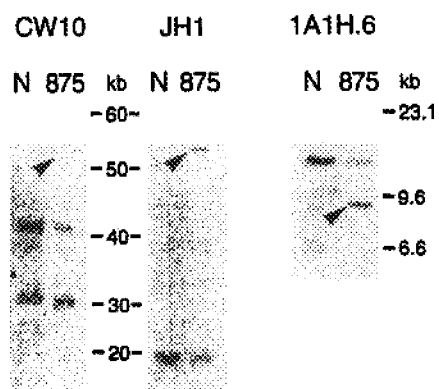

FIG. 5a: FIGE of DNA from: normal (N) and ADPKD patient OX875 (875), digested with EcoR I and hybridised with, left panel, CW10; middle panel, JH1. Normal fragments of 41 kb (plus a 31 kb fragment from the 16p13.1 site), CW10, and 18kb, JHI, are identified with these probes; OX875 has an additional 53kb band (arrowed). The EcoR I site separating these two fragments is removed by the deletion (see FIG. 3a). The right panel shows a Southern blot of BamH I digested DNA (as above) hybridised with 1A1H.6. A novel fragment of 9.5 kb is seen in OX875 DNA, as well as the normal 15 kb fragment. These results indicate that OX875 has a 5.5 kb deletion; its position was determined more precisely by mapping relative to two Xba I sites which flank the deletion (see FIG. 3a).

Figure 5B:
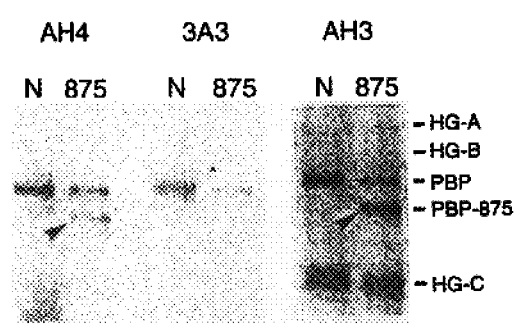

FIG. 5b: Northern blot of total fibroblast RNA, as (a), hybridised with the cDNAs, AH4, 3A3 and AH3. A novel transcript (PBP-875) of about 11 kb is seen with AH4 (the band is reduced in intensity because the probe is partly deleted) and AH3 (arrowed), which flank the deletion, but not 3A3 which is entirely deleted (see FIG. 3a). The transcripts HG-A, HG-B and HG-C, from the duplicated area, are seen with AH3 (see FIG. 4b).

Figure 5C:
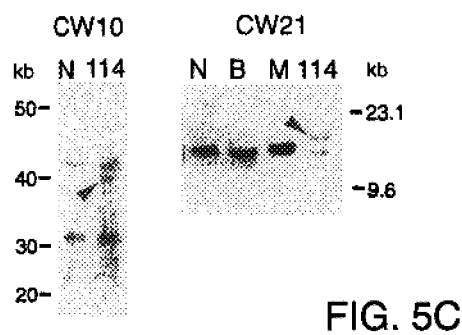

FIG. 5c: Left panel; FIGE of DNA from: normal (N) and ADPKD patient OX114 (114), digested with ECOR I and hybridised with CW10; a novel fragment of 39 kb (arrowed) is seen in OX114. Middle panel; DNA, as above, plus the normal mother (M) and brother (B) of OX114 digested with BamH I and hybridised with CW21. A larger than normal fragment of 19 kb (arrowed) was detected in OX114 but not other family members due to deletion of a BamH I site; together these results are consistent with a 2 kb deletion (see FIG. 3a). Right panel; RT-PCR of RNA, as above, with primers flanking the OX114 deletion (see Experimental Procedures). A novel fragment of 810 bp (arrowed) is seen in OX114, indicating a deletion of 446 bp in the PBP transcript.

Figure 5D:
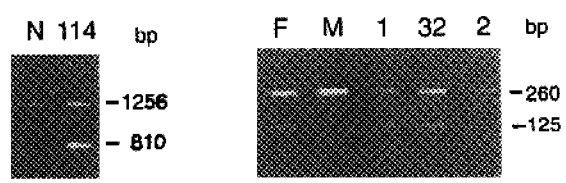

FIG. 5d: RT-PCR of RNA from: ADPKD patient OX32 (32) plus the probands, normal mother (M) and affected father (F) and sibs (1) and (2) using the C primer pair from 3A3 (SEQ. I.D. Nos. 11 and 12) (see Experimental Procedures). A novel fragment of 125 bp is detected in each of the affected individuals.

Figure 6:
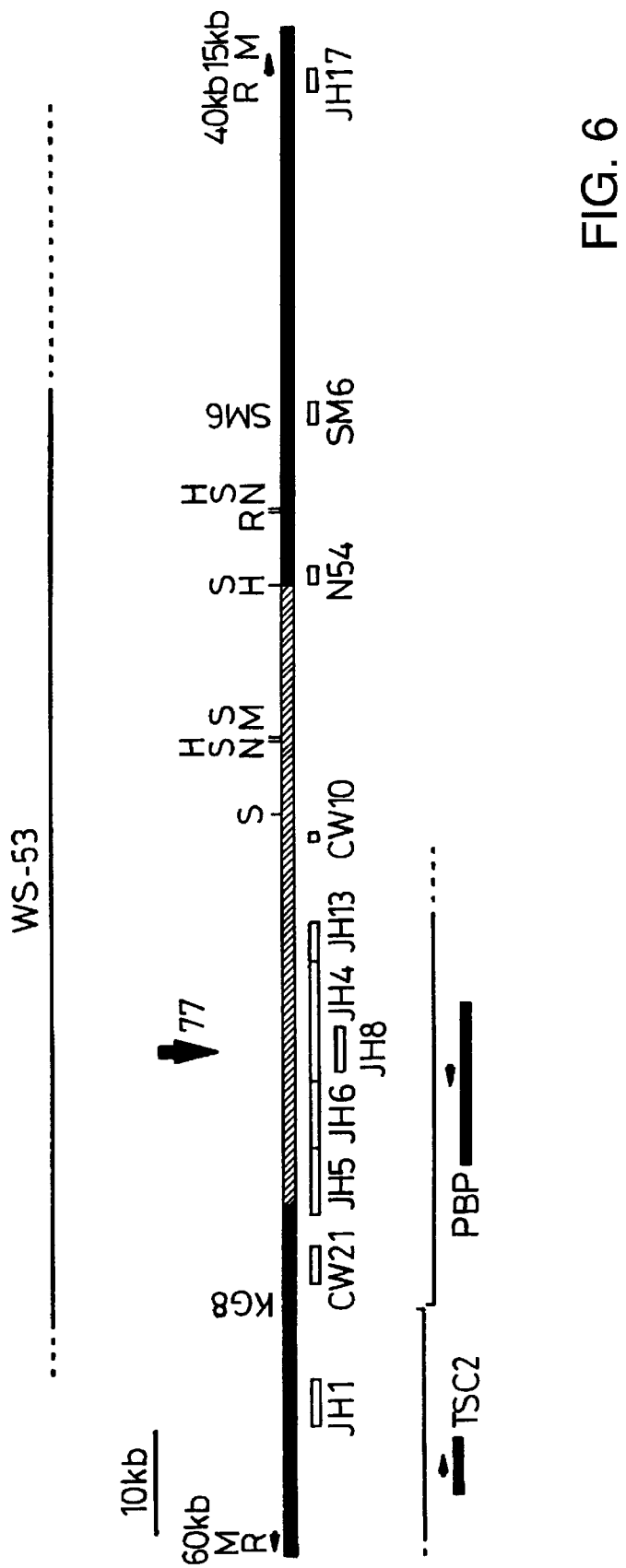

FIG. 6: Map of the region containing the TSC2 and PBP genes showing the area deleted in patient WS-53 and the position of the 77 translocation breakpoint. Localisation of the distal end of the WS-53 deletion was described (European Chromosome 16 Tuberous Sclerosis Consortium, 1993) and we have now localised the proximal end between SM6 and JH17. The size of the aberrant Mlu I fragment in WS-53, detected by JH1 and JH17, is 90kb and these probes lie on adjacent Mlu I fragments of 120kb and 70kb, respectively. Therefore the WS-53 deletion is about 100kb. Restriction sites for: Mlu I (M); Nru I (R); Not I (N); and partial maps for Sac II (S) and BssH II (H) are shown. DNA probes (open boxes) and the TSC2 and PBP transcripts (filled boxes) are indicated below the line with their known genomic extents (brackets). The locations of the microsatellites KG8 and SM6 are also indicated.

FIG. 7: The partial nucleotide sequence (cDNA) of the PKD1 transcript extending 5631bp to the 3' end of the gene (SEQ. I.D. NO. 1). The corresponding predicted protein (SEQ. I.D. NO. 2) is shown below the sequence and extends from the start of the nucleotide sequence. The GT-repeat, KG8, is in the 3' untranslated region between 5430–5448 bp. This sequence corresponds to GenBank Accession No. L33243. Also shown is probe 1A1H0.6 (SEQ. I.D. NO. 3].

FIG. 8: The sequence of the probe 1AIH.6 (SEQ. I.D. NO. 19].

FIG. 9: The sequence of the probe CW10 (SEQ. I.D. NO. 4) which is about 0.5kb. Also shown are the sequences of probes CW10F (SEQ. I.D. NO. 10) and CW10R (SEQ. I.D. NO. 21].

Figure 10:
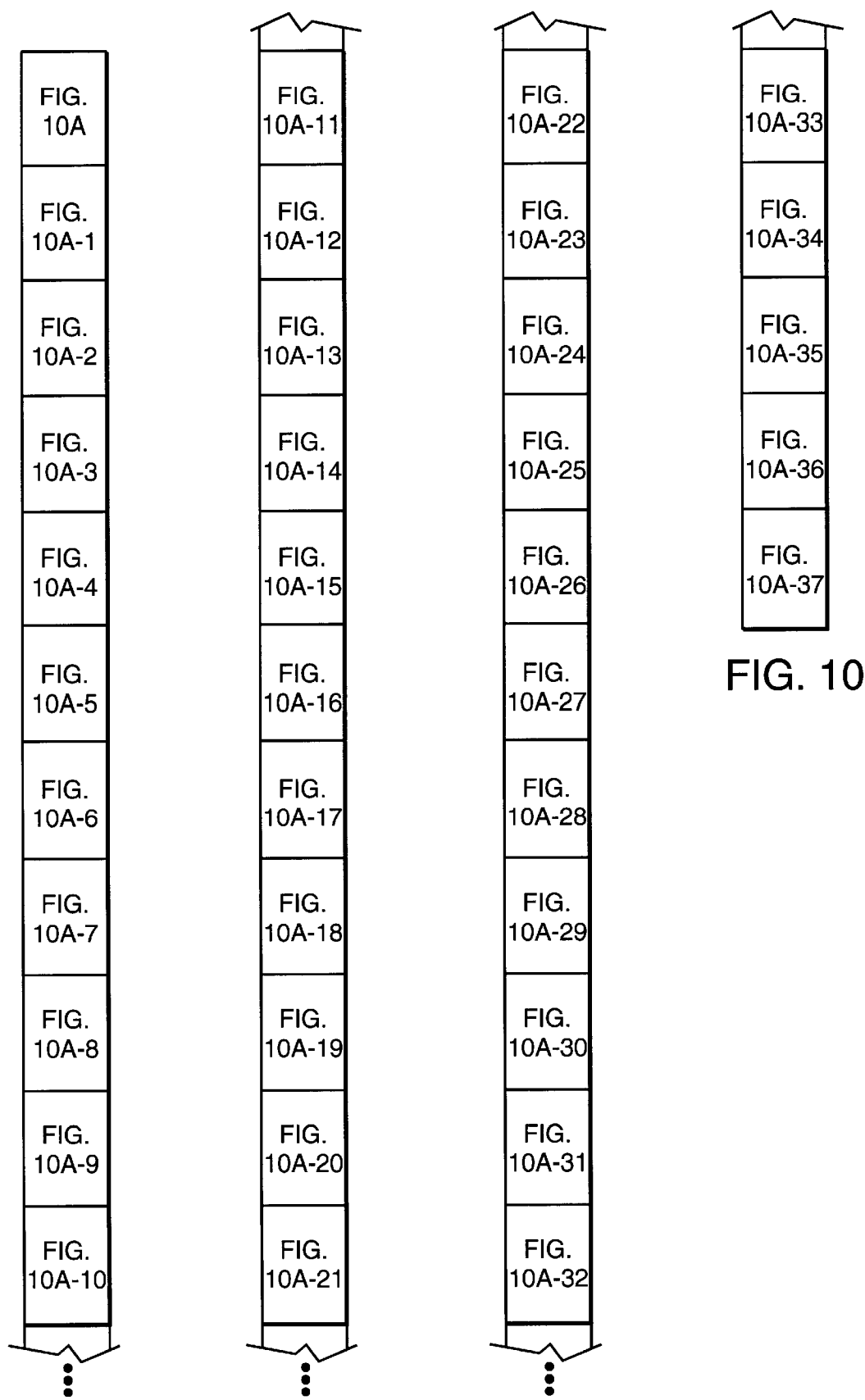

FIG. 10: Panels 10A-10A-36 the larger partial nucleotide sequence (SEQ. I.D. NO. 5) of the PKD1 transcript (cDNA) extending from bp 2 to 13807bp to the 3' end of the gene together with the corresponding predicted protein also shown in SEQ I.D. NO. 6. This larger partial sequence encompasses the (smaller) partial sequence of FIG. 7 from amino acid no. 2726 in SEQ. I.D. NO. 2 and relates to the entire PKD1 gene sequence (SEQ. I.D. NO. 7) apart from its extreme 5' end.

Figure 11:
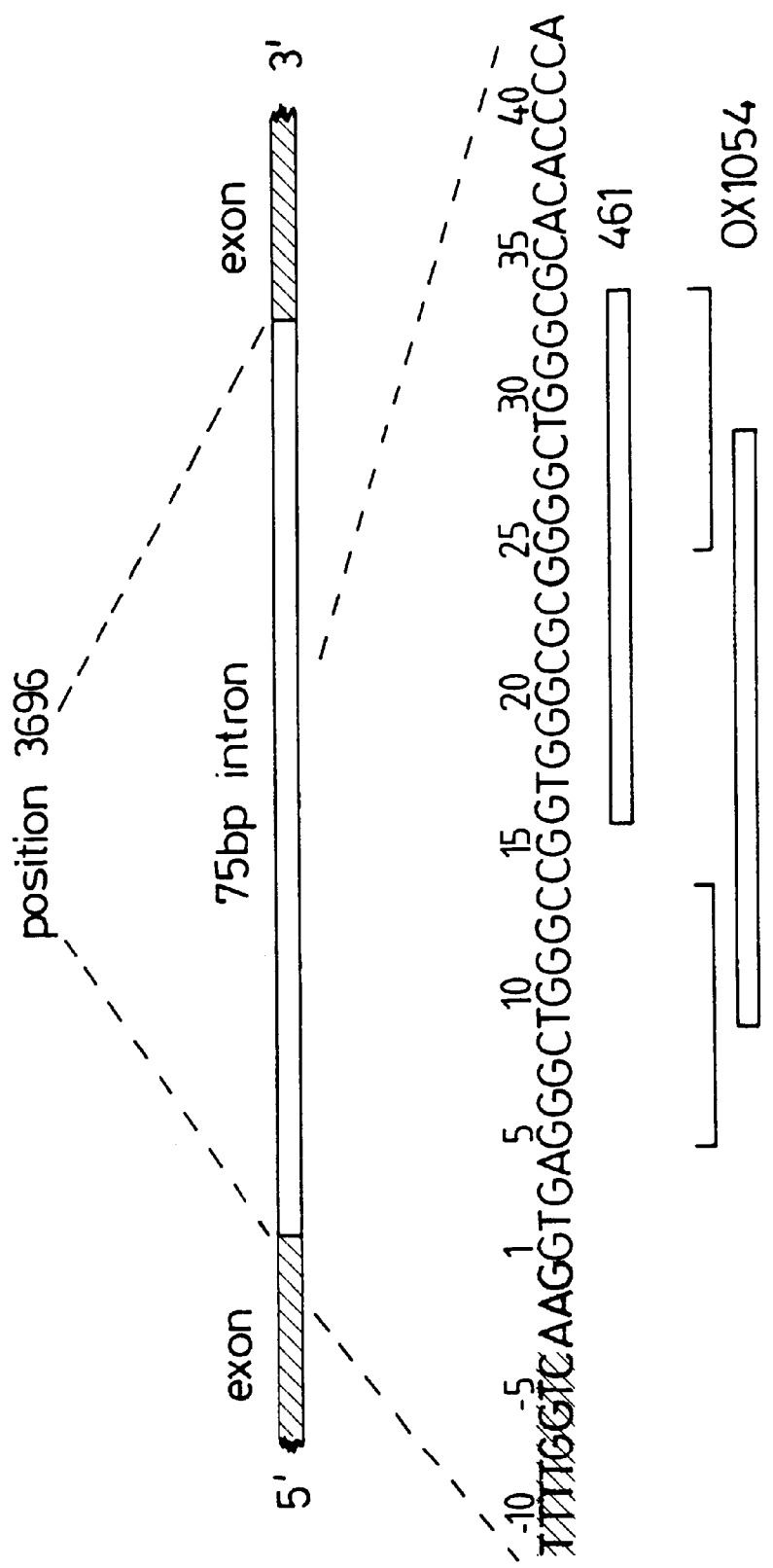

FIG. 11: A map of the 75bp intron amplified by the primer set 3A3C (SEQ. I.D. Nos. 11 and 12) insert (SEQ. I.D. NO. 18) at position 3696 of the 3' sequence (SEQ. I.D. NO. 1) showing the positions of genomic deletions found in PKD1 patients 461 and OX1054.

Figure 12:
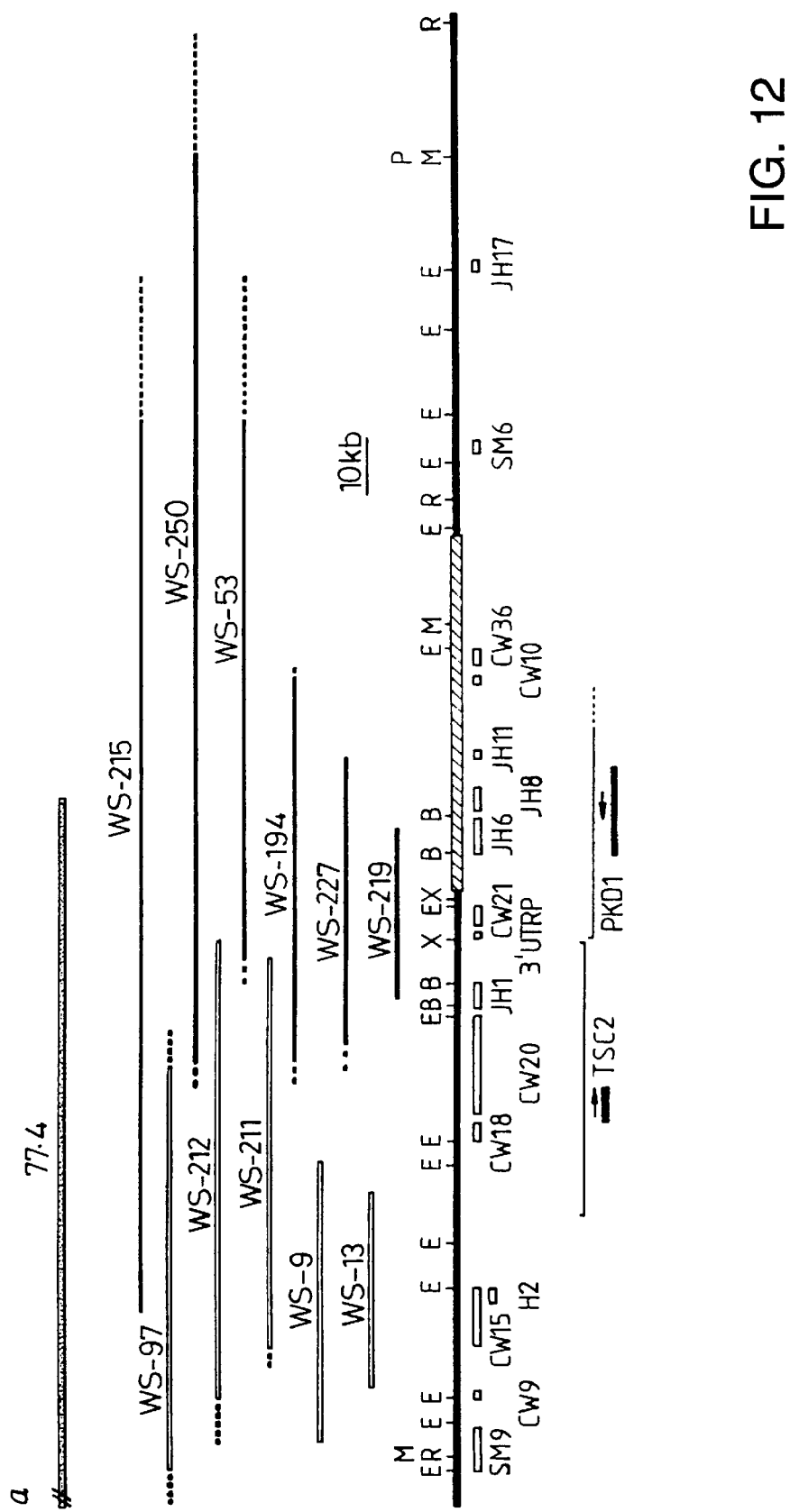

FIG. 12: A map of the region of chromosome 16 containing the TSC2 and PKD1 genes showing the areas affected in patients WS-215, WS-250, WS-212, WS-194, WS-227 and WS-219; also WS-53 (but cf. FIG. 6). Genomic sites for the enzymes Mlul (M), Clal (C), Pvul (P) and Nrul (R) are shown. Positions of single copy probes and cosmids used to screen for deletions are shown below the line which represents about 400kb of genomic DNA. The genomic distribution of the approximately 45kb TSC2 gene and known extent of the PKD1 gene are indicated above. The hatched area represents an about 50kb region which is duplicated more proximally on chromosome 16p.

Figure 13:
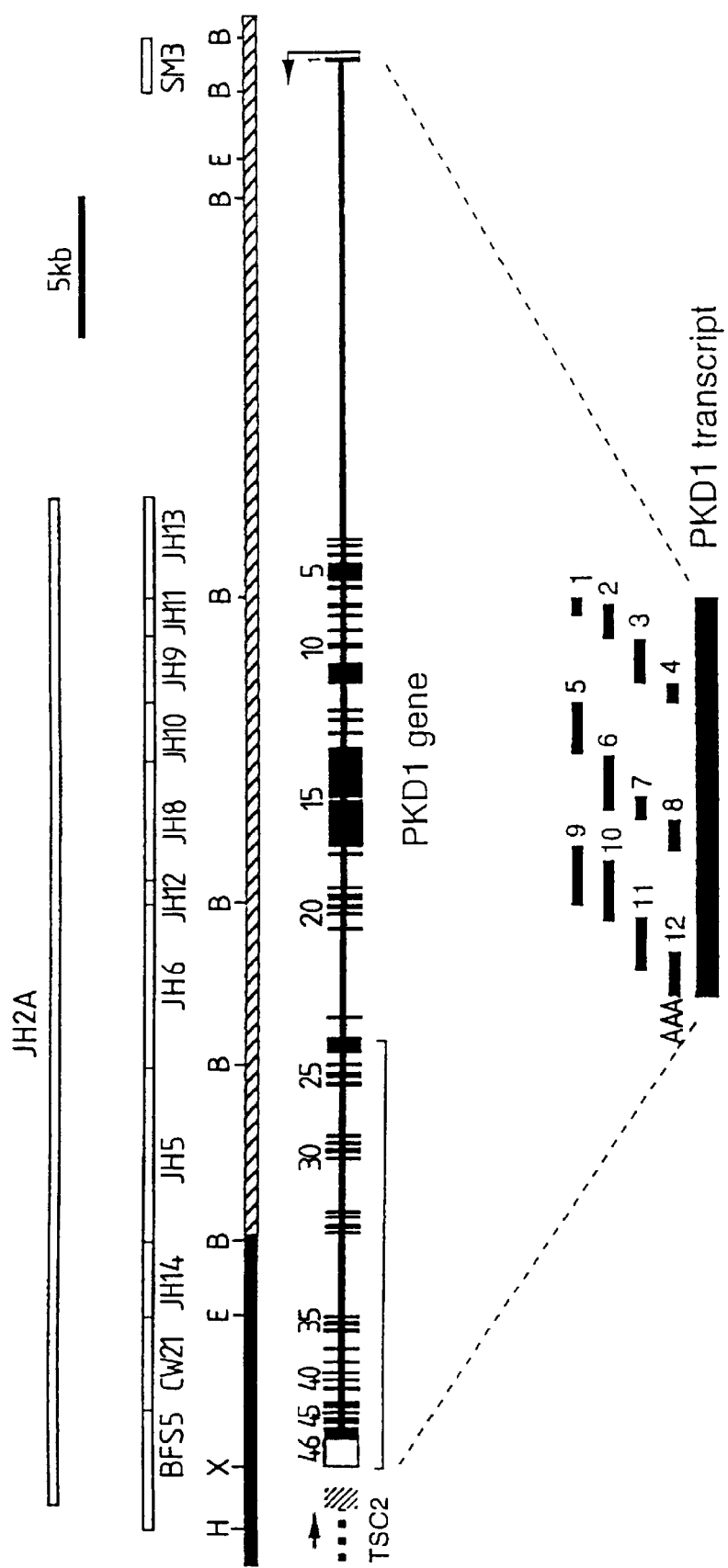

FIG. 13 is a genomic map of the PKD1 gene. (Top) A restriction map of the genomic area containing the PKD1 gene shows sites for Bam H1 (B), EcoRI (E) and partial maps for Xbal (X) and Hind III(H), and the duplicated area (hatched). The position of genomic clones and the cosmid JH2A are shown above the map (open boxes). The positions of the 46 exons of the PKD1 gene are shown below the map (solid boxes, translated areas; open boxes, untranslated regions; UTRs). Each 5th exon is numbered and the direction of transcription arrowed. The area sequenced in FIGS. 7 and 10 is bracketed and the approximate location of the 3' end of the TSC2 gene is shown on the left (dashed line and hatched box). (Bottom) The cDNA contig covering the PKD1 transcript. The cDNAs are: 1, rev1; 2, S13;3, S3/4; 4, S1/3;5, GAP e; 6, GAP d; 7, GAP g; 8, GAP a (see table 2 for details); 9, A1C; 10, AH3; 11, 3A3; 12, AH4.

Figure 14A:
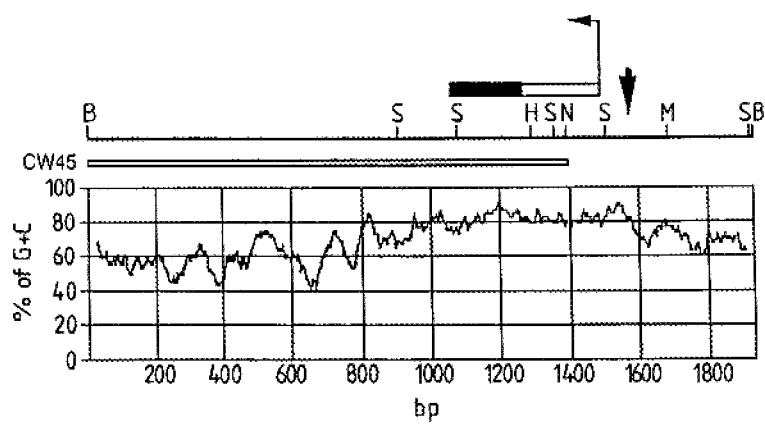

FIG. 14(a) (Top) Map of the genomic BamH I fragment, SM3 which contains the CpG island at the 5' end of the PKD1 gene, showing the probe CW45 (open box). Genomic restriction sites for the methylation sensitive enzymes: SacII (S), Notl (N), Mlul (M) and BssHII (H) are illustrated. The approximate position of the DNaseI hypersensitive site is also shown (large arrow), plus the location of the first exon including the proposed transcription start site (small arrow), the 5'UTR (open box) and the translated region (solid bar). (Bottom) The GC content across the area is plotted with a window size of 50 nt. A peak of GC content of over 80% is seen in the area of the transcriptional start site and the first exon. A corresponding lack of CpG suppression was also found with an average CpG/GC ratio of 0.84 between 800–1,800 bp.

Figure 14B:
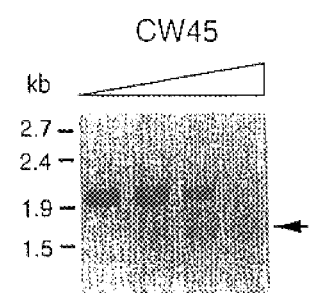

FIG. 14(b). Analysis of DNase I hypersensitivity at the PKD1 CpG island. DNA isolated from HeLa cells treated with an increasing amount of DNase I (left to right; first lane contains no DNase 1), digested with BamH I and hybridised with CW45. A fragment about 400 bp smaller than the restriction fragment is seen with increasing DNase 1, indicating a hypersensitive site as shown in (a). SM3 is within the duplicated area and so both the PKD1 and HG loci are assayed together. The degree of DNase1 digestion seen at the end of the assay indicates that cleavage occurs at the PKD1 and HG loci.

Figure 15:
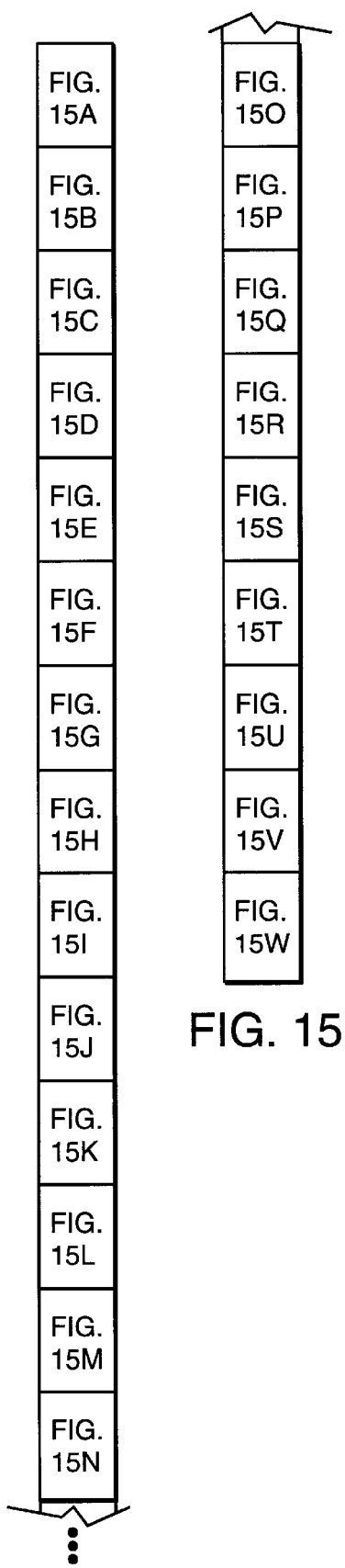

FIG. 15 provides the sequence of the PKD1 transcript (SEQ. I.D. NO. 7) and predicted protein (SEQ. I.D. NO. 8). The full sequence of 14,148 bp from the transcription start site to the poly A tail is shown. The probable signal sequence of 23 amino acids is shown after the first methionine (underlined) plus the cleavage site (arrow). The predicted transmembrane (TM) domains (double underlined and numbered) and N-linked glycosylation sites (asterisk) are indicated. The position of a possible hinge sequence is underlined and tyrosine kinase and protein kinase C phosphorylation sites marked with a box and circle, respectively.

FIG. 16(a). The leucine rich repeats (LRRs) found in the PKD1 protein (72–125aa) are compared with each other and to the LRR consensus (Rothberg, 1990; Kobe, 1994); a, aliphatic. A total of just over 2 full repeats are present in PKD1 but they have been arranged into 3 incomplete repeats to show their similarity to those found in slit (Rothberg, 1990). The black boxes show identity to the LRR consensus and shaded boxes other regions of similarity between the repeats which have also been noted in other LRRs (Kobe, 1994).

FIG. 16(b). The amino flanking region to the LRR in the PKD1 protein (33–71aa) is compared similar regions from a variety of other proteins. Black boxes shown identity with the consensus (adapted from [Rothberg, 1990 #1126]) and shaded boxes conserved amino acids. The different types of residue indicated in the consensus are: a, as above; p, polar or turn-like; h, hydrophobic. The listed proteins, with the species and Protein Identification Resource no. (PIR) shown in brackets, are: OMgp, oligodendrocyte myelin glycoprotein (Human, A34210); Slit (Drosophila; A36665); Chaoptin (Drosophila; A29943); GP-IB Beta, platelet glycoprotein 1βchain (Human; A31929); Pg1, proteoglycan-1 (mouse; 520811); Biglycan (Human; A40757); Trk (Human; A25184) and LH-CF, lutropinchoriogonadotrophin receptor (Rat; A41343).

FIG. 16(c). The carboxy flanking region of the LRR repeat from the PKD1 protein (126–180 aa) compared to similar regions in other proteins and a consensus accepted from [Rothberg, 1990 #1126). The shading and amino acid types are as above. The proteins not described above are: Toll (Drosophila; A29943) and GP IX, platelet glycoprotein IX (Human; A46606).

FIG. 17 is a sequence comparison of the C-type lectin domain. The PKD1 lectin domain (403–532aa) is compared to those of: BRA3, acorn barnacle lectin (JC1503); Kupffer cell carbohydrate-binding receptor (Rat; A28166), CSP, cartilage specific protoglycan (Bovine; A27752); Agp; asialoglycoprotein receptor (Human; 55283), E-Selectin (Mouse; B42755) and glycoprotein gp120 (Human; A46274). Black squares show identify with the consensus and shaded boxes conserved residues. Amino acid types are: Very highly conserved residues are shown in bold in the consensus which is adapted from Drickamer 1987, Drickamer 1988.

FIG. 18 is a sequence analysis of the Ig-like repeat. The 16 copies of the PKD1 Ig-like repeat (PKDI 273–356 aa; PKDII-XVI, 851–2145aa) are compared to each other and to: V.a. colAi, and C.p. colA collagenases of Vibrio alginolyticus (S19658) and Clostridium perfringens (D13791), respectively; Pmel17, melanocyte specific glycoprotein (Human; A41234), FLT4, Ig repeat IV of fms-like tyrosine kinase 4 (Human; X68203), CaVPT, Ig repeat I of target protein of the calcium vector protein (CAVP) (amphioxius; P05548). black boxes shown amino acids identical in more than 5 repeats and shaded boxes related residues. An Ig consensus determined from Harpaz et al. 1994 and Takagi et al. 1990 is shown in the symbols: a, aliphatic; h, hydrophobic; s, small and b, base with the predicted positions of the β-strands indicated below. The PKD repeat IV has an extra repetition of 20 aa in the centre of the repeat while all of the others are between 84–87 aa.

Figure 19B:
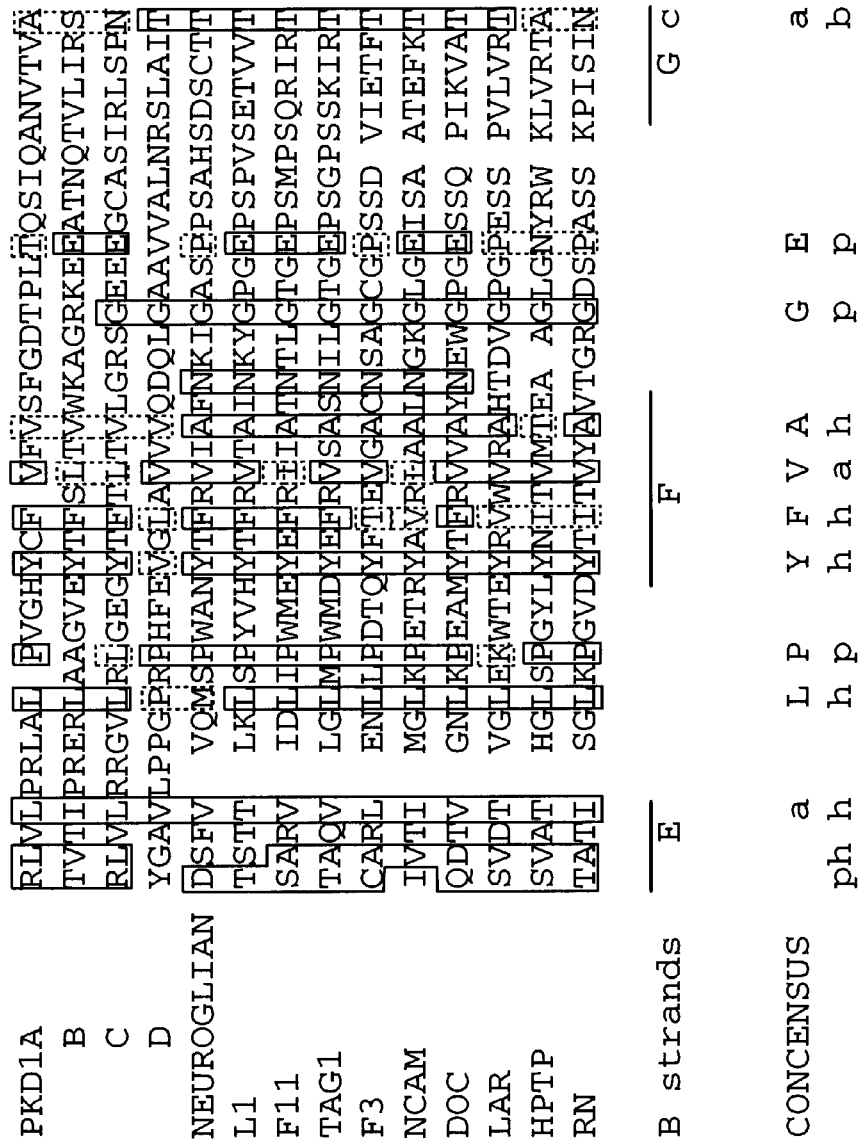

FIG. 19 reveals type III-related fibronectin domains. The four fibronectin-related domains from the PKD1 protein (2169–2573aa) are compared to similar domains in: Neuroglian (Drosophila; A32579); L1, neural recognition molecule L1 (X59847); F11, neural cell recognition molecule F11 (X14877); TAG 1, transiently expressed axonal surface glycoprotein-1 (Human; S28830); F3, Neuro-1 antigen (mouse; SO5944); NCAM, neural cell adhesion molecule (Rat; X06564); DCC, deleted in colorectal cancer (Human; X76132); LAR, Leukocyte-common antigen related molecule (Human; Y00815) HPTP, β protein tyrosine phosphate beta (Human; X54131) and FN, fibronectin (Human; X02761). The consensus sequence is compiled from Borh and Doolittle (1993), Kuma et al. (1993), Baron et al. (1992) and Borh and Doolittle (1992). Black boxes show identity to highly conserved residues and shaded boxes conserved changes or similarity in less highly conserved positions. The approximate positions of the β strands are illustrated. The fibronectin repeats in the PKD1 protein are linked by sequences of 27aa (A-B), 22aa (B-C) and 7aa (C-D) which are not shown.

Figure 20:
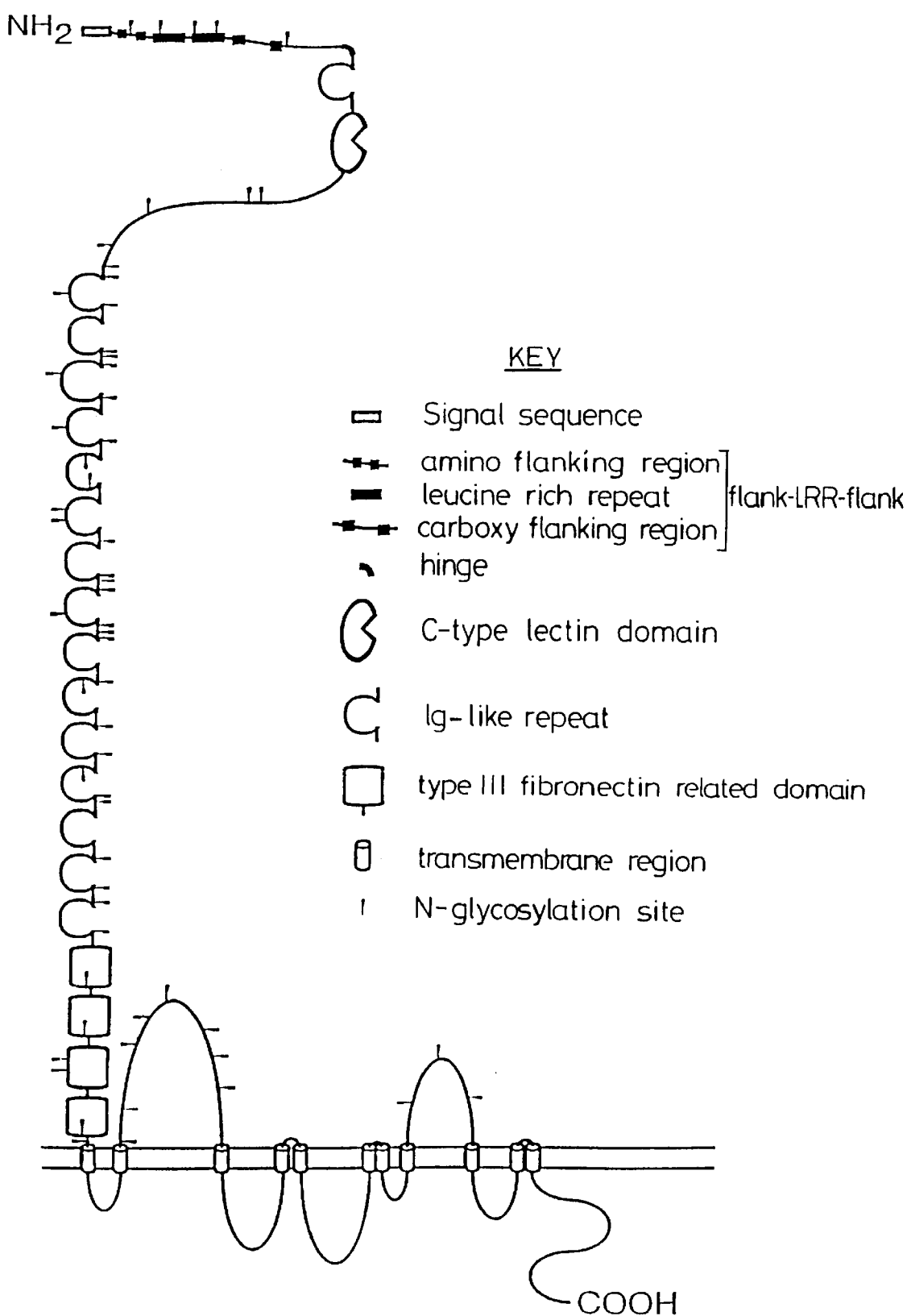

FIG. 20 presents a proposed model of the PKD1 protein, polycystin. The predicted structure of the PKD1 protein is shown.

DETAILED DESCRIPTION

All references mentioned herein are listed in full at the end of the description which are herein incorporated by reference in their entirety. Except where the context clearly indicates otherwise, references to the PBP gene, transcript, sequence, protein or the like can be read as referring to the PKD1 gene, transcript, sequence, protein or the like, respectively.

A Translocation Associated with ADPKD

A major pointer to the identity of the PKD1 gene was provided by a Portuguese pedigree (family 77) with both ADPKD and TSC (FIG. 1b). Cytogenetic analysis showed-that the mother, 77-2, has a balanced translocation, 46XX t(16;22) (p13.3;q11. 21) which was inherited by her daughter, 77-3. The son, 77-4, has the unbalanced karyotype, 45XY-16-22+der(16) (16qter→16p13.3: :22q11. 21→2qter) and consequently is monosomic for 16p13.3→16pter as well as for 22q11.21→pter. This individual has the clinical phenotype of TSC (see Experimental Procedures); the most likely explanation is that the TSC2 locus located within 16p13.3 is deleted in the unbalanced karyotype.

Further analysis revealed that the mother (77-2), and the daughter (77-3) with the balanced translocation, have the clinical features of ADPKD (see Experimental Procedures), while the parents of 77-2 were cytogenetically normal, with no clinical features of TSC and no renal cysts on ultrasound examination (aged 67 and 82 years). Although kidney cysts can be a feature of TSC, no other clinical signs of TSC were identified in 77-2 or 77-3, making it unlikely that the polycystic kidneys were due to TSC. We therefore investigated the possibility that the translocation disrupted the PKD1 locus in 16p13.3 and proceeded to identify and clone the region containing the breakpoint.

The 77 family was analyzed with polymorphic markers from 16p13.3. Individual 77-4 was hemizygous for MS205.2 and GGG1, but heterozygous for SM6 and more proximal markers, locating the translocation breakpoint between GGG1 and SM6 (see FIG. 1a). Fluorescence in situ hybridization (FISH) of a cosmid from the TSC2 region, CW9D (cosmid 1 in FIG. 1a), to metaphase spreads showed that it hybridized to the der(22) chromosome of 77-2; placing the breakpoint proximal to CW9D and indicating that 77-4 was hemizygous for this region consistent with his TSC phenotype. DNA from members of the 77 family was digested with Cla I, separated by PFGE and hybridized with SM6; revealing a breakpoint fragment of about 100 kb in individuals with the der(16) chromosome (FIG. 1c). The small size of this novel fragment enabled the breakpoint to be localized distal to SM6 in a region of just 60 kb (FIG. 1a). A cosmid contig covering this region was therefore constructed (see Experimental Procedures for details).

The Translocation Breakpoint Lies within a Region Duplicated Elsewhere on Chromosome 16p (16p13.1)

It is noted hereabove that the region between CW21 and N54 (FIG. 1a) was duplicated at a more proximal site on the short arm of chromosome 16 (Germino, et al., 1992; European Chromosome 16 Tuberous Sclerosis Consortium, 1993). FIG. 2 shows that a cosmid, CW10III, from the duplicated region hybridized to two points on 16p; the distal, PKD1 region and a proximal site positioned in 16p13.1 The structure of the duplicated area is complex with each fragment present once in 16p13.3 re-iterated two–four times in 16p13.1 (see FIG. 2). Cosmids spanning the duplicated area in 16p13.3 were subcloned (see FIG. 3a and Experimental Procedures for details) and a restriction map was generated. A genomic map of the PKD1 region was constructed using a radiation hybrid, Hy145.19 which contains the distal portion of 16p but not the duplicate site in 16p13.1.

To localize the 77 translocation breakpoint, subclones from the target region were hybridized to 77-2 DNA, digested with Cla I and separated by PFGE. Once probes mapping across the breakpoint were identified they were hybridized to conventional Southern blots of 77 family DNA. FIG. 3b shows that novel BamH I fragments were detected from the centromeric and telomeric side of the breakpoint, which was localized to the distal part of the probe 8S1 (FIG. 3a). Hence, the balanced translocation was not associated with a substantial deletion, and the breakpoint was located more than 20 kb proximal to the TSC2 locus (FIG. 3a). These results supported the hypothesis that polycystic kidney disease in individuals with the balanced translocation (77-2 and 77-3) was not due to disruption of the TSC2 gene, but indicated that a separate gene mapping just proximal to TSC2, was likely to be the PKD1 gene.

The Polycystic Breakpoint (PBP) Gene is Disrupted by the Translocation

Localization of the 77 breakpoint identified a precise region in which to look for a candidate or the PKD1 gene. During the search for the TSC2 gene we identified other transcripts not associated with TSC including a large transcript (about 14 kb) partially represented in the cDNAs 3A3 and AH4 which mapped to the genomic fragments CW23 and CW21 (FIG. 3a). The orientation of the gene encoding this transcript had been determined by the identification of a polyA tract in the cDNA, AH4: the 3' end of this gene lies very close to the TSC gene, in a tail to tail orientation (European Chromosome 16 Tuberous Sclerosis Consortium, 1993). To determine whether this gene crossed the translocation breakpoint genomic probes from within the duplicated area and flanking the breakpoint were hybridized to Northern blots. Probes from both sides of the breakpoint, between JH5 and JH13 identified the 14 kb transcript (FIG. 3a and see below for details) Therefore, this gene, called 3A3, but not designated the PBP gene extended over the 77 breakpoint and consequently was a candidate for the PKD1 gene. A walk was initiated to increase the extent of the PBP cDNA contig and several new cDNAs were identified using probes from the single copy (non-duplicated) region (see Experimental Procedures for details). A cDNA contig was constructed which extended about 5.7 kb, including about 2kb into the area that is duplicated ((FIG. 3a).

Expression of the PBP Gene

Initial studies of the expression pattern of the PBP gene were undertaken with cDNAs that map entirely within the single copy region (e.g. AH4 and 3A3). FIG. 4a shows that the about 14 kb transcript was identified by 3A3 in various tissue-specific cell lines. From this and other Northern blots we concluded that the PBP gene was expressed in all of the cell lines tested, although often at a low level. The two cell lines which showed the highest level of expression were fibroblasts and a cell line derived from an astrocytoma, G-CCM. Significant levels of expression were also obtained in cell lines derived from kidney (G401) and liver (Hep3B). Measuring the expression of the PBP gene in tissue samples by Northern blotting proved difficult because such a large transcript is susceptible to minor RNA degradation. However, initial results with an RNAse protection assay, using a region of the gene located in the single copy area (see Experimental Procedures), showed a moderate level of expression of the PBP gene in tissue obtained from normal and polycystic kidney (data not shown). The widespread expression of the PBP is consistent with the systemic nature of ADPKD.

Identification of Transcripts that are Partially Homologous to the PBP Transcript New cDNAs were identified with the genomic fragments, JH4 and JH8, that map to the duplicated region (FIG. 3a and see Experimental Procedures). However, when these cDNAs were hybridized to Northern blots a more complex pattern than that seen with 3A3 was observed. As well as the ~14 kb PBP transcript, three other, partially homologous transcripts were identified designated homologous gene-A (HG-A; ~21 kb), HG-B (~17 kb) and HG-C (8.5 kb) FIG. 4b). There were two possible explanations for these results, either the HG transcripts were alternatively spliced forms of the PBP gene, or the HG transcripts were encoded by gene located in 16p13.1 To determine the genomic location of the HG loci a fragment from the 3' end of one HG cDNA (HG-4/1.1) was isolated. HG-4/1.1 hybridized to all three HG transcripts, but not to the PBP transcript and on a hybrid panel it mapped to 16p13.1 (not the PKD1 area). These results show that all the HG transcripts are related to each other outside the region of homology with the PBP transcript and that the HG loci map to the proximal site (16p13.1).

An Abnormal Transcript Associated with the 77 Translocation

As the PBP gene was transcribed across the region disrupted by the 77 translocation breakpoint, in a proximal to distal direction on the chromosome (see FIG. 3a) it was possible that a novel transcript originating from the PBP promotor would be found in this family. FIG. 4c shows that using a probe to the PBP transcript that mapped mainly proximal to the breakpoint, a novel transcript of approximately 9 kb (PBP-77) derived from the der(16) product of the translocation was detected. Interestingly, the PBP-77 transcript appears to be expressed at a higher level than the normal PBP product. These results confirmed that the 77 translocation disrupts the PBP gene and supports the hypothesis that this is the PKD1 gene.

Mutations of the PBP Gene in Other ADPKD Patients

To prove that the PBP gene is the defective gene at the PKD1 locus, we analyzed this region for mutations in patients with typical ADPKD. The 3' end of the PBP gene was most accessible to study as it maps outside the duplicated area. To screen this region BamH I digests of DNA from 282 apparently unrelated ADPKD patients were hybridized with the probe 1A1H.6 (SEQ. I.D. NO. 3), (see (FIG. 3a). In addition, a large EcoR I fragment (41 kb)

which contains a significant proportion of the PBP gene was assayed by field inversion gel electrophoresis (FIGE) in 167 ADPKD patients, using the probe CW10 (SEQ. I.D. NO. 4). Two genomic rearrangements were identified in ADPKD patients by these procedures; each identified by both methods.

The first rearrangement was identified in patient OX875 (see Experimental Procedures for clinical details) who was shown to have a 5.5 kb genomic deletion without the 3' end of the PBP gene, producing a smaller transcript (PBP-875) (see FIGS. 5a, b and 3a for details). This genomic deletion results in a ~3 kb internal deletion of the transcript with the ~500 bp adjacent to the polyA tail intact. In this family linkage of ADPKD to chromosome 16 could not be proven because although OX875 has a positive family history of ADPKD there were no living, affected relatives. However, paraffin-embedded tissue from her affected father (now deceased) was available. We demonstrated that this individual has the same rearrangement as OX875 by PCR amplification of a 220bp fragment spanning the deletion (data not shown). This result and analysis of two unaffected sibs of OX875, that did not have the deletion, showed that this mutation was transmitted with ADPKD.

The second rearrangement detected by hybridization was a 2 kb genomic deletion within the PBP gene, in ADPKD patient OX114 (see Experimental Procedures for clinical details and FIGS. 5c and 3a). No abnormal PBP transcript was identified by Northern blot analysis, but using primers flanking the deletion (see Experimental Procedures) a shortened product was detected by RT-PCR (FIG. 5c). This was cloned and sequenced and shown to have a frame-shift deletion of 446 bp (between base pair 1746 and 2192 of the sequence shown in FIG. 7 (SEQ. I.D. NO. 1)). OX114 is the only member of the family with ADPKD (she has no children) and ultrasound analysis of her parents at age 78 (father) and 73 years old (mother) showed no evidence of renal cysts. Somatic cell hybrids were produced from OX114 and the deleted chromosome was found to be of paternal origin by haplotype analysis. The father of OX114 (OX984) with seven microsatellite markers from the PKD1 region, as OX114. Renal ultrasound revealed no cysts in OX984 at age 53 and no deletion was detected by DNA analysis (FIG. 5c). Hence, the deletion in OX114 is a de novo event associated with the development of ADPKD. Although it is not possible to show that the ADPKD is chromosome 16-linked, the location of the PBP gene indicated that this is a de novo PKD1 mutation.

To identify more PKD1 associated mutations, single copy regions of the PBP gene were analyzed by T-PCR using RNA isolated from lymphoblastoid cell lines established from ADPKD patients. cDNA from 48 unrelated patients was amplified with the primer pair 3A3 C (SEQ. I.D. Nos: 11 and 12) (see Experimental Procedures) and the product of 260 bp was analyzed on an agarose gel. In one patient, OX32, an additional smaller product (125bp) was identified, consistent with a deletion or splicing mutation. OX32 comes from a large family in which the disease can be traced through three generations. Analysis of RNA from two affected sibs of OX32 and his parents showed that the abnormal transcript segregates with PKD1 (FIG. 5d).

Amplification of normal genomic DNA with the 3A3 C (SEQ. I.D. 1) primers generates a product of 418 bp; sequencing showed that this region contains two small introns (5', 75 bp and 3', 83 bp) flanking a 135 bp exon. The product amplified from OX32 genomic DNA was normal in size, excluding a genomic deletion. However, heteroduplex analysis of that DNA revealed larger heteroduplex bands, consistent with a mutation within that genomic interval. The abnormal OX32, RT-PCR product was cloned and sequenced: this demonstrated that, although present in genomic DNA, the 135 bp exon was missing from the abnormal transcript. SEQuencing of OX32 genomic DNA demonstrated a G→C transition at +1 of the splice donor site following the 135 bp exon. This mutation was confirmed in all available affected family members by digesting amplified genomic DNA with the enzyme Bst NI: a site is destroyed by the base substitution. The splicing defect results in an in-frame deletion of 135 bp from the PBP transcript (3696 bp to 3831 bp of the sequence shown in FIG. 7 (SEQ. I.D. NO. 1)). Together, the three intragenic mutations confirm that the PBP gene is the defective gene at the PKD1 locus.

Deletions that Disrupt the TSC2 and the PKD1 Gene

The deletion called WS-53 disrupts both the TSC2 gene and the PKD1 gene (European Chromosome 16 Tuberous Sclerosis Consortium, 1993), although the full proximal extent of the deletion was not determined. Further study has shown that the deletion extends ~100 kb (see FIG. 6 for details) and deletes most if not all of the PKD1 gene. This patient has TSC but also has unusually severe polycystic disease of the kidneys. Other patients with a similar phenotype have also been under investigation. Deletions involving both TSC2 and PKD1 were identified and characterized in six patients in whom TSC was associated with infantile polycystic kidney disease. As well as the deletion in WS-53, those in WS-215 and WS-250 also extended proximally well beyond the known distribution of PKD1 and probably delete the entire gene. The deletion in WS-194 extended over the known extent of PKD1, but not much further proximally, while the proximal breakpoints in WS-219 and WS-227 lay within PKD1 itself. Northern analysis of case WS-227 lay within PKD1 itself. Northern analysis of case WS-219 with probe JH8, which lies outside the deletion, showed a reduced level of the PKD1 transcript but no evidence of an abnormally sized transcript (data not shown). Analysis of samples from the clinically unaffected parents of patients WS-53, WS-215, WS-219, WS-227 and WS-250 showed the deletions in these patients to be de novo. The father of WS-194 was unavailable for study.

In a further case (WS-212), renal ultrasound showed no cysts at four years of age but a deletion was identified which removed the entire TSC2 gene and deleted an XbaI site which is located 42bp 5' to the polyadenylation signal of PKD1. To determine the precise position of the proximal breakpoint in PKD1, a 587bp probe from the 3' untranslated region 3'UTR was hybridized to XbaI digested DNA. A 15kb XbaI breakpoint fragment was detected with an approximately equal intensity to the normal fragment of 6kb, indicating that most of the PKDI3'UTR was preserved on the mutant chromosome. Evidence that a PKD1 transcript is produced from the deleted chromosome in WS-212 was obtained by 3' rapid identification of cDNA ends (RACE) with a novel, smaller product generated from WS-212 cDNA. Characterization of this product showed that polyadenylation occurs 546bp 5' to the normal position, within the 3'UTR of PKD1 (231bp 3' to the stop codon at 5073bp of the described PKD1 sequence[14] (SEQ. I.D. NO. 1)). A transcript with an intact open reading frame is thus produced from the deleted WS-212 chromosome. It is likely that a functional PKD1 protein in produced from this transcript, explaining the lack of cystic disease in this patient. The sequence preceding the novel site of polyA addition is: AGTCAGT<u>AATTTA</u>TATGGTGTGTTAAAATGTG(A)n (SEQ. I.D. NO. 22). Although not conforming precisely to the consensus of AATAAA, it is likely that part of this AT rich region acts as an alternative polyadenylation signal if, as in this case, the normal signal is deleted (a possible sequence is underlined).

The WS-212 deletion is 75kb between SM9-CW9 distally and the PKD1 3'UTR proximally. The WS-215 deletion is 160kb between CW15 and SM6-JH17. WS-194 has 65kb deleted between CW20 and CW10- CW36. WS-227 has a 50kb deletion between CW20 and JH11 and WS-219 has a 27kb deletion between JH1 and JH6. The distal end of the WS-250 deletion is in CW20 but the precise location of the proximal end is not known. However, the same breakpoint fragment of 320kb is seen with Pvul-digested DNA using probes on adjacent Pvul fragments, CE18 (which normally detects a 245kb fragment) and Blu24 (235kb ). Hence this deletion can be estimated ~160kb. b. PFGE analysis of the deletion in WS-219. Mlul digested DNA from a normal control (N) and WS-219 probed with the clones H2, JH1, CW21 and CW10 (SEQ. I.D. NO. 4) which detect an ~130kb fragment in normal individuals. CW10(SEQ. I.D. NO. 4) also detects a much smaller fragment from the duplicated region situated more proximally on 16p. A novel fragment of ~100kb is seen in WS-219 with probes H2 and CW10 (SEQ. I.D. NO. 4) which flank the deletion in this patient. JH1 is partially deleted but detects the novel band weakly. The aberrant fragment is not detected by CW-21, which is deleted on the mutant chromosome. BamHl digested DNA of normal control (N) and WS-219 separated by conventional gel electrophoresis and hybridized to probes JH1 and JH6 which flank the deletion. The same breakpoint fragment of ~3kb is seen with both probes, consistent with a deletion of ~27kb ending within the BamHl fragments seen by these probes.

Two Further Deletions

In addition we have characterized two further mutations of this gene which were identified in typical PKD1 families. In both cases the mutation is a deletion in the 75bp intron amplified by the primer pair 3A3C (European Polycystic Kidney Disease Consortium, 1994). The deletions are of 18bp and 20bp, respectively, in the patients 461 and OX1054. Although these deletions do not disrupt the highly conserved sequences flanking the exon/intron boundaries, they do result in aberrant splicing of the transcript. In both cases, two abnormal mRNAs are produced, one larger and one smaller than normal. SEQuencing of these cDNAs showed that the larger transcript includes the deleted intron, and so has an in-frame insertion of 57bp in 461, while OX1054 has a frameshift insertion of 55bp. The smaller transcript is due to activation of a cryptic splice site in the exon preceding the deleted intron and results in an in-frame deletion of 66bp in both patients. The demonstration of two additional mutations of this gene in PKD1 patients further confirms that this is the PKD1 gene.

Partial Characterization of the PKD1 Gene

To characterize the PKD1 gene further, evolutionary conservation was analyzed by 'zoo blotting'. Using probes from the single copy, 3' region (3A3) and from the duplicated area (JH4, JH8) the PKD1 gene was conserved in other mammalian species, including horse, dog, pig and rodents (data not shown). No evidence of related sequences were seen in chicken, frog or drosophila by hybridization at normal stringency. The degree of conservation was similar when probes from the single copy of the duplicated region were employed.

Although the full genomic extent of the PKD1 gene was not yet known, results obtained by hybridization to Northern blots showed that it extended from at least as far as JH13. Several CpG islands were localized 5' of the known extent of the PKD1 gene (FIG. 6), although there was no direct evidence that any of these are associated with this gene.

The cDNA contig extending 5631bp to the 3' end of the PKD1 transcript was sequenced; where possible more than one cDNA was analyzed and in all regions both strands were sequenced (FIG. 7 (SEQ. I.D. NO. 1)). We estimated that this accounts for ~40% of the PKD1 transcript. An open reading frame was detected which runs from the 5' end of the region sequenced and spans 4842 bp, leaving a 3' untranslated region of 789 bp which contains the previously described microsatellite, KG8 (Peral, et al., 1994; Snarey, et al., 1994). A polyadenylation signal is present at nucleotides 5598–5603 and a polyA tail was detected in two independent cDNAs (AH4 and AH6) at position, 5620. Comparison with the cDNAs HG-4 and 11BHS21, which are encoded by genes in the duplicate, 16p13.1 region, show that 1866bp at the 5' end of the partial PKD1 sequence shown in FIG. 7 (SEQ. I.D. NO. 1) lies within the duplicated area. The predicted amino acid sequence from the available open reading frame extends 1614 residues, and is shown in FIG. 7 (SEQ I.D. NO. 27). A search of the swissprot and NBRF data bases with the available protein sequence, using the Blast program (Altschul, et al., 1990) identified only short regions of similarity (notably, between amino-acids 690–770 and 1390–1530) to a diverse group of proteins; no highly significant areas of homology were recognized. The importance of the short regions of similarity is unclear as the search for protein motifs with the ProSite Program did not identify any recognized functional protein domains within the PKD1 gene.

The test of identifying and characterizing the PKD1 gene has been more difficult than for other disorders because more than three quarters of the gene is embedded in a region of DNA that is duplicated elsewhere on chromosome 16. This segment of 40–50 kb of DNA, present as a single copy in the PKD1 area (16p13.1), is re-iterated as several divergent copies in the more proximal region, 16p13.1 This proximal site contains three gene loci (HG-A, -B and -C) that each produce polyadenylated mRNAs and share substantial homology to the PKD1 gene; it is not known whether these partially homologous transcripts are translated into functional proteins.

Although gene amplification is known as a major mechanism for creating protein diversity during evolution, the discovery of a human disease locus embedded within an area duplicated relatively recently is a new observation. In this case because of the recent nature of the reiteration the whole duplicated genomic region retains a high level of homology, not just the exons. The sequence of events leading to the duplication and which sequence represents the original gene locus are not yet clear. However, early evidence of homology of the 3' ends of the three HG transcripts which are different from the 3' end of the PKD1 gene indicated that the loci in 16p13.1 have probably arisen by further reiteration of sequences at this site, after it separated from the distal locus.

To try to overcome the duplication problem we employed an exon linking approach using RNA isolated from a radiation hybrid, HY145.19, that contains just the PKD1 part of chromosome 16, and not the duplicate site in 16p13.1. Hence, this hybrid produces transcripts from the PKD1 gene but not from the homologous genes (HG-A, HG-B and HG-C). We have also sequenced much of the genomic region containing the PKD1 gene, from the cosmid JH2A, and have sequenced a number of cDNAs from the HG locus. To determine the likely position of PKD1 exons in the genomic DNA we compared HG cDNAs, (HG-4 and HG-7) to the genomic sequence. We then designed primers with sequences corresponding to the genomic DNA, to regions identified by the HG exons and employing DNA generated from the hybrid HY145.19, we amplified sections of the PKD1 transcript. The polymerase Pfu was used to minimise incorporation errors. These amplified fragments were then cloned and sequenced. The PKD1 cDNA contig whose sequence is shown in FIG. 10 is made up of (3'–5') the original 5.7 kb of sequence shown in FIG. 7, and the cDNAs: gap α 22 (890 bp ), gap gamma (872 bp ), a section of genomic DNA from the clone JH8 (2, 724 bp ) which corresponds to a large exon, S1-S3 (733 bp ), S3-S4 (1,589 bp ) and S4-S13 (1,372 bp ). Together these make a cDNA of 13,807nt. When these cDNAs from the PKD1 contig were sequenced an open reading frame was found to run from the start of the contig to the stop codon, a region of 13,018 bp (SEQ. I.D. NO. 5). The predicted protein encoded by the PKD1 transcript is also shown in FIG. 10 (SEQ. NO. 6) and has 4,339 amino acid residues.

Cloning a Full Length PKD1 cDNA cDNAs known to originate from the PKD1 or HG transcripts show on average a sequence divergence of less than 3%. Consequently, although many cDNAs were identified by hybridisation of various PKD1 genomic probes to cDNA libraries, it proved difficult to differentiate genuine PKD1 clones from those of the HG transcripts. For this reason a novel strategy was employed to clone the PKD1 transcript.

To obtain a template of genomic sequence of the PKD1 gene, clones which contain the transcribed region, JH6 and JH8-JH13, were sequentially truncated and sequenced. These clones were isolated from the cosmid JH2A, which extends into the single copy area containing the 3' portion of the PKD1 gene (FIG. 13) and hence represents the PKD1 and not the HG loci. As a result of this analysis a contig of about 18 kb of genomic sequence was generated, which was ultimately found to encode >95% of the unsequenced portion of the PKD1 transcript.

A number of HG cDNA clones identified by the DNA probes JH8 or JH13 (including HG-4, HG-7C and 13A1) were sequenced. Clones identified by JH8 were chosen because this genomic area is duplicated fewer times than the surrounding DNA, with only the HG-A and HG-B transcripts (not HG-C) homologous to this region. The comparison of these cDNA and genomic sequences showed a characteristic intron/exon pattern and we concluded that the exons highlighted in the genomic sequence were likely to be exons of the PKD1 gene. To prove this, pairs of primers matching the sequence of the putative PKD1 exons and spaced 0.7–2kb apart in the proposed transcript, were synthesised. Employing RNA from a radiation hybrid, HY145.19, that contains the PKD1 but not the HG loci, PKD1 specific cDNAs were amplified by RT-PCR and cloned (see Experimental Procedures for details). In this way, a number of overlapping cDNAs spanning the PKD1 transcript, for the cDNAs at the 3' end to those homologous to JH13 were cloned (FIG. 13).

Analysis of a further cDNA, HG-6 showed that a short region (-100bp ) of HG-6 lay 5' to the sequenced genomic region and this was located by hybridisation to the genomic clone SM3 (FIG. 13); SM3 was subsequently sequenced. The position of the cDNA in SM3 was identified and the possible 5' extent of this exon was determined in the genomic sequence; and in-frame stop codon was identified hear the 3' end of the exon. This exon lay at a CpG island (described hereinafter) suggesting, along with the presence of the stop codon, that this may be the first exon of the PKD1 gene. to determine the likely transcriptional start site the method of primer extension from three different oligos within the first exon was employed (see Experimental Procedures). In all cases, a transcriptional start was identified at the same G nucleotide and showed the first exon to be 426 bp. The structure of the PKD1 transcript was confirmed by a final exon link, rev1 which starts 3 bp3' to the proposed transcriptional start (see FIG. 13 and Experimental Procedures for details).

The Intron/exon Structure of the PKD1 Gene

SEQuencing the cDNA contig revealed a total sequence of 14, 148bp which extends over approximately 52bp of genomic sequence from SM3 to BFS5 (FIG. 13). We were able to determine the intron/exon structure of much of the gene by direct comparison between the cDNA and genomic sequence. In the 3' region of the gene (JH5-BFS5), a partial genomic sequence was obtained at intron/exon borders by sequencing the corresponding genomic clone from exonic primer.

The PKD1 CpG Island

The 5' end of the gene lies at CpG island SM3. SM3 is located entirely within the duplicated region, but this clone was isolated from the cosmid SMll which extends through the duplicated area into the proximal flanking single copy region and therefore is known to originate from this area. FIG. 14 shows a map of the PKD1 CpG island including genomic sites for several methylation sensitive enzymes, the location of the first exon and the GC content across the island. Evidence that the enzyme sites in the PKD1 region (and not just the HG area) digest, was obtained by pulsed field gel electrophoresis with the enzymes Mlul, Notl and BssHll using probes outside the duplicated area. Digestion of the Sacll sites and confirmation of the Notl site was made with a panel of somatic cell hybrids which either contain just the HG (P-MWH2A) or just the PKD1 locus (Hy145.19). These results showed that the Sacll and Notl sites digest in both sets of hybrids (data not shown), indicating that this region is a CpG island in the HG as well as the PKD1 area. Further proof that this is the likely position of a functional promoter was obtained analysis for DNAase 1 hypersensitivity. A DNAase hypersensitive site in the region 5' to the transcription start site in SM3 was detected (FIGS. 14a and b).

Analysis of the PKD1 Transcript

Analysis of the sequence shows an open reading frame running from the start of the sequence to position 13,117 bp (FIG. 15 (SEQ. I.D. NO. 7)). Detailed sequencing of the genomic region containing the 3' portion of the gene revealed two extra Cs at positions 13,081–2 (FIG. 15 (SEQ. I.D. NO. 7). An in-frame start codon which is consistent with the Kozak consensus was detected at position 212 bp ; just 3' to the stop codon in the 5'UTR. Analysis for a signal sequence cleavage site using the von Hinge (von Hinge 1986) algorithm showed a high probability of a hydrophobic signal sequence with cleavage at amino acid 23 (see FIG. 15) (SEQ. I.D. NO. 8). The total length of the predicted protein is 4302 aa with a calculated molecular mass after excision of the signal peptide of 460 kD and an estimated isoelectric point of 6.26. However, this may be an underestimate of the total mass of the protein as many potential sites for N-linked glycosylation are present (FIG. 15) (SEQ. I.D. NO. 8].

Homologies with the PKD1 Protein

The predicted PKD1 protein was analysed for homologies with know proteins in the SwissProt and NBRF databases using the BLAST Altschul et al 1990) and FASTA algorithms. This analysis revealed two clear homologies and also a number of other potential similarities which were studied on detail.

Leucine Rich Repeat

Near the 5' end of the PKD1 protein is a region of leucine rich-repeats (LRRs). LRRs are a highly conserved motif usually of 24 residues with precisely spaced leucines (or other aliphatic amino acids) and an asparagine at position 19 (FIG. 16a and reviewed in Kobe and Reisenhofer (1994)). Two complete LRRs plus a partial repeat unit are found in the PKD1 protein, which have complete homology with the LRR consensus.

Surrounding the LRRs are distinctive cysteine-rich amino and carboxy flanking regions (FIGS. 16b and c). This flank-LRR-flank structure is exclusively found on proteins in extracellular locations and is thought to be involved in protein-protein interactions such as adhesion to other cells or to components of the extracellular matrix or as a receptor concerned with binding or signal transduction. The structure found in the PKD1 protein is similar to that found in the Drosophila protein, slit, which is important for normal central nervous system development (Rothberg, 1990). Although slit contains far more LRRs than the PKD1 protein, with four blocks each consisting of 4 or 5 repeat units, the structure of each block is similar as they finish on the amino and carboxy side with shortened LRRs which are immediately flanked by the cysteine rich regions. In the PKD1 protein two shortened LRRs surround one complete repeat unit and immediately abut the amino and carboxy flanking regions.

The amino flanking region consists of four invariant cysteines and a number of other highly conserved residues in an area of 30–40 amino acids; comparison of the PKD1 region to amino flanking motifs of other proteins is shown in FIG. 4b. The carboxy flanking region extends over an area of between 50–60 residues and consists of an invariant proline and four cysteines plus several other highly conserved amino acids. The similarity of the PKD1 region to carboxy flanking regions from other proteins is shown in FIG. 4c.

Some LRR proteins, such as slit (Rothberg 1990) and small proteoglycans are wholly extracellular but others including Toll (Hashimoto et al, 1990) and trkc (Lamballe 1991) have a single transmembrane sequence, while the LH-CRG receptor and related proteins have seven transmembrane segments and are involved in signal transduction.

C type Lectin Domain

Analysis of the sequence from exons 6 and 7 showed a high level of homology with a C type lectin domain. C type lectins are found in a variety of proteins in extracellular locations where they bind specific carbohydrates in the presence of $Ca^{2+}$ ion (Drickamer 1987, 1988; Weiss 1992). FIG. 17 illustrates the similarity of the PKDI lectin domain to those found in a number of proteins including: proteogylcans, which interact with collagens and other components of the extracellular matrix; endocytic receptors, and selectins which are involved in cell adhesion and recognition. Three different selectins have been identified: E-selectin (endothelium), P-selectin (platelets) and L-selectin (lymphocytes) and these work with other cell adhesion molecules to promote binding of the cell carrying the selectin to various other target cells.

Immunoglobulin-like Repeat Motif

Significant homologies were detected between a region of exon 5 and three regions of exon 15, with the same conserved sequence, WDFGDGS (SEQ. I.D. NO. 8), which is also found in a melanocyte-specific secreted glycoprotein, Pmel17 (Kwon et al, 1991) and three prokaryotic collagenases or proteinases (Ohara et al, 1989, Takeuchi et al, 1992 and Matsushita et al, 1994). Further analysis of the amino acid sequence of the PKD1 protein showed that a conserved region of approximately 85 bp could be discerned around this central sequence and that 16 copies of this repeat were present in the PKD1 protein; 1 in exon 5 and the other 15 as a tandem array in exons 11 to 15. FIG. 18 shows that a highly conserved structure is maintained between the repeats although in some cases less similarity is noted with the WDFGDGS (SEQ. I.D. NO. 8) sequence. Further analysis of the most conserved residues found in the repeat units showed similarity to various immunoglobulin (Ig) domains; two Ig repeats which show particular homology to the PKD1 protein are shown (FIG. 18). The repeat unit is most similar to that found in a number of cell adhesion and surface receptors which have recently been defined as the I set of Ig domains (Harpaz 1994). Ig repeats consist of 7–9 β strands of 5–10 residues linked by turns which are packed into two β sheets. The B, C, F and G β-strands of the I set are particularly similar to the PKD1 repeat, although the highly conserved cystine residues which stabilise the two β sheets through a disulphide bond are absent. The D and E β strands, however, seem less similar and in some cases are significantly shortened or apparently absent.

Further evidence that this PKD1 repeat has an Ig-like structure is found by analysis of the secondary structure with the predominant configuration found of β strands linked by turns. The WDFGDS (SEQ. I.D. NO. 23) area of the Ig molecule is one that often has a specific binding function (Jones et al., 1995) and this sequence may have a specific binding role in polycystin.

Type III Fibronectin-related Domains

Analysis of the secondary structure of the PKD1 protein beyond the carboxy end of the region of Ig-like repeats showed a continuation of the β stand and turn structure. No evidence of further Ig-like repeats could be found in this area but three pairs of evenly spaced (38–40aa) tryptophan and tyrosine residues was noted which are the most highly conserved positions of the type III fibronectin repeat which has a similar secondary structure to Ig domains. Further analysis and comparison with other type III fibronectin domains showed that in total four fibronectin repeats (one with leucine replacing the conserved tyrosine) could be recognised in this area with many of the most highly conserved residues of this domain found in the PKD1 repeat (FIG. 20).

A large number of proteins with Ig-like repeats have now been described which are involved in cell-cell interactions and cell adhesion (reviewed in Brummendork and Rathjen, 1994), while type III fibronectin (FNIII) domains are found on extracellular matrix molecules and adhesion proteins. A number of cell adhesion proteins which are located mainly on neural cells, have both Ig-like and FNIII-related domains. In these cases the FNIII repeats are always positioned C-terminal of the Ig-like units and close to a transmembrane domain; a similar pattern is seen in the proposed structure of polycystin. These Ig/FNIII containing proteins such as neuroglican and NrCAM are thought to be involved in neuron-neuron interactions and the patterning of the axonal network.

Many cell adhesion proteins of the Ig superfamily are also involved in communication and signal transduction mediated through their cytoplasmic tails. These cytoplasmic regions are known to bind to cytoskeletal proteins and other intracellular components, and phosphorylation of this part of the molecule is also thought to affect adhesive properties of the protein; potential phosphorylation sites are found in the cytoplasmic tail and one intracellular loop of polycystin (FIG. 20).

Transmembrane Regions

Analysis of hydrophobicity predicted that the deduced protein is an integral membrane protein with a signal peotide and multiple transmembrane (TM) domains located in the C-terminal region. From this analysis 11 regions (including the signal peptide) had a mean hydrophobicity indice higher than 1.4 and therefore were considered as certain membrane spanning domains (see-Experimental Procedures for details). Three others with a mean hydrophobicity indice between 0.75–1.0 were considered as putative TM domains. The most likely topology of the protein was predicted using TopPed II programme (see Experimental Procedures for details) and the resulting model included one putative segment plus the 10 certain transmembrane domains and the signal peptide. According to this model the N-terminal end is extracellular and the (highly hydrophobic) carboxy-terminal region is anchored to the membrane by 11 membrane-spanning segments, with the highly charged carboxy end located in the cytoplasm. This topology is supported by the study of N-glycosylation sites with all but one site, out of a total of 61 predicted, in an extracellular location according to the model, including 11 in the two large extracellular loops between TM regions.

However, if degree of hydrophobicity required to define a certain putative transmembrane region is altered within the model, the predicted number of such domains can change to 9 (excluding the most N-terminal pair) or 13 (with two new domains defined between TM7 and TM8). This can be ascertained by studies with specific antibodies.

Most transmembrane proteins containing the types of cell adhesion domain found on polycystin have a single transmembrane domain. The role of the multiple membrane spanning domains found in polycystin is not yet clear.

Proposed Structure of the PKD1 Protein

From the detailed analysis of the predicted PKD1 protein sequence a model of the likely structure of the protein can be formulated (FIG. 20). This model predicts an extracellular N-terminal region of approximately 2550 aa containing several distinctive extracellular domains and an intracellular C-terminus of approximately 225 aa. The intervening region of nearly 1500 aa is associated with the membrane with 11 transmembrane regions predicted and 10 variously sized extracellular and cytoplasmic loops (see FIG. 20). A proline rich hinge is found between the flank-LRR-flank region and the first Ig-like repeat. Two phosphorylation sites for tyrosine kinase and protein kinase C are found in cytoplasmic locations (FIGS. 15 (SEQ. I.D. NO. 8) and 20).

Therefore, the PKD1 protein, named polycystin, has highlighted several clear domains, plus a reiterated motif that occupies over 30% of the protein.

Characterisation of the PKD1 gene has proven to be a uniquely difficult problem because most of the gene lies in a region which is reiterated elsewhere on the chromosome. The high degree of similarity between the two areas (>97%) both in exons and introns has meant that a novel approach has been required to clone the full length transcript; involving extensive genomic sequencing and generating cDNAs from a cell line with the PKD1 but not the HG loci. In this way a contig containing the entire PKD1 transcript has now been cloned.

Preliminary analysis shows that the HG genes are very similar to PKD1 both in terms of genomic structure and sequence over most of their length (apart from the novel 3' regions). The 5' end of the PKD1 gene is at a CpG island which lies within the duplicated area. Homologous areas to this island, in the HG region, also have cleavable sites for methylation sensitive enzymes; these duplicate islands probably lie at the 5' ends of the various HG genes. Analysis for DNAase hypersensitivity also indicates that the HG, CpG islands probably contain active promoters. These results are consistent with the observation of polyadenylated mRNA from the HG genes on Northern blots and the similarity of the expression pattern of the HG and PKD1 genes in different tissue specific cell lines. The HG genes may have complete open reading frames and may encode functional proteins. Antibodies to their 'unique' 3' regions will be required to determine this. Although the PKD1 transcript is large, the overall size of the gene, at 52 kb, is not (the Duchenne muscular dystrophy (DMD) gene which encodes a slightly smaller transcript has a genomic size of over 2 Mb). Indeed, if the first intron of PKD1 is excluded from the analysis, 40.3% of the remainder of the gene is found in the mature mRNA. In the compact structure of the PKD1 gene, some of the introns are close to or smaller than the minimal size of 80 bp thought to be required for efficient splicing, although they are presumably excised effectively. We have shown that deletion of 18 or 10 bp from one small intron (intron 43), resulting in an intron of 55 or 57 bp, leads to aberrant splicing (Peral, 1995). Similar mutations may be found in the other small introns of this gene. The compact nature of the PKD1 gene probably reflects the GC rich area of the genome in which it is found (the PKD1 transcript has a total GC content of about 65%); a similar organisation is seen in other genes from the area of chromosome 16 (Vyas, 1992) is in an AT rich genomic region.

It is clear that polycystin has many features of a cell adhesion or recognition molecule with multiple different extracellular domains. These various binding domains are likely to have different specificities so that it can be envisaged that it will bind to a variety of different proteins (and carbohydrates) both on other cells and possibly in the extracellular matrix. Although provisional evidence indicates a wide range of expression of polycystin in tissue specific cell lines, detailed analysis by in situ of the mRNA and with antibodies to determine the cells expressing this protein both in adult tissue and during development will provide further evidence.

Initial analysis has revealed little clear evidence of alternate splicing, although one cDNA (out of 6 studied) had an extra exon of 255 bp positioned in intron 16. This exon contains an in-frame stop codon and it is not known at this stage if this represents an incompletely spliced mRNA or a splice form of polycystin which terminates at this point. Truncation of the protein here would leave a secreted protein lacking all of the transmembrane and cytoplasmic regions. Interestingly, a similar secreted form of the neural adhesion protein, NCAM, which is normally attached to the cell membrane, is produced by alternate splicing by insertion of an exon containing a stop codon (Gower et al., 1988).

The initial changes that have been noted in ADPKD kidneys are abnormal thickening and splitting of the basement membrane (BM) and simultaneous de-differentiation of associated epithelial cells at the point of tubular dilation. Similar results have been noted in the heterozygote Han:SPRD rat (Schafer et al., 1994) which is a dominant model of PKD, although it is not known if it is a rat model of PKD1. Concurrent changes in cellular characteristics and the BM suggests that a disruption or alteration of communication between the cell and the BM may be the primary change in this disease. Polycystin could play an important role in interaction and communication between epithelial cells and the BM. It is known that signals are required from cells to the extracellular matrix (ECM) for normal BM development and also that communication from the ECM to cells is required for control of cellular differentiation. Communication between the ECM and cells occurs by several different means including through integrins and so polycystin may bind to integrins, although it may interact directly with components of the ECM. Although ADPKD is generally a disease of adulthood, there is plenty of evidence that the cystic changes in the kidney may start much earlier (Milutinovic et al., 1970), even in utero (Reeders, 1986). Expression of polycystin during renal development may be when its major role occurs, perhaps in assembly of the BM and it is then that the errors, which later lead to cyst development, occur.

The plethora of connective tissue abnormalities associated with ADPKD indicate that the adhesion/communication roles of polycystin may be important for assembly and/or maintenance of the BM in many tissues, as well as the kidney. Hence, it is possible that disruption of normal cell adhesion and communication mediated by polycystin may explain the primary defects seen in the kidney and other organs in ADPKD. Clearly molecules that interact with polycystin or have a similar role are candidates for the other renal polycystic diseases of man.

A study of the mutations of the PKD1 gene highlight important functional regions of the protein. All of the mutations described so far in typical PKD1 families involve deletion or other disruption in the 3' end of gene. Two large deletions detected on Southern blots remove a large part of the protein (or make an out of frame product) including the last 6 transmembrane domains and the C-terminal end. The in-frame splicing change described in the same paper would remove most of TM10 and part of the preceding cytoplasmic loop. Two recently described splicing mutations (Peral, 1995) create three different products which either delete part of the cytoplasmic loop between TM7 and TM8 or a larger region of this loop including part of TM7 or insert an extra region into that loop. These mutated genes may make functional protein (they all produce abnormal mRNA) and it is interesting to note that, in each case, these proteins would have an intact extracellular region with disrupted cytoplasmic and transmembrane areas. Such proteins may bind to extracellular targets but are unable to communicate in a normal way.

A group of mutations of PKD1 which completely delete the gene and hence are clearly inactivating have been described (Brook-Carter, 1994). However, in each of these cases the deletions also disrupt the adjacent TSC2 gene making interpretation of these cases difficult (TSC2 mutations alone can cause the development of renal cysts). Nevertheless, the severity of the polycystic disease in these patients indicate that inactivation of one PKD1 allele does promote cyst development. Further more, all these children are often severely affected at birth, cyst formation must occur in utero in these cases and hence polycystin has an important developmental role. A second somatic hit in the target tissue may also be required in these cases (and normal PKD1 patients) before cyst development can occur.

PKD1 Gene and Polycystic Kidney Disease

We have therefore compelling evidence that mutations of the PKD1 gene give rise to the typical phenotype of ADPKD. The location of this gene within the PKD1 candidate region and the available genetic evidence from the families with mutations show that this is the PKD1 gene. The present invention therefore includes the complete PKD1 gene itself and the six PKD1—associated mutations which have been described: a de novo translocation, which was subsequently transmitted with the phenotype; two intragenic deletions (one a de novo event); two further deletions; and a splicing defect.

It has been argued that PKD1 could be recessive at the cellular level, with a second somatic mutation required to give rise to cystic epithelium (Reeders, 1992). This "two hit" process is thought to be the mutational mechanism giving rise to several dominant diseases, such as neurofibromatosis (Legius, et al., 1993) and tuberous sclerosis (Green, et al., 1994) which result from a defect in the control of cellular growth. If this were the case, however, we might expect that a proportion of constitutional PKD1 mutations would be inactivating deletions as seen in these other disorders.

The location of the PKD1 mutations may, however, reflect some ascertainment bias as it is this single copy area which has been screened most intensively for mutations. Nevertheless, no additional deletions were detected when a large part of the gene was screened by FIGE, and studies by PFGE showed no large deletions of this area in 75 PKD1 patients. It is possible that the mutations detected so far result in the production of an abnormal protein which causes disease through a gain of function. However, it is also possible that these mutations eliminate the production of functional protein from this chromosome and result in the PKD1 phenotype by haploinsufficiency, or only after loss of the second PKD1 homologue by somatic mutation.

At least one mutation which seems to delete the entire PKD1 gene has been identified (WS-53) but in this case it also disrupts the adjacent TSC2 gene and the resulting phenotype is of TSC with severe cystic kidney disease. Renal cysts are common in TSC so that the phenotypic significance of deletion of the PKD1 gene in this case is difficult to assess. It is clear that not all cases of renal cystic disease in TSC are due to disruption of the PKD1 gene; chromosome 9 linked TSC (TSC1) families also manifest cystic kidneys and we have analysed many TSC2 patients with kidney cysts who do not have deletion of the PKD1 gene.

Preliminary analysis of the PKD1 protein sequence (SEQ. I.D. NO. 8) has highlighted two regions which provide some clues to the possible function of the PKD1 gene. At the extreme 5' end of the characterised region are two leucine-rich repeats (LRRs) (amino acids 29–74) flanked by characteristic amino flanking (amino acids 6–28) and carboxy flanking sequences (amino acids 76–133) (Rothberg et al., 1990). LRRs are thought to be involved in protein-protein interations (Kobe and Deisenhofer, 1994) and the flanking sequences are only found in extracellular proteins. Other proteins with LRRs flanked on the amino and carboxy sides are receptors or are involved in adhesion or cellular signalling. Further 3' on the protein (amino acids 350–515) is a C-type lectin domain (Curtis et al., 1992). This indicates that this region binds carbohydrates and is also likely to be extracellular. These two regions of homology indicate that the 5' part of the PKD1 protein is extracellular and involved in protein-protein interactions. It is possible that this protein is a constituent of, or plays a role in assembling, the extracellular matrix (ECM) and may act as an adhesive protein in the ECM. It is also possible that the extracellular portion of this protein is important in signalling to other cells. The function of much of the PKD1 protein is still not fully known but the presence of several hydrophobic regions indicates that the protein may be threaded through the cell membrane.

Familial studies indicate that de novo mutations probably account for only a small minority of all ADPKD cases; a recent study detected 5 possible new mutations in 209 families (Davies, et al., 1991). However in our study one of three intragenic muttions detected was a new mutation and the PKD1 associated translocation was also a de novo event.

Furthermore, the mutations detected in the two familial cases do not account for a significant proportion of the local PKD1. The OX875 deletion was only detected in 1 of 282 unrelated cases, and the splicing defect was seen in only 1 of 48 unrelated cases. Nevertheless, studies of linkage disequilibrium have found evidence of common haplotypes associated with PKD1 in a proportion of some populations (Peral, et al., 1994; Snarey, et al., 1994) suggesting that common mutations will be identified.

Once a larger range of mutations have been characterised it will be possible to evaluate whether the type and location of mutation determines disease severity, and if there is a correlation between mutation and extra-renal manifestations. Previous studies have provided some evidence that the risk of cerebral aneurysms 'runs true' in families (Huston, et al., 1993) and that some PKD1 families exhibit a consistently mild phenotype (Ryynanen, et al., 1987). A recent study has concluded that there is evidence of anticipation in ADPKD families, especially if the disease is transmitted through the mother (Fink, et al., 1994). Furthermore, analysis of families with early manifestations of ADPKD show that there is a significant intra-familial recurrence risk and that childhood cases are most often transmitted maternally (Rink, et al., 1993; Zerres, et al., 1993). This pattern of inheritance is reminiscent of that seen in diseases in which an expanded trinucleotide repeat was found to be the mutational mechanism (reviewed in Mandel, 1993). However, no evidence for an expanding repeat correlating with PKD1 has been found in this region although such a sequence cannot be excluded.

There is ample evidence that early presymptomatic diagnosis of PKD1 is helpful because it allows complications such as hypertension and urinary tract infections to be monitored and treated quickly (Ravine, et al., 1991). The identification of mutations within a family allow rapid screening of that and other families with the same mutation. However, genetic linkage analysis is likely to remain important for presymptomatic diagnosis. The accuracy and ease of linkage based diagnosis will be improved by the identification of the PKD1 gene as a microsatellite lies in the 3' untranslated region of this gene (KG-8) and several CA repeats are located 5' of the gene (see FIGS. 1a and 6; Peral, et al., 1994; Snarey, et al., 1994).

Experimental Procedures

Clinical Details of Patients

Family 77

77-2 and 77-3 are 48 and 17 years old, respectively and have typical ADPKD. Both have bilateral polycystic kidneys and 77-2 has impaired renal function. Neither patient manifests any signs of TSC (apart from cystic kidneys) on clinical and ophthalmological examination or by CT scan of the brain.

77-4 is 13 years old, severely mentally retarded and has multiple signs of tSC including adenoma sebaceum, depigmented macules and periventricular calcification on CT scan. Renal ultrasound reveals a small number of bilateral renal cysts.

ADPKD Patients

OX875 developed ESRD from ADPKD, aged 46. Progressive decline in renal function had been observed over 17 years; ultrasound examinations documented enlarging polycystic kidneys with less extensive hepatic cystic disease. Both kidneys were removed after renal transplantation and pathological examination showed typical advanced cystic disease in kidneys weighing 1920 g and 340 g (normal average 120 g).

OX114 developed ESRD from ADPKD aged 54: diagnosis was made by radiological investigation during an episode of abdominal pain aged 25. A progressive decline in renal function and the development of hypertension was subsequently observed. Ultrasonic examination demonstrated enlarged kidneys with typical cystic disease, with less severe hepatic involvement.

OX32 is a member of a large kindred affected by typical ADPKD in which several members have developed ESRD. The patient himself has been observed for 12 years with progressive renal failure and hypertension following ultrasonic demonstration of polycystic kidneys.

No signs of TSC were observed on clinical examination of any of the ADPKD patients.

DNA Electrophoresis and Hybridisation

DNA extraction, restriction digests, electrophoresis, Southern blotting, hybridisation and washing were performed by standard methods or as previously described (Harris, et al., 1990). FIGE was performed with the Biorad FIGE Mapper using programme 5 to separate fragments from 25–50 kb. High molecular weight DNA for PFGE was isolated in agarose blocks and separated on the Biorad a CHEF DRII apparatus using appropriate conditions.

Genomic DNA Probes and Somatic Cell Hybrids

Many of the DNA probes used in this study have been described previously: MS205.2 (D16S309; Royle, et al., 1992); GGG1 (D16S259; Germino, et al., 1990); N54 (D16S139; Himmelbauer, et al., 1991); SM6 (D16S665), CW23, CW21, and JH1 (European Chromosome 16 Tuberous Sclerosis Consortium, 1993). Microsatellite probes for haplotype analysis were KG8 and W5.2 (Snarey, et al., 1994)SM6, CW3 and CW2, (Peral, et al., 1994), 16AC2.5 (Thompson, et al., 1992); SM7 (Harris, et al., 1991), VK5AC (Aksentijevich, et al., 1993).

New probes isolated during this study were: JH4, JH5, JH6, 11 kb, 6 kb and 6 kb BamH I fragments, respectively, and JH13 and JH14, 4 kb and 2.8 kb BamH I-EcoR I fragments, respectively, all from the cosmid JH2A; JH8 and JH10 are 4.5kb and 2 kb Sac I fragments, respectively and JH12 a 0.6 Sac I-BamH I fragment, all from JH4; 8S1 and 8S3 are 2.4 kb and 0.6 kb Sac II fragments, respectively, from JH8; CW10 (SEQ. I.D. NO. 4) is a 0.5 kb Not I-Mlu I fragment of SM25A; JH17 is a 2 kb EcoR I fragment of NM17.

The somatic cell hybrids N-OH1 (Germino, et al., 1990), P-MWH2A (European Chromosome 16 Tuberous Sclerosis Consortium, 1993) and Hy145.19 (Himmelbauer, et al., 1991) have previously been described. Somatic cell hybrids containing the paternally derived (BP2-10) and maternally derived (BP2-9) chromosomes from OX114 were produced by the method of Deisseroth and Hendrick (1979).

Constructing a Cosmid Contig

Cosmids were isolated from chromosome 16 specific and total genomic libraries, and a contig was constructed using the methods and libraries previously described (European Chromosome 16 Tuberous Sclerosis Consortium, 1993). To ensure that cosmids were derived from the 16p13.3 region (not the duplicate 16p13.1 area) initially, probes from the single copy area were used to screen libraries (e.g. CW21 and N54). Two cosmids mapped entirely within the area duplicated, CW10III and JC10.2B. To establish that these were from the PKD1 area, they were restriction mapped and hybridised with the probe CW10. The fragment sizes detected were compared to results obtained with hybrids containing only the 16p13.3. are (Hy145.19) or only the 16p13.1 region (P-MWH2A).

Fish

FISH was performed essentially as previously described (Buckle and Rack, 1993). The hybridisation mixture contained 100 ng of biotin-II-dUTP labelled cosmid DNA and 2.5 mg human Cot-1 DNA (BRL), which was denatured and annealled at 37° C. for 15 min prior to hybridisation at 42° C. overnight. After stringent washes the site of hybridisation was detected with successive layers of fluorescein-conjugated avidin (5 mg/ml) and biotinylated ani-avidin (5 mg/ML) Vector Laboratories). Slides were mounted in Vectashield (Vector Laboratories) containing 1 mg/ml pro-pidium iodide and 1 mg/ml 4', 6-diamidino-2-phenylindole (DAPI), to allow concurrent G-banded analysis under UV light. Results were analysed and images captured using a Bio-Rad MRC 600 confocal laser scanning microscope.

cDNA Screening and Characterisation

Foetal brain cDNAs libraries in 7 phage (Clonetech and Stratagene) were screened by standard methods with genomic fragments in the single copy area (equivalent to CW23 and CW21) or with a 0.8 kb Pvu II-Eco RI single copy fragment of AH3. Six PBP cDNAs were characterised; AH4 (1.7 kb ) and 3A3 (2.0kb ) are described in European Chromosome 16 Tuberous Sclerosis Consortium, 1993, and four novel cDNAs AH3 (2.2 kb ), AH6 (2.0 kb ), A1C (2.2 kb ) and B1E (2.9 kb ). A Striatum library (Stratagene) was screened with JH4 and a HG-C cDNA, 11BHS21 (3.8 KB) WAS ISOLATED, 21 p.9 is a 0.9 kb Pvu II-EcoR I subclone of this cDNA. A HG-A or HG-B cDNA, HG-4 (7 kb ) was also isolated by screening the foetal brain library (Stratagene) with JH8. HG-4/1.1 is a 1.1 kb Pvu II-EcoR I fragment from the 3' end of HG-4. 1A1H.6 (SEQ. I.D. NO. 3) is a 0.6 kb Hind III-EcoR I subclone of a TSC2 cDNA, 1A-1 (1.7 kb ), which was isolated from the Clonetech library. Each cDNA was subcloned into Bluescript and sequenced utilising a combination of sequential truncation and liigonucleotide primers using DyeDeoxy Terminators (Applied Biosystems) and an ABI 373A DNA SEQuencer (Applied Biosystems) or by hand with 'SEQuenase' T7 DNA polymerase OUSB).

RNA Procedures

Total RNA was isolated from cell lines and tissues by the method of Chomczynskiand Sacchi (1987) and enrichment for mRNA made using the PolyAT tract mRNA Isolation System (Promega). For RNA electrophoresis 0.5% agarose denaturing formaldehyde gels were used which were Northern blotted, hybridised and washed by standard procedures. The 0.24–9.5kb RNA (Gibco BRL) size standard was used and hybridisation of the probe (1-9B3) to the 13kb Utrophin transcript (Love, et al., 1989) in total fibroblast RNA was used as a size marker for the large transcripts.

RT-PCR was performed with 2.5 mg of total RNA by the method of Brown et al. (1990) with random hexamer primers, except that AMV-reverse transcriptase (Life Sciences) was employed. To characterise the deletion of the PBP transcript in OX114 we used the primers:

```
                                         [Seq. I.D. No.9]
AH#F9  5'TTT GAC AAG CAC ATC TGG CTC TC 3'
                                         [Seq. I.D. No.10]
AH3B7  5'TAC ACC AGG AGG CTC CGC AG 3'
``` in a DMSO containing PCR buffer (Dode, et al., 1990) with 0.5 mM MgCl$_2$ and 36 cycles of: 94° C., 1 min; 61° C., 1 min; 72° C., 2 min plus a final extension of 10 min. The 3A3 C primers used to amplify the OX32 cDNA and DNA were:

```
                                         [Seq. I.D. No.11]
3A3C1  5'CGC CGC TTC ACT AGC TTC GAC 3'
```

```
                                         [Seq. I.D. No.12]
3A3C2  5'ACG CTC CAG AGG GAG TCC AC 3'
```

These were employed in a PCR buffer and cycle previously described (Harris, et al., 1991) with 1 mM MgCl$_2$ and an annealing temperature of 61° C.

PCR products for sequencing were amplified with Pfu-1 (Stratagene) and ligated into the Srf-1 site in PCR-Script (Stratagene) in the presence of Srf-1.

RNAse Protection

Tissues from normal and end-stage polycystic kidneys were immediately homogenised in guanidinium thiocyanate. RNA was purified on a cesium chloride gradient and 30 mg total RNA was assayed by RNAse protection by the method of Melton, et al., (1984) using a genomic template generated with the 3A3, C primers (SEQ. I.D. Nos. 11 and 12].

Heteroduplex Analysis

Heteroduplex analysis was performed essentially as described by Keen et al. (1991). Samples were amplified from genomic DNA with the 3A3, C primers (SEQ. I.D. Nos. 11 and 12), heated at 95° C. for 5 minutes and incubated at room temperature for at least 30 minutes before loading on a Hydrolink gel (AT Biochem). Hydrolink gels were run for 12–18 hours at 250V and fragments observed after staining with ethidium bromide.

Extraction and Amplification of Paraffin-embedded DNA

DNA from formalin fixed, paraffin wax embedded kidney tissue was prepared by the method of Wright and Manos (1990), except that after proteinase K digestion overnight at 55° C., the DNA was extracted with phenol plus chloroform before ethanol precipitation. Approximately 50 ng of DNA was used for PCR with 1.5 mM MgCl$_2$ and 40 cycles of 94° C. for 1 min, 50° C. for 1 min and 72° C. for 40 s, plus a 10 min extension at 72° C.

The oligonucleotide primers designed to amplify across the genomic deletion of OX875 were:

AHF42: 5'-GGG CAA GGG AGG ATG ACA AG-3' (SEQ. I.D. NO. 13]

JH14B3: 5'-GGG TTT ATC AGC AGC AAG CGG-3' (SEQ. I.D. NO. 14]

which produced a product of about 220 bp in individuals with the OX875 deletion.

3' RACE analysis of WS-212

3' RACE was completed essentially as described (European Polycystic Kidney Disease Consortium (1994)). Reverse transcription was performed with 5 μg total RNA with 0.5 μg of the hybrid dT$_{17}$ adapter primer using conditions previously described (Fronman et al., (1988)). A specific 3' RACE product was amplified with the primer F5 and adapter primer in 0.5 mM MgCl$_2$ with the program: 57° C., 60s; 72° C., 15 minutes and 30 cycles of 95° C., 40s; 57° C., 60s; 720° C., 60s plus 720° C., 10 minutes. The amplified product was cloned using the TA cloning system (Invitrogen) and sequenced by conventional methods.

Genomic and cDNA Probes and Somatic Cell Hybrids

The genomic clones CW21, JH5, JH6, JH8, JH10, JH12, JH13 and JH14 and the cDNAs A1C, AH3, 3A3 and AH4 are described herein. Newly described probes are: SM3 a 2.0kb BamH 1 subclone of the cosmid SM11, JH9, 2.4 kb Sac 1 fragment and JH11, 1.2kn Sac 1—BamHl fragment, both from JH4. See Eur. Polycystic Kidney Disease Consortium, 1994 and Eur. Chromosome 16 Tuberous Sclerosis Consortium 1993 for all above clones. DFS5 is a 4.2kb Not l -Hind lll fragment of CW23 (Eur. Chromosome 16 Tuberous Sclerosis Consortium, 1993). The cDNAs; BPG4, BPG6, BPG7 and 13-A were isolated from a fetal brain cDNA library in λ phage (Stratagene) and are 7 kb, 2 kb, 4.5 kb and 1.2 kb respectively.

The somatic cell hybrids have previously been described, P-MWH2A (Eur. Chromosome 16 Tuberous Sclerosis Consortium, 1993) and Hy145.19 (Himmelbauer et al., 1991).

Exon Linking

Total cellular RNA from the radiation hybrid Hy145.19 was reverse-transcribed using random hexamers (Eur. Polycystic Kidney Disease Consortium, 1994). This material was used as a template for PCR using the proof reading polymerase Pfu-1 with the primer pairs described in Table 2 (SEQ. I.D. NO. 7). The resultant products were cloned into the Srf-1 site of pPCRscript (SK+) plasmid.

SEQuencing

Full length sequence was obtained from the genomic clones, HG cDNAs and exon link clones using the progressive unidirectional deletion technique of Henikoff, (1984). Both strands were then sequenced using DyeDeoxy Terminator Cycle SEQuencing and an Applied Biosystems SEQuencer 373A. Contig assembly was done using the programmes Assembly line (vs 1.0.7), SEQEd (vs 1.03) and MacVector (4.1.4).

Primer Extension

Primer extension was performed on total cellular fibroblast RNA. 25 μg of RNA was annealed at 60° C. in the presence of 400mM NaCl to 0.01 pM of HPLC pure oligonucleotide which had been end labelled to a specific activity of $3 \times 10^7$ cpm/pM with $^{32}$P. Primer extension was then performed in the presence of 50 mM Tris pH8.2, 10 mM DTT, 6 mM MgCl$_2$, 25 mg/ml Actinomycin D, 0.5 mM dNTPs, and 8 units of AMV reverse transcriptase. The extension reaction was continued for 60 min at 42° C. The extension products were compared to a sequencing ladder generated using the same primer on the genomic clone SM3. The primers used were:

N2765:5'-
GGCGCGGCGGGCGGCATCGTTAGGGCAGCG-3'
(SEQ. I.D. NO. 15]
N5496:5'-
GGCGGGCGGCATCGTTAGGGCAGCGCGCGC-3'
(SEQ. I.D. NO. 16]
N5495:5'-
ACCTGCTGCTGAGCGACGCCCGCTCGGGGC-3'
(SEQ. I.D. NO. 17].

Analysis of SEQuence Homology

The predicted PKD1 protein was analyzed for homologies with known proteins in the SwissProt and NBRF database using the BLAST (Altschul et al., 1990) and FASTA (Pearson et al., 1988) algorithms. Layouts were prepared by hand and using the programme Pileup.

Transmembrane Regions

Potential transmembrane segments were identified by the method of Sipos and von Heljne (Sipos et al. 1993), using the GES hydrophobicity scale (Engelmen et al., 1986) and a trapezoid sliding window (a full window of 21 residues and a core window of 11 residues), as recommended. Candidate transmembrane domains were selected on the basis of their average hydrophobicity <H>, and were classified as-certain (<H≧≦1.0) or putative (0.6, <H> <1).

The best topology for the protein was predicted on the basis of three different criteria: a) the net charge difference between the 15 N-terminal and the 15C-terminal residues flanking the most N-terminal transmembrane segment (Hartmann et al., 1989); b) the difference in positively charged residues between the two sides of the membrane in loops smaller than 60 residues, and c) the analysis of the overall amino acid composition of loops longer than 60 residues by the compositional distance method (Nakashima et al., 1992). Using the above criteria the TopPred II program (Sipos wt al., 1993) calculated all the possible topologies of the proteins including the certain transmembrane segments and either included or excluded each of the putative segments to determine the most likely structure.

PKD1 Protein Purification

The PKD1 protein may be purified according to conventional protein purification procedures well known in the art. Alternatively, the protein may be purified from cells harboring a plasmid containing an expressible PKD1 gene. For example, the protein may be expressed in an E.coli expression system and purified as follows.

Cells are grown in a 10 liter volume in a Chemap Fermentor (Chemapec, Woodbury, N.Y.) in 2% medium. Fermentation temperature may be 37'C, pH 6.8, and air as provided at 1 vvm. Plasmid selection may be provided using ampicillin for a plasmid containing an ampicillin resistance gene. Typical yield (wet weight) is 30 g/l.

For cell lysis, 50 g wet cell weight of E.coli containing the recombinant PKD1 plasmid may be resuspended in a final volume of 100 ml in 50 mM Tris-HCl pH 8.0, 5 mM EDTA, 5 mM DTT, 15 mM mercaptoethanol, 0.5% triton X-100, and 5 mM PMSF. 300 mg lysozyme is added to the suspension, and incubated for 30 min at room temperature. The material is then lyzed using a BEAD BEATER (R) (Biospec Products, Bartlesville, OK) containing an equal volume of 0.1–0.15 um glass beads. The liquid is separated from the beads and the supernatant removed, the pellet dissolved in 20 mM Tris-Cl pH 8.0.

The protein may be purified from the supernatant using DEAE chromatography, as is well known in the art.

Preparation of Antibodies

Antibodies specific for PDK1 protein or a fragment thereof are prepared as follows. A peptide corresponding to at least 8 amino acid residues of the PKD1 sequence of FIG. 15 (SEQ. I.D. NO. 8), are synthesized. Coupling of the peptide to carrier protein and immunizations is performed as described (Dymecki, S. M., J. Biol. Chem 267:4815–4823, 1992). Rabbit antibodies against this peptide are raised and sera are titered against peptide antigen by ELISA. The sera exhibiting the highest titer (1:27,000) are most useful.

Techniques for preparing monoclonal antibodies are well known, and monoclonal antibodies of this invention may be prepared by using the synthetic polypeptides of this invention, preferably bound to a carrier, as the immunogen as was done by Arnheiter et al., Nature, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" the synthetic polypeptides of this invention or their conjugates with a carrier. Antibodies are utilized along with an "indicating group" also sometimes referred to as a "label". The indicating group or label is utilized in conjunction with the antibody as a means for determining whether an immune reaction has taken place, and in some instances for determining the extent of such a reaction.

The indicating group may be a single atom as in the case of radioactive elements such as iodine 125 or 131, hydrogen 3 or sulfur 35, or NMR-active elements such as fluorine 19 or nitrogen 15. The indicating group may also be a molecule such as a fluorescent dye like fluorescein, or an enzyme, such as horseradish peroxidase (HRP), or the like.

The terms "indicating group" or "label" are used herein to include single atoms and molecules that are linked to the antibody or used separately, and whether those atoms or molecules are used alone or in conjunction with additional reagents. Such indicating groups or labels are themselves well-known in immunochemistry and constitute a part of this invention only insofar as they are utilized with otherwise novel antibodies, methods and/or systems.

Detection of PKD1 and Subcellular Localization

Another embodiment of this invention relates to an assay for the presence of PKD1 protein in cells. Here, an above-described antibody is raised and harvested. The antibody or idiotype-containing polyamide portion thereof is then admixed with candidate tissue and an indicating group. The presence of the naturally occurring amino acid sequence is ascertained by the formation of an immune reaction as signaled by the indicating group. Candidate tissues include any tissue or cell line or bodily fluid to be tested for the presence of PKD1.

Metabolic labeling immunoprecipitation, and immunolocalization assays are performed in cells as described previously (Furth, M. E., et al., Oncogene 1:47–58, 1987; Laemmli, U. K., Nature 227:680–685, 1970; Yarden, Y., et al., EMBO J. 6:3341–3351, 1987; Konopka, J. B., et al., Mol. Cell. Biol. 5:3116–3123, 1985). For immunoblot analysis, total lysates are prepared (using Fruth's lysis buffer) (Fruth, M. E., et al., Oncogene, 1:47–58, 1987). Relative protein concentrations are determined with a colorimetric assay kit (Bio-Rad) with bovine serum albumin as the standard. A protein of lysate containing approximately 0.05 mg of protein is mixed with an equal volume of 2×SDS sample buffer containing 2 mercaptoethanol, boiled for 5 min., fractioned on 10% polyacrylamide-SDS gels (Konopka, J. B., et al., J. Virol., 51:223–232, 1984) and transferred to immunobilon polyvinyldine difluoride (Millipore Corp., Bedford, Mass.) filters. Protein blots are treated with specific antipeptide antibodies (see below). Primary binding of the PKD1-specific antibodies is detected using anti-IgG second antibodies conjugated to horseradish peroxidase and subsequent chemiluminescence development ECL Western blotting system (Amersham International).

For metabolic labeling, $10^6$ cells are labeled with 100 $\mu$Ci of $^{35}$S-methionine in 1 ml of Dulbecco's modified Eagles medium minus methionine (Amersham Corp.) for 16 h. Immunoprecipitation of PKD1 protein from labeled cells with antipeptide antiserum is performed as described (Dymecki, S. M., et al., supra). Portions of lysates containing $10^7$ cpm of acid-insoluble $^{35}$S-methionine are incubated with 1 $\mu$g of the antiserum in 0.5 ml of reaction mixture. Immunoprecipitation samples are analyzed by SDS-polylarcylamide gel electrophoresis and autoradiography.

For immunolocalization studies, $10^7$ CMK cells are resuspended in 1 ml of sonication buffer (60 mM Tris-HCl, pH 7.5, 6 mM EDTA, 15 mM EGTA, 0.75M sucrose, 0.03% leupeptin 12 mM phenylmethylsulfonyl fluoride, 30 mM 2-mercaptoethanol). Cells are sonicated 6 times for 10 seconds each and centrifuged at 25,000×g for 10 min at 40° C. The pellet is dissolved in 1 ml of sonication buffer and centrifuged at 25,000×g for 10 min at 4° C.

The pellet (nucleus fraction) is resuspended in 1 ml of sonication buffer and added to an equal volume of 2×SDS sample buffer. The supernatant obtained above (after the first sonication) is again centrifuged at 100,000×g for 40 min at 4° C. The supernatant (cytosolic fraction) is removed and added to an equal volume of 2×concentrated SDS sample buffer. The remaining pellet (membrane fraction) is washed and dissolved in sonication buffer and SDS sample buffer as described above. Protein samples are analyzed by electrophoresis on 10% polyacrylamide gels, according to the Laemmli method (Konopka, J. B., supra). The proteins are transferred from the gels on a 0.45-$\mu$polyvinylidene difluoride membrane for subsequent immunoblot analysis. Primary binding of the PKD1 specific antibodies is detected using anti-IgG second antibodies conjugated to horseradish peroxidase.

For immunohistochemical localization of PKD1 protein, CMK cells or U3T3 are grown on cover slips to approximately 50% confluence and are washed with PBS (pH 7.4) after removing the medium. The cells are prefixed for 1 min at 37° C. in 1% paraformaldehyde containing 0.075% Triton X-100, rinsed with PBS and then fixed for 10 min with 4% paraformaldehyde. After the fixation step, cells are rinsed in PBS, quenched in PBS with 0.1 and finally rinsed again in PBS. For antibody staining, the cells are first blocked with a blocking solution (3% bovine serum albumin in PBS) and incubated for 1 h at 37° C. The cells are then incubated for 1 h at 37° C. with antiserum (1:100 dilution or with preimmune rabbit serum (1:100). After the incubation with the primary antibody, the cells are washed in PBS containing 3% bovine and serum albumin and 0.1% Tween 20 and incubated for 1 h at 37° C. in fluorescein-conjugated donkey anti-rabbit IgGs (Jackson Immunoresearch, Maine) diluted 1:100 in blocking solution.

The coverslips are washed in PBS (pH 8.0), and glycerol is added to each coverslip before mounting on glass slides and sealing with clear nail polish. All glass slides are examined with a Zeiss Axiophot microscope.

An indicating group or label is preferably supplied along with the antibody and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

Pharmaceutical Compositions of the Invention; Dosage and Administration

Pharmaceutical formulations comprising PKD1 nucleic acid or protein, or mutants thereof, can be prepared by procedures well known in the art. For example, as injectables, e.g., liquid solutions or suspensions. Solid forms for solution in, or suspension in, a liquid prior to injection also can be prepared. Optionally, the preparation also can be emulsified. The active ingredient can be mixed with excipients which are pharmaceutically acceptable and compatible with the active ingredient. For example, water, saline, dextrose, glycerol, ethanol, etc. or combinations thereof. Also useful are wetting or emulsifying agents, pH buffering agents or adjuvants. PKD1 protein or DNA can be administered parenterally, by injection, for example, either subcutaneously or intramuscularly. Additional formulations which are suitable for other modes of administration include suppositories and, in some cases, oral formulations. In each case, the active protein or the nucleic acid will be present in the range of about 0.05% to about 10%, preferably in the range of about 1–20% by weight. Alternatively, the active protein or the nucleic acid will be administered at a dosage of about 10 mg–2 kg/kg body weight, preferably 50 mg–400 mg/kg/body weight. Administration may be daily, weekly, or in a single dosage, as determined by the physician.

TABLE 1

Details of the exons and introns of the PKD1 gene

| Exons | | | Introns | |
|---|---|---|---|---|
| Exon No. | position (bp) | Size (nt) bp | positions (aa) | Intron No. | Size (bp) |
| 1 | 1–426 | 426 | 1–72 | 1 | ~17 kb |
| 2 | 427–498 | 72 | 73–96 | 2 | 121 |
| 3 | 499–570 | 72 | 97–120 | 3 | 268 |
| 4 | 571–740 | 170 | 121–177 | 4 | 213 |
| 5 | 741–1412 | 672 | 177–401 | 5 | 117 |
| 6 | 1413–1596 | 184 | 401–462 | 6 | 435 |
| 7 | 1597–1817 | 221 | 463–536 | 7 | 188 |
| 8 | 1818–1933 | 118 | 536–575 | 8 | 410 |
| 9 | 1934–2060 | 127 | 525–617 | 9 | 363 |
| 10 | 2061–2308 | 248 | 617–700 | 10 | 452 |
| 11 | 2309–3064 | 756 | 700–952 | 11 | 877 |
| 12 | 3065–3196 | 132 | 952–996 | 12 | 196 |
| 13 | 3197–3372 | 176 | 996–1054 | 13 | 314 |
| 14 | 3373–3506 | 134 | 1055–1099 | 14 | 468 |
| 15 | 3507–7126 | 3,620 | 1099–2306 | 15 | 219 |
| 16 | 7127–7276 | 150 | 2306–2356 | 16 | ? |
| 17 | 7277–7420 | 144 | 2356–2404 | 17 | 127 |
| 18 | 7421–7700 | 280 | 2404–2497 | 18 | 93 |
| 19 | 7701–7914 | 214 | 2497–2568 | 19 | 66 |
| 20 | 7915–8074 | 160 | 2569–2622 | 20 | ~400 bp |
| 21 | 8075–8227 | 153 | 2622–2673 | 21 | 3.1 kb |
| 22 | 8228–8372 | 145 | 2673–2721 | 22 | 650 |
| 23 | 8373–9002 | 630 | 2721–2931 | 23 | 295 |
| 24 | 9003–9159 | 158 | 2931–2983 | 24 | 180 |

TABLE 1-continued

Details of the exons and introns of the PKD1 gene

| Exons | | | Introns | |
|---|---|---|---|---|
| Exon No. | position (bp) | Size (nt) bp | positions (aa) | Intron No. | Size (bp) |
| 25 | 9160–9412 | 254 | 2984–3068 | 25 | 123 |
| 26 | 9413–9608 | 196 | 3068–3133 | 26 | ~1.7 kb |
| 27 | 9609–9779 | 171 | 3133–3190 | 27 | 86 |
| 28 | 9780–9923 | 144 | 3190–3238 | 28 | 93 |
| 29 | 9924–10134 | 211 | 3238–3308 | 29 | 90 |
| 30 | 10135–10261 | 127 | 3309–3351 | 30 | ~1.5 kb |
| 31 | 10262–10378 | 117 | 3351–3390 | 31 | 88 |
| 32 | 10379–10428 | 50 | 3390–3406 | 32 | 224 |
| 33 | 10429–10613 | 185 | 3407–3468 | 33 | 77 |
| 34 | 10614–10707 | 94 | 3468–3499 | 34 | ~3 kb |
| 35 | 10708–10826 | 119 | 3500–3539 | 35 | 78 |
| 36 | 10827–11029 | 203 | 3539–3607 | 36 | 72 |
| 37 | 11030–11224 | 195 | 3607–3672 | 37 | 450 |
| 38 | 11225–11364 | 140 | 3672–3718 | 38 | 361 |
| 39 | 11365–11477 | 113 | 3719–3756 | 39 | 290 |
| 40 | 11478–11619 | 142 | 3756–3803 | 40 | 139 |
| 41 | 11620–11745 | 126 | 3804–3845 | 41 | 183 |
| 42 | 11746–11920 | 175 | 3846–3904 | 42 | ~320 |
| 43 | 11921–12211 | 291 | 3904–4001 | 43 | 75 |
| 44 | 12212–12346 | 135 | 4001–4046 | 44 | 83 |
| 45 | 12347–12652 | 306 | 4046–4148 | 45 | 88 |
| 46 | 12653–14148 | 1,496 | 4148–4302 | | |

TABLE 2

Details of the exon link cDNAs

| Product Name | Product Size (bp) | Oligonucleotide Sequences | Position in cDNA | Exon Position |
|---|---|---|---|---|
| rev1 | 652 | AGCGCCAGCGTCCGAGCGG<br>CTGCACCACCCGCACCTGC | 8–658<br>200–658 | 1–4 |
| S13 | 1285 | CCGGGCGCTGGACGTTGGGCT<br>AGTGCTCGGCTGTGGCTGGGT | 448–1733 | 2–7 |
| S3/4 | 1608 | CACCCAGCCACAGCCGAGCACT<br>GTGTGGCATTGGGGGACAGCAC | 1712–3320 | 7–13 |
| S1/3 | 732 | TGCTGTCCCCCAATGCCAC<br>ACGGTCACTGTGCAGTTC | 3300–4032 | 13–15 |
| GAP e | 1983 | CCAATGCCACACTGGTACTGACG<br>TGGTAGGTGCCGGCCTCGAG | 3309–5292 | 13–15 |
| GAP d | 2036 | CCGGCACCTACCATGTGCAGC<br>CCAAGGACACAATGGGCACC | 5280–7316 | 15–17 |
| GAP g | 884 | GAGGTGTATCGCACCGCCAG<br>GCCCAGTGGGAAGAGGCGGC | 6773–7657 | 15–18 |
| GAP a | 1211 | TCTTGCCGCCTCTTCCCA<br>GCAGCCCAGTCCGAGTTG | 7634–8862 | 18–23 |

Other Embodiments

Other embodiments will be evident to those of skill in the arm It should be understood that the foregoing detailed description is provided for clarity only and is merely exemplary. The spirit and scope of the present invention are not limited thereto, being defined by the claims set forth below.

REFERENCES

Aksentijevich et al., Am. J. Hum. Genet. 53:451–461, (1993).
Altschul et al., J. Mol. Biol. 215:403–410, (1990).
Bevilacqua, M. P., et al., Science 243:1160–1165, (1989).
Bork et al., Protein Science 2:1185–1187, (1993).
Breuning et al., Lancet ii, 1359–1361, (1987).
Breuning et al., J. Med. Genet. 27:603–613, (1990).
Brook-Carter et al., Nature Genetics 8:328–332, (1994).
Brown et al., Nucl. Acids Res. 18:4191–4195, (1990).
Brümmendork, T., et al., Protein Profile 1:951–1058, (1994).
Buckle et al., Human Genetic Disease Analysis; IRL Press (K. E.
Davies, Ed.) 2:59–82, Oxford, (1993).
Carone, F. A., et al., Laboratory Investigations 70:437–448, (1994).
Carone, F. A., et al., Kidney International 47:861–868, (1995).
Calvet, J. P., Kidney International 43:101–108, (1993).
Chapman et al., N. Eng. J. Med. 327:916–920, (1992).
Chao, M. V., Neuron 9:583–593, (1992).
Chomczynski et al., Anal. Biochem. 162:156–159, (1987).
Curtis et al., Proc. of the Nat'l. Acad. of Sci., USA 89:8356–8360, (1992).
Dalgaard, O. Z., Acta Medica Scandinavica 158:1–251, (1957).
Daoust, M. C., et al., Genomics 25:733-736, (1995).
Davies et al., Q. J. Med. 79:477–485, (1991).
Deisseroth et al., Proc. Natl. Acad. Sci. USA 76:2185–2189, (1979).
Dode et al., Brit. J. Haemat. 76:275–281, (1990).
Drickamer, K., Kidney Int'l. 32:167–180, (1987).
Drickamer, K., J. Biol. Chem. 263:9557–9560, (1988).
Ekblom, P., FASEB Journal 3:2141–2150, (1989).
Engelman et al., Ann. Rev. Bioph. Chem. 15:321–353, (1986).
European Polycystic Kidney Disease Consortium, Cell 77:881–894, (1994).
European Chromosome 16 Tuberous Sclerosis Consortium, Cell 75:1305–1315, (1993).
Fink et al., J. Amer. Soc. Nephrology 3:1863–1870, (1993).
Fink et al., Kidney Int. 45:1153–1162, (1994).
Fronman et al., Biochemistry 85:8998–9002, (1988).
Gabow, P. A., Kidney Int. 40:989–996, (1991).
Gabow, P. A., N. E. J. of Medicine 329:332–342, (1993).
Gabow, P. A., Amer. J. of Kidney Diseases 16:403–413, (1990).
Germino et al., Am. J. Hum. Genet. 46:925–933, (1990).
Germino et al., Genomics 13:144–151, (1992).
Gower, H. J., et al., Cell 55:955–964, (1988).
Green et al., Nature Genet. 6:193–196, (1994).
Harpaz, Y., et al., J. of the Mol. Biol. 238:528–539 (1994).
Harris et al., Genomics 7:195–206, (1990).
Harris et al., Lancet 338:1484–1487, (1991).
Hartmann et al., Proc. Nat'l. Acad. Sci. USA 86:5786–5790, (1989).
Henikoff, S., Gene 28:351–359, (1984).
Himmelbauer et al., Amer. J. Human Genetics 48:325–334, (1991).
Hossack et al., N. Eng. J. Med. 319:907–912, (1988).
Huston et al., J. Amer. Soc. of Nephrology 3:1871–1877, (1993).
Hyland et al., Hum. Genet. 84:286–288, (1990).
Jia, R., et al., J. of Biol. Chem. 269:1839–1844 (1994).
Jones, E. Y., et al., Nature 373:539–544, (1995).
Keen et al., Trend Genet. 7:5, (1991).
Kimberly, W. J., et al., Genomics 18:467–472, (1993).
Kimberling et al., N. Eng. J. Med. 319:913–918, (1988).
Kobe et al., Trends in Bioch. Sci. 19:415–421, (1994).
Kornblihtt, A. R., et al., EMBO Journal 4:1755–1759, (1985).
Kozak, M., Nucleic Acids Res. 15:8125–8148, (1987).
Kuma et al., Mol. Biol. and Evolution 10:539–551, (1993).
Kwon, B. S., et al., Proc. of the Nat' l. Acad. of Sci., USA 88:9228–9232, (1991).
Lamballe et al., Cell 66:967–979, (1991).
Legius et al., Nature Genet. 3:122–126, (1993).
Love et al., Nature 339:55–58, (1989).
Mandel, J-L, Nature Genetics 4:8–9.
Matsushita, O., et al., Journal of Bacteriology 176:149–156, (1994).
McFarland, K. C., et al., Science 245:494–499, (1989).
Melton et al., Nuc. Acid Res. 12:7035–7056.
Milutinovic, J., et al., Amer. J. of Med. 68:741–744, (1980).
Milutinovic, J., et al., Amer. J. of Clin. Path. 73: 740–747, (1979).
Nakashima et al., FEBS Letters 303:141–146, (1992).
Oldberg, et al., EMBO J. 8:2601–2604, (1989).
Oldberg et al., Biochemical J. 243:255–259, (1987).
Parfrey et al., N. Eng. J. Med. 323:1085–1090, (1990).
Pearson et al., Proc. Nat'l Acad. Sci. USA 85:2444–2448, (1988).
Peral et al., Am. J. Hum. Genet. 54:899–908.
Peral et al., Human Molecular Genetics (in press), (1995).
Peters, D. J. M., et al., Nature Genetics 5:359–362, (1993).
Peters, D. J. M., et al., Contributions to Nephrology: Polychystic
Kidney Disease (eds. Breuning, M. H., Devoto, M. & Romeo, G), p. 128–139 (1992).
Pound et al., J. Med. Genet. 29:247–248, (1992).
Ravine et al., Lancet 337:127–129, (1991).
Ravine D., et al., Lancet 340:1330–1333, (1992).
Reeders, S. T., Nature Genet. 1:235–237, (1992).
Reeders et al., Lancet i, 6–8, (1986).
Reeders et al., Nature 317:542–544, (1985).
Reeders et al., Genomics 3:150–155, (1988).
Romeo et al., Lancet ii, 8–10, (1988).
Roth, G. J., Blood 77:5–19, (1991).
Rothberg et al., Genes and Development 4:2169–2187, (1990).
Royle et al., Nucl. Acids Res. 20:1164, (1992).
Ryynanen et al., J. Med. Genet. 24:462–465, (1987).
Schäfer, K., et al., Kidney International 46:134–152, (1994).
Scheff et al., Ann. Intern. Med. 92:202–204, (1980).
Sipos et al., European J. Biochemistry 213:1333–1340, (1993).
Snarey et al., Am. J. Hum. Genet. (in press), (1994).
Somlo et al., Genomics 13:152–158, (1992).
Somlo, S., et al., J. of the Amer. Soc. of Nephrology 4: 1371–1378, (1993).
Streuli, M., et al., Journal of Experimental Medicine 168:1523–1530, (1988).
Takagi et al., J. Bioch. Chem. 265:19721–19727, (1990).
Taylor, M. E., et al., J. of Biol. Chem. 265:12156–12162, (1990).
Thompson et al., Genomics 13:402–408, (1992).

Volkmer H., et al., Journal of Cell Biology 118:149–161, (1992).
von Heijne, G., Nuc. Acids Res. 14:4683–4691, (1986).
Wieringa, B., et al., Cell 37:915–925, (1984).
Weis et al., Nature 360:127–134, (1992).
Williams, A. F., et al., Annual Review of Immunology 6:381–405 (1988).

Wilson, P. D., et al., Kidney International 39:450–463, (1991).

Wright et al., PCR Protocols: A Guide to Methods and Applications, 153–166, (1990).

Zerres et al., J. Med. Genet. 30:583–588, (1993).

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 5631 base pairs
      (B) TYPE: nucleic acid
      (C) STRANDEDNESS: unknown
      (D) TOPOLOGY: unknown (ii) MOLECULE TYPE: cDNA (vi) ORIGINAL SOURCE:
      (A) ORGANISM: Homo sapiens (ix) FEATURE:
      (A) NAME/KEY: CDS
      (B) LOCATION:1..4842

(ix) FEATURE:
      (A) NAME/KEY: misc_feature
      (B) LOCATION:1..5631
      (D) OTHER INFORMATION:/function= "Original 3' end of the PKD1 gene"

(xi) SEQUENCE DESCRIPTION: SEQ ID NO: 1:

```
CTC AAC GAG GAG CCC CTG ACG CTG GCG GGC GAG GAG ATC GTG GCC CAG        48
Leu Asn Glu Glu Pro Leu Thr Leu Ala Gly Glu Glu Ile Val Ala Gln
 1               5                  10                  15

GGC AAG CGC TCG GAC CCG CGG AGC CTG CTG TGC TAT GGC GGC GCC CCA        96
Gly Lys Arg Ser Asp Pro Arg Ser Leu Leu Cys Tyr Gly Gly Ala Pro
             20                  25                  30

GGG CCT GGC TGC CAC TTC TCC ATC CCC GAG GCT TTC AGC GGG GCC CTG       144
Gly Pro Gly Cys His Phe Ser Ile Pro Glu Ala Phe Ser Gly Ala Leu
         35                  40                  45

GCC AAC CTC AGT GAC GTG GTG CAG CTC ATC TTT CTG GTG GAC TCC AAT       192
Ala Asn Leu Ser Asp Val Val Gln Leu Ile Phe Leu Val Asp Ser Asn
     50                  55                  60

CCC TTT CCC TTT GGC TAT ATC AGC AAC TAC ACC GTC TCC ACC AAG GTG       240
Pro Phe Pro Phe Gly Tyr Ile Ser Asn Tyr Thr Val Ser Thr Lys Val
 65                  70                  75                  80

GCC TCG ATG GCA TTC CAG ACA CAG GCC GGC GCC CAG ATC CCC ATC GAG       288
Ala Ser Met Ala Phe Gln Thr Gln Ala Gly Ala Gln Ile Pro Ile Glu
                 85                  90                  95

CGG CTG GCC TCA GAG CGC GCC ATC ACC GTG AAG GTG CCC AAC AAC TCG       336
Arg Leu Ala Ser Glu Arg Ala Ile Thr Val Lys Val Pro Asn Asn Ser
            100                 105                 110

GAC TGG GCT GCC CGG GGC CAC CGC AGC TCC GCC AAC TCC GCC AAC TCC       384
Asp Trp Ala Ala Arg Gly His Arg Ser Ser Ala Asn Ser Ala Asn Ser
        115                 120                 125

GTT GTG GTC CAG CCC CAG GCC TCC GTC GGT GCT GTG GTC ACC CTG GAC       432
Val Val Val Gln Pro Gln Ala Ser Val Gly Ala Val Val Thr Leu Asp
    130                 135                 140
```

```
AGC AGC AAC CCT GCG GCC GGG CTG CAT CTG CAG CTC AAC TAT ACG CTG        480
Ser Ser Asn Pro Ala Ala Gly Leu His Leu Gln Leu Asn Tyr Thr Leu
145                 150                 155                 160

CTG GAC GGC CAC TAC CTG TCT GAG GAA CCT GAG CCC TAC CTG GCA GTC        528
Leu Asp Gly His Tyr Leu Ser Glu Glu Pro Glu Pro Tyr Leu Ala Val
                    165                 170                 175

TAC CTA CAC TCG GAG CCC CGG CCC AAT GAG CAC AAC TGC TCG GCT AGC        576
Tyr Leu His Ser Glu Pro Arg Pro Asn Glu His Asn Cys Ser Ala Ser
            180                 185                 190

AGG AGG ATC CGC CCA GAG TCA CTC CAG GGT GCT GAC CAC CGG CCC TAC        624
Arg Arg Ile Arg Pro Glu Ser Leu Gln Gly Ala Asp His Arg Pro Tyr
                195                 200                 205

ACC TTC TTC ATT TCC CCG GGG AGC AGA GAC CCA GCG GGG AGT TAC CAT        672
Thr Phe Phe Ile Ser Pro Gly Ser Arg Asp Pro Ala Gly Ser Tyr His
        210                 215                 220

CTG AAC CTC TCC AGC CAC TTC CGC TGG TCG GCG CTG CAG GTG TCC GTG        720
Leu Asn Leu Ser Ser His Phe Arg Trp Ser Ala Leu Gln Val Ser Val
225                 230                 235                 240

GGC CTG TAC ACG TCC CTG TGC CAG TAC TTC AGC GAG GAG GAC ATG GTG        768
Gly Leu Tyr Thr Ser Leu Cys Gln Tyr Phe Ser Glu Glu Asp Met Val
                    245                 250                 255

TGG CGG ACA GAG GGG CTG CTG CCC CTG GAG GAG ACC TCG CCC CGC CAG        816
Trp Arg Thr Glu Gly Leu Leu Pro Leu Glu Glu Thr Ser Pro Arg Gln
            260                 265                 270

GCC GTC TGC CTC ACC CGC CAC CTC ACC GCC TTC GGC GCC AGC CTC TTC        864
Ala Val Cys Leu Thr Arg His Leu Thr Ala Phe Gly Ala Ser Leu Phe
                275                 280                 285

GTG CCC CCA AGC CAT GTC CGC TTT GTG TTT CCT GAG CCG ACA GCG GAT        912
Val Pro Pro Ser His Val Arg Phe Val Phe Pro Glu Pro Thr Ala Asp
        290                 295                 300

GTA AAC TAC ATC GTC ATG CTG ACA TGT GCT GTG TGC CTG GTG ACC TAC        960
Val Asn Tyr Ile Val Met Leu Thr Cys Ala Val Cys Leu Val Thr Tyr
305                 310                 315                 320

ATG GTC ATG GCC GCC ATC CTG CAC AAG CTG GAC CAG TTG GAT GCC AGC       1008
Met Val Met Ala Ala Ile Leu His Lys Leu Asp Gln Leu Asp Ala Ser
                    325                 330                 335

CGG GGC CGC GCC ATC CCT TTC TGT GGG CAG CGG GGC CGC TTC AAG TAC       1056
Arg Gly Arg Ala Ile Pro Phe Cys Gly Gln Arg Gly Arg Phe Lys Tyr
            340                 345                 350

GAG ATC CTC GTC AAG ACA GGC TGG GGC CGG GGC TCA GGT ACC ACG GCC       1104
Glu Ile Leu Val Lys Thr Gly Trp Gly Arg Gly Ser Gly Thr Thr Ala
                355                 360                 365

CAC GTG GGC ATC ATG CTG TAT GGG GTG GAC AGC CGG AGC GGC CAC CGG       1152
His Val Gly Ile Met Leu Tyr Gly Val Asp Ser Arg Ser Gly His Arg
        370                 375                 380

CAC CTG GAC GGC GAC AGA GCC TTC CAC CGC AAC AGC CTG GAC ATC TTC       1200
His Leu Asp Gly Asp Arg Ala Phe His Arg Asn Ser Leu Asp Ile Phe
385                 390                 395                 400

CGG ATC GCC ACC CCG CAC AGC CTG GGT AGC GTG TGG AAG ATC CGA GTG       1248
Arg Ile Ala Thr Pro His Ser Leu Gly Ser Val Trp Lys Ile Arg Val
                    405                 410                 415

TGG CAC GAC AAC AAA GGG CTC AGC CCT GCC TGG TTC CTG CAG CAC GTC       1296
Trp His Asp Asn Lys Gly Leu Ser Pro Ala Trp Phe Leu Gln His Val
            420                 425                 430

ATC GTC AGG GAC CTG CAG ACG GCA CGC AGC GCC TTC TTC CTG GTC AAT       1344
Ile Val Arg Asp Leu Gln Thr Ala Arg Ser Ala Phe Phe Leu Val Asn
                435                 440                 445

GAC TGG CTT TCG GTG GAG ACG GAG GCC AAC GGG GGC CTG GTG GAG AAG       1392
Asp Trp Leu Ser Val Glu Thr Glu Ala Asn Gly Gly Leu Val Glu Lys
        450                 455                 460
```

```
GAG GTG CTG GCC GCG AGC GAC GCA GCC CTT TTG CGC TTC CGG CGC CTG          1440
Glu Val Leu Ala Ala Ser Asp Ala Ala Leu Leu Arg Phe Arg Arg Leu
465                 470                 475                 480

CTG GTG GCT GAG CTG CAG CGT GGC TTC TTT GAC AAG CAC ATC TGG CTC          1488
Leu Val Ala Glu Leu Gln Arg Gly Phe Phe Asp Lys His Ile Trp Leu
                485                 490                 495

TCC ATA TGG GAC CGG CCG CCT CGT AGC CGT TTC ACT CGC ATC CAG AGG          1536
Ser Ile Trp Asp Arg Pro Pro Arg Ser Arg Phe Thr Arg Ile Gln Arg
            500                 505                 510

GCC ACC TGC TGC GTT CTC CTC ATC TGC CTC TTC CTG GGC GCC AAC GCC          1584
Ala Thr Cys Cys Val Leu Leu Ile Cys Leu Phe Leu Gly Ala Asn Ala
        515                 520                 525

GTG TGG TAC GGG GCT GTT GGC GAC TCT GCC TAC AGC ACG GGG CAT GTG          1632
Val Trp Tyr Gly Ala Val Gly Asp Ser Ala Tyr Ser Thr Gly His Val
    530                 535                 540

TCC AGG CTG AGC CCG CTG AGC GTC GAC ACA GTC GCT GTT GGC CTG GTG          1680
Ser Arg Leu Ser Pro Leu Ser Val Asp Thr Val Ala Val Gly Leu Val
545                 550                 555                 560

TCC AGC GTG GTT GTC TAT CCC GTC TAC CTG GCC ATC CTT TTT CTC TTC          1728
Ser Ser Val Val Val Tyr Pro Val Tyr Leu Ala Ile Leu Phe Leu Phe
                565                 570                 575

CGG ATG TCC CGG AGC AAG GTG GCT GGG AGC CCG AGC CCC ACA CCT GCC          1776
Arg Met Ser Arg Ser Lys Val Ala Gly Ser Pro Ser Pro Thr Pro Ala
            580                 585                 590

GGG CAG CAG GTG CTG GAC ATC GAC AGC TGC CTG GAC TCG TCC GTG CTG          1824
Gly Gln Gln Val Leu Asp Ile Asp Ser Cys Leu Asp Ser Ser Val Leu
        595                 600                 605

GAC AGC TCC TTC CTC ACG TTC TCA GGC CTC CAC GCT GAG GCC TTT GTT          1872
Asp Ser Ser Phe Leu Thr Phe Ser Gly Leu His Ala Glu Ala Phe Val
    610                 615                 620

GGA CAG ATG AAG AGT GAC TTG TTT CTG GAT GAT TCT AAG AGT CTG GTG          1920
Gly Gln Met Lys Ser Asp Leu Phe Leu Asp Asp Ser Lys Ser Leu Val
625                 630                 635                 640

TGC TGG CCC TCC GGC GAG GGA ACG CTC AGT TGG CCG GAC CTG CTC AGT          1968
Cys Trp Pro Ser Gly Glu Gly Thr Leu Ser Trp Pro Asp Leu Leu Ser
                645                 650                 655

GAC CCG TCC ATT GTG GGT AGC AAT CTG CGG CAG CTG GCA CGG GGC CAG          2016
Asp Pro Ser Ile Val Gly Ser Asn Leu Arg Gln Leu Ala Arg Gly Gln
            660                 665                 670

GCG GGC CAT GGG CTG GGC CCA GAG GAG GAC GGC TTC TCC CTG GCC AGC          2064
Ala Gly His Gly Leu Gly Pro Glu Glu Asp Gly Phe Ser Leu Ala Ser
        675                 680                 685

CCC TAC TCG CCT GCC AAA TCC TTC TCA GCA TCA GAT GAA GAC CTG ATC          2112
Pro Tyr Ser Pro Ala Lys Ser Phe Ser Ala Ser Asp Glu Asp Leu Ile
    690                 695                 700

CAG CAG GTC CTT GCC GAG GGG GTC AGC AGC CCA GCC CCT ACC CAA GAC          2160
Gln Gln Val Leu Ala Glu Gly Val Ser Ser Pro Ala Pro Thr Gln Asp
705                 710                 715                 720

ACC CAC ATG GAA ACG GAC CTG CTC AGC AGC CTG TCC AGC ACT CCT GGG          2208
Thr His Met Glu Thr Asp Leu Leu Ser Ser Leu Ser Ser Thr Pro Gly
                725                 730                 735

GAG AAG ACA GAG ACG CTG GCG CTG CAG AGG CTG GGG GAG CTG GGG CCA          2256
Glu Lys Thr Glu Thr Leu Ala Leu Gln Arg Leu Gly Glu Leu Gly Pro
            740                 745                 750

CCC AGC CCA GGC CTG AAC TGG GAA CAG CCC CAG GCA GCG AGG CTG TCC          2304
Pro Ser Pro Gly Leu Asn Trp Glu Gln Pro Gln Ala Ala Arg Leu Ser
        755                 760                 765

AGG ACA GGA CTG GTG GAG GGT CTG CGG AAG CGC CTG CTG CCG GCC TGG          2352
Arg Thr Gly Leu Val Glu Gly Leu Arg Lys Arg Leu Leu Pro Ala Trp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 770 |     |     |     |     | 775 |     |     |     |     | 780 |     |     |     |     |      |
| TGT | GCC | TCC | CTG | GCC | CAC | GGG | CTC | AGC | CTG | CTC | CTG | GTG | GCT | GTG | GCT | 2400 |
| Cys | Ala | Ser | Leu | Ala | His | Gly | Leu | Ser | Leu | Leu | Leu | Val | Ala | Val | Ala |      |
| 785 |     |     |     |     | 790 |     |     |     |     | 795 |     |     |     |     | 800 |      |
| GTG | GCT | GTC | TCA | GGG | TGG | GTG | GGT | GCG | AGC | TTC | CCC | CCG | GGC | GTG | AGT | 2448 |
| Val | Ala | Val | Ser | Gly | Trp | Val | Gly | Ala | Ser | Phe | Pro | Pro | Gly | Val | Ser |      |
|     |     |     |     | 805 |     |     |     |     | 810 |     |     |     |     | 815 |     |      |
| GTT | GCG | TGG | CTC | CTG | TCC | AGC | AGC | GCC | AGC | TTC | CTG | GCC | TCA | TTC | CTC | 2496 |
| Val | Ala | Trp | Leu | Leu | Ser | Ser | Ser | Ala | Ser | Phe | Leu | Ala | Ser | Phe | Leu |      |
|     |     |     | 820 |     |     |     |     | 825 |     |     |     |     | 830 |     |     |      |
| GGC | TGG | GAG | CCA | CTG | AAG | GTC | TTG | CTG | GAA | GCC | CTG | TAC | TTC | TCA | CTG | 2544 |
| Gly | Trp | Glu | Pro | Leu | Lys | Val | Leu | Leu | Glu | Ala | Leu | Tyr | Phe | Ser | Leu |      |
|     |     | 835 |     |     |     |     | 840 |     |     |     |     | 845 |     |     |     |      |
| GTG | GCC | AAG | CGG | CTG | CAC | CCG | GAT | GAA | GAT | GAC | ACC | CTG | GTA | GAG | AGC | 2592 |
| Val | Ala | Lys | Arg | Leu | His | Pro | Asp | Glu | Asp | Asp | Thr | Leu | Val | Glu | Ser |      |
| 850 |     |     |     |     | 855 |     |     |     |     | 860 |     |     |     |     |     |      |
| CCG | GCT | GTG | ACG | CCT | GTG | AGC | GCA | CGT | GTG | CCC | CGC | GTA | CGG | CCA | CCC | 2640 |
| Pro | Ala | Val | Thr | Pro | Val | Ser | Ala | Arg | Val | Pro | Arg | Val | Arg | Pro | Pro |      |
| 865 |     |     |     | 870 |     |     |     |     | 875 |     |     |     |     |     | 880 |      |
| CAC | GGC | TTT | GCA | CTC | TTC | CTG | GCC | AAG | GAA | GAA | GCC | CGC | AAG | GTC | AAG | 2688 |
| His | Gly | Phe | Ala | Leu | Phe | Leu | Ala | Lys | Glu | Glu | Ala | Arg | Lys | Val | Lys |      |
|     |     |     |     | 885 |     |     |     |     | 890 |     |     |     |     | 895 |     |      |
| AGG | CTA | CAT | GGC | ATG | CTG | CGG | AGC | CTC | CTG | GTG | TAC | ATG | CTT | TTT | CTG | 2736 |
| Arg | Leu | His | Gly | Met | Leu | Arg | Ser | Leu | Leu | Val | Tyr | Met | Leu | Phe | Leu |      |
|     |     |     | 900 |     |     |     |     | 905 |     |     |     |     | 910 |     |     |      |
| CTG | GTG | ACC | CTG | CTG | GCC | AGC | TAT | GGG | GAT | GCC | TCA | TGC | CAT | GGG | CAC | 2784 |
| Leu | Val | Thr | Leu | Leu | Ala | Ser | Tyr | Gly | Asp | Ala | Ser | Cys | His | Gly | His |      |
|     |     | 915 |     |     |     |     | 920 |     |     |     |     | 925 |     |     |     |      |
| GCC | TAC | CGT | CTG | CAA | AGC | GCC | ATC | AAG | CAG | GAG | CTG | CAC | AGC | CGG | GCC | 2832 |
| Ala | Tyr | Arg | Leu | Gln | Ser | Ala | Ile | Lys | Gln | Glu | Leu | His | Ser | Arg | Ala |      |
| 930 |     |     |     |     | 935 |     |     |     |     | 940 |     |     |     |     |     |      |
| TTC | CTG | GCC | ATC | ACG | CGG | TCT | GAG | GAG | CTC | TGG | CCA | TGG | ATG | GCC | CAC | 2880 |
| Phe | Leu | Ala | Ile | Thr | Arg | Ser | Glu | Glu | Leu | Trp | Pro | Trp | Met | Ala | His |      |
| 945 |     |     |     |     | 950 |     |     |     |     | 955 |     |     |     |     | 960 |      |
| GTG | CTG | CTG | CCC | TAC | GTC | CAC | GGG | AAC | CAG | TCC | AGC | CCA | GAG | CTG | GGG | 2928 |
| Val | Leu | Leu | Pro | Tyr | Val | His | Gly | Asn | Gln | Ser | Ser | Pro | Glu | Leu | Gly |      |
|     |     |     |     | 965 |     |     |     |     | 970 |     |     |     |     | 975 |     |      |
| CCC | CCA | CGG | CTG | CGG | CAG | GTG | CGG | CTG | CAG | GAA | GCA | CTC | TAC | CCA | GAC | 2976 |
| Pro | Pro | Arg | Leu | Arg | Gln | Val | Arg | Leu | Gln | Glu | Ala | Leu | Tyr | Pro | Asp |      |
|     |     |     | 980 |     |     |     |     | 985 |     |     |     |     | 990 |     |     |      |
| CCT | CCC | GGC | CCC | AGG | GTC | CAC | ACG | TGC | TCG | GCC | GCA | GGA | GGC | TTC | AGC | 3024 |
| Pro | Pro | Gly | Pro | Arg | Val | His | Thr | Cys | Ser | Ala | Ala | Gly | Gly | Phe | Ser |      |
|     |     | 995 |     |     |     |     | 1000|     |     |     |     | 1005|     |     |     |      |
| ACC | AGC | GAT | TAC | GAC | GTT | GGC | TGG | GAG | AGT | CCT | CAC | AAT | GGC | TCG | GGG | 3072 |
| Thr | Ser | Asp | Tyr | Asp | Val | Gly | Trp | Glu | Ser | Pro | His | Asn | Gly | Ser | Gly |      |
|     | 1010|     |     |     | 1015|     |     |     |     | 1020|     |     |     |     |     |      |
| ACG | TGG | GCC | TAT | TCA | GCG | CCG | GAT | CTG | CTG | GGG | GCA | TGG | TCC | TGG | GGC | 3120 |
| Thr | Trp | Ala | Tyr | Ser | Ala | Pro | Asp | Leu | Leu | Gly | Ala | Trp | Ser | Trp | Gly |      |
| 1025|     |     |     | 1030|     |     |     |     | 1035|     |     |     |     | 1040|     |      |
| TCC | TGT | GCC | GTG | TAT | GAC | AGC | GGG | GGC | TAC | GTG | CAG | GAG | CTG | GGC | CTG | 3168 |
| Ser | Cys | Ala | Val | Tyr | Asp | Ser | Gly | Gly | Tyr | Val | Gln | Glu | Leu | Gly | Leu |      |
|     |     |     |     | 1045|     |     |     |     | 1050|     |     |     |     | 1055|     |      |
| AGC | CTG | GAG | GAG | AGC | CGC | GAC | CGG | CTG | CGC | TTC | CTG | CAG | CTG | CAC | AAC | 3216 |
| Ser | Leu | Glu | Glu | Ser | Arg | Asp | Arg | Leu | Arg | Phe | Leu | Gln | Leu | His | Asn |      |
|     |     |     | 1060|     |     |     |     | 1065|     |     |     |     | 1070|     |     |      |
| TGG | CTG | GAC | AAC | AGG | AGC | CGC | GCT | GTG | TTC | CTG | GAG | CTC | ACG | CGC | TAC | 3264 |
| Trp | Leu | Asp | Asn | Arg | Ser | Arg | Ala | Val | Phe | Leu | Glu | Leu | Thr | Arg | Tyr |      |
|     |     | 1075|     |     |     |     | 1080|     |     |     |     | 1085|     |     |     |      |
| AGC | CCG | GCC | GTG | GGG | CTG | CAC | GCC | GCC | GTC | ACG | CTG | CGC | CTC | GAG | TTC | 3312 |

```
Ser Pro Ala Val Gly Leu His Ala Ala Val Thr Leu Arg Leu Glu Phe
    1090                1095                1100

CCG GCG GCC GGC CGC GCC CTG GCC GCC CTC AGC GTC CGC CCC TTT GCG      3360
Pro Ala Gly Arg Ala Leu Ala Ala Leu Ser Val Arg Pro Phe Ala
1105                1110                1115                1120

CTG CGC CGC CTC AGC GCG GGC CTC TCG CTG CCT CTG CTC ACC TCG GTG      3408
Leu Arg Arg Leu Ser Ala Gly Leu Ser Leu Pro Leu Leu Thr Ser Val
                1125                1130                1135

TGC CTG CTG CTG TTC GCC GTG CAC TTC GCC GTG GCC GAG GCC CGT ACT      3456
Cys Leu Leu Leu Phe Ala Val His Phe Ala Val Ala Glu Ala Arg Thr
            1140                1145                1150

TGG CAC AGG GAA GGG CGC TGG CGC GTG CTG CGG CTC GGA GCC TGG GCG      3504
Trp His Arg Glu Gly Arg Trp Arg Val Leu Arg Leu Gly Ala Trp Ala
        1155                1160                1165

CGG TGG CTG CTG GTG GCG CTG ACG GCG GCC ACG GCA CTG GTA CGC CTC      3552
Arg Trp Leu Leu Val Ala Leu Thr Ala Ala Thr Ala Leu Val Arg Leu
    1170                1175                1180

GCC CAG CTG GGT GCC GCT GAC CGC CAG TGG ACC CGT TTC GTG CGC GGC      3600
Ala Gln Leu Gly Ala Ala Asp Arg Gln Trp Thr Arg Phe Val Arg Gly
1185                1190                1195                1200

CGC CCG CGC CGC TTC ACT AGC TTC GAC CAG GTG GCG CAC GTG AGC TCC      3648
Arg Pro Arg Arg Phe Thr Ser Phe Asp Gln Val Ala His Val Ser Ser
                1205                1210                1215

GCA GCC CGT GGC CTG GCG GCC TCG CTG CTC TTC CTG CTT TTG GTC AAG      3696
Ala Ala Arg Gly Leu Ala Ala Ser Leu Leu Phe Leu Leu Leu Val Lys
            1220                1225                1230

GCT GCC CAG CAC GTA CGC TTC GTG CGC CAG TGG TCC GTC TTT GGC AAG      3744
Ala Ala Gln His Val Arg Phe Val Arg Gln Trp Ser Val Phe Gly Lys
        1235                1240                1245

ACA TTA TGC CGA GCT CTG CCA GAG CTC CTG GGG GTC ACC TTG GGC CTG      3792
Thr Leu Cys Arg Ala Leu Pro Glu Leu Leu Gly Val Thr Leu Gly Leu
    1250                1255                1260

GTG GTG CTC GGG GTA GCC TAC GCC CAG CTG GCC ATC CTG CTC GTG TCT      3840
Val Val Leu Gly Val Ala Tyr Ala Gln Leu Ala Ile Leu Leu Val Ser
1265                1270                1275                1280

TCC TGT GTG GAC TCC CTC TGG AGC GTG GCC CAG GCC CTG TTG GTG CTG      3888
Ser Cys Val Asp Ser Leu Trp Ser Val Ala Gln Ala Leu Leu Val Leu
                1285                1290                1295

TGC CCT GGG ACT GGG CTC TCT ACC CTG TGT CCT GCC GAG TCC TGG CAC      3936
Cys Pro Gly Thr Gly Leu Ser Thr Leu Cys Pro Ala Glu Ser Trp His
            1300                1305                1310

CTG TCA CCC CTG CTG TGT GTG GGG CTC TGG GCA CTG CGG CTG TGG GGC      3984
Leu Ser Pro Leu Leu Cys Val Gly Leu Trp Ala Leu Arg Leu Trp Gly
        1315                1320                1325

GCC CTA CGG CTG GGG GCT GTT ATT CTC CGC TGG CGC TAC CAC GCC TTG      4032
Ala Leu Arg Leu Gly Ala Val Ile Leu Arg Trp Arg Tyr His Ala Leu
    1330                1335                1340

CGT GGA GAG CTG TAC CGG CCG GCC TGG GAG CCC CAG GAC TAC GAG ATG      4080
Arg Gly Glu Leu Tyr Arg Pro Ala Trp Glu Pro Gln Asp Tyr Glu Met
1345                1350                1355                1360

GTG GAG TTG TTC CTG CGC AGG CTG CGC CTC TGG ATG GGC CTC AGC AAG      4128
Val Glu Leu Phe Leu Arg Arg Leu Arg Leu Trp Met Gly Leu Ser Lys
                1365                1370                1375

GTC AAG GAG TTC CGC CAC AAA GTC CGC TTT GAA GGG ATG GAG CCG CTG      4176
Val Lys Glu Phe Arg His Lys Val Arg Phe Glu Gly Met Glu Pro Leu
            1380                1385                1390

CCC TCT CGC TCC TCC AGG GGC TCC AAG GTA TCC CCG GAT GTG CCC CCA      4224
Pro Ser Arg Ser Ser Arg Gly Ser Lys Val Ser Pro Asp Val Pro Pro
        1395                1400                1405
```

| | |
|---|---:|
| CCC AGC GCT GGC TCC GAT GCC TCG CAC CCC TCC ACC TCC TCC AGC CAG<br>Pro Ser Ala Gly Ser Asp Ala Ser His Pro Ser Thr Ser Ser Ser Gln<br>    1410                    1415                  1420 | 4272 |
| CTG GAT GGG CTG AGC GTG AGC CTG GGC CGG CTG GGA ACA AGG TGT GAG<br>Leu Asp Gly Leu Ser Val Ser Leu Gly Arg Leu Gly Thr Arg Cys Glu<br>1425                  1430                  1435                  1440 | 4320 |
| CCT GAG CCC TCC CGC CTC CAA GCC GTG TTC GAG GCC CTG CTC ACC CAG<br>Pro Glu Pro Ser Arg Leu Gln Ala Val Phe Glu Ala Leu Leu Thr Gln<br>                  1445                  1450                  1455 | 4368 |
| TTT GAC CGA CTC AAC CAG GCC ACA GAG GAC GTC TAC CAG CTG GAG CAG<br>Phe Asp Arg Leu Asn Gln Ala Thr Glu Asp Val Tyr Gln Leu Glu Gln<br>                  1460                  1465                  1470 | 4416 |
| CAG CTG CAC AGC CTG CAA GGC CGC AGG AGC AGC CGG GCG CCC GCC GGA<br>Gln Leu His Ser Leu Gln Gly Arg Arg Ser Ser Arg Ala Pro Ala Gly<br>        1475                  1480                  1485 | 4464 |
| TCT TCC CGT GGC CCA TCC CCG GGC CTG CGG CCA GCA CTG CCC AGC CGC<br>Ser Ser Arg Gly Pro Ser Pro Gly Leu Arg Pro Ala Leu Pro Ser Arg<br>        1490                  1495                  1500 | 4512 |
| CTT GCC CGG GCC AGT CGG GGT GTG GAC CTG GCC ACT GGC CCC AGC AGG<br>Leu Ala Arg Ala Ser Arg Gly Val Asp Leu Ala Thr Gly Pro Ser Arg<br>1505                  1510                  1515                  1520 | 4560 |
| ACA CCT TCG GGC CAA GAA CAA GGT CCA CCC CAG CAG CAC TTA GTC CTC<br>Thr Pro Ser Gly Gln Glu Gln Gly Pro Pro Gln Gln His Leu Val Leu<br>                  1525                  1530                  1535 | 4608 |
| CTT CCT GGC GGG GGT GGG CCG TGG AGT CGG AGT GGA CAC CGC TCA GTA<br>Leu Pro Gly Gly Gly Gly Pro Trp Ser Arg Ser Gly His Arg Ser Val<br>        1540                  1545                  1550 | 4656 |
| TTA CTT TCT GCC GCT GTC AAG GCC GAG GGC CAG GCA GAA TGG CTG CAC<br>Leu Leu Ser Ala Ala Val Lys Ala Glu Gly Gln Ala Glu Trp Leu His<br>                1555                  1560                  1565 | 4704 |
| GTA GGT TCC CCA GAG AGC AGG CAG GGG CAT CTG TCT GTC TGT GGG CTT<br>Val Gly Ser Pro Glu Ser Arg Gln Gly His Leu Ser Val Cys Gly Leu<br>    1570                  1575                  1580 | 4752 |
| CAG CAC TTT AAA GAG GCT GTG TGG CCA ACC AGG ACC CAG GGT CCC CTC<br>Gln His Phe Lys Glu Ala Val Trp Pro Thr Arg Thr Gln Gly Pro Leu<br>1585                  1590                  1595                  1600 | 4800 |
| CCC AGC TCC CTT GGG AAG GAC ACA GCA GTA TTG GAC GGT TTC<br>Pro Ser Ser Leu Gly Lys Asp Thr Ala Val Leu Asp Gly Phe<br>                  1605                  1610 | 4842 |
| TAGCCTCTGA GATGCTAATT TATTTCCCCG AGTCCTCAGG TACAGCGGGC TGTGCCCGGC | 4902 |
| CCCACCCCCT GGGCAGATGT CCCCCACTGC TAAGGCTGCT GGCTTCAGGG AGGGTTAGCC | 4962 |
| TGCACCGCCG CCACCCTGCC CCTAAGTTAT TACCTCTCCA GTTCCTACCG TACTCCCTGC | 5022 |
| ACCGTCTCAC TGTGTGTCTC GTGTCAGTAA TTTATATGGT GTTAAAATGT GTATATTTTT | 5082 |
| GTATGTCACT ATTTTCACTA GGGCTGAGGG GCCTGCGCCC AGAGCTGGCC TCCCCCAACA | 5142 |
| CCTGCTGCGC TTGGTAGGTG TGGTGGCGTT ATGGCAGCCC GGCTGCTGCT TGGATGCGAG | 5202 |
| CTTGGCCTTG GGCCGGTGCT GGGGGCACAG CTGTCTGCCA GGCACTCTCA TCACCCCAGA | 5262 |
| GGCCTTGTCA TCCTCCCTTG CCCCAGGCCA GGTAGCAAGA GAGCAGCGCC CAGGCCTGCT | 5322 |
| GGCATCAGGT CTGGGCAAGT AGCAGGACTA GGCATGTCAG AGGACCCCAG GGTGGTTAGA | 5382 |
| GGAAAAGACT CCTCCTGGGG GCTGGCTCCC AGGGTGGAGG AAGGTGACTG TGTGTGTGTG | 5442 |
| TGTGTGCGCG CGCGACGCGC GAGTGTGCTG TATGGCCCAG GCAGCCTCAA GGCCCTCGGA | 5502 |
| GCTGGCTGTG CCTGCTTCTG TGTACCACTT CTGTGGGCAT GGCCGCTTCT AGAGCCTCGA | 5562 |
| CACCCCCCCA ACCCCCGCAC CAAGCAGACA AAGTCAATAA AAGAGCTGTC TGACTGCAAA | 5622 |
| AAAAAAAAA | 5631 |

(2) INFORMATION FOR SEQ ID NO: 2:

(i) SEQUENCE CHARACTERISTICS:
        (A) LENGTH: 1614 amino acids
        (B) TYPE: amino acid
        (D) TOPOLOGY: linear (ii) MOLECULE TYPE: protein (xi) SEQUENCE DESCRIPTION: SEQ ID NO: 2:

```
Leu Asn Glu Glu Pro Leu Thr Leu Ala Gly Glu Glu Ile Val Ala Gln
 1               5                  10                  15

Gly Lys Arg Ser Asp Pro Arg Ser Leu Leu Cys Tyr Gly Gly Ala Pro
             20                  25                  30

Gly Pro Gly Cys His Phe Ser Ile Pro Glu Ala Phe Ser Gly Ala Leu
         35                  40                  45

Ala Asn Leu Ser Asp Val Val Gln Leu Ile Phe Leu Val Asp Ser Asn
     50                  55                  60

Pro Phe Pro Phe Gly Tyr Ile Ser Asn Tyr Thr Val Ser Thr Lys Val
 65                  70                  75                  80

Ala Ser Met Ala Phe Gln Thr Gln Ala Gly Ala Gln Ile Pro Ile Glu
             85                  90                  95

Arg Leu Ala Ser Glu Arg Ala Ile Thr Val Lys Val Pro Asn Asn Ser
            100                 105                 110

Asp Trp Ala Ala Arg Gly His Arg Ser Ser Ala Asn Ser Ala Asn Ser
        115                 120                 125

Val Val Val Gln Pro Gln Ala Ser Val Gly Ala Val Thr Leu Asp
    130                 135                 140

Ser Ser Asn Pro Ala Ala Gly Leu His Leu Gln Leu Asn Tyr Thr Leu
145                 150                 155                 160

Leu Asp Gly His Tyr Leu Ser Glu Glu Pro Glu Pro Tyr Leu Ala Val
                165                 170                 175

Tyr Leu His Ser Glu Pro Arg Pro Asn Glu His Asn Cys Ser Ala Ser
            180                 185                 190

Arg Arg Ile Arg Pro Glu Ser Leu Gln Gly Ala Asp His Arg Pro Tyr
        195                 200                 205

Thr Phe Phe Ile Ser Pro Gly Ser Arg Asp Pro Ala Gly Ser Tyr His
    210                 215                 220

Leu Asn Leu Ser Ser His Phe Arg Trp Ser Ala Leu Gln Val Ser Val
225                 230                 235                 240

Gly Leu Tyr Thr Ser Leu Cys Gln Tyr Phe Ser Glu Glu Asp Met Val
                245                 250                 255

Trp Arg Thr Glu Gly Leu Leu Pro Leu Glu Glu Thr Ser Pro Arg Gln
            260                 265                 270

Ala Val Cys Leu Thr Arg His Leu Thr Ala Phe Gly Ala Ser Leu Phe
        275                 280                 285

Val Pro Pro Ser His Val Arg Phe Val Phe Pro Glu Pro Thr Ala Asp
    290                 295                 300

Val Asn Tyr Ile Val Met Leu Thr Cys Ala Val Cys Leu Val Thr Tyr
305                 310                 315                 320

Met Val Met Ala Ala Ile Leu His Lys Leu Asp Gln Leu Asp Ala Ser
                325                 330                 335

Arg Gly Arg Ala Ile Pro Phe Cys Gly Gln Arg Gly Arg Phe Lys Tyr
            340                 345                 350
```

```
Glu Ile Leu Val Lys Thr Gly Trp Gly Arg Gly Ser Gly Thr Thr Ala
            355                 360                 365

His Val Gly Ile Met Leu Tyr Gly Val Asp Ser Arg Ser Gly His Arg
        370                 375                 380

His Leu Asp Gly Asp Arg Ala Phe His Arg Asn Ser Leu Asp Ile Phe
385                 390                 395                 400

Arg Ile Ala Thr Pro His Ser Leu Gly Ser Val Trp Lys Ile Arg Val
                405                 410                 415

Trp His Asp Asn Lys Gly Leu Ser Pro Ala Trp Phe Leu Gln His Val
            420                 425                 430

Ile Val Arg Asp Leu Gln Thr Ala Arg Ser Ala Phe Phe Leu Val Asn
        435                 440                 445

Asp Trp Leu Ser Val Glu Thr Glu Ala Asn Gly Gly Leu Val Glu Lys
450                 455                 460

Glu Val Leu Ala Ala Ser Asp Ala Ala Leu Leu Arg Phe Arg Arg Leu
465                 470                 475                 480

Leu Val Ala Glu Leu Gln Arg Gly Phe Phe Asp Lys His Ile Trp Leu
                485                 490                 495

Ser Ile Trp Asp Arg Pro Arg Ser Arg Phe Thr Arg Ile Gln Arg
            500                 505                 510

Ala Thr Cys Cys Val Leu Leu Ile Cys Leu Phe Leu Gly Ala Asn Ala
        515                 520                 525

Val Trp Tyr Gly Ala Val Gly Asp Ser Ala Tyr Ser Thr Gly His Val
        530                 535                 540

Ser Arg Leu Ser Pro Leu Ser Val Asp Thr Val Ala Val Gly Leu Val
545                 550                 555                 560

Ser Ser Val Val Val Tyr Pro Val Tyr Leu Ala Ile Leu Phe Leu Phe
                565                 570                 575

Arg Met Ser Arg Ser Lys Val Ala Gly Ser Pro Ser Pro Thr Pro Ala
            580                 585                 590

Gly Gln Gln Val Leu Asp Ile Asp Ser Cys Leu Asp Ser Ser Val Leu
        595                 600                 605

Asp Ser Ser Phe Leu Thr Phe Ser Gly Leu His Ala Glu Ala Phe Val
        610                 615                 620

Gly Gln Met Lys Ser Asp Leu Phe Leu Asp Asp Ser Lys Ser Leu Val
625                 630                 635                 640

Cys Trp Pro Ser Gly Glu Gly Thr Leu Ser Trp Pro Asp Leu Leu Ser
                645                 650                 655

Asp Pro Ser Ile Val Gly Ser Asn Leu Arg Gln Leu Ala Arg Gly Gln
            660                 665                 670

Ala Gly His Gly Leu Gly Pro Glu Glu Asp Gly Phe Ser Leu Ala Ser
        675                 680                 685

Pro Tyr Ser Pro Ala Lys Ser Phe Ser Ala Ser Asp Glu Asp Leu Ile
        690                 695                 700

Gln Gln Val Leu Ala Glu Gly Val Ser Ser Pro Ala Pro Thr Gln Asp
705                 710                 715                 720

Thr His Met Glu Thr Asp Leu Leu Ser Ser Leu Ser Ser Thr Pro Gly
                725                 730                 735

Glu Lys Thr Glu Thr Leu Ala Leu Gln Arg Leu Gly Leu Gly Pro
            740                 745                 750

Pro Ser Pro Gly Leu Asn Trp Glu Gln Pro Gln Ala Ala Arg Leu Ser
        755                 760                 765

Arg Thr Gly Leu Val Glu Gly Leu Arg Lys Arg Leu Leu Pro Ala Trp
```

```
        770             775             780
Cys Ala Ser Leu Ala His Gly Leu Ser Leu Leu Val Ala Val Ala
785             790             795             800

Val Ala Val Ser Gly Trp Val Gly Ala Ser Phe Pro Gly Val Ser
            805             810             815

Val Ala Trp Leu Leu Ser Ser Ala Ser Phe Leu Ala Ser Phe Leu
            820             825             830

Gly Trp Glu Pro Leu Lys Val Leu Glu Ala Leu Tyr Phe Ser Leu
            835             840             845

Val Ala Lys Arg Leu His Pro Asp Glu Asp Thr Leu Val Glu Ser
850             855             860

Pro Ala Val Thr Pro Val Ser Ala Arg Val Pro Arg Val Arg Pro Pro
865             870             875             880

His Gly Phe Ala Leu Phe Leu Ala Lys Glu Glu Ala Arg Lys Val Lys
            885             890             895

Arg Leu His Gly Met Leu Arg Ser Leu Leu Val Tyr Met Leu Phe Leu
            900             905             910

Leu Val Thr Leu Leu Ala Ser Tyr Gly Asp Ala Ser Cys His Gly His
    915             920             925

Ala Tyr Arg Leu Gln Ser Ala Ile Lys Gln Glu Leu His Ser Arg Ala
930             935             940

Phe Leu Ala Ile Thr Arg Ser Glu Glu Leu Trp Pro Trp Met Ala His
945             950             955             960

Val Leu Leu Pro Tyr Val His Gly Asn Gln Ser Ser Pro Glu Leu Gly
            965             970             975

Pro Pro Arg Leu Arg Gln Val Arg Leu Gln Glu Ala Leu Tyr Pro Asp
            980             985             990

Pro Pro Gly Pro Arg Val His Thr Cys Ser Ala Ala Gly Gly Phe Ser
    995             1000            1005

Thr Ser Asp Tyr Asp Val Gly Trp Glu Ser Pro His Asn Gly Ser Gly
    1010            1015            1020

Thr Trp Ala Tyr Ser Ala Pro Asp Leu Leu Gly Ala Trp Ser Trp Gly
1025            1030            1035            1040

Ser Cys Ala Val Tyr Asp Ser Gly Gly Tyr Val Gln Glu Leu Gly Leu
            1045            1050            1055

Ser Leu Glu Glu Ser Arg Asp Arg Leu Arg Phe Leu Gln Leu His Asn
            1060            1065            1070

Trp Leu Asp Asn Arg Ser Arg Ala Val Phe Leu Glu Leu Thr Arg Tyr
            1075            1080            1085

Ser Pro Ala Val Gly Leu His Ala Ala Val Thr Leu Arg Leu Glu Phe
            1090            1095            1100

Pro Ala Ala Gly Arg Ala Leu Ala Ala Leu Ser Val Arg Pro Phe Ala
1105            1110            1115            1120

Leu Arg Arg Leu Ser Ala Gly Leu Ser Leu Pro Leu Leu Thr Ser Val
            1125            1130            1135

Cys Leu Leu Leu Phe Ala Val His Phe Ala Val Ala Glu Ala Arg Thr
            1140            1145            1150

Trp His Arg Glu Gly Arg Trp Arg Val Leu Arg Leu Gly Ala Trp Ala
            1155            1160            1165

Arg Trp Leu Leu Val Ala Leu Thr Ala Ala Thr Ala Leu Val Arg Leu
            1170            1175            1180

Ala Gln Leu Gly Ala Ala Asp Arg Gln Trp Thr Arg Phe Val Arg Gly
1185            1190            1195            1200
```

-continued

```
Arg Pro Arg Arg Phe Thr Ser Phe Asp Gln Val Ala His Val Ser Ser
            1205                1210                1215
Ala Ala Arg Gly Leu Ala Ala Ser Leu Leu Phe Leu Leu Leu Val Lys
            1220                1225                1230
Ala Ala Gln His Val Arg Phe Val Arg Gln Trp Ser Val Phe Gly Lys
            1235                1240                1245
Thr Leu Cys Arg Ala Leu Pro Glu Leu Leu Gly Val Thr Leu Gly Leu
            1250                1255                1260
Val Val Leu Gly Val Ala Tyr Ala Gln Leu Ala Ile Leu Leu Val Ser
1265                1270                1275                1280
Ser Cys Val Asp Ser Leu Trp Ser Val Ala Gln Ala Leu Leu Val Leu
            1285                1290                1295
Cys Pro Gly Thr Gly Leu Ser Thr Leu Cys Pro Ala Glu Ser Trp His
            1300                1305                1310
Leu Ser Pro Leu Leu Cys Val Gly Leu Trp Ala Leu Arg Leu Trp Gly
            1315                1320                1325
Ala Leu Arg Leu Gly Ala Val Ile Leu Arg Trp Arg Tyr His Ala Leu
            1330                1335                1340
Arg Gly Glu Leu Tyr Arg Pro Ala Trp Glu Pro Gln Asp Tyr Glu Met
1345                1350                1355                1360
Val Glu Leu Phe Leu Arg Arg Leu Arg Leu Trp Met Gly Leu Ser Lys
            1365                1370                1375
Val Lys Glu Phe Arg His Lys Val Arg Phe Glu Gly Met Glu Pro Leu
            1380                1385                1390
Pro Ser Arg Ser Ser Arg Gly Ser Lys Val Ser Pro Asp Val Pro Pro
            1395                1400                1405
Pro Ser Ala Gly Ser Asp Ala Ser His Pro Ser Thr Ser Ser Ser Gln
            1410                1415                1420
Leu Asp Gly Leu Ser Val Ser Leu Gly Arg Leu Gly Thr Arg Cys Glu
1425                1430                1435                1440
Pro Glu Pro Ser Arg Leu Gln Ala Val Phe Glu Ala Leu Leu Thr Gln
            1445                1450                1455
Phe Asp Arg Leu Asn Gln Ala Thr Glu Asp Val Tyr Gln Leu Glu Gln
            1460                1465                1470
Gln Leu His Ser Leu Gln Gly Arg Arg Ser Ser Arg Ala Pro Ala Gly
            1475                1480                1485
Ser Ser Arg Gly Pro Ser Pro Gly Leu Arg Pro Ala Leu Pro Ser Arg
            1490                1495                1500
Leu Ala Arg Ala Ser Arg Gly Val Asp Leu Ala Thr Gly Pro Ser Arg
1505                1510                1515                1520
Thr Pro Ser Gly Gln Glu Gln Gly Pro Pro Gln Gln His Leu Val Leu
            1525                1530                1535
Leu Pro Gly Gly Gly Pro Trp Ser Arg Ser Gly His Arg Ser Val
            1540                1545                1550
Leu Leu Ser Ala Ala Val Lys Ala Glu Gly Gln Ala Glu Trp Leu His
            1555                1560                1565
Val Gly Ser Pro Glu Ser Arg Gln Gly His Leu Ser Val Cys Gly Leu
            1570                1575                1580
Gln His Phe Lys Glu Ala Val Trp Pro Thr Arg Thr Gln Gly Pro Leu
1585                1590                1595                1600
Pro Ser Ser Leu Gly Lys Asp Thr Ala Val Leu Asp Gly Phe
            1605                1610
```

(2) INFORMATION FOR SEQ ID NO: 3:

(i) SEQUENCE CHARACTERISTICS:
        (A) LENGTH: 553 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..533
        (D) OTHER INFORMATION:/function= "1A1 H.6 probe"

(xi) SEQUENCE DESCRIPTION: SEQ ID NO: 3:

```
AGCTTGGCAC CATCAAGGGC CAGTTCAACT TTGTCCACGT GATCGTCACC CCGCTGGACT      60

ACGAGTGCAA CCTGGTGTCC CTGCAGTGCA GGAAAGACAT GGAGGGCCTT GTGGACACCA     120

GCGTGGCCAA GATCGTGTCT GACCGCAACC TGCCCTTCGT GGCCCGCCAG ATGGCCCTGC     180

ACGCAAATAT GGCCTCACAG GTGCATCATA GCCGCTCCAA CCCCACCGAT ATCTACCCCT     240

CCAAGTGGAT TGCCCGGCTC CGCCACATCA AGCGGCTCCG CCAGCGGATC TGCGAGGAAG     300

CCGCCTACTC CAACCCCAGC CTACCTCTGG TGCACCCTCC GTCCCATAGC AAAGCCCCTG     360

CACAGACTCC AGCCGAGCCC ACACCTGGCT ATGAGGTGGG CCAGCGGAAG CGCCTCATCT     420

CCTCGGTGGA GGACTTCACC GAGTTTGTGT GAGGCCGGGG CCCTCCCTCC TGCACTGGCC     480

TTGGACGGTA TTGCCTGTCA GTGAAATAAA TAAAGTCCTG ACCCCAGTGC ACAGACATAG     540

AGGCACAGAT TGC                                                        553
```

(2) INFORMATION FOR SEQ ID NO: 4:

(i) SEQUENCE CHARACTERISTICS:
        (A) LENGTH: 517 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION:1..517
        (D) OTHER INFORMATION:/function= "CW10 probe"

(xi) SEQUENCE DESCRIPTION: SEQ ID NO: 4:

```
CTGGTGTGTG TGAGACGTGC GGGGCTGGGA AGTGTTGGCA GAGCCGCGAG TACCGTCCTC      60

ACTCCTTTTG TTCTTTTGAC GTAAGCTGGC GAGTGGCACT GCCTGAGTTC CGCTCAGTGC     120

CCGCCCTGAT GTGCGGACCC CGCTGCATTC TTGCTGTTAG GTGGTGGCGG TGTGCGCTGT     180

CGCTGGTGGG CACCGAGAGT CTTTGGGAGC TTTGGGGAGG TTGTGCCAAG CCTGAGCCTC     240

GACGTCCCCC TTCCCGGCTT TCTGTTGGCT CTTCTGAGGC CAGGGCATCT CTATGAGGGC     300

CTCCTGCTGG AGCCGTCTCT GTGGATCTCC TCTGCCATCC TGGCCCATGA GTGGGTGATG     360

CGCTGGCCAC CATCTGGTGA CAGTGGCCGG GCACCGCTGC CAAATGTGGG TCCCGCATCT     420

GCAAGCCCCT CCCTGGGTCC CCTAGGGTAT GGGGTGGTTC TGCCACTGCC CTCGCTCCCC     480

CACCTTGGGG TGCCTCTCCC CCTGCTCGTG GGGGAGA                              517
```

```
(2) INFORMATION FOR SEQ ID NO: 5:

(i) SEQUENCE CHARACTERISTICS:
        (A) LENGTH: 13807 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION:2..13018

(ix) FEATURE:
        (A) NAME/KEY: misc_feature
        (B) LOCATION:7295..8184
        (D) OTHER INFORMATION:/function= "g alpha 22 fragment"

(ix) FEATURE:
        (A) NAME/KEY: misc_feature
        (B) LOCATION:6422..7294
        (D) OTHER INFORMATION:/function= "GAP GAMMA PETER fragment"

(ix) FEATURE:
        (A) NAME/KEY: misc_feature
        (B) LOCATION:3697..6421
        (D) OTHER INFORMATION:/function= "JH8 fragment"

(ix) FEATURE:
        (A) NAME/KEY: misc_feature
        (B) LOCATION:1373..1701
        (D) OTHER INFORMATION:/function= "S3/S4 PETER fragment"

(ix) FEATURE:
        (A) NAME/KEY: misc_feature
        (B) LOCATION:2176..2962
        (D) OTHER INFORMATION:/function= "S3/S4 CON2 PETER fragment"

(ix) FEATURE:
        (A) NAME/KEY: misc_feature
        (B) LOCATION:2963..3696
        (D) OTHER INFORMATION:/function= "S1/S3 PETER fragment"

(ix) FEATURE:
        (A) NAME/KEY: misc_feature
        (B) LOCATION:118..1372
        (D) OTHER INFORMATION:/function= "S4/JH13 fragment"

(ix) FEATURE:
        (A) NAME/KEY: misc_feature
        (B) LOCATION:1..85
        (D) OTHER INFORMATION:/function= "5' COMPLETE [Split]
            fragment"

(ix) FEATURE:
        (A) NAME/KEY: misc_feature
        (B) LOCATION:87..3696
        (D) OTHER INFORMATION:/function= "5' COMPLETE [Split]
            fragment"

(ix) FEATURE:
        (A) NAME/KEY: misc_feature
        (B) LOCATION:1..85
        (D) OTHER INFORMATION:/function= "6 (5) R cDNA [Split]
            fragment"

(ix) FEATURE:
        (A) NAME/KEY: misc_feature
        (B) LOCATION:87..117
        (D) OTHER INFORMATION:/product= "6 (5) R cDNA [Split]
            fragment"

(xi) SEQUENCE DESCRIPTION: SEQ ID NO: 5:
```

```
C GGC GCC GCC TGC CGC GTC AAC TGC TCG GGC CGC GGG CTG CGG ACG        46
  Gly Ala Ala Cys Arg Val Asn Cys Ser Gly Arg Gly Leu Arg Thr
  1615            1620                1625

CTC GGT CCC GCG CTG CGC ATC CCC GCG GAC GCC ACA GCG CTA GAC GTC      94
Leu Gly Pro Ala Leu Arg Ile Pro Ala Asp Ala Thr Ala Leu Asp Val
1630            1635             1640            1645

TCC CAC AAC CTG CTC CGG GCG CTG GAC GTT GGG CTC CTG GCG AAC CTC     142
Ser His Asn Leu Leu Arg Ala Leu Asp Val Gly Leu Leu Ala Asn Leu
                1650            1655            1660

TCG GCG CTG GCA GAG CTG GAT ATA AGC AAC AAC AAG ATT TCT ACG TTA     190
Ser Ala Leu Ala Glu Leu Asp Ile Ser Asn Asn Lys Ile Ser Thr Leu
                1665            1670            1675

GAA GAA GGA ATA TTT GCT AAT TTA TTT AAT TTA AGT GAA ATA AAC CTG     238
Glu Glu Gly Ile Phe Ala Asn Leu Phe Asn Leu Ser Glu Ile Asn Leu
            1680            1685            1690

AGT GGG AAC CCG TTT GAG TGT GAC TGT GGC CTG GCG TGG CTG CCG CGA     286
Ser Gly Asn Pro Phe Glu Cys Asp Cys Gly Leu Ala Trp Leu Pro Arg
        1695            1700            1705

TGG GCG GAG GAG CAG CAG GTG CGG GTG GTG CAG CCC GAG GCA GCC ACG     334
Trp Ala Glu Glu Gln Gln Val Arg Val Val Gln Pro Glu Ala Ala Thr
1710            1715            1720            1725

TGT GCT GGG CCT GGC TCC CTG GCT GGC CAG CCT CTG CTT GGC ATC CCC     382
Cys Ala Gly Pro Gly Ser Leu Ala Gly Gln Pro Leu Leu Gly Ile Pro
                1730            1735            1740

TTG CTG GAC AGT GGC TGT GGT GAG GAG TAT GTC GCC TGC CTC CCT GAC     430
Leu Leu Asp Ser Gly Cys Gly Glu Glu Tyr Val Ala Cys Leu Pro Asp
                1745            1750            1755

AAC AGC TCA GGC ACC GTG GCA GCA GTG TCC TTT TCA GCT GCC CAC GAA     478
Asn Ser Ser Gly Thr Val Ala Ala Val Ser Phe Ser Ala Ala His Glu
                1760            1765            1770

GGC CTG CTT CAG CCA GAG GCC TGC AGC GCC TTC TGC TTC TCC ACC GGC     526
Gly Leu Leu Gln Pro Glu Ala Cys Ser Ala Phe Cys Phe Ser Thr Gly
        1775            1780            1785

CAG GGC CTC GCA GCC CTC TCG GAG CAG GGC TGG TGC CTG TGT GGG GCG     574
Gln Gly Leu Ala Ala Leu Ser Glu Gln Gly Trp Cys Leu Cys Gly Ala
1790            1795            1800            1805

GCC CAG CCC TCC AGT GCC TCC TTT GCC TGC CTG TCC CTC TGC TCC GGC     622
Ala Gln Pro Ser Ser Ala Ser Phe Ala Cys Leu Ser Leu Cys Ser Gly
                1810            1815            1820

CCC CCG CCA CCT CCT GCC CCC ACC TGT AGG GGC CCC ACC CTC CTC CAG     670
Pro Pro Pro Pro Pro Ala Pro Thr Cys Arg Gly Pro Thr Leu Leu Gln
            1825            1830            1835

CAC GTC TTC CCT GCC TCC CCA GGG GCC ACC CTG GTG GGG CCC CAC GGA     718
His Val Phe Pro Ala Ser Pro Gly Ala Thr Leu Val Gly Pro His Gly
            1840            1845            1850

CCT CTG GCC TCT GGC CAG CTA GCA GCC TTC CAC ATC GCT GCC CCG CTC     766
Pro Leu Ala Ser Gly Gln Leu Ala Ala Phe His Ile Ala Ala Pro Leu
    1855            1860            1865

CCT GTC ACT GCC ACA CGC TGG GAC TTC GGA GAC GGC TCC GCC GAG GTG     814
Pro Val Thr Ala Thr Arg Trp Asp Phe Gly Asp Gly Ser Ala Glu Val
1870            1875            1880            1885

GAT GCC GCT GGG CCG GCT GCC TCG CAT CGC TAT GTG CTG CCT GGG CGC     862
Asp Ala Ala Gly Pro Ala Ala Ser His Arg Tyr Val Leu Pro Gly Arg
                1890            1895            1900

TAT CAC GTG ACG GCC GTG CTG GCC CTG GGG GCC GGC TCA GCC CTG CTG     910
Tyr His Val Thr Ala Val Leu Ala Leu Gly Ala Gly Ser Ala Leu Leu
                1905            1910            1915

GGG ACA GAC GTG CAG GTG GAA GCG GCA CCT GCC GCC CTG GAG CTC GTG     958
Gly Thr Asp Val Gln Val Glu Ala Ala Pro Ala Ala Leu Glu Leu Val
```

-continued

```
             1920                1925                1930
TGC CCG TCC TCG GTG CAG AGT GAC GAG AGC CTT GAC CTC AGC ATC CAG      1006
Cys Pro Ser Ser Val Gln Ser Asp Glu Ser Leu Asp Leu Ser Ile Gln
        1935                1940                1945

AAC CGC GGT GGT TCA GGC CTG GAG GCC GCC TAC AGC ATC GTG GCC CTG      1054
Asn Arg Gly Gly Ser Gly Leu Glu Ala Ala Tyr Ser Ile Val Ala Leu
1950                1955                1960                1965

GGC GAG GAG CCG GCC CGA GCG GTG CAC CCG CTC TGC CCC TCG GAC ACG      1102
Gly Glu Glu Pro Ala Arg Ala Val His Pro Leu Cys Pro Ser Asp Thr
        1970                1975                1980

GAG ATC TTC CCT GGC AAC GGG CAC TGC TAC CGC CTG GTG GTG GAG AAG      1150
Glu Ile Phe Pro Gly Asn Gly His Cys Tyr Arg Leu Val Val Glu Lys
        1985                1990                1995

GCG GCC TGG CTG CAG GCG CAG GAG CAG TGT CAG GCC TGG GCC GGG GCC      1198
Ala Ala Trp Leu Gln Ala Gln Glu Gln Cys Gln Ala Trp Ala Gly Ala
        2000                2005                2010

GCC CTG GCA ATG GTG GAC AGT CCC GCC GTG CAG CGC TTC CTG GTC TCC      1246
Ala Leu Ala Met Val Asp Ser Pro Ala Val Gln Arg Phe Leu Val Ser
        2015                2020                2025

CGG GTC ACC AGG AGC CTA GAC GTG TGG ATC GGC TTC TCG ACT GTG CAG      1294
Arg Val Thr Arg Ser Leu Asp Val Trp Ile Gly Phe Ser Thr Val Gln
2030                2035                2040                2045

GGG GTG GAG GTG GGC CCA GCG CCG CAG GGC GAG GCC TTC AGC CTG GAG      1342
Gly Val Glu Val Gly Pro Ala Pro Gln Gly Glu Ala Phe Ser Leu Glu
        2050                2055                2060

AGC TGC CAG AAC TGG CTG CCC GGG GAG CCA CAC CCA GCC ACA GCC GAG      1390
Ser Cys Gln Asn Trp Leu Pro Gly Glu Pro His Pro Ala Thr Ala Glu
        2065                2070                2075

CAC TGC GTC CGG CTC GGG CCC ACC GGG TGG TGT AAC ACC GAC CTG TGC      1438
His Cys Val Arg Leu Gly Pro Thr Gly Trp Cys Asn Thr Asp Leu Cys
        2080                2085                2090

TCA GCG CCG CAC AGC TAC GTC TGC GAG CTG CAG CCC GGA GGC CCA GTG      1486
Ser Ala Pro His Ser Tyr Val Cys Glu Leu Gln Pro Gly Gly Pro Val
        2095                2100                2105

CAG GAT GCC GAG AAC CTC CTC GTG GGA GCG CCC AGT GGG GAC CTG CAG      1534
Gln Asp Ala Glu Asn Leu Leu Val Gly Ala Pro Ser Gly Asp Leu Gln
2110                2115                2120                2125

GGA CCC CTG ACG CCT CTG GCA CAG CAG GAC GGC CTC TCA GCC CCG CAC      1582
Gly Pro Leu Thr Pro Leu Ala Gln Gln Asp Gly Leu Ser Ala Pro His
        2130                2135                2140

GAG CCC GTG GAG GTC ATG GTA TTC CCG GGC CTG CGT CTG AGC CGT GAA      1630
Glu Pro Val Glu Val Met Val Phe Pro Gly Leu Arg Leu Ser Arg Glu
        2145                2150                2155

GCC TTC CTC ACC ACG GCC GAA TTT GGG ACC CAG GAG CTC CGG CGG CCC      1678
Ala Phe Leu Thr Thr Ala Glu Phe Gly Thr Gln Glu Leu Arg Arg Pro
        2160                2165                2170

GCC CAG CTG CGG CTG CAG GTG TAC CGG CTC CTC AGC ACA GCA GGG ACC      1726
Ala Gln Leu Arg Leu Gln Val Tyr Arg Leu Leu Ser Thr Ala Gly Thr
        2175                2180                2185

CCG GAG AAC GGC AGC GAG CCT GAG AGC AGG TCC CCG GAC AAC AGG ACC      1774
Pro Glu Asn Gly Ser Glu Pro Glu Ser Arg Ser Pro Asp Asn Arg Thr
2190                2195                2200                2205

CAG CTG GCC CCC GCG TGC ATG CCA GGG GGA CGC TGG TGC CCT GGA GCC      1822
Gln Leu Ala Pro Ala Cys Met Pro Gly Gly Arg Trp Cys Pro Gly Ala
        2210                2215                2220

AAC ATC TGC TTG CCG CTG GAC GCC TCT TGC CAC CCC AGG CC TGC GCC       1870
Asn Ile Cys Leu Pro Leu Asp Ala Ser Cys His Pro Gln Ala Cys Ala
        2225                2230                2235

AAT GGC TGC ACG TCA GGG CCA GGG CTA CCC GGG GCC CCC TAT GCG CTA      1918
```

```
Asn Gly Cys Thr Ser Gly Pro Gly Leu Pro Gly Ala Pro Tyr Ala Leu
         2240                2245                2250

TGG AGA GAG TTC CTC TTC TCC GTT GCC GCG GGG CCC CCC GCG CAG TAC        1966
Trp Arg Glu Phe Leu Phe Ser Val Ala Ala Gly Pro Pro Ala Gln Tyr
    2255                2260                2265

TCG GTC ACC CTC CAC GGC CAG GAT GTC CTC ATG CTC CCT GGT GAC CTC        2014
Ser Val Thr Leu His Gly Gln Asp Val Leu Met Leu Pro Gly Asp Leu
2270                2275                2280                2285

GTT GGC TTG CAG CAC GAC GCT GGC CCT GGC GCC CTC CTG CAC TGC TCG        2062
Val Gly Leu Gln His Asp Ala Gly Pro Gly Ala Leu Leu His Cys Ser
                2290                2295                2300

CCG GCT CCC GGC CAC CCT GGT CCC CAG GCC CCG TAC CTC TCC GCC AAC        2110
Pro Ala Pro Gly His Pro Gly Pro Gln Ala Pro Tyr Leu Ser Ala Asn
            2305                2310                2315

GCC TCG TCA TGG CTG CCC CAC TTG CCA GCC CAG CTG GAG GGC ACT TGG        2158
Ala Ser Ser Trp Leu Pro His Leu Pro Ala Gln Leu Glu Gly Thr Trp
        2320                2325                2330

GCC TGC CCT GCC TGT GCC CTG CGG CTG CTT GCA GCC ACG GAA CAG CTC        2206
Ala Cys Pro Ala Cys Ala Leu Arg Leu Leu Ala Ala Thr Glu Gln Leu
    2335                2340                2345

ACC GTG CTG CTG GGC TTG AGG CCC AAC CCT GGA CTG CGG ATG CCT GGG        2254
Thr Val Leu Leu Gly Leu Arg Pro Asn Pro Gly Leu Arg Met Pro Gly
2350                2355                2360                2365

CGC TAT GAG GTC CGG GCA GAG GTG GGC AAT GGC GTG TCC AGG CAC AAC        2302
Arg Tyr Glu Val Arg Ala Glu Val Gly Asn Gly Val Ser Arg His Asn
                2370                2375                2380

CTC TCC TGC AGC TTT GAC GTG GTC TCC CCA GTG GCT GGG CTG CGG GTC        2350
Leu Ser Cys Ser Phe Asp Val Val Ser Pro Val Ala Gly Leu Arg Val
            2385                2390                2395

ATC TAC CCT GCC CCC CGC GAC GGC CGC CTC TAC GTG CCC ACC AAC GGC        2398
Ile Tyr Pro Ala Pro Arg Asp Gly Arg Leu Tyr Val Pro Thr Asn Gly
        2400                2405                2410

TCA GCC TTG GTG CTC CAG GTG GAC TCT GGT GCC AAC GCC ACG GCC ACG        2446
Ser Ala Leu Val Leu Gln Val Asp Ser Gly Ala Asn Ala Thr Ala Thr
    2415                2420                2425

GCT CGC TGG CCT GGG GGC AGT GTC AGC GCC CGC TTT GAG AAT GTC TGC        2494
Ala Arg Trp Pro Gly Gly Ser Val Ser Ala Arg Phe Glu Asn Val Cys
2430                2435                2440                2445

CCT GCC CTG GTG GCC ACC TTC GTG CCC GGC TGC CCC TGG GAG ACC AAC        2542
Pro Ala Leu Val Ala Thr Phe Val Pro Gly Cys Pro Trp Glu Thr Asn
                2450                2455                2460

GAT ACC CTG TTC TCA GTG GTA GCA CTG CCG TGG CTC AGT GAG GGG GAG        2590
Asp Thr Leu Phe Ser Val Val Ala Leu Pro Trp Leu Ser Glu Gly Glu
            2465                2470                2475

CAC GTG GTG GAC GTG GTG GTG GAA AAC AGC GCC AGC CGG GCC AAC CTC        2638
His Val Val Asp Val Val Val Glu Asn Ser Ala Ser Arg Ala Asn Leu
        2480                2485                2490

AGC CTG CGG GTG ACG GCG GAG GAG CCC ATC TGT GGC CTC CGC GCC ACG        2686
Ser Leu Arg Val Thr Ala Glu Glu Pro Ile Cys Gly Leu Arg Ala Thr
    2495                2500                2505

CCC AGC CCC GAG GCC CGT GTA CTG CAG GGA GTC CTA GTG AGG TAC AGC        2734
Pro Ser Pro Glu Ala Arg Val Leu Gln Gly Val Leu Val Arg Tyr Ser
2510                2515                2520                2525

CCC GTG GTG GAG GCC GGC TCG GAC ATG GTC TTC CGG TGG ACC ATC AAC        2782
Pro Val Val Glu Ala Gly Ser Asp Met Val Phe Arg Trp Thr Ile Asn
                2530                2535                2540

GAC AAG CAG TCC CTG ACC TTC CAG AAC GTG GTC TTC AAT GTC ATT TAT        2830
Asp Lys Gln Ser Leu Thr Phe Gln Asn Val Val Phe Asn Val Ile Tyr
            2545                2550                2555
```

-continued

```
CAG AGC GCG GCG GTC TTC AAG CTC TCA CTG ACG GCC TCC AAC CAC GTG      2878
Gln Ser Ala Ala Val Phe Lys Leu Ser Leu Thr Ala Ser Asn His Val
        2560            2565                2570

AGC AAC GTC ACC GTG AAC TAC AAC GTA ACC GTG GAG CGG ATG AAC AGG      2926
Ser Asn Val Thr Val Asn Tyr Asn Val Thr Val Glu Arg Met Asn Arg
        2575            2580                2585

ATG CAG GGT CTG CAG GTC TCC ACA GTG CCG GCC GTG CTG TCC CCC AAT      2974
Met Gln Gly Leu Gln Val Ser Thr Val Pro Ala Val Leu Ser Pro Asn
2590            2595                2600                2605

GCC ACA CTG GTA CTG ACG GGT GGT GTG CTG GTG GAC TCA GCT GTG GAG      3022
Ala Thr Leu Val Leu Thr Gly Gly Val Leu Val Asp Ser Ala Val Glu
            2610                2615                2620

GTG GCC TTC CTG TGG AAC TTT GGG GAT GGG GAG CAG GCC CTC CAC CAG      3070
Val Ala Phe Leu Trp Asn Phe Gly Asp Gly Glu Gln Ala Leu His Gln
        2625            2630                2635

TTC CAG CCT CCG TAC AAC GAG TCC TTC CCG GTT CCA GAC CCC TCG GTG      3118
Phe Gln Pro Pro Tyr Asn Glu Ser Phe Pro Val Pro Asp Pro Ser Val
        2640            2645                2650

GCC CAG GTG CTG GTG GAG CAC AAT GTC ATG CAC ACC TAC GCT GCC CCA      3166
Ala Gln Val Leu Val Glu His Asn Val Met His Thr Tyr Ala Ala Pro
        2655            2660                2665

GGT GAG TAC CTC CTG ACC GTG CTG GCA TCT AAT GCC TTC GAG AAC CTG      3214
Gly Glu Tyr Leu Leu Thr Val Leu Ala Ser Asn Ala Phe Glu Asn Leu
2670            2675                2680                2685

ACG CAG CAG GTG CCT GTG AGC GTG CGC GCC TCC CTG CCC TCC GTG GCT      3262
Thr Gln Gln Val Pro Val Ser Val Arg Ala Ser Leu Pro Ser Val Ala
        2690            2695                2700

GTG GGT GTG AGT GAC GGC GTC CTG GTG GCC GGC CGG CCC GTC ACC TTC      3310
Val Gly Val Ser Asp Gly Val Leu Val Ala Gly Arg Pro Val Thr Phe
        2705            2710                2715

TAC CCG CAC CCG CTG CCC TCG CCT GGG GGT GTT CTT TAC ACG TGG GAC      3358
Tyr Pro His Pro Leu Pro Ser Pro Gly Gly Val Leu Tyr Thr Trp Asp
        2720            2725                2730

TTC GGG GAC GGC TCC CCT GTC CTG ACC CAG AGC CAG CCG GCT GCC AAC      3406
Phe Gly Asp Gly Ser Pro Val Leu Thr Gln Ser Gln Pro Ala Ala Asn
        2735            2740                2745

CAC ACC TAT GCC TCG AGG GGC ACC TAC CAC GTG CGC CTG GAG GTC AAC      3454
His Thr Tyr Ala Ser Arg Gly Thr Tyr His Val Arg Leu Glu Val Asn
2750            2755                2760                2765

AAC ACG GTG AGC GGT GCG GCG GCC CAG GCG GAT GTG CGC GTC TTT GAG      3502
Asn Thr Val Ser Gly Ala Ala Ala Gln Ala Asp Val Arg Val Phe Glu
        2770            2775                2780

GAG CTC CGC GGA CTC AGC GTG GAC ATG AGC CTG GCC GTG GAG CAG GGC      3550
Glu Leu Arg Gly Leu Ser Val Asp Met Ser Leu Ala Val Glu Gln Gly
        2785            2790                2795

GCC CCC GTG GTG GTC AGC GCC GCG GTG CAG ACG GGC GAC AAC ATC ACG      3598
Ala Pro Val Val Val Ser Ala Ala Val Gln Thr Gly Asp Asn Ile Thr
        2800            2805                2810

TGG ACC TTC GAC ATG GGG GAC GGC ACC GTG CTG TCG GGC CCG GAG GCA      3646
Trp Thr Phe Asp Met Gly Asp Gly Thr Val Leu Ser Gly Pro Glu Ala
        2815            2820                2825

ACA GTG GAG CAT GTG TAC CTG CGG GCA CAG AAC TGC ACA GTG ACC GTG      3694
Thr Val Glu His Val Tyr Leu Arg Ala Gln Asn Cys Thr Val Thr Val
2830            2835                2840                2845

GGT GCG GCC AGC CCC GCC GGC CAC CTG GCC CGG AGC CTG CAC GTG CTG      3742
Gly Ala Ala Ser Pro Ala Gly His Leu Ala Arg Ser Leu His Val Leu
        2850            2855                2860

GTC TTC GTC CTG GAG GTG CTG CGC GTT GAA CCC GCC GCC TGC ATC CCC      3790
Val Phe Val Leu Glu Val Leu Arg Val Glu Pro Ala Ala Cys Ile Pro
        2865            2870                2875
```

```
                                                            -continued

ACG CAG CCT GAC GCG CGG CTC ACG GCC TAC GTC ACC GGG AAC CCG GCC          3838
Thr Gln Pro Asp Ala Arg Leu Thr Ala Tyr Val Thr Gly Asn Pro Ala
            2880                2885                2890

CAC TAC CTC TTC GAC TGG ACC TTC GGG GAT GGC TCC TCC AAC ACG ACC          3886
His Tyr Leu Phe Asp Trp Thr Phe Gly Asp Gly Ser Ser Asn Thr Thr
        2895                2900                2905

GTG CGG GGG TGC CCG ACG GTG ACA CAC AAC TTC ACG CGG AGC GGC ACG          3934
Val Arg Gly Cys Pro Thr Val Thr His Asn Phe Thr Arg Ser Gly Thr
2910                2915                2920                2925

TTC CCC CTG GCG CTG GTG CTG TCC AGC CGC GTG AAC AGG GCG CAT TAC          3982
Phe Pro Leu Ala Leu Val Leu Ser Ser Arg Val Asn Arg Ala His Tyr
                2930                2935                2940

TTC ACC AGC ATC TGC GTG GAG CCA GAG GTG GGC AAC GTC ACC CTG CAG          4030
Phe Thr Ser Ile Cys Val Glu Pro Glu Val Gly Asn Val Thr Leu Gln
            2945                2950                2955

CCA GAG AGG CAG TTT GTG CAG CTC GGG GAC GAG GCC TGG CTG GTG GCA          4078
Pro Glu Arg Gln Phe Val Gln Leu Gly Asp Glu Ala Trp Leu Val Ala
        2960                2965                2970

TGT GCC TGG CCC CCG TTC CCC TAC CGC TAC ACC TGG GAC TTT GGC ACC          4126
Cys Ala Trp Pro Pro Phe Pro Tyr Arg Tyr Thr Trp Asp Phe Gly Thr
2975                2980                2985

GAG GAA GCC GCC CCC ACC CGT GCC AGG GGC CCT GAG GTG ACG TTC ATC          4174
Glu Glu Ala Ala Pro Thr Arg Ala Arg Gly Pro Glu Val Thr Phe Ile
2990                2995                3000                3005

TAC CGA GAC CCA GGC TCC TAT CTT GTG ACA GTC ACC GCG TCC AAC AAC          4222
Tyr Arg Asp Pro Gly Ser Tyr Leu Val Thr Val Thr Ala Ser Asn Asn
                3010                3015                3020

ATC TCT GCT GCC AAT GAC TCA GCC CTG GTG GAG GTG CAG GAG CCC GTG          4270
Ile Ser Ala Ala Asn Asp Ser Ala Leu Val Glu Val Gln Glu Pro Val
            3025                3030                3035

CTG GTC ACC AGC ATC AAG GTC AAT GGC TCC CTT GGG CTG GAG CTG CAG          4318
Leu Val Thr Ser Ile Lys Val Asn Gly Ser Leu Gly Leu Glu Leu Gln
        3040                3045                3050

CAG CCG TAC CTG TTC TCT GCT GTG GGC CGT GGG CGC CCC GCC AGC TAC          4366
Gln Pro Tyr Leu Phe Ser Ala Val Gly Arg Gly Arg Pro Ala Ser Tyr
3055                3060                3065

CTG TGG GAT CTG GGG GAC GGT GGG TGG CTC GAG GGT CCG GAG GTC ACC          4414
Leu Trp Asp Leu Gly Asp Gly Gly Trp Leu Glu Gly Pro Glu Val Thr
3070                3075                3080                3085

CAC GCT TAC AAC AGC ACA GGT GAC TTC ACC GTT AGG GTG GCC GGC TGG          4462
His Ala Tyr Asn Ser Thr Gly Asp Phe Thr Val Arg Val Ala Gly Trp
                3090                3095                3100

AAT GAG GTG AGC CGC AGC GAG GCC TGG CTC AAT GTG ACG GTG AAG CGG          4510
Asn Glu Val Ser Arg Ser Glu Ala Trp Leu Asn Val Thr Val Lys Arg
            3105                3110                3115

CGC GTG CGG GGG CTC GTC GTC AAT GCA AGC CGC ACG GTG GTG CCC CTG          4558
Arg Val Arg Gly Leu Val Val Asn Ala Ser Arg Thr Val Val Pro Leu
        3120                3125                3130

AAT GGG AGC GTG AGC TTC AGC ACG TCG CTG GAG GCC GGC AGT GAT GTG          4606
Asn Gly Ser Val Ser Phe Ser Thr Ser Leu Glu Ala Gly Ser Asp Val
3135                3140                3145

CGC TAT TCC TGG GTG CTC TGT GAC CGC TGC ACG CCC ATC CCT GGG GGT          4654
Arg Tyr Ser Trp Val Leu Cys Asp Arg Cys Thr Pro Ile Pro Gly Gly
3150                3155                3160                3165

CCT ACC ATC TCT TAC ACC TTC CGC TCC GTG GGC ACC TTC AAT ATC ATC          4702
Pro Thr Ile Ser Tyr Thr Phe Arg Ser Val Gly Thr Phe Asn Ile Ile
                3170                3175                3180

GTC ACG GCT GAG AAC GAG GTG GGC TCC GCC CAG GAC AGC ATC TTC GTC          4750
Val Thr Ala Glu Asn Glu Val Gly Ser Ala Gln Asp Ser Ile Phe Val
```

```
              3185                  3190                  3195
TAT GTC CTG CAG CTC ATA GAG GGG CTG CAG GTG GTG GGC GGT GGC CGC    4798
Tyr Val Leu Gln Leu Ile Glu Gly Leu Gln Val Val Gly Gly Gly Arg
        3200                  3205                  3210

TAC TTC CCC ACC AAC CAC ACG GTA CAG CTG CAG GCC GTG GTT AGG GAT    4846
Tyr Phe Pro Thr Asn His Thr Val Gln Leu Gln Ala Val Val Arg Asp
        3215                  3220                  3225

GGC ACC AAC GTC TCC TAC AGC TGG ACT GCC TGG AGG GAC AGG GGC CCG    4894
Gly Thr Asn Val Ser Tyr Ser Trp Thr Ala Trp Arg Asp Arg Gly Pro
3230                  3235                  3240                  3245

GCC CTG GCC GGC AGC GGC AAA GGC TTC TCG CTC ACC GTG CTC GAG GCC    4942
Ala Leu Ala Gly Ser Gly Lys Gly Phe Ser Leu Thr Val Leu Glu Ala
            3250                  3255                  3260

GGC ACC TAC CAT GTG CAG CTG CGG GCC ACC AAC ATG CTG GGC AGC GCC    4990
Gly Thr Tyr His Val Gln Leu Arg Ala Thr Asn Met Leu Gly Ser Ala
            3265                  3270                  3275

TGG GCC GAC TGC ACC ATG GAC TTC GTG GAG CCT GTG GGG TGG CTG ATG    5038
Trp Ala Asp Cys Thr Met Asp Phe Val Glu Pro Val Gly Trp Leu Met
        3280                  3285                  3290

GTG ACC GCC TCC CCG AAC CCA GCT GCC GTC AAC ACA AGC GTC ACC CTC    5086
Val Thr Ala Ser Pro Asn Pro Ala Ala Val Asn Thr Ser Val Thr Leu
    3295                  3300                  3305

AGT GCC GAG CTG GCT GGT GGC AGT GGT GTC GTA TAC ACT TGG TCC TTG    5134
Ser Ala Glu Leu Ala Gly Gly Ser Gly Val Val Tyr Thr Trp Ser Leu
3310                  3315                  3320                  3325

GAG GAG GGG CTG AGC TGG GAG ACC TCC GAG CCA TTT ACC ACC CAT AGC    5182
Glu Glu Gly Leu Ser Trp Glu Thr Ser Glu Pro Phe Thr Thr His Ser
            3330                  3335                  3340

TTC CCC ACA CCC GGC CTG CAC TTG GTC ACC ATG ACG GCA GGG AAC CCG    5230
Phe Pro Thr Pro Gly Leu His Leu Val Thr Met Thr Ala Gly Asn Pro
        3345                  3350                  3355

CTG GGC TCA GCC AAC GCC ACC GTG GAA GTG GAT GTG CAG GTG CCT GTG    5278
Leu Gly Ser Ala Asn Ala Thr Val Glu Val Asp Val Gln Val Pro Val
        3360                  3365                  3370

AGT GGC CTC AGC ATC AGG GCC AGC GAG CCC GGA GGC AGC TTC GTG GCG    5326
Ser Gly Leu Ser Ile Arg Ala Ser Glu Pro Gly Gly Ser Phe Val Ala
    3375                  3380                  3385

GCC GGG TCC TCT GTG CCC TTT TGG GGG CAG CTG GCC ACG GGC ACC AAT    5374
Ala Gly Ser Ser Val Pro Phe Trp Gly Gln Leu Ala Thr Gly Thr Asn
3390                  3395                  3400                  3405

GTG AGC TGG TGC TGG GCT GTG CCC GGC GGC AGC AGC AAG CGT GGC CCT    5422
Val Ser Trp Cys Trp Ala Val Pro Gly Gly Ser Ser Lys Arg Gly Pro
            3410                  3415                  3420

CAT GTC ACC ATG GTC TTC CCG GAT GCT GGC ACC TTC TCC ATC CGG CTC    5470
His Val Thr Met Val Phe Pro Asp Ala Gly Thr Phe Ser Ile Arg Leu
        3425                  3430                  3435

AAT GCC TCC AAC GCA GTC AGC TGG GTC TCA GCC ACG TAC AAC CTC ACG    5518
Asn Ala Ser Asn Ala Val Ser Trp Val Ser Ala Thr Tyr Asn Leu Thr
        3440                  3445                  3450

GCG GAG GAG CCC ATC GTG GGC CTG GTG CTG TGG GCC AGC AGC AAG GTG    5566
Ala Glu Glu Pro Ile Val Gly Leu Val Leu Trp Ala Ser Ser Lys Val
    3455                  3460                  3465

GTG GCG CCC GGG CAG CTG GTC CAT TTT CAG ATC CTG CTG GCT GCC GGC    5614
Val Ala Pro Gly Gln Leu Val His Phe Gln Ile Leu Leu Ala Ala Gly
3470                  3475                  3480                  3485

TCA GCT GTC ACC TTC CGC CTG CAG GTC GGC GGG GCC AAC CCC GAG GTG    5662
Ser Ala Val Thr Phe Arg Leu Gln Val Gly Gly Ala Asn Pro Glu Val
            3490                  3495                  3500

CTC CCC GGG CCC CGT TTC TCC CAC AGC TTC CCC CGC GTC GGA GAC CAC    5710
```

```
Leu Pro Gly Pro Arg Phe Ser His Ser Phe Pro Arg Val Gly Asp His
            3505                3510                3515

GTG GTG AGC GTG CGG GGC AAA AAC CAC GTG AGC TGG GCC CAG GCG CAG          5758
Val Val Ser Val Arg Gly Lys Asn His Val Ser Trp Ala Gln Ala Gln
            3520                3525                3530

GTG CGC ATC GTG GTG CTG GAG GCC GTG AGT GGG CTG CAG ATG CCC AAC          5806
Val Arg Ile Val Val Leu Glu Ala Val Ser Gly Leu Gln Met Pro Asn
            3535                3540                3545

TGC TGC GAG CCT GGC ATC GCC ACG GGC ACT GAG AGG AAC TTC ACA GCC          5854
Cys Cys Glu Pro Gly Ile Ala Thr Gly Thr Glu Arg Asn Phe Thr Ala
3550            3555                3560                3565

CGC GTG CAG CGC GGC TCT CGG GTC GCC TAC GCC TGG TAC TTC TCG CTG          5902
Arg Val Gln Arg Gly Ser Arg Val Ala Tyr Ala Trp Tyr Phe Ser Leu
            3570                3575                3580

CAG AAG GTC CAG GGC GAC TCG CTG GTC ATC CTG TCG GGC CGC GAC GTC          5950
Gln Lys Val Gln Gly Asp Ser Leu Val Ile Leu Ser Gly Arg Asp Val
            3585                3590                3595

ACC TAC ACG CCC GTG GCC GCG GGG CTG TTG GAG ATC CAG GTG CGC GCC          5998
Thr Tyr Thr Pro Val Ala Ala Gly Leu Leu Glu Ile Gln Val Arg Ala
            3600                3605                3610

TTC AAC GCC CTG GGC AGT GAG AAC CGC ACG CTG GTG CTG GAG GTT CAG          6046
Phe Asn Ala Leu Gly Ser Glu Asn Arg Thr Leu Val Leu Glu Val Gln
            3615                3620                3625

GAC GCC GTC CAG TAT GTG GCC CTG CAG AGC GGC CCC TGC TTC ACC AAC          6094
Asp Ala Val Gln Tyr Val Ala Leu Gln Ser Gly Pro Cys Phe Thr Asn
3630            3635                3640                3645

CGC TCG GCG CAG TTT GAG GCC GCC ACC AGC CCC AGC CCC CGG CGT GTG          6142
Arg Ser Ala Gln Phe Glu Ala Ala Thr Ser Pro Ser Pro Arg Arg Val
            3650                3655                3660

GCC TAC CAC TGG GAC TTT GGG GAT GGG TCG CCA GGG CAG GAC ACA GAT          6190
Ala Tyr His Trp Asp Phe Gly Asp Gly Ser Pro Gly Gln Asp Thr Asp
            3665                3670                3675

GAG CCC AGG GCC GAG CAC TCC TAC CTG AGG CCT GGG GAC TAC CGC GTG          6238
Glu Pro Arg Ala Glu His Ser Tyr Leu Arg Pro Gly Asp Tyr Arg Val
            3680                3685                3690

CAG GTG AAC GCC TCC AAC CTG GTG AGC TTC TTC GTG GCG CAG GCC ACG          6286
Gln Val Asn Ala Ser Asn Leu Val Ser Phe Phe Val Ala Gln Ala Thr
            3695                3700                3705

GTG ACC GTC CAG GTG CTG GCC TGC CGG GAG CCG GAG GTG GAC GTG GTC          6334
Val Thr Val Gln Val Leu Ala Cys Arg Glu Pro Glu Val Asp Val Val
3710            3715                3720                3725

CTG CCC CTG CAG GTG CTG ATG CGG CGA TCA CAG CGC AAC TAC TTG GAG          6382
Leu Pro Leu Gln Val Leu Met Arg Arg Ser Gln Arg Asn Tyr Leu Glu
            3730                3735                3740

GCC CAC GTT GAC CTG CGC GAC TGC GTC ACC TAC CAG ACT GAG TAC CGC          6430
Ala His Val Asp Leu Arg Asp Cys Val Thr Tyr Gln Thr Glu Tyr Arg
            3745                3750                3755

TGG GAG GTG TAT CGC ACC GCC AGC TGC CAG CGG CCG GGG CGC CCA GCG          6478
Trp Glu Val Tyr Arg Thr Ala Ser Cys Gln Arg Pro Gly Arg Pro Ala
            3760                3765                3770

CGT GTG GCC CTG CCC GGC GTG GAC GTG AGC CGG CCT CGG CTG GTG CTG          6526
Arg Val Ala Leu Pro Gly Val Asp Val Ser Arg Pro Arg Leu Val Leu
            3775                3780                3785

CCG CGG CTG GCG CTG CCT GTG GGG CAC TAC TGC TTT GTG TTT GTC GTG          6574
Pro Arg Leu Ala Leu Pro Val Gly His Tyr Cys Phe Val Phe Val Val
3790            3795                3800                3805

TCA TTT GGG GAC ACG CCA CTG ACA CAG AGC ATC CAG GCC AAT GTG ACG          6622
Ser Phe Gly Asp Thr Pro Leu Thr Gln Ser Ile Gln Ala Asn Val Thr
            3810                3815                3820
```

```
                                                       -continued

GTG GCC CCC GAG CGC CTG GTG CCC ATC ATT GAG GGT GGC TCA TAC CGC        6670
Val Ala Pro Glu Arg Leu Val Pro Ile Ile Glu Gly Gly Ser Tyr Arg
              3825                3830                3835

GTG TGG TCA GAC ACA CGG GAC CTG GTG CTG GAT GGG AGC GAG TCC TAC        6718
Val Trp Ser Asp Thr Arg Asp Leu Val Leu Asp Gly Ser Glu Ser Tyr
              3840                3845                3850

GAC CCC AAC CTG GAG GAC GGC GAC CAG ACG CCG CTC AGT TTC CAC TGG        6766
Asp Pro Asn Leu Glu Asp Gly Asp Gln Thr Pro Leu Ser Phe His Trp
              3855                3860                3865

GCC TGT GTG GCT TCG ACA CAG AGG GAG GCT GGC GGG TGT GCG CTG AAC        6814
Ala Cys Val Ala Ser Thr Gln Arg Glu Ala Gly Gly Cys Ala Leu Asn
3870                3875                3880                3885

TTT GGG CCC CGC GGG AGC AGC ACG GTC ACC ATT CCA CGG GAG CGG CTG        6862
Phe Gly Pro Arg Gly Ser Ser Thr Val Thr Ile Pro Arg Glu Arg Leu
              3890                3895                3900

GCG GCT GGC GTG GAG TAC ACC TTC AGC CTG ACC GTG TGG AAG GCC GGC        6910
Ala Ala Gly Val Glu Tyr Thr Phe Ser Leu Thr Val Trp Lys Ala Gly
              3905                3910                3915

CGC AAG GAG GAG GCC ACC AAC CAG ACG GTG CTG ATC CGG AGT GGC CGG        6958
Arg Lys Glu Glu Ala Thr Asn Gln Thr Val Leu Ile Arg Ser Gly Arg
              3920                3925                3930

GTG CCC ATT GTG TCC TTG GAG TGT GTG TCC TGC AAG GCA CAG GCC GTG        7006
Val Pro Ile Val Ser Leu Glu Cys Val Ser Cys Lys Ala Gln Ala Val
              3935                3940                3945

TAC GAA GTG AGC CGC AGC TCC TAC GTG TAC TTG GAG GGC CGC TGC CTC        7054
Tyr Glu Val Ser Arg Ser Ser Tyr Val Tyr Leu Glu Gly Arg Cys Leu
3950                3955                3960                3965

AAT TGC AGC AGC GGC TCC AAG CGA GGG CGG TGG GCT GCA CGT ACG TTC        7102
Asn Cys Ser Ser Gly Ser Lys Arg Gly Arg Trp Ala Ala Arg Thr Phe
              3970                3975                3980

AGC AAC AAG ACG CTG GTG CTG GAT GAG ACC ACC ACA TCC ACG GGC AGT        7150
Ser Asn Lys Thr Leu Val Leu Asp Glu Thr Thr Thr Ser Thr Gly Ser
              3985                3990                3995

GCA GGC ATG CGA CTG GTG CTG CGG CGG GGC GTG CTG CGG GAC GGC GAG        7198
Ala Gly Met Arg Leu Val Leu Arg Arg Gly Val Leu Arg Asp Gly Glu
              4000                4005                4010

GGA TAC ACC TTC ACG CTC ACG GTG CTG GGC CGC TCT GGC GAG GAG GAG        7246
Gly Tyr Thr Phe Thr Leu Thr Val Leu Gly Arg Ser Gly Glu Glu Glu
              4015                4020                4025

GGC TGC GCC TCC ATC CGC CTG TCC CCC AAC CGC CCG CCG CTG GGG GGC        7294
Gly Cys Ala Ser Ile Arg Leu Ser Pro Asn Arg Pro Pro Leu Gly Gly
4030                4035                4040                4045

TCT TGC CGC CTC TTC CCA CTG GGC GCT GTG CAC GCC CTC ACC ACC AAG        7342
Ser Cys Arg Leu Phe Pro Leu Gly Ala Val His Ala Leu Thr Thr Lys
              4050                4055                4060

GTG CAC TTC GAA TGC ACG GGC TGG CAT GAC GCG GAG GAT GCT GGC GCC        7390
Val His Phe Glu Cys Thr Gly Trp His Asp Ala Glu Asp Ala Gly Ala
              4065                4070                4075

CCG CTG GTG TAC GCC CTG CTG CTG CGG CGC TGT CGC CAG GGC CAC TGC        7438
Pro Leu Val Tyr Ala Leu Leu Leu Arg Arg Cys Arg Gln Gly His Cys
              4080                4085                4090

GAG GAG TTC TGT GTC TAC AAG GGC AGC CTC TCC AGC TAC GGA GCC GTG        7486
Glu Glu Phe Cys Val Tyr Lys Gly Ser Leu Ser Ser Tyr Gly Ala Val
              4095                4100                4105

CTG CCC CCG GGT TTC AGG CCA CAC TTC GAG GTG GGC CTG GCC GTG GTG        7534
Leu Pro Pro Gly Phe Arg Pro His Phe Glu Val Gly Leu Ala Val Val
4110                4115                4120                4125

GTG CAG GAC CAG CTG GGA GCC GCT GTG GTC GCC CTC AAC AGG TCT TTG        7582
Val Gln Asp Gln Leu Gly Ala Ala Val Val Ala Leu Asn Arg Ser Leu
              4130                4135                4140
```

```
GCC ATC ACC CTC CCA GAG CCC AAC GGC AGC GCA ACG GGC CTC ACA GTC      7630
Ala Ile Thr Leu Pro Glu Pro Asn Gly Ser Ala Thr Gly Leu Thr Val
            4145                4150                4155

TGG CTG CAC GGG CTC ACC GCT AGT GTG CTC CCA GGG CTG CTG CGG CAG      7678
Trp Leu His Gly Leu Thr Ala Ser Val Leu Pro Gly Leu Leu Arg Gln
            4160                4165                4170

GCC GAT CCC CAG CAC GTC ATC GAG TAC TCG TTG GCC CTG GTC ACC GTG      7726
Ala Asp Pro Gln His Val Ile Glu Tyr Ser Leu Ala Leu Val Thr Val
            4175                4180                4185

CTG AAC GAG TAC GAG CGG GCC CTG GAC GTG GCG GCA GAG CCC AAG CAC      7774
Leu Asn Glu Tyr Glu Arg Ala Leu Asp Val Ala Ala Glu Pro Lys His
4190                4195                4200                4205

GAG CGG CAG CAC CGA GCC CAG ATA CGC AAG AAC ATC ACG GAG ACT CTG      7822
Glu Arg Gln His Arg Ala Gln Ile Arg Lys Asn Ile Thr Glu Thr Leu
            4210                4215                4220

GTG TCC CTG AGG GTC CAC ACT GTG GAT GAC ATC CAG CAG ATC GCT GCT      7870
Val Ser Leu Arg Val His Thr Val Asp Asp Ile Gln Gln Ile Ala Ala
            4225                4230                4235

GCG CTG GCC CAG TGC ATG GGG CCC AGC AGG GAG CTC GTA TGC CGC TCG      7918
Ala Leu Ala Gln Cys Met Gly Pro Ser Arg Glu Leu Val Cys Arg Ser
            4240                4245                4250

TGC CTG AAG CAG ACG CTG CAC AAG CTG GAG GCC ATG ATG CTC ATC CTG      7966
Cys Leu Lys Gln Thr Leu His Lys Leu Glu Ala Met Met Leu Ile Leu
            4255                4260                4265

CAG GCA GAG ACC ACC GCG GGC ACC GTG ACG CCC ACC GCC ATC GGA GAC      8014
Gln Ala Glu Thr Thr Ala Gly Thr Val Thr Pro Thr Ala Ile Gly Asp
4270                4275                4280                4285

AGC ATC CTC AAC ATC ACA GGA GAC CTC ATC CAC CTG GCC AGC TCG GAC      8062
Ser Ile Leu Asn Ile Thr Gly Asp Leu Ile His Leu Ala Ser Ser Asp
            4290                4295                4300

GTG CGG GCA CCA CAG CCC TCA GAG CTG GGA GCC GAG TCA CCA TCT CGG      8110
Val Arg Ala Pro Gln Pro Ser Glu Leu Gly Ala Glu Ser Pro Ser Arg
            4305                4310                4315

ATG GTG GCG TCC CAG GCC TAC AAC CTG ACC TCT GCC CTC ATG CGC ATC      8158
Met Val Ala Ser Gln Ala Tyr Asn Leu Thr Ser Ala Leu Met Arg Ile
            4320                4325                4330

CTC ATG CGC TCC CGC GTG CTC AAC GAG GAG CCC CTG ACG CTG GCG GGC      8206
Leu Met Arg Ser Arg Val Leu Asn Glu Glu Pro Leu Thr Leu Ala Gly
            4335                4340                4345

GAG GAG ATC GTG GCC CAG GGC AAG CGC TCG GAC CCG CGG AGC CTG CTG      8254
Glu Glu Ile Val Ala Gln Gly Lys Arg Ser Asp Pro Arg Ser Leu Leu
4350                4355                4360                4365

TGC TAT GGC GGC GCC CCA GGG CCT GGC TGC CAC TTC TCC ATC CCC GAG      8302
Cys Tyr Gly Gly Ala Pro Gly Pro Gly Cys His Phe Ser Ile Pro Glu
            4370                4375                4380

GCT TTC AGC GGG GCC CTG GCC AAC CTC AGT GAC GTG GTG CAG CTC ATC      8350
Ala Phe Ser Gly Ala Leu Ala Asn Leu Ser Asp Val Val Gln Leu Ile
            4385                4390                4395

TTT CTG GTG GAC TCC AAT CCC TTT CCC TTT GGC TAT ATC AGC AAC TAC      8398
Phe Leu Val Asp Ser Asn Pro Phe Pro Phe Gly Tyr Ile Ser Asn Tyr
            4400                4405                4410

ACC GTC TCC ACC AAG GTG GCC TCG ATG GCA TTC CAG ACA CAG GCC GGC      8446
Thr Val Ser Thr Lys Val Ala Ser Met Ala Phe Gln Thr Gln Ala Gly
            4415                4420                4425

GCC CAG ATC CCC ATC GAG CGG CTG GCC TCA GAG CGC GCC ATC ACC GTG      8494
Ala Gln Ile Pro Ile Glu Arg Leu Ala Ser Glu Arg Ala Ile Thr Val
4430                4435                4440                4445

AAG GTG CCC AAC AAC TCG GAC TGG GCT GCC CGG GGC CAC CGC AGC TCC      8542
Lys Val Pro Asn Asn Ser Asp Trp Ala Ala Arg Gly His Arg Ser Ser
```

-continued

```
                    4450                  4455                  4460
GCC AAC TCC GCC AAC TCC GTT GTG GTC CAG CCC CAG GCC TCC GTC GGT      8590
Ala Asn Ser Ala Asn Ser Val Val Val Gln Pro Gln Ala Ser Val Gly
            4465                  4470                  4475

GCT GTG GTC ACC CTG GAC AGC AGC AAC CCT GCG GCC GGG CTG CAT CTG      8638
Ala Val Val Thr Leu Asp Ser Ser Asn Pro Ala Ala Gly Leu His Leu
            4480                  4485                  4490

CAG CTC AAC TAT ACG CTG CTG GAC GGC CAC TAC CTG TCT GAG GAA CCT      8686
Gln Leu Asn Tyr Thr Leu Leu Asp Gly His Tyr Leu Ser Glu Glu Pro
            4495                  4500                  4505

GAG CCC TAC CTG GCA GTC TAC CTA CAC TCG GAG CCC CGG CCC AAT GAG      8734
Glu Pro Tyr Leu Ala Val Tyr Leu His Ser Glu Pro Arg Pro Asn Glu
4510                  4515                  4520                  4525

CAC AAC TGC TCG GCT AGC AGG AGG ATC CGC CCA GAG TCA CTC CAG GGT      8782
His Asn Cys Ser Ala Ser Arg Arg Ile Arg Pro Glu Ser Leu Gln Gly
            4530                  4535                  4540

GCT GAC CAC CGG CCC TAC ACC TTC TTC ATT TCC CCG GGG AGC AGA GAC      8830
Ala Asp His Arg Pro Tyr Thr Phe Phe Ile Ser Pro Gly Ser Arg Asp
            4545                  4550                  4555

CCA GCG GGG AGT TAC CAT CTG AAC CTC TCC AGC CAC TTC CGC TGG TCG      8878
Pro Ala Gly Ser Tyr His Leu Asn Leu Ser Ser His Phe Arg Trp Ser
            4560                  4565                  4570

GCG CTG CAG GTG TCC GTG GGC CTG TAC ACG TCC CTG TGC CAG TAC TTC      8926
Ala Leu Gln Val Ser Val Gly Leu Tyr Thr Ser Leu Cys Gln Tyr Phe
            4575                  4580                  4585

AGC GAG GAG GAC ATG GTG TGG CGG ACA GAG GGG CTG CTG CCC CTG GAG      8974
Ser Glu Glu Asp Met Val Trp Arg Thr Glu Gly Leu Leu Pro Leu Glu
4590                  4595                  4600                  4605

GAG ACC TCG CCC CGC CAG GCC GTC TGC CTC ACC CGC CAC CTC ACC GCC      9022
Glu Thr Ser Pro Arg Gln Ala Val Cys Leu Thr Arg His Leu Thr Ala
            4610                  4615                  4620

TTC GGC GCC AGC CTC TTC GTG CCC CCA AGC CAT GTC CGC TTT GTG TTT      9070
Phe Gly Ala Ser Leu Phe Val Pro Pro Ser His Val Arg Phe Val Phe
            4625                  4630                  4635

CCT GAG CCG ACA GCG GAT GTA AAC TAC ATC GTC ATG CTG ACA TGT GCT      9118
Pro Glu Pro Thr Ala Asp Val Asn Tyr Ile Val Met Leu Thr Cys Ala
            4640                  4645                  4650

GTG TGC CTG GTG ACC TAC ATG GTC ATG GCC GCC ATC CTG CAC AAG CTG      9166
Val Cys Leu Val Thr Tyr Met Val Met Ala Ala Ile Leu His Lys Leu
            4655                  4660                  4665

GAC CAG TTG GAT GCC AGC CGG GGC CGC GCC ATC CCT TTC TGT GGG CAG      9214
Asp Gln Leu Asp Ala Ser Arg Gly Arg Ala Ile Pro Phe Cys Gly Gln
4670                  4675                  4680                  4685

CGG GGC CGC TTC AAG TAC GAG ATC CTC GTC AAG ACA GGC TGG GGC CGG      9262
Arg Gly Arg Phe Lys Tyr Glu Ile Leu Val Lys Thr Gly Trp Gly Arg
            4690                  4695                  4700

GGC TCA GGT ACC ACG GCC CAC GTG GGC ATC ATG CTG TAT GGG GTG GAC      9310
Gly Ser Gly Thr Thr Ala His Val Gly Ile Met Leu Tyr Gly Val Asp
            4705                  4710                  4715

AGC CGG AGC GGC CAC CGG CAC CTG GAC GGC GAC AGA GCC TTC CAC CGC      9358
Ser Arg Ser Gly His Arg His Leu Asp Gly Asp Arg Ala Phe His Arg
            4720                  4725                  4730

AAC AGC CTG GAC ATC TTC CGG ATC GCC ACC CCG CAC AGC CTG GGT AGC      9406
Asn Ser Leu Asp Ile Phe Arg Ile Ala Thr Pro His Ser Leu Gly Ser
            4735                  4740                  4745

GTG TGG AAG ATC CGA GTG TGG CAC GAC AAC AAA GGG CTC AGC CCT GCC      9454
Val Trp Lys Ile Arg Val Trp His Asp Asn Lys Gly Leu Ser Pro Ala
4750                  4755                  4760                  4765

TGG TTC CTG CAG CAC GTC ATC GTC AGG GAC CTG CAG ACG GCA CGC AGC      9502
```

```
Trp Phe Leu Gln His Val Ile Val Arg Asp Leu Gln Thr Ala Arg Ser
            4770                4775                4780

GCC TTC TTC CTG GTC AAT GAC TGG CTT TCG GTG GAG ACG GAG GCC AAC        9550
Ala Phe Phe Leu Val Asn Asp Trp Leu Ser Val Glu Thr Glu Ala Asn
            4785                4790                4795

GGG GGC CTG GTG GAG AAG GAG GTG CTG GCC GCG AGC GAC GCA GCC CTT        9598
Gly Gly Leu Val Glu Lys Glu Val Leu Ala Ala Ser Asp Ala Ala Leu
            4800                4805                4810

TTG CGC TTC CGG CGC CTG CTG GTG GCT GAG CTG CAG CGT GGC TTC TTT        9646
Leu Arg Phe Arg Arg Leu Leu Val Ala Glu Leu Gln Arg Gly Phe Phe
            4815                4820                4825

GAC AAG CAC ATC TGG CTC TCC ATA TGG GAC CGG CCG CCT CGT AGC CGT        9694
Asp Lys His Ile Trp Leu Ser Ile Trp Asp Arg Pro Pro Arg Ser Arg
4830                4835                4840                4845

TTC ACT CGC ATC CAG AGG GCC ACC TGC TGC GTT CTC CTC ATC TGC CTC        9742
Phe Thr Arg Ile Gln Arg Ala Thr Cys Cys Val Leu Leu Ile Cys Leu
            4850                4855                4860

TTC CTG GGC GCC AAC GCC GTG TGG TAC GGG GCT GTT GGC GAC TCT GCC        9790
Phe Leu Gly Ala Asn Ala Val Trp Tyr Gly Ala Val Gly Asp Ser Ala
            4865                4870                4875

TAC AGC ACG GGG CAT GTG TCC AGG CTG AGC CCG CTG AGC GTC GAC ACA        9838
Tyr Ser Thr Gly His Val Ser Arg Leu Ser Pro Leu Ser Val Asp Thr
            4880                4885                4890

GTC GCT GTT GGC CTG GTG TCC AGC GTG GTT GTC TAT CCC GTC TAC CTG        9886
Val Ala Val Gly Leu Val Ser Ser Val Val Val Tyr Pro Val Tyr Leu
            4895                4900                4905

GCC ATC CTT TTT CTC TTC CGG ATG TCC CGG AGC AAG GTG GCT GGG AGC        9934
Ala Ile Leu Phe Leu Phe Arg Met Ser Arg Ser Lys Val Ala Gly Ser
4910                4915                4920                4925

CCG AGC CCC ACA CCT GCC GGG CAG CAG GTG CTG GAC ATC GAC AGC TGC        9982
Pro Ser Pro Thr Pro Ala Gly Gln Gln Val Leu Asp Ile Asp Ser Cys
            4930                4935                4940

CTG GAC TCG TCC GTG CTG GAC AGC TCC TTC CTC ACG TTC TCA GGC CTC       10030
Leu Asp Ser Ser Val Leu Asp Ser Ser Phe Leu Thr Phe Ser Gly Leu
            4945                4950                4955

CAC GCT GAG GCC TTT GTT GGA CAG ATG AAG AGT GAC TTG TTT CTG GAT       10078
His Ala Glu Ala Phe Val Gly Gln Met Lys Ser Asp Leu Phe Leu Asp
            4960                4965                4970

GAT TCT AAG AGT CTG GTG TGC TGG CCC TCC GGC GAG GGA ACG CTC AGT       10126
Asp Ser Lys Ser Leu Val Cys Trp Pro Ser Gly Glu Gly Thr Leu Ser
            4975                4980                4985

TGG CCG GAC CTG CTC AGT GAC CCG TCC ATT GTG GGT AGC AAT CTG CGG       10174
Trp Pro Asp Leu Leu Ser Asp Pro Ser Ile Val Gly Ser Asn Leu Arg
4990                4995                5000                5005

CAG CTG GCA CGG GGC CAG GCG GGC CAT GGG CTG GGC CCA GAG GAG GAC       10222
Gln Leu Ala Arg Gly Gln Ala Gly His Gly Leu Gly Pro Glu Glu Asp
            5010                5015                5020

GGC TTC TCC CTG GCC AGC CCC TAC TCG CCT GCC AAA TCC TTC TCA GCA       10270
Gly Phe Ser Leu Ala Ser Pro Tyr Ser Pro Ala Lys Ser Phe Ser Ala
            5025                5030                5035

TCA GAT GAA GAC CTG ATC CAG CAG GTC CTT GCC GAG GGG GTC AGC AGC       10318
Ser Asp Glu Asp Leu Ile Gln Gln Val Leu Ala Glu Gly Val Ser Ser
            5040                5045                5050

CCA GCC CCT ACC CAA GAC ACC CAC ATG GAA ACG GAC CTG CTC AGC AGC       10366
Pro Ala Pro Thr Gln Asp Thr His Met Glu Thr Asp Leu Leu Ser Ser
            5055                5060                5065

CTG TCC AGC ACT CCT GGG GAG AAG ACA GAG ACG CTG GCG CTG CAG AGG       10414
Leu Ser Ser Thr Pro Gly Glu Lys Thr Glu Thr Leu Ala Leu Gln Arg
5070                5075                5080                5085
```

-continued

```
CTG GGG GAG CTG GGG CCA CCC AGC CCA GGC CTG AAC TGG GAA CAG CCC        10462
Leu Gly Glu Leu Gly Pro Pro Ser Pro Gly Leu Asn Trp Glu Gln Pro
            5090                5095                5100

CAG GCA GCG AGG CTG TCC AGG ACA GGA CTG GTG GAG GGT CTG CGG AAG        10510
Gln Ala Ala Arg Leu Ser Arg Thr Gly Leu Val Glu Gly Leu Arg Lys
            5105                5110                5115

CGC CTG CTG CCG GCC TGG TGT GCC TCC CTG GCC CAC GGG CTC AGC CTG        10558
Arg Leu Leu Pro Ala Trp Cys Ala Ser Leu Ala His Gly Leu Ser Leu
            5120                5125                5130

CTC CTG GTG GCT GTG GCT GTG GCT GTC TCA GGG TGG GTG GGT GCG AGC        10606
Leu Leu Val Ala Val Ala Val Ala Val Ser Gly Trp Val Gly Ala Ser
            5135                5140                5145

TTC CCC CCG GGC GTG AGT GTT GCG TGG CTC CTG TCC AGC AGC GCC AGC        10654
Phe Pro Pro Gly Val Ser Val Ala Trp Leu Leu Ser Ser Ser Ala Ser
5150                5155                5160                5165

TTC CTG GCC TCA TTC CTC GGC TGG GAG CCA CTG AAG GTC TTG CTG GAA        10702
Phe Leu Ala Ser Phe Leu Gly Trp Glu Pro Leu Lys Val Leu Leu Glu
            5170                5175                5180

GCC CTG TAC TTC TCA CTG GTG GCC AAG CGG CTG CAC CCG GAT GAA GAT        10750
Ala Leu Tyr Phe Ser Leu Val Ala Lys Arg Leu His Pro Asp Glu Asp
            5185                5190                5195

GAC ACC CTG GTA GAG AGC CCG GCT GTG ACG CCT GTG AGC GCA CGT GTG        10798
Asp Thr Leu Val Glu Ser Pro Ala Val Thr Pro Val Ser Ala Arg Val
            5200                5205                5210

CCC CGC GTA CGG CCA CCC CAC GGC TTT GCA CTC TTC CTG GCC AAG GAA        10846
Pro Arg Val Arg Pro Pro His Gly Phe Ala Leu Phe Leu Ala Lys Glu
            5215                5220                5225

GAA GCC CGC AAG GTC AAG AGG CTA CAT GGC ATG CTG CGG AGC CTC CTG        10894
Glu Ala Arg Lys Val Lys Arg Leu His Gly Met Leu Arg Ser Leu Leu
5230                5235                5240                5245

GTG TAC ATG CTT TTT CTG CTG GTG ACC CTG CTG GCC AGC TAT GGG GAT        10942
Val Tyr Met Leu Phe Leu Leu Val Thr Leu Leu Ala Ser Tyr Gly Asp
            5250                5255                5260

GCC TCA TGC CAT GGG CAC GCC TAC CGT CTG CAA AGC GCC ATC AAG CAG        10990
Ala Ser Cys His Gly His Ala Tyr Arg Leu Gln Ser Ala Ile Lys Gln
            5265                5270                5275

GAG CTG CAC AGC CGG GCC TTC CTG GCC ATC ACG CGG TCT GAG GAG CTC        11038
Glu Leu His Ser Arg Ala Phe Leu Ala Ile Thr Arg Ser Glu Glu Leu
            5280                5285                5290

TGG CCA TGG ATG GCC CAC GTG CTG CTG CCC TAC GTC CAC GGG AAC CAG        11086
Trp Pro Trp Met Ala His Val Leu Leu Pro Tyr Val His Gly Asn Gln
            5295                5300                5305

TCC AGC CCA GAG CTG GGG CCC CCA CGG CTG CGG CAG GTG CGG CTG CAG        11134
Ser Ser Pro Glu Leu Gly Pro Pro Arg Leu Arg Gln Val Arg Leu Gln
5310                5315                5320                5325

GAA GCA CTC TAC CCA GAC CCT CCC GGC CCC AGG GTC CAC ACG TGC TCG        11182
Glu Ala Leu Tyr Pro Asp Pro Pro Gly Pro Arg Val His Thr Cys Ser
            5330                5335                5340

GCC GCA GGA GGC TTC AGC ACC AGC GAT TAC GAC GTT GGC TGG GAG AGT        11230
Ala Ala Gly Gly Phe Ser Thr Ser Asp Tyr Asp Val Gly Trp Glu Ser
            5345                5350                5355

CCT CAC AAT GGC TCG GGG ACG TGG GCC TAT TCA GCG CCG GAT CTG CTG        11278
Pro His Asn Gly Ser Gly Thr Trp Ala Tyr Ser Ala Pro Asp Leu Leu
            5360                5365                5370

GGG GCA TGG TCC TGG GGC TCC TGT GCC GTG TAT GAC AGC GGG GGC TAC        11326
Gly Ala Trp Ser Trp Gly Ser Cys Ala Val Tyr Asp Ser Gly Gly Tyr
            5375                5380                5385

GTG CAG GAG CTG GGC CTG AGC CTG GAG GAG AGC CGC GAC CGG CTG CGC        11374
Val Gln Glu Leu Gly Leu Ser Leu Glu Glu Ser Arg Asp Arg Leu Arg
5390                5395                5400                5405
```

-continued

| | |
|---|---|
| TTC CTG CAG CTG CAC AAC TGG CTG GAC AAC AGG AGC CGC GCT GTG TTC<br>Phe Leu Gln Leu His Asn Trp Leu Asp Asn Arg Ser Arg Ala Val Phe<br>               5410                     5415                    5420 | 11422 |
| CTG GAG CTC ACG CGC TAC AGC CCG GCC GTG GGG CTG CAC GCC GCC GTC<br>Leu Glu Leu Thr Arg Tyr Ser Pro Ala Val Gly Leu His Ala Ala Val<br>               5425                     5430                    5435 | 11470 |
| ACG CTG CGC CTC GAG TTC CCG GCG GCC GGC CGC GCC CTG GCC GCC CTG<br>Thr Leu Arg Leu Glu Phe Pro Ala Ala Gly Arg Ala Leu Ala Ala Leu<br>             5440                     5445                    5450 | 11518 |
| AGC GTC CGC CCC TTT GCG CTG CGC CGC CTC AGC GCG GGC CTC TCG CTG<br>Ser Val Arg Pro Phe Ala Leu Arg Arg Leu Ser Ala Gly Leu Ser Leu<br>             5455                     5460                    5465 | 11566 |
| CCT CTG CTC ACC TCG GTG TGC CTG CTG CTG TTC GCC GTG CAC TTC GCC<br>Pro Leu Leu Thr Ser Val Cys Leu Leu Leu Phe Ala Val His Phe Ala<br>5470                  5475                     5480                    5485 | 11614 |
| GTG GCC GAG GCC CGT ACT TGG CAC AGG GAA GGG CGC TGG CGC GTG CTG<br>Val Ala Glu Ala Arg Thr Trp His Arg Glu Gly Arg Trp Arg Val Leu<br>             5490                     5495                    5500 | 11662 |
| CGG CTC GGA GCC TGG GCG CGG TGG CTG CTG GTG GCG CTG ACG GCG GCC<br>Arg Leu Gly Ala Trp Ala Arg Trp Leu Leu Val Ala Leu Thr Ala Ala<br>               5505                     5510                    5515 | 11710 |
| ACG GCA CTG GTA CGC CTC GCC CAG CTG GGT GCC GCT GAC CGC CAG TGG<br>Thr Ala Leu Val Arg Leu Ala Gln Leu Gly Ala Ala Asp Arg Gln Trp<br>             5520                     5525                    5530 | 11758 |
| ACC CGT TTC GTG CGC GGC CGC CCG CGC CGC TTC ACT AGC TTC GAC CAG<br>Thr Arg Phe Val Arg Gly Arg Pro Arg Arg Phe Thr Ser Phe Asp Gln<br>             5535                     5540                    5545 | 11806 |
| GTG GCG CAC GTG AGC TCC GCA GCC CGT GGC CTG GCG GCC TCG CTG CTC<br>Val Ala His Val Ser Ser Ala Ala Arg Gly Leu Ala Ala Ser Leu Leu<br>5550                  5555                     5560                    5565 | 11854 |
| TTC CTG CTT TTG GTC AAG GCT GCC CAG CAC GTA CGC TTC GTG CGC CAG<br>Phe Leu Leu Leu Val Lys Ala Ala Gln His Val Arg Phe Val Arg Gln<br>             5570                     5575                    5580 | 11902 |
| TGG TCC GTC TTT GGC AAG ACA TTA TGC CGA GCT CTG CCA GAG CTC CTG<br>Trp Ser Val Phe Gly Lys Thr Leu Cys Arg Ala Leu Pro Glu Leu Leu<br>             5585                     5590                    5595 | 11950 |
| GGG GTC ACC TTG GGC CTG GTG GTG CTC GGG GTA GCC TAC GCC CAG CTG<br>Gly Val Thr Leu Gly Leu Val Val Leu Gly Val Ala Tyr Ala Gln Leu<br>             5600                     5605                    5610 | 11998 |
| GCC ATC CTG CTC GTG TCT TCC TGT GTG GAC TCC CTC TGG AGC GTG GCC<br>Ala Ile Leu Leu Val Ser Ser Cys Val Asp Ser Leu Trp Ser Val Ala<br>             5615                     5620                    5625 | 12046 |
| CAG GCC CTG TTG GTG CTG TGC CCT GGG ACT GGG CTC TCT ACC CTG TGT<br>Gln Ala Leu Leu Val Leu Cys Pro Gly Thr Gly Leu Ser Thr Leu Cys<br>5630                  5635                     5640                    5645 | 12094 |
| CCT GCC GAG TCC TGG CAC CTG TCA CCC CTG CTG TGT GTG GGG CTC TGG<br>Pro Ala Glu Ser Trp His Leu Ser Pro Leu Leu Cys Val Gly Leu Trp<br>             5650                     5655                    5660 | 12142 |
| GCA CTG CGG CTG TGG GGC GCC CTA CGG CTG GGG GCT GTT ATT CTC CGC<br>Ala Leu Arg Leu Trp Gly Ala Leu Arg Leu Gly Ala Val Ile Leu Arg<br>             5665                     5670                    5675 | 12190 |
| TGG CGC TAC CAC GCC TTG CGT GGA GAG CTG TAC CGG CCG GCC TGG GAG<br>Trp Arg Tyr His Ala Leu Arg Gly Glu Leu Tyr Arg Pro Ala Trp Glu<br>             5680                     5685                    5690 | 12238 |
| CCC CAG GAC TAC GAG ATG GTG GAG TTG TTC CTG CGC AGG CTG CGC CTC<br>Pro Gln Asp Tyr Glu Met Val Glu Leu Phe Leu Arg Arg Leu Arg Leu<br>             5695                     5700                    5705 | 12286 |
| TGG ATG GGC CTC AGC AAG GTC AAG GAG TTC CGC CAC AAA GTC CGC TTT<br>Trp Met Gly Leu Ser Lys Val Lys Glu Phe Arg His Lys Val Arg Phe | 12334 |

```
5710              5715              5720              5725
GAA GGG ATG GAG CCG CTG CCC TCT CGC TCC TCC AGG GGC TCC AAG GTA    12382
Glu Gly Met Glu Pro Leu Pro Ser Arg Ser Ser Arg Gly Ser Lys Val
                5730              5735              5740

TCC CCG GAT GTG CCC CCA CCC AGC GCT GGC TCC GAT GCC TCG CAC CCC    12430
Ser Pro Asp Val Pro Pro Pro Ser Ala Gly Ser Asp Ala Ser His Pro
                5745              5750              5755

TCC ACC TCC TCC AGC CAG CTG GAT GGG CTG AGC GTG AGC CTG GGC CGG    12478
Ser Thr Ser Ser Ser Gln Leu Asp Gly Leu Ser Val Ser Leu Gly Arg
                5760              5765              5770

CTG GGG ACA AGG TGT GAG CCT GAG CCC TCC CGC CTC CAA GCC GTG TTC    12526
Leu Gly Thr Arg Cys Glu Pro Glu Pro Ser Arg Leu Gln Ala Val Phe
            5775              5780              5785

GAG GCC CTG CTC ACC CAG TTT GAC CGA CTC AAC CAG GCC ACA GAG GAC    12574
Glu Ala Leu Leu Thr Gln Phe Asp Arg Leu Asn Gln Ala Thr Glu Asp
5790              5795              5800              5805

GTC TAC CAG CTG GAG CAG CAG CTG CAC AGC CTG CAA GGC CGC AGG AGC    12622
Val Tyr Gln Leu Glu Gln Gln Leu His Ser Leu Gln Gly Arg Arg Ser
                5810              5815              5820

AGC CGG GCG CCC GCC GGA TCT TCC CGT GGC CCA TCC CCG GGC CTG CGG    12670
Ser Arg Ala Pro Ala Gly Ser Ser Arg Gly Pro Ser Pro Gly Leu Arg
                5825              5830              5835

CCA GCA CTG CCC AGC CGC CTT GCC CGG GCC AGT CGG GGT GTG GAC CTG    12718
Pro Ala Leu Pro Ser Arg Leu Ala Arg Ala Ser Arg Gly Val Asp Leu
            5840              5845              5850

GCC ACT GGC CCC AGC AGG ACA CCT TCG GGC CAA GAA CAA GGT CCA CCC    12766
Ala Thr Gly Pro Ser Arg Thr Pro Ser Gly Gln Glu Gln Gly Pro Pro
            5855              5860              5865

CAG CAG CAC TTA GTC CTC CTT CCT GGC GGG GGT GGG CCG TGG AGT CGG    12814
Gln Gln His Leu Val Leu Leu Pro Gly Gly Gly Gly Pro Trp Ser Arg
5870              5875              5880              5885

AGT GGA CAC CGC TCA GTA TTA CTT TCT GCC GCT GTC AAG GCC GAG GGC    12862
Ser Gly His Arg Ser Val Leu Leu Ser Ala Ala Val Lys Ala Glu Gly
                5890              5895              5900

CAG GCA GAA TGG CTG CAC GTA GGT TCC CCA GAG AGC AGG CAG GGG CAT    12910
Gln Ala Glu Trp Leu His Val Gly Ser Pro Glu Ser Arg Gln Gly His
                5905              5910              5915

CTG TCT GTC TGT GGG CTT CAG CAC TTT AAA GAG GCT GTG TGG CCA ACC    12958
Leu Ser Val Cys Gly Leu Gln His Phe Lys Glu Ala Val Trp Pro Thr
                5920              5925              5930

AGG ACC CAG GGT CCC CTC CCC AGC TCC CTT GGG AAG GAC ACA GCA GTA    13006
Arg Thr Gln Gly Pro Leu Pro Ser Ser Leu Gly Lys Asp Thr Ala Val
                5935              5940              5945

TTG GAC GGT TTC TAGCCTCTGA GATGCTAATT TATTTCCCCG AGTCCTCAGG        13058
Leu Asp Gly Phe
5950

TACAGCGGGC TGTGCCCGGC CCCACCCCCT GGGCAGATGT CCCCCACTGC TAAGGCTGCT  13118

GGCTTCAGGG AGGGTTAGCC TGCACCGCCG CCACCCTGCC CCTAAGTTAT ACCTCTCCA   13178

GTTCCTACCG TACTCCCTGC ACCGTCTCAC TGTGTGTCTC GTGTCAGTAA TTTATATGGT  13238

GTTAAAATGT GTATATTTTT GTATGTCACT ATTTTCACTA GGGCTGAGGG GCCTGCGCCC  13298

AGAGCTGGCC TCCCCCAACA CCTGCTGCGC TTGGTAGGTG TGGTGGCGTT ATGGCAGCCC  13358

GGCTGCTGCT TGGATGCGAG CTTGGCCTTG GCCGGTGCT GGGGGCACAG CTGTCTGCCA   13418

GGCACTCTCA TCACCCCAGA GGCCTTGTCA TCCTCCCTTG CCCCAGGCCA GGTAGCAAGA  13478

GAGCAGCGCC CAGGCCTGCT GGCATCAGGT CTGGGCAAGT AGCAGGACTA GGCATGTCAG  13538

AGGACCCCAG GGTGGTTAGA GGAAAAGACT CCTCCTGGGG GCTGGCTCCC AGGGTGGAGG  13598
```

```
AAGGTGACTG TGTGTGTGTG TGTGTGCGCG CGCGACGCGC GAGTGTGCTG TATGGCCCAG     13658

GCAGCCTCAA GGCCCTCGGA GCTGGCTGTG CCTGCTTCTG TGTACCACTT CTGTGGGCAT     13718

GGCCGCTTCT AGAGCCTCGA CACCCCCCCA ACCCCCGCAC CAAGCAGACA AAGTCAATAA     13778

AAGAGCTGTC TGACTGCAAA AAAAAAAA                                       13807
```

(2) INFORMATION FOR SEQ ID NO: 6:

(i) SEQUENCE CHARACTERISTICS:
        (A) LENGTH: 4339 amino acids
        (B) TYPE: amino acid
        (D) TOPOLOGY: linear (ii) MOLECULE TYPE: protein (xi) SEQUENCE DESCRIPTION: SEQ ID NO: 6:

```
Gly Ala Ala Cys Arg Val Asn Cys Ser Gly Arg Gly Leu Arg Thr Leu
 1               5                  10                  15

Gly Pro Ala Leu Arg Ile Pro Ala Asp Ala Thr Ala Leu Asp Val Ser
            20                  25                  30

His Asn Leu Leu Arg Ala Leu Asp Val Gly Leu Leu Ala Asn Leu Ser
        35                  40                  45

Ala Leu Ala Glu Leu Asp Ile Ser Asn Asn Lys Ile Ser Thr Leu Glu
50                  55                  60

Glu Gly Ile Phe Ala Asn Leu Phe Asn Leu Ser Glu Ile Asn Leu Ser
65                  70                  75                  80

Gly Asn Pro Phe Glu Cys Asp Cys Gly Leu Ala Trp Leu Pro Arg Trp
                85                  90                  95

Ala Glu Glu Gln Gln Val Arg Val Val Gln Pro Glu Ala Ala Thr Cys
            100                 105                 110

Ala Gly Pro Gly Ser Leu Ala Gly Gln Pro Leu Leu Gly Ile Pro Leu
        115                 120                 125

Leu Asp Ser Gly Cys Gly Glu Glu Tyr Val Ala Cys Leu Pro Asp Asn
130                 135                 140

Ser Ser Gly Thr Val Ala Ala Val Ser Phe Ser Ala Ala His Glu Gly
145                 150                 155                 160

Leu Leu Gln Pro Glu Ala Cys Ser Ala Phe Cys Phe Ser Thr Gly Gln
                165                 170                 175

Gly Leu Ala Ala Leu Ser Glu Gln Gly Trp Cys Leu Cys Gly Ala Ala
            180                 185                 190

Gln Pro Ser Ser Ala Ser Phe Ala Cys Leu Ser Leu Cys Ser Gly Pro
        195                 200                 205

Pro Pro Pro Ala Pro Thr Cys Arg Gly Pro Thr Leu Leu Gln His
210                 215                 220

Val Phe Pro Ala Ser Pro Gly Ala Thr Leu Val Gly Pro His Gly Pro
225                 230                 235                 240

Leu Ala Ser Gly Gln Leu Ala Ala Phe His Ile Ala Ala Pro Leu Pro
                245                 250                 255

Val Thr Ala Thr Arg Trp Asp Phe Gly Asp Gly Ser Ala Glu Val Asp
            260                 265                 270

Ala Ala Gly Pro Ala Ala Ser His Arg Tyr Val Leu Pro Gly Arg Tyr
        275                 280                 285

His Val Thr Ala Val Leu Ala Leu Gly Ala Gly Ser Ala Leu Leu Gly
    290                 295                 300

Thr Asp Val Gln Val Glu Ala Ala Pro Ala Ala Leu Glu Leu Val Cys
```

-continued

```
305                 310                 315                 320
Pro Ser Ser Val Gln Ser Asp Glu Ser Leu Asp Leu Ser Ile Gln Asn
                325                 330                 335
Arg Gly Gly Ser Gly Leu Glu Ala Ala Tyr Ser Ile Val Ala Leu Gly
                340                 345                 350
Glu Glu Pro Ala Arg Ala Val His Pro Leu Cys Pro Ser Asp Thr Glu
                355                 360                 365
Ile Phe Pro Gly Asn Gly His Cys Tyr Arg Leu Val Glu Lys Ala
    370                 375                 380
Ala Trp Leu Gln Ala Gln Glu Gln Cys Gln Ala Trp Ala Gly Ala Ala
385                 390                 395                 400
Leu Ala Met Val Asp Ser Pro Ala Val Gln Arg Phe Leu Val Ser Arg
                405                 410                 415
Val Thr Arg Ser Leu Asp Val Trp Ile Gly Phe Ser Thr Val Gln Gly
                420                 425                 430
Val Glu Val Gly Pro Ala Pro Gln Gly Glu Ala Phe Ser Leu Glu Ser
                435                 440                 445
Cys Gln Asn Trp Leu Pro Gly Glu Pro His Pro Ala Thr Ala Glu His
        450                 455                 460
Cys Val Arg Leu Gly Pro Thr Gly Trp Cys Asn Thr Asp Leu Cys Ser
465                 470                 475                 480
Ala Pro His Ser Tyr Val Cys Glu Leu Gln Pro Gly Gly Pro Val Gln
                485                 490                 495
Asp Ala Glu Asn Leu Leu Val Gly Ala Pro Ser Gly Asp Leu Gln Gly
                500                 505                 510
Pro Leu Thr Pro Leu Ala Gln Gln Asp Gly Leu Ser Ala Pro His Glu
        515                 520                 525
Pro Val Glu Val Met Val Phe Pro Gly Leu Arg Leu Ser Arg Glu Ala
        530                 535                 540
Phe Leu Thr Thr Ala Glu Phe Gly Thr Gln Glu Leu Arg Arg Pro Ala
545                 550                 555                 560
Gln Leu Arg Leu Gln Val Tyr Arg Leu Leu Ser Thr Ala Gly Thr Pro
                565                 570                 575
Glu Asn Gly Ser Glu Pro Glu Ser Arg Ser Pro Asp Asn Arg Thr Gln
                580                 585                 590
Leu Ala Pro Ala Cys Met Pro Gly Gly Arg Trp Cys Pro Gly Ala Asn
                595                 600                 605
Ile Cys Leu Pro Leu Asp Ala Ser Cys His Pro Gln Ala Cys Ala Asn
        610                 615                 620
Gly Cys Thr Ser Gly Pro Gly Leu Pro Gly Ala Pro Tyr Ala Leu Trp
625                 630                 635                 640
Arg Glu Phe Leu Phe Ser Val Ala Ala Gly Pro Pro Ala Gln Tyr Ser
                645                 650                 655
Val Thr Leu His Gly Gln Asp Val Leu Met Leu Pro Gly Asp Leu Val
            660                 665                 670
Gly Leu Gln His Asp Ala Gly Pro Gly Ala Leu Leu His Cys Ser Pro
            675                 680                 685
Ala Pro Gly His Pro Gly Pro Gln Ala Pro Tyr Leu Ser Ala Asn Ala
            690                 695                 700
Ser Ser Trp Leu Pro His Leu Pro Ala Gln Leu Glu Gly Thr Trp Ala
705                 710                 715                 720
Cys Pro Ala Cys Ala Leu Arg Leu Leu Ala Ala Thr Glu Gln Leu Thr
                725                 730                 735
```

```
Val Leu Leu Gly Leu Arg Pro Asn Pro Gly Leu Arg Met Pro Gly Arg
                740                 745                 750

Tyr Glu Val Arg Ala Glu Val Gly Asn Gly Val Ser Arg His Asn Leu
        755                 760                 765

Ser Cys Ser Phe Asp Val Val Ser Pro Val Ala Gly Leu Arg Val Ile
    770                 775                 780

Tyr Pro Ala Pro Arg Asp Gly Arg Leu Tyr Val Pro Thr Asn Gly Ser
785                 790                 795                 800

Ala Leu Val Leu Gln Val Asp Ser Gly Ala Asn Ala Thr Ala Thr Ala
                805                 810                 815

Arg Trp Pro Gly Gly Ser Val Ser Ala Arg Phe Glu Asn Val Cys Pro
                820                 825                 830

Ala Leu Val Ala Thr Phe Val Pro Gly Cys Pro Trp Glu Thr Asn Asp
                835                 840                 845

Thr Leu Phe Ser Val Val Ala Leu Pro Trp Leu Ser Glu Gly Glu His
                850                 855                 860

Val Val Asp Val Val Glu Asn Ser Ala Ser Arg Ala Asn Leu Ser
865                 870                 875                 880

Leu Arg Val Thr Ala Glu Pro Ile Cys Gly Leu Arg Ala Thr Pro
                885                 890                 895

Ser Pro Glu Ala Arg Val Leu Gln Gly Val Leu Val Arg Tyr Ser Pro
                900                 905                 910

Val Val Glu Ala Gly Ser Asp Met Val Phe Arg Trp Thr Ile Asn Asp
                915                 920                 925

Lys Gln Ser Leu Thr Phe Gln Asn Val Val Phe Asn Val Ile Tyr Gln
    930                 935                 940

Ser Ala Val Phe Lys Leu Ser Leu Thr Ala Ser Asn His Val Ser
945                 950                 955                 960

Asn Val Thr Val Asn Tyr Asn Val Thr Val Glu Arg Met Asn Arg Met
                965                 970                 975

Gln Gly Leu Gln Val Ser Thr Val Pro Ala Val Leu Ser Pro Asn Ala
                980                 985                 990

Thr Leu Val Leu Thr Gly Gly Val Leu Val Asp Ser Ala Val Glu Val
            995                 1000                1005

Ala Phe Leu Trp Asn Phe Gly Asp Gly Glu Gln Ala Leu His Gln Phe
        1010                1015                1020

Gln Pro Pro Tyr Asn Glu Ser Phe Pro Val Pro Asp Pro Ser Val Ala
1025                1030                1035                1040

Gln Val Leu Val Glu His Asn Val Met His Thr Tyr Ala Ala Pro Gly
            1045                1050                1055

Glu Tyr Leu Leu Thr Val Leu Ala Ser Asn Ala Phe Glu Asn Leu Thr
        1060                1065                1070

Gln Gln Val Pro Val Ser Val Arg Ala Ser Leu Pro Ser Val Ala Val
        1075                1080                1085

Gly Val Ser Asp Gly Val Leu Val Ala Gly Arg Pro Val Thr Phe Tyr
        1090                1095                1100

Pro His Pro Leu Pro Ser Pro Gly Gly Val Leu Tyr Thr Trp Asp Phe
1105                1110                1115                1120

Gly Asp Gly Ser Pro Val Leu Thr Gln Ser Gln Pro Ala Ala Asn His
                1125                1130                1135

Thr Tyr Ala Ser Arg Gly Thr Tyr His Val Arg Leu Glu Val Asn Asn
                1140                1145                1150
```

-continued

```
Thr Val Ser Gly Ala Ala Gln Ala Asp Val Arg Val Phe Glu Glu
        1155                1160                1165
Leu Arg Gly Leu Ser Val Asp Met Ser Leu Ala Val Glu Gln Gly Ala
    1170                1175                1180
Pro Val Val Ser Ala Ala Val Gln Thr Gly Asp Asn Ile Thr Trp
1185                1190                1195                1200
Thr Phe Asp Met Gly Asp Gly Thr Val Leu Ser Gly Pro Glu Ala Thr
                1205                1210                1215
Val Glu His Val Tyr Leu Arg Ala Gln Asn Cys Thr Val Thr Val Gly
                1220                1225                1230
Ala Ala Ser Pro Ala Gly His Leu Ala Arg Ser Leu His Val Leu Val
            1235                1240                1245
Phe Val Leu Glu Val Leu Arg Val Glu Pro Ala Ala Cys Ile Pro Thr
        1250                1255                1260
Gln Pro Asp Ala Arg Leu Thr Ala Tyr Val Thr Gly Asn Pro Ala His
1265                1270                1275                1280
Tyr Leu Phe Asp Trp Thr Phe Gly Asp Gly Ser Ser Asn Thr Thr Val
                1285                1290                1295
Arg Gly Cys Pro Thr Val Thr His Asn Phe Thr Arg Ser Gly Thr Phe
                1300                1305                1310
Pro Leu Ala Leu Val Leu Ser Ser Arg Val Asn Arg Ala His Tyr Phe
            1315                1320                1325
Thr Ser Ile Cys Val Glu Pro Glu Val Gly Asn Val Thr Leu Gln Pro
        1330                1335                1340
Glu Arg Gln Phe Val Gln Leu Gly Asp Glu Ala Trp Leu Val Ala Cys
1345                1350                1355                1360
Ala Trp Pro Pro Phe Pro Tyr Arg Tyr Thr Trp Asp Phe Gly Thr Glu
                1365                1370                1375
Glu Ala Ala Pro Thr Arg Ala Arg Gly Pro Glu Val Thr Phe Ile Tyr
            1380                1385                1390
Arg Asp Pro Gly Ser Tyr Leu Val Thr Val Thr Ala Ser Asn Asn Ile
            1395                1400                1405
Ser Ala Ala Asn Asp Ser Ala Leu Val Glu Val Gln Glu Pro Val Leu
        1410                1415                1420
Val Thr Ser Ile Lys Val Asn Gly Ser Leu Gly Leu Glu Leu Gln Gln
1425                1430                1435                1440
Pro Tyr Leu Phe Ser Ala Val Gly Arg Gly Arg Pro Ala Ser Tyr Leu
                1445                1450                1455
Trp Asp Leu Gly Asp Gly Gly Trp Leu Glu Gly Pro Glu Val Thr His
                1460                1465                1470
Ala Tyr Asn Ser Thr Gly Asp Phe Thr Val Arg Val Ala Gly Trp Asn
            1475                1480                1485
Glu Val Ser Arg Ser Glu Ala Trp Leu Asn Val Thr Val Lys Arg Arg
        1490                1495                1500
Val Arg Gly Leu Val Val Asn Ala Ser Arg Thr Val Val Pro Leu Asn
1505                1510                1515                1520
Gly Ser Val Ser Phe Ser Thr Ser Leu Glu Ala Gly Ser Asp Val Arg
                1525                1530                1535
Tyr Ser Trp Val Leu Cys Asp Arg Cys Thr Pro Ile Pro Gly Gly Pro
                1540                1545                1550
Thr Ile Ser Tyr Thr Phe Arg Ser Val Gly Thr Phe Asn Ile Ile Val
            1555                1560                1565
Thr Ala Glu Asn Glu Val Gly Ser Ala Gln Asp Ser Ile Phe Val Tyr
```

-continued

```
            1570                1575                1580
Val Leu Gln Leu Ile Glu Gly Leu Gln Val Val Gly Gly Arg Tyr
1585                1590                1595                1600
Phe Pro Thr Asn His Thr Val Gln Leu Gln Ala Val Val Arg Asp Gly
                    1605                1610                1615
Thr Asn Val Ser Tyr Ser Trp Thr Ala Trp Arg Asp Arg Gly Pro Ala
                    1620                1625                1630
Leu Ala Gly Ser Gly Lys Gly Phe Ser Leu Thr Val Leu Glu Ala Gly
                    1635                1640                1645
Thr Tyr His Val Gln Leu Arg Ala Thr Asn Met Leu Gly Ser Ala Trp
                    1650                1655                1660
Ala Asp Cys Thr Met Asp Phe Val Glu Pro Val Gly Trp Leu Met Val
1665                1670                1675                1680
Thr Ala Ser Pro Asn Pro Ala Ala Val Asn Thr Ser Val Thr Leu Ser
                    1685                1690                1695
Ala Glu Leu Ala Gly Gly Ser Gly Val Val Tyr Thr Trp Ser Leu Glu
                    1700                1705                1710
Glu Gly Leu Ser Trp Glu Thr Ser Glu Pro Phe Thr Thr His Ser Phe
                    1715                1720                1725
Pro Thr Pro Gly Leu His Leu Val Thr Met Thr Ala Gly Asn Pro Leu
                    1730                1735                1740
Gly Ser Ala Asn Ala Thr Val Glu Val Asp Val Gln Val Pro Val Ser
1745                1750                1755                1760
Gly Leu Ser Ile Arg Ala Ser Glu Pro Gly Gly Ser Phe Val Ala Ala
                    1765                1770                1775
Gly Ser Ser Val Pro Phe Trp Gly Gln Leu Ala Thr Gly Thr Asn Val
                    1780                1785                1790
Ser Trp Cys Trp Ala Val Pro Gly Gly Ser Ser Lys Arg Gly Pro His
                    1795                1800                1805
Val Thr Met Val Phe Pro Asp Ala Gly Thr Phe Ser Ile Arg Leu Asn
                    1810                1815                1820
Ala Ser Asn Ala Val Ser Trp Val Ser Ala Thr Tyr Asn Leu Thr Ala
1825                1830                1835                1840
Glu Glu Pro Ile Val Gly Leu Val Leu Trp Ala Ser Ser Lys Val Val
                    1845                1850                1855
Ala Pro Gly Gln Leu Val His Phe Gln Ile Leu Leu Ala Ala Gly Ser
                    1860                1865                1870
Ala Val Thr Phe Arg Leu Gln Val Gly Gly Ala Asn Pro Glu Val Leu
                    1875                1880                1885
Pro Gly Pro Arg Phe Ser His Ser Phe Pro Arg Val Gly Asp His Val
                    1890                1895                1900
Val Ser Val Arg Gly Lys Asn His Val Ser Trp Ala Gln Ala Gln Val
1905                1910                1915                1920
Arg Ile Val Val Leu Glu Ala Val Ser Gly Leu Gln Met Pro Asn Cys
                    1925                1930                1935
Cys Glu Pro Gly Ile Ala Thr Gly Thr Glu Arg Asn Phe Thr Ala Arg
                    1940                1945                1950
Val Gln Arg Gly Ser Arg Val Ala Tyr Ala Trp Tyr Phe Ser Leu Gln
                    1955                1960                1965
Lys Val Gln Gly Asp Ser Leu Val Ile Leu Ser Gly Arg Asp Val Thr
                    1970                1975                1980
Tyr Thr Pro Val Ala Ala Gly Leu Leu Glu Ile Gln Val Arg Ala Phe
1985                1990                1995                2000
```

-continued

Asn Ala Leu Gly Ser Glu Asn Arg Thr Leu Val Leu Glu Val Gln Asp
                2005                2010                2015

Ala Val Gln Tyr Val Ala Leu Gln Ser Gly Pro Cys Phe Thr Asn Arg
                2020                2025                2030

Ser Ala Gln Phe Glu Ala Ala Thr Ser Pro Ser Pro Arg Arg Val Ala
                2035                2040                2045

Tyr His Trp Asp Phe Gly Asp Gly Ser Pro Gly Gln Asp Thr Asp Glu
                2050                2055                2060

Pro Arg Ala Glu His Ser Tyr Leu Arg Pro Gly Asp Tyr Arg Val Gln
2065                2070                2075                2080

Val Asn Ala Ser Asn Leu Val Ser Phe Phe Val Ala Gln Ala Thr Val
                2085                2090                2095

Thr Val Gln Val Leu Ala Cys Arg Glu Pro Glu Val Asp Val Val Leu
                2100                2105                2110

Pro Leu Gln Val Leu Met Arg Arg Ser Gln Arg Asn Tyr Leu Glu Ala
                2115                2120                2125

His Val Asp Leu Arg Asp Cys Val Thr Tyr Gln Thr Glu Tyr Arg Trp
                2130                2135                2140

Glu Val Tyr Arg Thr Ala Ser Cys Gln Arg Pro Gly Arg Pro Ala Arg
2145                2150                2155                2160

Val Ala Leu Pro Gly Val Asp Val Ser Arg Pro Arg Leu Val Leu Pro
                2165                2170                2175

Arg Leu Ala Leu Pro Val Gly His Tyr Cys Phe Val Phe Val Val Ser
                2180                2185                2190

Phe Gly Asp Thr Pro Leu Thr Gln Ser Ile Gln Ala Asn Val Thr Val
                2195                2200                2205

Ala Pro Glu Arg Leu Val Pro Ile Ile Glu Gly Gly Ser Tyr Arg Val
                2210                2215                2220

Trp Ser Asp Thr Arg Asp Leu Val Leu Asp Gly Ser Glu Ser Tyr Asp
2225                2230                2235                2240

Pro Asn Leu Glu Asp Gly Asp Gln Thr Pro Leu Ser Phe His Trp Ala
                2245                2250                2255

Cys Val Ala Ser Thr Gln Arg Glu Ala Gly Gly Cys Ala Leu Asn Phe
                2260                2265                2270

Gly Pro Arg Gly Ser Ser Thr Val Thr Ile Pro Arg Glu Arg Leu Ala
                2275                2280                2285

Ala Gly Val Glu Tyr Thr Phe Ser Leu Thr Val Trp Lys Ala Gly Arg
                2290                2295                2300

Lys Glu Glu Ala Thr Asn Gln Thr Val Leu Ile Arg Ser Gly Arg Val
2305                2310                2315                2320

Pro Ile Val Ser Leu Glu Cys Val Ser Cys Lys Ala Gln Ala Val Tyr
                2325                2330                2335

Glu Val Ser Arg Ser Ser Tyr Val Tyr Leu Glu Gly Arg Cys Leu Asn
                2340                2345                2350

Cys Ser Ser Gly Ser Lys Arg Gly Arg Trp Ala Ala Arg Thr Phe Ser
                2355                2360                2365

Asn Lys Thr Leu Val Leu Asp Glu Thr Thr Ser Thr Gly Ser Ala
                2370                2375                2380

Gly Met Arg Leu Val Leu Arg Arg Gly Val Leu Arg Asp Gly Glu Gly
2385                2390                2395                2400

Tyr Thr Phe Thr Leu Thr Val Leu Gly Arg Ser Gly Glu Glu Glu Gly
                2405                2410                2415

```
Cys Ala Ser Ile Arg Leu Ser Pro Asn Arg Pro Pro Leu Gly Gly Ser
            2420                2425                2430

Cys Arg Leu Phe Pro Leu Gly Ala Val His Ala Leu Thr Thr Lys Val
            2435                2440                2445

His Phe Glu Cys Thr Gly Trp His Asp Ala Glu Asp Ala Gly Ala Pro
            2450                2455                2460

Leu Val Tyr Ala Leu Leu Leu Arg Arg Cys Arg Gln Gly His Cys Glu
2465                2470                2475                2480

Glu Phe Cys Val Tyr Lys Gly Ser Leu Ser Ser Tyr Gly Ala Val Leu
            2485                2490                2495

Pro Pro Gly Phe Arg Pro His Phe Glu Val Gly Leu Ala Val Val Val
            2500                2505                2510

Gln Asp Gln Leu Gly Ala Ala Val Ala Leu Asn Arg Ser Leu Ala
            2515                2520                2525

Ile Thr Leu Pro Glu Pro Asn Gly Ser Ala Thr Gly Leu Thr Val Trp
            2530                2535                2540

Leu His Gly Leu Thr Ala Ser Val Leu Pro Gly Leu Leu Arg Gln Ala
2545                2550                2555                2560

Asp Pro Gln His Val Ile Glu Tyr Ser Leu Ala Leu Val Thr Val Leu
            2565                2570                2575

Asn Glu Tyr Glu Arg Ala Leu Asp Val Ala Ala Glu Pro Lys His Glu
            2580                2585                2590

Arg Gln His Arg Ala Gln Ile Arg Lys Asn Ile Thr Glu Thr Leu Val
            2595                2600                2605

Ser Leu Arg Val His Thr Val Asp Asp Ile Gln Gln Ile Ala Ala Ala
            2610                2615                2620

Leu Ala Gln Cys Met Gly Pro Ser Arg Glu Leu Val Cys Arg Ser Cys
2625                2630                2635                2640

Leu Lys Gln Thr Leu His Lys Leu Glu Ala Met Met Leu Ile Leu Gln
            2645                2650                2655

Ala Glu Thr Thr Ala Gly Thr Val Thr Pro Thr Ala Ile Gly Asp Ser
            2660                2665                2670

Ile Leu Asn Ile Thr Gly Asp Leu Ile His Leu Ala Ser Ser Asp Val
            2675                2680                2685

Arg Ala Pro Gln Pro Ser Glu Leu Gly Ala Glu Ser Pro Ser Arg Met
            2690                2695                2700

Val Ala Ser Gln Ala Tyr Asn Leu Thr Ser Ala Leu Met Arg Ile Leu
2705                2710                2715                2720

Met Arg Ser Arg Val Leu Asn Glu Glu Pro Leu Thr Leu Ala Gly Glu
            2725                2730                2735

Glu Ile Val Ala Gln Gly Lys Arg Ser Asp Pro Arg Ser Leu Leu Cys
            2740                2745                2750

Tyr Gly Gly Ala Pro Gly Pro Gly Cys His Phe Ser Ile Pro Glu Ala
            2755                2760                2765

Phe Ser Gly Ala Leu Ala Asn Leu Ser Asp Val Val Gln Leu Ile Phe
            2770                2775                2780

Leu Val Asp Ser Asn Pro Phe Pro Phe Gly Tyr Ile Ser Asn Tyr Thr
2785                2790                2795                2800

Val Ser Thr Lys Val Ala Ser Met Ala Phe Gln Thr Gln Ala Gly Ala
            2805                2810                2815

Gln Ile Pro Ile Glu Arg Leu Ala Ser Glu Arg Ala Ile Thr Val Lys
            2820                2825                2830

Val Pro Asn Asn Ser Asp Trp Ala Ala Arg Gly His Arg Ser Ser Ala
```

-continued

```
            2835                2840                2845
Asn Ser Ala Asn Ser Val Val Gln Pro Gln Ala Ser Val Gly Ala
            2850                2855                2860
Val Val Thr Leu Asp Ser Ser Asn Pro Ala Ala Gly Leu His Leu Gln
2865                2870                2875                2880
Leu Asn Tyr Thr Leu Leu Asp Gly His Tyr Leu Ser Glu Glu Pro Glu
                2885                2890                2895
Pro Tyr Leu Ala Val Tyr Leu His Ser Glu Pro Arg Pro Asn Glu His
                2900                2905                2910
Asn Cys Ser Ala Ser Arg Arg Ile Arg Pro Glu Ser Leu Gln Gly Ala
                2915                2920                2925
Asp His Arg Pro Tyr Thr Phe Phe Ile Ser Pro Gly Ser Arg Asp Pro
                2930                2935                2940
Ala Gly Ser Tyr His Leu Asn Leu Ser Ser His Phe Arg Trp Ser Ala
2945                2950                2955                2960
Leu Gln Val Ser Val Gly Leu Tyr Thr Ser Leu Cys Gln Tyr Phe Ser
                2965                2970                2975
Glu Glu Asp Met Val Trp Arg Thr Glu Gly Leu Leu Pro Leu Glu Glu
                2980                2985                2990
Thr Ser Pro Arg Gln Ala Val Cys Leu Thr Arg His Leu Thr Ala Phe
                2995                3000                3005
Gly Ala Ser Leu Phe Val Pro Pro Ser His Val Arg Phe Val Phe Pro
                3010                3015                3020
Glu Pro Thr Ala Asp Val Asn Tyr Ile Val Met Leu Thr Cys Ala Val
3025                3030                3035                3040
Cys Leu Val Thr Tyr Met Val Met Ala Ala Ile Leu His Lys Leu Asp
                3045                3050                3055
Gln Leu Asp Ala Ser Arg Gly Arg Ala Ile Pro Phe Cys Gly Gln Arg
                3060                3065                3070
Gly Arg Phe Lys Tyr Glu Ile Leu Val Lys Thr Gly Trp Gly Arg Gly
                3075                3080                3085
Ser Gly Thr Thr Ala His Val Gly Ile Met Leu Tyr Gly Val Asp Ser
                3090                3095                3100
Arg Ser Gly His Arg His Leu Asp Gly Asp Arg Ala Phe His Arg Asn
3105                3110                3115                3120
Ser Leu Asp Ile Phe Arg Ile Ala Thr Pro His Ser Leu Gly Ser Val
                3125                3130                3135
Trp Lys Ile Arg Val Trp His Asp Asn Lys Gly Leu Ser Pro Ala Trp
                3140                3145                3150
Phe Leu Gln His Val Ile Val Arg Asp Leu Gln Thr Ala Arg Ser Ala
                3155                3160                3165
Phe Phe Leu Val Asn Asp Trp Leu Ser Val Glu Thr Glu Ala Asn Gly
                3170                3175                3180
Gly Leu Val Glu Lys Glu Val Leu Ala Ala Ser Asp Ala Ala Leu Leu
3185                3190                3195                3200
Arg Phe Arg Arg Leu Leu Val Ala Glu Leu Gln Arg Gly Phe Phe Asp
                3205                3210                3215
Lys His Ile Trp Leu Ser Ile Ser Asp Arg Pro Pro Arg Ser Arg Phe
                3220                3225                3230
Thr Arg Ile Gln Arg Ala Thr Cys Cys Val Leu Leu Ile Cys Leu Phe
                3235                3240                3245
Leu Gly Ala Asn Ala Val Trp Tyr Gly Ala Val Gly Asp Ser Ala Tyr
                3250                3255                3260
```

-continued

```
Ser Thr Gly His Val Ser Arg Leu Ser Pro Leu Ser Val Asp Thr Val
3265                3270                3275                3280

Ala Val Gly Leu Val Ser Ser Val Val Tyr Pro Val Tyr Leu Ala
        3285                3290                3295

Ile Leu Phe Leu Phe Arg Met Ser Arg Ser Lys Val Ala Gly Ser Pro
            3300                3305                3310

Ser Pro Thr Pro Ala Gly Gln Gln Val Leu Asp Ile Asp Ser Cys Leu
            3315                3320                3325

Asp Ser Ser Val Leu Asp Ser Ser Phe Leu Thr Phe Ser Gly Leu His
        3330                3335                3340

Ala Glu Ala Phe Val Gly Gln Met Lys Ser Asp Leu Phe Leu Asp Asp
3345                3350                3355                3360

Ser Lys Ser Leu Val Cys Trp Pro Ser Gly Glu Gly Thr Leu Ser Trp
            3365                3370                3375

Pro Asp Leu Leu Ser Asp Pro Ser Ile Val Gly Ser Asn Leu Arg Gln
            3380                3385                3390

Leu Ala Arg Gly Gln Ala Gly His Gly Leu Gly Pro Glu Glu Asp Gly
            3395                3400                3405

Phe Ser Leu Ala Ser Pro Tyr Ser Pro Ala Lys Ser Phe Ser Ala Ser
    3410                3415                3420

Asp Glu Asp Leu Ile Gln Gln Val Leu Ala Glu Gly Val Ser Ser Pro
3425                3430                3435                3440

Ala Pro Thr Gln Asp Thr His Met Glu Thr Asp Leu Leu Ser Ser Leu
            3445                3450                3455

Ser Ser Thr Pro Gly Glu Lys Thr Glu Thr Leu Ala Leu Gln Arg Leu
            3460                3465                3470

Gly Glu Leu Gly Pro Pro Ser Pro Gly Leu Asn Trp Glu Gln Pro Gln
            3475                3480                3485

Ala Ala Arg Leu Ser Arg Thr Gly Leu Val Glu Gly Leu Arg Lys Arg
            3490                3495                3500

Leu Leu Pro Ala Trp Cys Ala Ser Leu Ala His Gly Leu Ser Leu Leu
3505                3510                3515                3520

Leu Val Ala Val Ala Val Ala Val Ser Gly Trp Val Gly Ala Ser Phe
            3525                3530                3535

Pro Pro Gly Val Ser Val Ala Trp Leu Leu Ser Ser Ser Ala Ser Phe
            3540                3545                3550

Leu Ala Ser Phe Leu Gly Trp Glu Pro Leu Lys Val Leu Leu Glu Ala
            3555                3560                3565

Leu Tyr Phe Ser Leu Val Ala Lys Arg Leu His Pro Asp Glu Asp Asp
            3570                3575                3580

Thr Leu Val Glu Ser Pro Ala Val Thr Pro Val Ser Ala Arg Val Pro
3585                3590                3595                3600

Arg Val Arg Pro Pro His Gly Phe Ala Leu Phe Leu Ala Lys Glu Glu
            3605                3610                3615

Ala Arg Lys Val Lys Arg Leu His Gly Met Leu Arg Ser Leu Leu Val
            3620                3625                3630

Tyr Met Leu Phe Leu Leu Val Thr Leu Leu Ala Ser Tyr Gly Asp Ala
            3635                3640                3645

Ser Cys His Gly His Ala Tyr Arg Leu Gln Ser Ala Ile Lys Gln Glu
    3650                3655                3660

Leu His Ser Arg Ala Phe Leu Ala Ile Thr Arg Ser Glu Glu Leu Trp
3665                3670                3675                3680
```

-continued

```
Pro Trp Met Ala His Val Leu Pro Tyr Val His Gly Asn Gln Ser
            3685                3690                3695

Ser Pro Glu Leu Gly Pro Pro Arg Leu Arg Gln Val Arg Leu Gln Glu
            3700                3705                3710

Ala Leu Tyr Pro Asp Pro Pro Gly Pro Arg Val His Thr Cys Ser Ala
            3715                3720                3725

Ala Gly Gly Phe Ser Thr Ser Asp Tyr Asp Val Gly Trp Glu Ser Pro
            3730                3735                3740

His Asn Gly Ser Gly Thr Trp Ala Tyr Ser Ala Pro Asp Leu Leu Gly
3745                3750                3755                3760

Ala Trp Ser Trp Gly Ser Cys Ala Val Tyr Asp Ser Gly Gly Tyr Val
            3765                3770                3775

Gln Glu Leu Gly Leu Ser Leu Glu Glu Ser Arg Asp Arg Leu Arg Phe
            3780                3785                3790

Leu Gln Leu His Asn Trp Leu Asp Asn Arg Ser Arg Ala Val Phe Leu
            3795                3800                3805

Glu Leu Thr Arg Tyr Ser Pro Ala Val Gly Leu His Ala Ala Val Thr
            3810                3815                3820

Leu Arg Leu Glu Phe Pro Ala Ala Gly Arg Ala Leu Ala Ala Leu Ser
3825                3830                3835                3840

Val Arg Pro Phe Ala Leu Arg Arg Leu Ser Ala Gly Leu Ser Leu Pro
            3845                3850                3855

Leu Leu Thr Ser Val Cys Leu Leu Phe Ala Val His Phe Ala Val
            3860                3865                3870

Ala Glu Ala Arg Thr Trp His Arg Glu Gly Arg Trp Arg Val Leu Arg
            3875                3880                3885

Leu Gly Ala Trp Ala Arg Trp Leu Leu Val Ala Leu Thr Ala Ala Thr
            3890                3895                3900

Ala Leu Val Arg Leu Ala Gln Leu Gly Ala Ala Asp Arg Gln Trp Thr
3905                3910                3915                3920

Arg Phe Val Arg Gly Arg Pro Arg Arg Phe Thr Ser Phe Asp Gln Val
            3925                3930                3935

Ala His Val Ser Ser Ala Ala Arg Gly Leu Ala Ala Ser Leu Leu Phe
            3940                3945                3950

Leu Leu Leu Val Lys Ala Ala Gln His Val Arg Phe Val Arg Gln Trp
            3955                3960                3965

Ser Val Phe Gly Lys Thr Leu Cys Arg Ala Leu Pro Glu Leu Leu Gly
            3970                3975                3980

Val Thr Leu Gly Leu Val Val Leu Gly Val Ala Tyr Ala Gln Leu Ala
3985                3990                3995                4000

Ile Leu Leu Val Ser Ser Cys Val Asp Ser Leu Trp Ser Val Ala Gln
            4005                4010                4015

Ala Leu Leu Val Leu Cys Pro Gly Thr Gly Leu Ser Thr Leu Cys Pro
            4020                4025                4030

Ala Glu Ser Trp His Leu Ser Pro Leu Leu Cys Val Gly Leu Trp Ala
            4035                4040                4045

Leu Arg Leu Trp Gly Ala Leu Arg Leu Gly Ala Val Ile Leu Arg Trp
            4050                4055                4060

Arg Tyr His Ala Leu Arg Gly Glu Leu Tyr Arg Pro Ala Trp Glu Pro
4065                4070                4075                4080

Gln Asp Tyr Glu Met Val Glu Leu Phe Leu Arg Arg Leu Arg Leu Trp
            4085                4090                4095

Met Gly Leu Ser Lys Val Lys Glu Phe Arg His Lys Val Arg Phe Glu
```

```
                     4100              4105              4110
Gly Met Glu Pro Leu Pro Ser Arg Ser Ser Arg Gly Ser Lys Val Ser
            4115              4120              4125
Pro Asp Val Pro Pro Pro Ser Ala Gly Ser Asp Ala Ser His Pro Ser
    4130              4135              4140
Thr Ser Ser Ser Gln Leu Asp Gly Leu Ser Val Ser Leu Gly Arg Leu
4145              4150              4155              4160
Gly Thr Arg Cys Glu Pro Glu Pro Ser Arg Leu Gln Ala Val Phe Glu
                4165              4170              4175
Ala Leu Leu Thr Gln Phe Asp Arg Leu Asn Gln Ala Thr Glu Asp Val
                4180              4185              4190
Tyr Gln Leu Glu Gln Gln Leu His Ser Leu Gln Gly Arg Arg Ser Ser
            4195              4200              4205
Arg Ala Pro Ala Gly Ser Ser Arg Gly Pro Ser Pro Gly Leu Arg Pro
    4210              4215              4220
Ala Leu Pro Ser Arg Leu Ala Arg Ala Ser Arg Gly Val Asp Leu Ala
4225              4230              4235              4240
Thr Gly Pro Ser Arg Thr Pro Ser Gly Gln Glu Gln Gly Pro Pro Gln
                4245              4250              4255
Gln His Leu Val Leu Leu Pro Gly Gly Gly Pro Trp Ser Arg Ser
            4260              4265              4270
Gly His Arg Ser Val Leu Leu Ser Ala Ala Val Lys Ala Glu Gly Gln
            4275              4280              4285
Ala Glu Trp Leu His Val Gly Ser Pro Glu Ser Arg Gln Gly His Leu
    4290              4295              4300
Ser Val Cys Gly Leu Gln His Phe Lys Glu Ala Val Trp Pro Thr Arg
4305              4310              4315              4320
Thr Gln Gly Pro Leu Pro Ser Ser Leu Gly Lys Asp Thr Ala Val Leu
                4325              4330              4335
Asp Gly Phe (2) INFORMATION FOR SEQ ID NO: 7:

(i) SEQUENCE CHARACTERISTICS:
        (A) LENGTH: 14148 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION:212..13117

(ix) FEATURE:
        (A) NAME/KEY: misc_feature
        (B) LOCATION:212..278
        (D) OTHER INFORMATION:/note= "Probable signal sequence"

(ix) FEATURE:
        (A) NAME/KEY: misc_feature
        (B) LOCATION:359..4574
        (D) OTHER INFORMATION:/note= "N-linked glycosylation sites at
            the following positions: 359, 476, 557, 572, 770, 2072,
            2105, 2447, 2639, 2732, 2771, 2879, 2972, 3221, 3311,
            3425, 3548, 3743, 3791, 3929, 4016, 4217, 4253, 4355, "

(ix) FEATURE:
        (A) NAME/KEY: misc_feature
```

```
        (B) LOCATION:4574..8144
        (D) OTHER INFORMATION:/note= "N-linked glycosylation sites at
            following locations: 4559, 4574, 4631, 4763, 4832, 4871,
            4898, 5150, 5192, 5408, 5582, 5711, 5810, 5849, 6182,
            6359, 6431, 6584, 6953, 7268, 7394, 7445, 7943, 8144 "

(ix) FEATURE:
        (A) NAME/KEY: misc_feature
        (B) LOCATION:8363..11741
        (D) OTHER INFORMATION:/note= "N-linked glycosylation sites at
            following locations: 8471, 8663, 8732, 8843, 8984, 9077,
            9191, 11420, 11576, 11741"

(ix) FEATURE:
        (A) NAME/KEY: misc_feature
        (B) LOCATION:7949..8009
        (D) OTHER INFORMATION:/note= "Predicted transmembrane domain"

(ix) FEATURE:
        (A) NAME/KEY: misc_feature
        (B) LOCATION:8288..8348
        (D) OTHER INFORMATION:/note= "Predicted transmembrane domain"

(ix) FEATURE:
        (A) NAME/KEY: misc_feature
        (B) LOCATION:9434..9494
        (D) OTHER INFORMATION:/note= "Predicted transmembrane domain"

(ix) FEATURE:
        (A) NAME/KEY: misc_feature
        (B) LOCATION:10052..10112
        (D) OTHER INFORMATION:/note= "Predicted transmembrane domain"

(ix) FEATURE:
        (A) NAME/KEY: misc_feature
        (B) LOCATION:10178..10238
        (D) OTHER INFORMATION:/note= "Predicted transmembrane domain"

(ix) FEATURE:
        (A) NAME/KEY: misc_feature
        (B) LOCATION:10886..10946
        (D) OTHER INFORMATION:/note= "Predicted transmembrane domain"

(ix) FEATURE:
        (A) NAME/KEY: misc_feature
        (B) LOCATION:10955..11015
        (D) OTHER INFORMATION:/note= "Predicted transmembrane domain"

(ix) FEATURE:
        (A) NAME/KEY: misc_feature
        (B) LOCATION:11216..11276
        (D) OTHER INFORMATION:/note= "Predicted transmembrane domain"

(ix) FEATURE:
        (A) NAME/KEY: misc_feature
        (B) LOCATION:11894..11954
        (D) OTHER INFORMATION:/note= "Predicted transmembrane domain"

(ix) FEATURE:
        (A) NAME/KEY: misc_feature
        (B) LOCATION:12293..12353
        (D) OTHER INFORMATION:/note= "Predicted transmembrane domain"

(ix) FEATURE:
        (A) NAME/KEY: misc_feature
        (B) LOCATION:12377..12437
        (D) OTHER INFORMATION:/note= "Predicted transmembrane domain"

(ix) FEATURE:
        (A) NAME/KEY: misc_feature
        (B) LOCATION:212..278
        (D) OTHER INFORMATION:/note= "Possible hinge sequence"

(ix) FEATURE:
        (A) NAME/KEY: misc_feature
        (B) LOCATION:279
        (D) OTHER INFORMATION:/note= "Cleavage site"

(xi) SEQUENCE DESCRIPTION: SEQ ID NO: 7:
```

```
GCACTGCAGC GCCAGCGTCC GAGCGGGCGG CCGAGCTCCC GGAGCGGCCT GGCCCCGAGC        60

CCCGAGCGGG CGTCGCTCAG CAGCAGGTCG CGGCCGCGCA GCCCCATCCA GCCCCGCGCC       120

CGCCATGCCG TCCGCGGGCC CCGCCTGAGC TGCGGTCTCC GCGCGCGGGC GGGCCTGGGG       180

ACGGCGGGGC CATGCGCGCG CTGCCCTAAC G ATG CCG CCC GCC GCG CCC GCC          232
                                  Met Pro Pro Ala Ala Pro Ala
                                  4340                4345

CGC CTG GCG CTG GCC CTG GGC CTG GGC CTG TGG CTC GGG GCG CTG GCG         280
Arg Leu Ala Leu Ala Leu Gly Leu Gly Leu Trp Leu Gly Ala Leu Ala
        4350                4355                4360

GGG GGC CCC GGG CGC GGC TGC GGG CCC TGC GAG CCC CCC TGC CTC TGC         328
Gly Gly Pro Gly Arg Gly Cys Gly Pro Cys Glu Pro Pro Cys Leu Cys
        4365                4370                4375

GGC CCA GCG CCC GGC GCC GCC TGC CGC GTC AAC TGC TCG GGC CGC GGG         376
Gly Pro Ala Pro Gly Ala Ala Cys Arg Val Asn Cys Ser Gly Arg Gly
        4380                4385                4390

CTG CGG ACG CTC GGT CCC GCG CTG CGC ATC CCC GCG GAC GCC ACA GCG         424
Leu Arg Thr Leu Gly Pro Ala Leu Arg Ile Pro Ala Asp Ala Thr Ala
4395                4400                4405                4410

CTA GAC GTC TCC CAC AAC CTG CTC CGG GCG CTG GAC GTT GGG CTC CTG         472
Leu Asp Val Ser His Asn Leu Leu Arg Ala Leu Asp Val Gly Leu Leu
                4415                4420                4425

GCG AAC CTC TCG GCG CTG GCA GAG CTG GAT ATA AGC AAC AAC AAG ATT         520
Ala Asn Leu Ser Ala Leu Ala Glu Leu Asp Ile Ser Asn Asn Lys Ile
                4430                4435                4440

TCT ACG TTA GAA GAA GGA ATA TTT GCT AAT TTA TTT AAT TTA AGT GAA         568
Ser Thr Leu Glu Glu Gly Ile Phe Ala Asn Leu Phe Asn Leu Ser Glu
                4445                4450                4455

ATA AAC CTG AGT GGG AAC CCG TTT GAG TGT GAC TGT GGC CTG GCG TGG         616
Ile Asn Leu Ser Gly Asn Pro Phe Glu Cys Asp Cys Gly Leu Ala Trp
        4460                4465                4470

CTG CCG CGA TGG GCG GAG GAG CAG CAG GTG CGG GTG GTG CAG CCC GAG         664
Leu Pro Arg Trp Ala Glu Glu Gln Gln Val Arg Val Val Gln Pro Glu
4475                4480                4485                4490

GCA GCC ACG TGT GCT GGG CCT GGC TCC CTG GCT GGC CAG CCT CTG CTT         712
Ala Ala Thr Cys Ala Gly Pro Gly Ser Leu Ala Gly Gln Pro Leu Leu
                4495                4500                4505

GGC ATC CCC TTG CTG GAC AGT GGC TGT GGT GAG GAG TAT GTC GCC TGC         760
Gly Ile Pro Leu Leu Asp Ser Gly Cys Gly Glu Glu Tyr Val Ala Cys
        4510                4515                4520

CTC CCT GAC AAC AGC TCA GGC ACC GTG GCA GCA GTG TCC TTT TCA GCT         808
Leu Pro Asp Asn Ser Ser Gly Thr Val Ala Ala Val Ser Phe Ser Ala
        4525                4530                4535

GCC CAC GAA GGC CTG CTT CAG CCA GAG GCC TGC AGC GCC TTC TGC TTC         856
Ala His Glu Gly Leu Leu Gln Pro Glu Ala Cys Ser Ala Phe Cys Phe
        4540                4545                4550

TCC ACC GGC CAG GGC CTC GCA GCC CTC TCG GAG CAG GGC TGG TGC CTG         904
Ser Thr Gly Gln Gly Leu Ala Ala Leu Ser Glu Gln Gly Trp Cys Leu
4555                4560                4565                4570

TGT GGG GCG GCC CAG CCC TCC AGT GCC TCC TTT GCC TGC CTG TCC CTC         952
Cys Gly Ala Ala Gln Pro Ser Ser Ala Ser Phe Ala Cys Leu Ser Leu
                4575                4580                4585

TGC TCC GGC CCC CCG CCA CCT CCT GCC CCC ACC TGT AGG GGC CCC ACC        1000
Cys Ser Gly Pro Pro Pro Pro Ala Pro Thr Cys Arg Gly Pro Thr
        4590                4595                4600

CTC CTC CAG CAC GTC TTC CCT GCC TCC CCA GGG GCC ACC CTG GTG GGG        1048
Leu Leu Gln His Val Phe Pro Ala Ser Pro Gly Ala Thr Leu Val Gly
                4605                4610                4615
```

```
CCC CAC GGA CCT CTG GCC TCT GGC CAG CTA GCA GCC TTC CAC ATC GCT      1096
Pro His Gly Pro Leu Ala Ser Gly Gln Leu Ala Ala Phe His Ile Ala
        4620                4625                4630

GCC CCG CTC CCT GTC ACT GCC ACA CGC TGG GAC TTC GGA GAC GGC TCC      1144
Ala Pro Leu Pro Val Thr Ala Thr Arg Trp Asp Phe Gly Asp Gly Ser
4635                4640                4645                4650

GCC GAG GTG GAT GCC GCT GGG CCG GCT GCC TCG CAT CGC TAT GTG CTG      1192
Ala Glu Val Asp Ala Ala Gly Pro Ala Ala Ser His Arg Tyr Val Leu
            4655                4660                4665

CCT GGG CGC TAT CAC GTG ACG GCC GTG CTG GCC CTG GGG GCC GGC TCA      1240
Pro Gly Arg Tyr His Val Thr Ala Val Leu Ala Leu Gly Ala Gly Ser
        4670                4675                4680

GCC CTG CTG GGG ACA GAC GTG CAG GTG GAA GCG GCA CCT GCC GCC CTG      1288
Ala Leu Leu Gly Thr Asp Val Gln Val Glu Ala Ala Pro Ala Ala Leu
            4685                4690                4695

GAG CTC GTG TGC CCG TCC TCG GTG CAG AGT GAC GAG AGC CTT GAC CTC      1336
Glu Leu Val Cys Pro Ser Ser Val Gln Ser Asp Glu Ser Leu Asp Leu
        4700                4705                4710

AGC ATC CAG AAC CGC GGT GGT TCA GGC CTG GAG GCC GCC TAC AGC ATC      1384
Ser Ile Gln Asn Arg Gly Gly Ser Gly Leu Glu Ala Ala Tyr Ser Ile
4715                4720                4725                4730

GTG GCC CTG GGC GAG GAG CCG GCC CGA GCG GTG CAC CCG CTC TGC CCC      1432
Val Ala Leu Gly Glu Glu Pro Ala Arg Ala Val His Pro Leu Cys Pro
        4735                4740                4745

TCG GAC ACG GAG ATC TTC CCT GGC AAC GGG CAC TGC TAC CGC CTG GTG      1480
Ser Asp Thr Glu Ile Phe Pro Gly Asn Gly His Cys Tyr Arg Leu Val
            4750                4755                4760

GTG GAG AAG GCG GCC TGG CTG CAG GCG CAG GAG CAG TGT CAG GCC TGG      1528
Val Glu Lys Ala Ala Trp Leu Gln Ala Gln Glu Gln Cys Gln Ala Trp
        4765                4770                4775

GCC GGG GCC GCC CTG GCA ATG GTG GAC AGT CCC GCC GTG CAG CGC TTC      1576
Ala Gly Ala Ala Leu Ala Met Val Asp Ser Pro Ala Val Gln Arg Phe
    4780                4785                4790

CTG GTC TCC CGG GTC ACC AGG AGC CTA GAC GTG TGG ATC GGC TTC TCG      1624
Leu Val Ser Arg Val Thr Arg Ser Leu Asp Val Trp Ile Gly Phe Ser
4795                4800                4805                4810

ACT GTG CAG GGG GTG GAG GTG GGC CCA GCG CCG CAG GGC GAG GCC TTC      1672
Thr Val Gln Gly Val Glu Val Gly Pro Ala Pro Gln Gly Glu Ala Phe
            4815                4820                4825

AGC CTG GAG AGC TGC CAG AAC TGG CTG CCC GGG GAG CCA CAC CCA GCC      1720
Ser Leu Glu Ser Cys Gln Asn Trp Leu Pro Gly Glu Pro His Pro Ala
        4830                4835                4840

ACA GCC GAG CAC TGC GTC CGG CTC GGG CCC ACC GGG TGG TGT AAC ACC      1768
Thr Ala Glu His Cys Val Arg Leu Gly Pro Thr Gly Trp Cys Asn Thr
            4845                4850                4855

GAC CTG TGC TCA GCG CCG CAC AGC TAC GTC TGC GAG CTG CAG CCC GGA      1816
Asp Leu Cys Ser Ala Pro His Ser Tyr Val Cys Glu Leu Gln Pro Gly
        4860                4865                4870

GGC CCA GTG CAG GAT GCC GAG AAC CTC CTC GTG GGA GCG CCC AGT GGG      1864
Gly Pro Val Gln Asp Ala Glu Asn Leu Leu Val Gly Ala Pro Ser Gly
4875                4880                4885                4890

GAC CTG CAG GGA CCC CTG ACG CCT CTG GCA CAG CAG GAC GGC CTC TCA      1912
Asp Leu Gln Gly Pro Leu Thr Pro Leu Ala Gln Gln Asp Gly Leu Ser
            4895                4900                4905

GCC CCG CAC GAG CCC GTG GAG GTC ATG GTA TTC CCG GGC CTG CGT CTG      1960
Ala Pro His Glu Pro Val Glu Val Met Val Phe Pro Gly Leu Arg Leu
        4910                4915                4920

AGC CGT GAA GCC TTC CTC ACC ACG GCC GAA TTT GGG ACC CAG GAG CTC      2008
Ser Arg Glu Ala Phe Leu Thr Thr Ala Glu Phe Gly Thr Gln Glu Leu
        4925                4930                4935
```

```
CGG CGG CCC GCC CAG CTG CGG CTG CAG GTG TAC CGG CTC CTC AGC ACA     2056
Arg Arg Pro Ala Gln Leu Arg Leu Gln Val Tyr Arg Leu Leu Ser Thr
        4940            4945            4950

GCA GGG ACC CCG GAG AAC GGC AGC GAG CCT GAG AGC AGG TCC CCG GAC     2104
Ala Gly Thr Pro Glu Asn Gly Ser Glu Pro Glu Ser Arg Ser Pro Asp
4955            4960            4965            4970

AAC AGG ACC CAG CTG GCC CCC GCG TGC ATG CCA GGG GGA CGC TGG TGC     2152
Asn Arg Thr Gln Leu Ala Pro Ala Cys Met Pro Gly Gly Arg Trp Cys
            4975            4980            4985

CCT GGA GCC AAC ATC TGC TTG CCG CTG GAC GCC TCT TGC CAC CCC CAG     2200
Pro Gly Ala Asn Ile Cys Leu Pro Leu Asp Ala Ser Cys His Pro Gln
        4990            4995            5000

GCC TGC GCC AAT GGC TGC ACG TCA GGG CCA GGG CTA CCC GGG GCC CCC     2248
Ala Cys Ala Asn Gly Cys Thr Ser Gly Pro Gly Leu Pro Gly Ala Pro
        5005            5010            5015

TAT GCG CTA TGG AGA GAG TTC CTC TTC TCC GTT GCC GCG GGG CCC CCC     2296
Tyr Ala Leu Trp Arg Glu Phe Leu Phe Ser Val Ala Ala Gly Pro Pro
        5020            5025            5030

GCG CAG TAC TCG GTC ACC CTC CAC GGC CAG GAT GTC CTC ATG CTC CCT     2344
Ala Gln Tyr Ser Val Thr Leu His Gly Gln Asp Val Leu Met Leu Pro
5035            5040            5045            5050

GGT GAC CTC GTT GGC TTG CAG CAC GAC GCT GGC CCT GGC GCC CTC CTG     2392
Gly Asp Leu Val Gly Leu Gln His Asp Ala Gly Pro Gly Ala Leu Leu
            5055            5060            5065

CAC TGC TCG CCG GCT CCC GGC CAC CCT GGT CCC CAG GCC CCG TAC CTC     2440
His Cys Ser Pro Ala Pro Gly His Pro Gly Pro Gln Ala Pro Tyr Leu
            5070            5075            5080

TCC GCC AAC GCC TCG TCA TGG CTG CCC CAC TTG CCA GCC CAG CTG GAG     2488
Ser Ala Asn Ala Ser Ser Trp Leu Pro His Leu Pro Ala Gln Leu Glu
        5085            5090            5095

GGC ACT TGG GCC TGC CCT GCC TGT GCC CTG CGG CTG CTT GCA GCC ACG     2536
Gly Thr Trp Ala Cys Pro Ala Cys Ala Leu Arg Leu Leu Ala Ala Thr
        5100            5105            5110

GAA CAG CTC ACC GTG CTG CTG GGC TTG AGG CCC AAC CCT GGA CTG CGG     2584
Glu Gln Leu Thr Val Leu Leu Gly Leu Arg Pro Asn Pro Gly Leu Arg
5115            5120            5125            5130

ATG CCT GGG CGC TAT GAG GTC CGG GCA GAG GTG GGC AAT GGC GTG TCC     2632
Met Pro Gly Arg Tyr Glu Val Arg Ala Glu Val Gly Asn Gly Val Ser
            5135            5140            5145

AGG CAC AAC CTC TCC TGC AGC TTT GAC GTG GTC TCC CCA GTG GCT GGG     2680
Arg His Asn Leu Ser Cys Ser Phe Asp Val Val Ser Pro Val Ala Gly
            5150            5155            5160

CTG CGG GTC ATC TAC CCT GCC CCC CGC GAC GGC CGC CTC TAC GTG CCC     2728
Leu Arg Val Ile Tyr Pro Ala Pro Arg Asp Gly Arg Leu Tyr Val Pro
        5165            5170            5175

ACC AAC GGC TCA GCC TTG GTG CTC CAG GTG GAC TCT GGT GCC AAC GCC     2776
Thr Asn Gly Ser Ala Leu Val Leu Gln Val Asp Ser Gly Ala Asn Ala
        5180            5185            5190

ACG GCC ACG GCT CGC TGG CCT GGG GGC AGT GTC AGC GCC CGC TTT GAG     2824
Thr Ala Thr Ala Arg Trp Pro Gly Gly Ser Val Ser Ala Arg Phe Glu
5195            5200            5205            5210

AAT GTC TGC CCT GCC CTG GTG GCC ACC TTC GTG CCC GGC TGC CCC TGG     2872
Asn Val Cys Pro Ala Leu Val Ala Thr Phe Val Pro Gly Cys Pro Trp
            5215            5220            5225

GAG ACC AAC GAT ACC CTG TTC TCA GTG GTA GCA CTG CCG TGG CTC AGT     2920
Glu Thr Asn Asp Thr Leu Phe Ser Val Val Ala Leu Pro Trp Leu Ser
            5230            5235            5240

GAG GGG GAG CAC GTG GTG GAC GTG GTG GTG GAA AAC AGC GCC AGC CGG     2968
Glu Gly Glu His Val Val Asp Val Val Val Glu Asn Ser Ala Ser Arg
```

```
                      -continued 5245               5250              5255

GCC AAC CTC AGC CTG CGG GTG ACG GCG GAG GAG CCC ATC TGT GGC CTC    3016
Ala Asn Leu Ser Leu Arg Val Thr Ala Glu Glu Pro Ile Cys Gly Leu
        5260              5265             5270

CGC GCC ACG CCC AGC CCC GAG GCC CGT GTA CTG CAG GGA GTC CTA GTG    3064
Arg Ala Thr Pro Ser Pro Glu Ala Arg Val Leu Gln Gly Val Leu Val
5275              5280             5285              5290

AGG TAC AGC CCC GTG GTG GAG GCC GGC TCG GAC ATG GTC TTC CGG TGG    3112
Arg Tyr Ser Pro Val Val Glu Ala Gly Ser Asp Met Val Phe Arg Trp
                  5295             5300             5305

ACC ATC AAC GAC AAG CAG TCC CTG ACC TTC CAG AAC GTG GTC TTC AAT    3160
Thr Ile Asn Asp Lys Gln Ser Leu Thr Phe Gln Asn Val Val Phe Asn
        5310              5315             5320

GTC ATT TAT CAG AGC GCG GCG GTC TTC AAG CTC TCA CTG ACG GCC TCC    3208
Val Ile Tyr Gln Ser Ala Ala Val Phe Lys Leu Ser Leu Thr Ala Ser
        5325              5330             5335

AAC CAC GTG AGC AAC GTC ACC GTG AAC TAC AAC GTA ACC GTG GAG CGG    3256
Asn His Val Ser Asn Val Thr Val Asn Tyr Asn Val Thr Val Glu Arg
        5340              5345             5350

ATG AAC AGG ATG CAG GGT CTG CAG GTC TCC ACA GTG CCG GCC GTG CTG    3304
Met Asn Arg Met Gln Gly Leu Gln Val Ser Thr Val Pro Ala Val Leu
5355              5360             5365              5370

TCC CCC AAT GCC ACA CTG GTA CTG ACG GGT GGT GTG CTG GTG GAC TCA    3352
Ser Pro Asn Ala Thr Leu Val Leu Thr Gly Gly Val Leu Val Asp Ser
        5375              5380             5385

GCT GTG GAG GTG GCC TTC CTG TGG AAC TTT GGG GAT GGG GAG CAG GCC    3400
Ala Val Glu Val Ala Phe Leu Trp Asn Phe Gly Asp Gly Glu Gln Ala
                  5390             5395             5400

CTC CAC CAG TTC CAG CCT CCG TAC AAC GAG TCC TTC CCG GTT CCA GAC    3448
Leu His Gln Phe Gln Pro Pro Tyr Asn Glu Ser Phe Pro Val Pro Asp
        5405              5410             5415

CCC TCG GTG GCC CAG GTG CTG GTG GAG CAC AAT GTC ATG CAC ACC TAC    3496
Pro Ser Val Ala Gln Val Leu Val Glu His Asn Val Met His Thr Tyr
        5420              5425             5430

GCT GCC CCA GGT GAG TAC CTC CTG ACC GTG CTG GCA TCT AAT GCC TTC    3544
Ala Ala Pro Gly Glu Tyr Leu Leu Thr Val Leu Ala Ser Asn Ala Phe
5435              5440             5445              5450

GAG AAC CTG ACG CAG CAG GTG CCT GTG AGC GTG CGC GCC TCC CTG CCC    3592
Glu Asn Leu Thr Gln Gln Val Pro Val Ser Val Arg Ala Ser Leu Pro
                  5455             5460             5465

TCC GTG GCT GTG GGT GTG AGT GAC GGC GTC CTG GTG GCC GGC CGG CCC    3640
Ser Val Ala Val Gly Val Ser Asp Gly Val Leu Val Ala Gly Arg Pro
                  5470             5475             5480

GTC ACC TTC TAC CCG CAC CCG CTG CCC TCG CCT GGG GGT GTT CTT TAC    3688
Val Thr Phe Tyr Pro His Pro Leu Pro Ser Pro Gly Gly Val Leu Tyr
        5485              5490             5495

ACG TGG GAC TTC GGG GAC GGC TCC CCT GTC CTG ACC CAG AGC CAG CCG    3736
Thr Trp Asp Phe Gly Asp Gly Ser Pro Val Leu Thr Gln Ser Gln Pro
        5500              5505             5510

GCT GCC AAC CAC ACC TAT GCC TCG AGG GGC ACC TAC CAC GTG CGC CTG    3784
Ala Ala Asn His Thr Tyr Ala Ser Arg Gly Thr Tyr His Val Arg Leu
5515              5520             5525              5530

GAG GTC AAC AAC ACG GTG AGC GGT GCG GCG GCC CAG GCG GAT GTG CGC    3832
Glu Val Asn Asn Thr Val Ser Gly Ala Ala Ala Gln Ala Asp Val Arg
                  5535             5540             5545

GTC TTT GAG GAG CTC CGC GGA CTC AGC GTG GAC ATG AGC CTG GCC GTG    3880
Val Phe Glu Glu Leu Arg Gly Leu Ser Val Asp Met Ser Leu Ala Val
                  5550             5555             5560

GAG CAG GGC GCC CCC GTG GTG GTC AGC GCC GCG GTG CAG ACG GGC GAC    3928
```

-continued

```
Glu Gln Gly Ala Pro Val Val Ser Ala Ala Val Gln Thr Gly Asp
        5565             5570             5575

AAC ATC ACG TGG ACC TTC GAC ATG GGG GAC GGC ACC GTG CTG TCG GGC    3976
Asn Ile Thr Trp Thr Phe Asp Met Gly Asp Gly Thr Val Leu Ser Gly
    5580             5585             5590

CCG GAG GCA ACA GTG GAG CAT GTG TAC CTG CGG GCA CAG AAC TGC ACA    4024
Pro Glu Ala Thr Val Glu His Val Tyr Leu Arg Ala Gln Asn Cys Thr
5595             5600             5605             5610

GTG ACC GTG GGT GCG GCC AGC CCC GCC GGC CAC CTG GCC CGG AGC CTG    4072
Val Thr Val Gly Ala Ala Ser Pro Ala Gly His Leu Ala Arg Ser Leu
                5615             5620             5625

CAC GTG CTG GTC TTC GTC CTG GAG GTG CTG CGC GTT GAA CCC GCC GCC    4120
His Val Leu Val Phe Val Leu Glu Val Leu Arg Val Glu Pro Ala Ala
            5630             5635             5640

TGC ATC CCC ACG CAG CCT GAC GCG CGG CTC ACG GCC TAC GTC ACC GGG    4168
Cys Ile Pro Thr Gln Pro Asp Ala Arg Leu Thr Ala Tyr Val Thr Gly
        5645             5650             5655

AAC CCG GCC CAC TAC CTC TTC GAC TGG ACC TTC GGG GAT GGC TCC TCC    4216
Asn Pro Ala His Tyr Leu Phe Asp Trp Thr Phe Gly Asp Gly Ser Ser
    5660             5665             5670

AAC ACG ACC GTG CGG GGG TGC CCG ACG GTG ACA CAC AAC TTC ACG CGG    4264
Asn Thr Thr Val Arg Gly Cys Pro Thr Val Thr His Asn Phe Thr Arg
5675             5680             5685             5690

AGC GGC ACG TTC CCC CTG GCG CTG GTG CTG TCC AGC CGC GTG AAC AGG    4312
Ser Gly Thr Phe Pro Leu Ala Leu Val Leu Ser Ser Arg Val Asn Arg
                5695             5700             5705

GCG CAT TAC TTC ACC AGC ATC TGC GTG GAG CCA GAG GTG GGC AAC GTC    4360
Ala His Tyr Phe Thr Ser Ile Cys Val Glu Pro Glu Val Gly Asn Val
            5710             5715             5720

ACC CTG CAG CCA GAG AGG CAG TTT GTG CAG CTC GGG GAC GAG GCC TGG    4408
Thr Leu Gln Pro Glu Arg Gln Phe Val Gln Leu Gly Asp Glu Ala Trp
        5725             5730             5735

CTG GTG GCA TGT GCC TGG CCC CCG TTC CCC TAC CGC TAC ACC TGG GAC    4456
Leu Val Ala Cys Ala Trp Pro Pro Phe Pro Tyr Arg Tyr Thr Trp Asp
    5740             5745             5750

TTT GGC ACC GAG GAA GCC GCC CCC ACC CGT GCC AGG GGC CCT GAG GTG    4504
Phe Gly Thr Glu Glu Ala Ala Pro Thr Arg Ala Arg Gly Pro Glu Val
5755             5760             5765             5770

ACG TTC ATC TAC CGA GAC CCA GGC TCC TAT CTT GTG ACA GTC ACC GCG    4552
Thr Phe Ile Tyr Arg Asp Pro Gly Ser Tyr Leu Val Thr Val Thr Ala
                5775             5780             5785

TCC AAC AAC ATC TCT GCT GCC AAT GAC TCA GCC CTG GTG GAG GTG CAG    4600
Ser Asn Asn Ile Ser Ala Ala Asn Asp Ser Ala Leu Val Glu Val Gln
            5790             5795             5800

GAG CCC GTG CTG GTC ACC AGC ATC AAG GTC AAT GGC TCC CTT GGG CTG    4648
Glu Pro Val Leu Val Thr Ser Ile Lys Val Asn Gly Ser Leu Gly Leu
        5805             5810             5815

GAG CTG CAG CAG CCG TAC CTG TTC TCT GCT GTG GGC CGT GGG CGC CCC    4696
Glu Leu Gln Gln Pro Tyr Leu Phe Ser Ala Val Gly Arg Gly Arg Pro
    5820             5825             5830

GCC AGC TAC CTG TGG GAT CTG GGG GAC GGT GGG TGG CTC GAG GGT CCG    4744
Ala Ser Tyr Leu Trp Asp Leu Gly Asp Gly Gly Trp Leu Glu Gly Pro
5835             5840             5845             5850

GAG GTC ACC CAC GCT TAC AAC AGC ACA GGT GAC TTC ACC GTT AGG GTG    4792
Glu Val Thr His Ala Tyr Asn Ser Thr Gly Asp Phe Thr Val Arg Val
                5855             5860             5865

GCC GGC TGG AAT GAG GTG AGC CGC AGC GAG GCC TGG CTC AAT GTG ACG    4840
Ala Gly Trp Asn Glu Val Ser Arg Ser Glu Ala Trp Leu Asn Val Thr
            5870             5875             5880
```

```
GTG AAG CGG CGC GTG CGG GGG CTC GTC GTC AAT GCA AGC CGC ACG GTG    4888
Val Lys Arg Arg Val Arg Gly Leu Val Val Asn Ala Ser Arg Thr Val
        5885            5890            5895

GTG CCC CTG AAT GGG AGC GTG AGC TTC AGC ACG TCG CTG GAG GCC GGC    4936
Val Pro Leu Asn Gly Ser Val Ser Phe Ser Thr Ser Leu Glu Ala Gly
        5900            5905            5910

AGT GAT GTG CGC TAT TCC TGG GTG CTC TGT GAC CGC TGC ACG CCC ATC    4984
Ser Asp Val Arg Tyr Ser Trp Val Leu Cys Asp Arg Cys Thr Pro Ile
5915            5920            5925            5930

CCT GGG GGT CCT ACC ATC TCT TAC ACC TTC CGC TCC GTG GGC ACC TTC    5032
Pro Gly Gly Pro Thr Ile Ser Tyr Thr Phe Arg Ser Val Gly Thr Phe
            5935            5940            5945

AAT ATC ATC GTC ACG GCT GAG AAC GAG GTG GGC TCC GCC CAG GAC AGC    5080
Asn Ile Ile Val Thr Ala Glu Asn Glu Val Gly Ser Ala Gln Asp Ser
            5950            5955            5960

ATC TTC GTC TAT GTC CTG CAG CTC ATA GAG GGG CTG CAG GTG GTG GGC    5128
Ile Phe Val Tyr Val Leu Gln Leu Ile Glu Gly Leu Gln Val Val Gly
            5965            5970            5975

GGT GGC CGC TAC TTC CCC ACC AAC CAC ACG GTA CAG CTG CAG GCC GTG    5176
Gly Gly Arg Tyr Phe Pro Thr Asn His Thr Val Gln Leu Gln Ala Val
        5980            5985            5990

GTT AGG GAT GGC ACC AAC GTC TCC TAC AGC TGG ACT GCC TGG AGG GAC    5224
Val Arg Asp Gly Thr Asn Val Ser Tyr Ser Trp Thr Ala Trp Arg Asp
5995            6000            6005            6010

AGG GGC CCG GCC CTG GCC GGC AGC GGC AAA GGC TTC TCG CTC ACC GTG    5272
Arg Gly Pro Ala Leu Ala Gly Ser Gly Lys Gly Phe Ser Leu Thr Val
            6015            6020            6025

CTC GAG GCC GGC ACC TAC CAT GTG CAG CTG CGG GCC ACC AAC ATG CTG    5320
Leu Glu Ala Gly Thr Tyr His Val Gln Leu Arg Ala Thr Asn Met Leu
            6030            6035            6040

GGC AGC GCC TGG GCC GAC TGC ACC ATG GAC TTC GTG GAG CCT GTG GGG    5368
Gly Ser Ala Trp Ala Asp Cys Thr Met Asp Phe Val Glu Pro Val Gly
            6045            6050            6055

TGG CTG ATG GTG ACC GCC TCC CCG AAC CCA GCT GCC GTC AAC ACA AGC    5416
Trp Leu Met Val Thr Ala Ser Pro Asn Pro Ala Ala Val Asn Thr Ser
        6060            6065            6070

GTC ACC CTC AGT GCC GAG CTG GCT GGT GGC AGT GGT GTC GTA TAC ACT    5464
Val Thr Leu Ser Ala Glu Leu Ala Gly Gly Ser Gly Val Val Tyr Thr
6075            6080            6085            6090

TGG TCC TTG GAG GAG GGG CTG AGC TGG GAG ACC TCC GAG CCA TTT ACC    5512
Trp Ser Leu Glu Glu Gly Leu Ser Trp Glu Thr Ser Glu Pro Phe Thr
            6095            6100            6105

ACC CAT AGC TTC CCC ACA CCC GGC CTG CAC TTG GTC ACC ATG ACG GCA    5560
Thr His Ser Phe Pro Thr Pro Gly Leu His Leu Val Thr Met Thr Ala
            6110            6115            6120

GGG AAC CCG CTG GGC TCA GCC AAC GCC ACC GTG GAA GTG GAT GTG CAG    5608
Gly Asn Pro Leu Gly Ser Ala Asn Ala Thr Val Glu Val Asp Val Gln
            6125            6130            6135

GTG CCT GTG AGT GGC CTC AGC ATC AGG GCC AGC GAG CCC GGA GGC AGC    5656
Val Pro Val Ser Gly Leu Ser Ile Arg Ala Ser Glu Pro Gly Gly Ser
        6140            6145            6150

TTC GTG GCG GCC GGG TCC TCT GTG CCC TTT TGG GGG CAG CTG GCC ACG    5704
Phe Val Ala Ala Gly Ser Ser Val Pro Phe Trp Gly Gln Leu Ala Thr
6155            6160            6165            6170

GGC ACC AAT GTG AGC TGG TGC TGG GCT GTG CCC GGC GGC AGC AGC AAG    5752
Gly Thr Asn Val Ser Trp Cys Trp Ala Val Pro Gly Gly Ser Ser Lys
            6175            6180            6185

CGT GGC CCT CAT GTC ACC ATG GTC TTC CCG GAT GCT GGC ACC TTC TCC    5800
Arg Gly Pro His Val Thr Met Val Phe Pro Asp Ala Gly Thr Phe Ser
            6190            6195            6200
```

```
ATC CGG CTC AAT GCC TCC AAC GCA GTC AGC TGG GTC TCA GCC ACG TAC    5848
Ile Arg Leu Asn Ala Ser Asn Ala Val Ser Trp Val Ser Ala Thr Tyr
        6205                6210                6215

AAC CTC ACG GCG GAG GAG CCC ATC GTG GGC CTG GTG CTG TGG GCC AGC    5896
Asn Leu Thr Ala Glu Glu Pro Ile Val Gly Leu Val Leu Trp Ala Ser
        6220                6225                6230

AGC AAG GTG GTG GCG CCC GGG CAG CTG GTC CAT TTT CAG ATC CTG CTG    5944
Ser Lys Val Val Ala Pro Gly Gln Leu Val His Phe Gln Ile Leu Leu
6235                6240                6245                6250

GCT GCC GGC TCA GCT GTC ACC TTC CGC CTG CAG GTC GGC GGG GCC AAC    5992
Ala Ala Gly Ser Ala Val Thr Phe Arg Leu Gln Val Gly Gly Ala Asn
                6255                6260                6265

CCC GAG GTG CTC CCC GGG CCC CGT TTC TCC CAC AGC TTC CCC CGC GTC    6040
Pro Glu Val Leu Pro Gly Pro Arg Phe Ser His Ser Phe Pro Arg Val
        6270                6275                6280

GGA GAC CAC GTG GTG AGC GTG CGG GGC AAA AAC CAC GTG AGC TGG GCC    6088
Gly Asp His Val Val Ser Val Arg Gly Lys Asn His Val Ser Trp Ala
        6285                6290                6295

CAG GCG CAG GTG CGC ATC GTG GTG CTG GAG GCC GTG AGT GGG CTG CAG    6136
Gln Ala Gln Val Arg Ile Val Val Leu Glu Ala Val Ser Gly Leu Gln
        6300                6305                6310

ATG CCC AAC TGC TGC GAG CCT GGC ATC GCC ACG GGC ACT GAG AGG AAC    6184
Met Pro Asn Cys Cys Glu Pro Gly Ile Ala Thr Gly Thr Glu Arg Asn
6315                6320                6325                6330

TTC ACA GCC CGC GTG CAG CGC GGC TCT CGG GTC GCC TAC GCC TGG TAC    6232
Phe Thr Ala Arg Val Gln Arg Gly Ser Arg Val Ala Tyr Ala Trp Tyr
                6335                6340                6345

TTC TCG CTG CAG AAG GTC CAG GGC GAC TCG CTG GTC ATC CTG TCG GGC    6280
Phe Ser Leu Gln Lys Val Gln Gly Asp Ser Leu Val Ile Leu Ser Gly
        6350                6355                6360

CGC GAC GTC ACC TAC ACG CCC GTG GCC GCG GGG CTG TTG GAG ATC CAG    6328
Arg Asp Val Thr Tyr Thr Pro Val Ala Ala Gly Leu Leu Glu Ile Gln
        6365                6370                6375

GTG CGC GCC TTC AAC GCC CTG GGC AGT GAG AAC CGC ACG CTG GTG CTG    6376
Val Arg Ala Phe Asn Ala Leu Gly Ser Glu Asn Arg Thr Leu Val Leu
        6380                6385                6390

GAG GTT CAG GAC GCC GTC CAG TAT GTG GCC CTG CAG AGC GGC CCC TGC    6424
Glu Val Gln Asp Ala Val Gln Tyr Val Ala Leu Gln Ser Gly Pro Cys
6395                6400                6405                6410

TTC ACC AAC CGC TCG GCG CAG TTT GAG GCC GCC ACC AGC CCC AGC CCC    6472
Phe Thr Asn Arg Ser Ala Gln Phe Glu Ala Ala Thr Ser Pro Ser Pro
                6415                6420                6425

CGG CGT GTG GCC TAC CAC TGG GAC TTT GGG GAT GGG TCG CCA GGG CAG    6520
Arg Arg Val Ala Tyr His Trp Asp Phe Gly Asp Gly Ser Pro Gly Gln
                6430                6435                6440

GAC ACA GAT GAG CCC AGG GCC GAG CAC TCC TAC CTG AGG CCT GGG GAC    6568
Asp Thr Asp Glu Pro Arg Ala Glu His Ser Tyr Leu Arg Pro Gly Asp
        6445                6450                6455

TAC CGC GTG CAG GTG AAC GCC TCC AAC CTG GTG AGC TTC TTC GTG GCG    6616
Tyr Arg Val Gln Val Asn Ala Ser Asn Leu Val Ser Phe Phe Val Ala
        6460                6465                6470

CAG GCC ACG GTG ACC GTC CAG GTG CTG GCC TGC CGG GAG CCG GAG GTG    6664
Gln Ala Thr Val Thr Val Gln Val Leu Ala Cys Arg Glu Pro Glu Val
6475                6480                6485                6490

GAC GTG GTC CTG CCC CTG CAG GTG CTG ATG CGG CGA TCA CAG CGC AAC    6712
Asp Val Val Leu Pro Leu Gln Val Leu Met Arg Arg Ser Gln Arg Asn
                6495                6500                6505

TAC TTG GAG GCC CAC GTT GAC CTG CGC GAC TGC GTC ACC TAC CAG ACT    6760
Tyr Leu Glu Ala His Val Asp Leu Arg Asp Cys Val Thr Tyr Gln Thr
```

-continued

```
              6510                  6515                  6520
GAG TAC CGC TGG GAG GTG TAT CGC ACC GCC AGC TGC CAG CGG CCG GGG         6808
Glu Tyr Arg Trp Glu Val Tyr Arg Thr Ala Ser Cys Gln Arg Pro Gly
            6525                  6530                  6535

CGC CCA GCG CGT GTG GCC CTG CCC GGC GTG GAC GTG AGC CGG CCT CGG         6856
Arg Pro Ala Arg Val Ala Leu Pro Gly Val Asp Val Ser Arg Pro Arg
            6540                  6545                  6550

CTG GTG CTG CCG CGG CTG GCG CTG CCT GTG GGG CAC TAC TGC TTT GTG         6904
Leu Val Leu Pro Arg Leu Ala Leu Pro Val Gly His Tyr Cys Phe Val
6555                  6560                  6565                  6570

TTT GTC GTG TCA TTT GGG GAC ACG CCA CTG ACA CAG AGC ATC CAG GCC         6952
Phe Val Val Ser Phe Gly Asp Thr Pro Leu Thr Gln Ser Ile Gln Ala
                  6575                  6580                  6585

AAT GTG ACG GTG GCC CCC GAG CGC CTG GTG CCC ATC ATT GAG GGT GGC         7000
Asn Val Thr Val Ala Pro Glu Arg Leu Val Pro Ile Ile Glu Gly Gly
            6590                  6595                  6600

TCA TAC CGC GTG TGG TCA GAC ACA CGG GAC CTG GTG CTG GAT GGG AGC         7048
Ser Tyr Arg Val Trp Ser Asp Thr Arg Asp Leu Val Leu Asp Gly Ser
            6605                  6610                  6615

GAG TCC TAC GAC CCC AAC CTG GAG GAC GGC GAC CAG ACG CCG CTC AGT         7096
Glu Ser Tyr Asp Pro Asn Leu Glu Asp Gly Asp Gln Thr Pro Leu Ser
            6620                  6625                  6630

TTC CAC TGG GCC TGT GTG GCT TCG ACA CAG AGG GAG GCT GGC GGG TGT         7144
Phe His Trp Ala Cys Val Ala Ser Thr Gln Arg Glu Ala Gly Gly Cys
6635                  6640                  6645                  6650

GCG CTG AAC TTT GGG CCC CGC GGG AGC AGC ACG GTC ACC ATT CCA CGG         7192
Ala Leu Asn Phe Gly Pro Arg Gly Ser Ser Thr Val Thr Ile Pro Arg
                  6655                  6660                  6665

GAG CGG CTG GCG GCT GGC GTG GAG TAC ACC TTC AGC CTG ACC GTG TGG         7240
Glu Arg Leu Ala Ala Gly Val Glu Tyr Thr Phe Ser Leu Thr Val Trp
            6670                  6675                  6680

AAG GCC GGC CGC AAG GAG GAG GCC ACC AAC CAG ACG GTG CTG ATC CGG         7288
Lys Ala Gly Arg Lys Glu Glu Ala Thr Asn Gln Thr Val Leu Ile Arg
            6685                  6690                  6695

AGT GGC CGG GTG CCC ATT GTG TCC TTG GAG TGT GTG TCC TGC AAG GCA         7336
Ser Gly Arg Val Pro Ile Val Ser Leu Glu Cys Val Ser Cys Lys Ala
            6700                  6705                  6710

CAG GCC GTG TAC GAA GTG AGC CGC AGC TCC TAC GTG TAC TTG GAG GGC         7384
Gln Ala Val Tyr Glu Val Ser Arg Ser Ser Tyr Val Tyr Leu Glu Gly
6715                  6720                  6725                  6730

CGC TGC CTC AAT TGC AGC AGC GGC TCC AAG CGA GGG CGG TGG GCT GCA         7432
Arg Cys Leu Asn Cys Ser Ser Gly Ser Lys Arg Gly Arg Trp Ala Ala
                  6735                  6740                  6745

CGT ACG TTC AGC AAC AAG ACG CTG GTG CTG GAT GAG ACC ACC ACA TCC         7480
Arg Thr Phe Ser Asn Lys Thr Leu Val Leu Asp Glu Thr Thr Thr Ser
            6750                  6755                  6760

ACG GGC AGT GCA GGC ATG CGA CTG GTG CTG CGG CGG GGC GTG CTG CGG         7528
Thr Gly Ser Ala Gly Met Arg Leu Val Leu Arg Arg Gly Val Leu Arg
            6765                  6770                  6775

GAC GGC GAG GGA TAC ACC TTC ACG CTC ACG GTG CTG GGC CGC TCT GGC         7576
Asp Gly Glu Gly Tyr Thr Phe Thr Leu Thr Val Leu Gly Arg Ser Gly
            6780                  6785                  6790

GAG GAG GAG GGC TGC GCC TCC ATC CGC CTG TCC CCC AAC CGC CCG CCG         7624
Glu Glu Glu Gly Cys Ala Ser Ile Arg Leu Ser Pro Asn Arg Pro Pro
6795                  6800                  6805                  6810

CTG GGG GGC TCT TGC CGC CTC TTC CCA CTG GGC GCT GTG CAC GCC CTC         7672
Leu Gly Gly Ser Cys Arg Leu Phe Pro Leu Gly Ala Val His Ala Leu
                  6815                  6820                  6825

ACC ACC AAG GTG CAC TTC GAA TGC ACG GGC TGG CAT GAC GCG GAG GAT         7720
```

```
Thr Thr Lys Val His Phe Glu Cys Thr Gly Trp His Asp Ala Glu Asp
            6830                6835                6840

GCT GGC GCC CCG CTG GTG TAC GCC CTG CTG CTG CGG CGC TGT CGC CAG       7768
Ala Gly Ala Pro Leu Val Tyr Ala Leu Leu Leu Arg Arg Cys Arg Gln
            6845                6850                6855

GGC CAC TGC GAG GAG TTC TGT GTC TAC AAG GGC AGC CTC TCC AGC TAC       7816
Gly His Cys Glu Glu Phe Cys Val Tyr Lys Gly Ser Leu Ser Ser Tyr
            6860                6865                6870

GGA GCC GTG CTG CCC CCG GGT TTC AGG CCA CAC TTC GAG GTG GGC CTG       7864
Gly Ala Val Leu Pro Pro Gly Phe Arg Pro His Phe Glu Val Gly Leu
6875                6880                6885                6890

GCC GTG GTG GTG CAG GAC CAG CTG GGA GCC GCT GTG GTC GCC CTC AAC       7912
Ala Val Val Val Gln Asp Gln Leu Gly Ala Ala Val Val Ala Leu Asn
                6895                6900                6905

AGG TCT TTG GCC ATC ACC CTC CCA GAG CCC AAC GGC AGC GCA ACG GGG       7960
Arg Ser Leu Ala Ile Thr Leu Pro Glu Pro Asn Gly Ser Ala Thr Gly
            6910                6915                6920

CTC ACA GTC TGG CTG CAC GGG CTC ACC GCT AGT GTG CTC CCA GGG CTG       8008
Leu Thr Val Trp Leu His Gly Leu Thr Ala Ser Val Leu Pro Gly Leu
            6925                6930                6935

CTG CGG CAG GCC GAT CCC CAG CAC GTC ATC GAG TAC TCG TTG GCC CTG       8056
Leu Arg Gln Ala Asp Pro Gln His Val Ile Glu Tyr Ser Leu Ala Leu
            6940                6945                6950

GTC ACC GTG CTG AAC GAG TAC GAG CGG GCC CTG GAC GTG GCG GCA GAG       8104
Val Thr Val Leu Asn Glu Tyr Glu Arg Ala Leu Asp Val Ala Ala Glu
6955                6960                6965                6970

CCC AAG CAC GAG CGG CAG CAC CGA GCC CAG ATA CGC AAG AAC ATC ACG       8152
Pro Lys His Glu Arg Gln His Arg Ala Gln Ile Arg Lys Asn Ile Thr
                6975                6980                6985

GAG ACT CTG GTG TCC CTG AGG GTC CAC ACT GTG GAT GAC ATC CAG CAG       8200
Glu Thr Leu Val Ser Leu Arg Val His Thr Val Asp Asp Ile Gln Gln
            6990                6995                7000

ATC GCT GCT GCG CTG GCC CAG TGC ATG GGG CCC AGC AGG GAG CTC GTA       8248
Ile Ala Ala Ala Leu Ala Gln Cys Met Gly Pro Ser Arg Glu Leu Val
            7005                7010                7015

TGC CGC TCG TGC CTG AAG CAG ACG CTG CAC AAG CTG GAG GCC ATG ATG       8296
Cys Arg Ser Cys Leu Lys Gln Thr Leu His Lys Leu Glu Ala Met Met
            7020                7025                7030

CTC ATC CTG CAG GCA GAG ACC ACC GCG GGC ACC GTG ACG CCC ACC GCC       8344
Leu Ile Leu Gln Ala Glu Thr Thr Ala Gly Thr Val Thr Pro Thr Ala
7035                7040                7045                7050

ATC GGA GAC AGC ATC CTC AAC ATC ACA GGA GAC CTC ATC CAC CTG GCC       8392
Ile Gly Asp Ser Ile Leu Asn Ile Thr Gly Asp Leu Ile His Leu Ala
                7055                7060                7065

AGC TCG GAC GTG CGG GCA CCA CAG CCC TCA GAG CTG GGA GCC GAG TCA       8440
Ser Ser Asp Val Arg Ala Pro Gln Pro Ser Glu Leu Gly Ala Glu Ser
            7070                7075                7080

CCA TCT CGG ATG GTG GCG TCC CAG GCC TAC AAC CTG ACC TCT GCC CTC       8488
Pro Ser Arg Met Val Ala Ser Gln Ala Tyr Asn Leu Thr Ser Ala Leu
            7085                7090                7095

ATG CGC ATC CTC ATG CGC TCC CGC GTG CTC AAC GAG GAG CCC CTG ACG       8536
Met Arg Ile Leu Met Arg Ser Arg Val Leu Asn Glu Glu Pro Leu Thr
            7100                7105                7110

CTG GCG GGC GAG GAG ATC GTG GCC CAG GGC AAG CGC TCG GAC CCG CGG       8584
Leu Ala Gly Glu Glu Ile Val Ala Gln Gly Lys Arg Ser Asp Pro Arg
7115                7120                7125                7130

AGC CTG CTG TGC TAT GGC GGC GCC CCA GGG CCT GGC TGC CAC TTC TCC       8632
Ser Leu Leu Cys Tyr Gly Gly Ala Pro Gly Pro Gly Cys His Phe Ser
                7135                7140                7145
```

-continued

```
ATC CCC GAG GCT TTC AGC GGG GCC CTG GCC AAC CTC AGT GAC GTG GTG      8680
Ile Pro Glu Ala Phe Ser Gly Ala Leu Ala Asn Leu Ser Asp Val Val
        7150                7155                7160

CAG CTC ATC TTT CTG GTG GAC TCC AAT CCC TTT CCC TTT GGC TAT ATC      8728
Gln Leu Ile Phe Leu Val Asp Ser Asn Pro Phe Pro Phe Gly Tyr Ile
        7165                7170                7175

AGC AAC TAC ACC GTC TCC ACC AAG GTG GCC TCG ATG GCA TTC CAG ACA      8776
Ser Asn Tyr Thr Val Ser Thr Lys Val Ala Ser Met Ala Phe Gln Thr
        7180                7185                7190

CAG GCC GGC GCC CAG ATC CCC ATC GAG CGG CTG GCC TCA GAG CGC GCC      8824
Gln Ala Gly Ala Gln Ile Pro Ile Glu Arg Leu Ala Ser Glu Arg Ala
7195                7200                7205                7210

ATC ACC GTG AAG GTG CCC AAC AAC TCG GAC TGG GCT GCC CGG GGC CAC      8872
Ile Thr Val Lys Val Pro Asn Asn Ser Asp Trp Ala Ala Arg Gly His
            7215                7220                7225

CGC AGC TCC GCC AAC TCC GCC AAC TCC GTT GTG GTC CAG CCC CAG GCC      8920
Arg Ser Ser Ala Asn Ser Ala Asn Ser Val Val Val Gln Pro Gln Ala
                7230                7235                7240

TCC GTC GGT GCT GTG GTC ACC CTG GAC AGC AGC AAC CCT GCG GCC GGG      8968
Ser Val Gly Ala Val Val Thr Leu Asp Ser Ser Asn Pro Ala Ala Gly
            7245                7250                7255

CTG CAT CTG CAG CTC AAC TAT ACG CTG CTG GAC GGC CAC TAC CTG TCT      9016
Leu His Leu Gln Leu Asn Tyr Thr Leu Leu Asp Gly His Tyr Leu Ser
        7260                7265                7270

GAG GAA CCT GAG CCC TAC CTG GCA GTC TAC CTA CAC TCG GAG CCC CGG      9064
Glu Glu Pro Glu Pro Tyr Leu Ala Val Tyr Leu His Ser Glu Pro Arg
7275                7280                7285                7290

CCC AAT GAG CAC AAC TGC TCG GCT AGC AGG AGG ATC CGC CCA GAG TCA      9112
Pro Asn Glu His Asn Cys Ser Ala Ser Arg Arg Ile Arg Pro Glu Ser
            7295                7300                7305

CTC CAG GGT GCT GAC CAC CGG CCC TAC ACC TTC TTC ATT TCC CCG GGG      9160
Leu Gln Gly Ala Asp His Arg Pro Tyr Thr Phe Phe Ile Ser Pro Gly
        7310                7315                7320

AGC AGA GAC CCA GCG GGG AGT TAC CAT CTG AAC CTC TCC AGC CAC TTC      9208
Ser Arg Asp Pro Ala Gly Ser Tyr His Leu Asn Leu Ser Ser His Phe
        7325                7330                7335

CGC TGG TCG GCG CTG CAG GTG TCC GTG GGC CTG TAC ACG TCC CTG TGC      9256
Arg Trp Ser Ala Leu Gln Val Ser Val Gly Leu Tyr Thr Ser Leu Cys
        7340                7345                7350

CAG TAC TTC AGC GAG GAG GAC ATG GTG TGG CGG ACA GAG GGG CTG CTG      9304
Gln Tyr Phe Ser Glu Glu Asp Met Val Trp Arg Thr Glu Gly Leu Leu
7355                7360                7365                7370

CCC CTG GAG GAG ACC TCG CCC CGC CAG GCC GTC TGC CTC ACC CGC CAC      9352
Pro Leu Glu Glu Thr Ser Pro Arg Gln Ala Val Cys Leu Thr Arg His
            7375                7380                7385

CTC ACC GCC TTC GGC GCC AGC CTC TTC GTG CCC CCA AGC CAT GTC CGC      9400
Leu Thr Ala Phe Gly Ala Ser Leu Phe Val Pro Pro Ser His Val Arg
        7390                7395                7400

TTT GTG TTT CCT GAG CCG ACA GCG GAT GTA AAC TAC ATC GTC ATG CTG      9448
Phe Val Phe Pro Glu Pro Thr Ala Asp Val Asn Tyr Ile Val Met Leu
        7405                7410                7415

ACA TGT GCT GTG TGC CTG GTG ACC TAC ATG GTC ATG GCC GCC ATC CTG      9496
Thr Cys Ala Val Cys Leu Val Thr Tyr Met Val Met Ala Ala Ile Leu
        7420                7425                7430

CAC AAG CTG GAC CAG TTG GAT GCC AGC CGG GGC CGC GCC ATC CCT TTC      9544
His Lys Leu Asp Gln Leu Asp Ala Ser Arg Gly Arg Ala Ile Pro Phe
7435                7440                7445                7450

TGT GGG CAG CGG GGC CGC TTC AAG TAC GAG ATC CTC GTC AAG ACA GGC      9592
Cys Gly Gln Arg Gly Arg Phe Lys Tyr Glu Ile Leu Val Lys Thr Gly
            7455                7460                7465
```

```
TGG GGC CGG GGC TCA GGT ACC ACG GCC CAC GTG GGC ATC ATG CTG TAT       9640
Trp Gly Arg Gly Ser Gly Thr Thr Ala His Val Gly Ile Met Leu Tyr
            7470                7475                7480

GGG GTG GAC AGC CGG AGC GGC CAC CGG CAC CTG GAC GGC GAC AGA GCC       9688
Gly Val Asp Ser Arg Ser Gly His Arg His Leu Asp Gly Asp Arg Ala
            7485                7490                7495

TTC CAC CGC AAC AGC CTG GAC ATC TTC CGG ATC GCC ACC CCG CAC AGC       9736
Phe His Arg Asn Ser Leu Asp Ile Phe Arg Ile Ala Thr Pro His Ser
            7500                7505                7510

CTG GGT AGC GTG TGG AAG ATC CGA GTG TGG CAC GAC AAC AAA GGG CTC       9784
Leu Gly Ser Val Trp Lys Ile Arg Val Trp His Asp Asn Lys Gly Leu
7515                7520                7525                7530

AGC CCT GCC TGG TTC CTG CAG CAC GTC ATC GTC AGG GAC CTG CAG ACG       9832
Ser Pro Ala Trp Phe Leu Gln His Val Ile Val Arg Asp Leu Gln Thr
                7535                7540                7545

GCA CGC AGC GCC TTC TTC CTG GTC AAT GAC TGG CTT TCG GTG GAG ACG       9880
Ala Arg Ser Ala Phe Phe Leu Val Asn Asp Trp Leu Ser Val Glu Thr
            7550                7555                7560

GAG GCC AAC GGG GGC CTG GTG GAG AAG GAG GTG CTG GCC GCG AGC GAC       9928
Glu Ala Asn Gly Gly Leu Val Glu Lys Glu Val Leu Ala Ala Ser Asp
            7565                7570                7575

GCA GCC CTT TTG CGC TTC CGG CGC CTG CTG GTG GCT GAG CTG CAG CGT       9976
Ala Ala Leu Leu Arg Phe Arg Arg Leu Leu Val Ala Glu Leu Gln Arg
            7580                7585                7590

GGC TTC TTT GAC AAG CAC ATC TGG CTC TCC ATA TGG GAC CGG CCG CCT      10024
Gly Phe Phe Asp Lys His Ile Trp Leu Ser Ile Trp Asp Arg Pro Pro
7595                7600                7605                7610

CGT AGC CGT TTC ACT CGC ATC CAG AGG GCC ACC TGC TGC GTT CTC CTC      10072
Arg Ser Arg Phe Thr Arg Ile Gln Arg Ala Thr Cys Cys Val Leu Leu
            7615                7620                7625

ATC TGC CTC TTC CTG GGC GCC AAC GCC GTG TGG TAC GGG GCT GTT GGC      10120
Ile Cys Leu Phe Leu Gly Ala Asn Ala Val Trp Tyr Gly Ala Val Gly
            7630                7635                7640

GAC TCT GCC TAC AGC ACG GGG CAT GTG TCC AGG CTG AGC CCG CTG AGC      10168
Asp Ser Ala Tyr Ser Thr Gly His Val Ser Arg Leu Ser Pro Leu Ser
            7645                7650                7655

GTC GAC ACA GTC GCT GTT GGC CTG GTG TCC AGC GTG GTT GTC TAT CCC      10216
Val Asp Thr Val Ala Val Gly Leu Val Ser Ser Val Val Val Tyr Pro
            7660                7665                7670

GTC TAC CTG GCC ATC CTT TTT CTC TTC CGG ATG TCC CGG AGC AAG GTG      10264
Val Tyr Leu Ala Ile Leu Phe Leu Phe Arg Met Ser Arg Ser Lys Val
7675                7680                7685                7690

GCT GGG AGC CCG AGC CCC ACA CCT GCC GGG CAG CAG GTG CTG GAC ATC      10312
Ala Gly Ser Pro Ser Pro Thr Pro Ala Gly Gln Gln Val Leu Asp Ile
                7695                7700                7705

GAC AGC TGC CTG GAC TCG TCC GTG CTG GAC AGC TCC TTC CTC ACG TTC      10360
Asp Ser Cys Leu Asp Ser Ser Val Leu Asp Ser Ser Phe Leu Thr Phe
            7710                7715                7720

TCA GGC CTC CAC GCT GAG GCC TTT GTT GGA CAG ATG AAG AGT GAC TTG      10408
Ser Gly Leu His Ala Glu Ala Phe Val Gly Gln Met Lys Ser Asp Leu
            7725                7730                7735

TTT CTG GAT GAT TCT AAG AGT CTG GTG TGC TGG CCC TCC GGC GAG GGA      10456
Phe Leu Asp Asp Ser Lys Ser Leu Val Cys Trp Pro Ser Gly Glu Gly
            7740                7745                7750

ACG CTC AGT TGG CCG GAC CTG CTC AGT GAC CCG TCC ATT GTG GGT AGC      10504
Thr Leu Ser Trp Pro Asp Leu Leu Ser Asp Pro Ser Ile Val Gly Ser
7755                7760                7765                7770

AAT CTG CGG CAG CTG GCA CGG GGC CAG GCG GGC CAT GGG CTG GGC CCA      10552
Asn Leu Arg Gln Leu Ala Arg Gly Gln Ala Gly His Gly Leu Gly Pro
```

```
                7775                7780                7785
GAG GAG GAC GGC TTC TCC CTG GCC AGC CCC TAC TCG CCT GCC AAA TCC    10600
Glu Glu Asp Gly Phe Ser Leu Ala Ser Pro Tyr Ser Pro Ala Lys Ser
                7790                7795                7800

TTC TCA GCA TCA GAT GAA GAC CTG ATC CAG CAG GTC CTT GCC GAG GGG    10648
Phe Ser Ala Ser Asp Glu Asp Leu Ile Gln Gln Val Leu Ala Glu Gly
            7805                7810                7815

GTC AGC AGC CCA GCC CCT ACC CAA GAC ACC CAC ATG GAA ACG GAC CTG    10696
Val Ser Ser Pro Ala Pro Thr Gln Asp Thr His Met Glu Thr Asp Leu
        7820                7825                7830

CTC AGC AGC CTG TCC AGC ACT CCT GGG GAG AAG ACA GAG ACG CTG GCG    10744
Leu Ser Ser Leu Ser Ser Thr Pro Gly Glu Lys Thr Glu Thr Leu Ala
7835                7840                7845                7850

CTG CAG AGG CTG GGG GAG CTG GGG CCA CCC AGC CCA GGC CTG AAC TGG    10792
Leu Gln Arg Leu Gly Glu Leu Gly Pro Pro Ser Pro Gly Leu Asn Trp
            7855                7860                7865

GAA CAG CCC CAG GCA GCG AGG CTG TCC AGG ACA GGA CTG GTG GAG GGT    10840
Glu Gln Pro Gln Ala Ala Arg Leu Ser Arg Thr Gly Leu Val Glu Gly
            7870                7875                7880

CTG CGG AAG CGC CTG CTG CCG GCC TGG TGT GCC TCC CTG GCC CAC GGG    10888
Leu Arg Lys Arg Leu Leu Pro Ala Trp Cys Ala Ser Leu Ala His Gly
        7885                7890                7895

CTC AGC CTG CTC CTG GTG GCT GTG GCT GTG GCT GTC TCA GGG TGG GTG    10936
Leu Ser Leu Leu Leu Val Ala Val Ala Val Ala Val Ser Gly Trp Val
            7900                7905                7910

GGT GCG AGC TTC CCC CCG GGC GTG AGT GTT GCG TGG CTC CTG TCC AGC    10984
Gly Ala Ser Phe Pro Pro Gly Val Ser Val Ala Trp Leu Leu Ser Ser
7915                7920                7925                7930

AGC GCC AGC TTC CTG GCC TCA TTC CTC GGC TGG GAG CCA CTG AAG GTC    11032
Ser Ala Ser Phe Leu Ala Ser Phe Leu Gly Trp Glu Pro Leu Lys Val
            7935                7940                7945

TTG CTG GAA GCC CTG TAC TTC TCA CTG GTG GCC AAG CGG CTG CAC CCG    11080
Leu Leu Glu Ala Leu Tyr Phe Ser Leu Val Ala Lys Arg Leu His Pro
            7950                7955                7960

GAT GAA GAT GAC ACC CTG GTA GAG AGC CCG GCT GTG ACG CCT GTG AGC    11128
Asp Glu Asp Asp Thr Leu Val Glu Ser Pro Ala Val Thr Pro Val Ser
            7965                7970                7975

GCA CGT GTG CCC CGC GTA CGG CCA CCC CAC GGC TTT GCA CTC TTC CTG    11176
Ala Arg Val Pro Arg Val Arg Pro Pro His Gly Phe Ala Leu Phe Leu
            7980                7985                7990

GCC AAG GAA GAA GCC CGC AAG GTC AAG AGG CTA CAT GGC ATG CTG CGG    11224
Ala Lys Glu Glu Ala Arg Lys Val Lys Arg Leu His Gly Met Leu Arg
7995                8000                8005                8010

AGC CTC CTG GTG TAC ATG CTT TTT CTG CTG GTG ACC CTG CTG GCC AGC    11272
Ser Leu Leu Val Tyr Met Leu Phe Leu Leu Val Thr Leu Leu Ala Ser
            8015                8020                8025

TAT GGG GAT GCC TCA TGC CAT GGG CAC GCC TAC CGT CTG CAA AGC GCC    11320
Tyr Gly Asp Ala Ser Cys His Gly His Ala Tyr Arg Leu Gln Ser Ala
        8030                8035                8040

ATC AAG CAG GAG CTG CAC AGC CGG GCC TTC CTG GCC ATC ACG CGG TCT    11368
Ile Lys Gln Glu Leu His Ser Arg Ala Phe Leu Ala Ile Thr Arg Ser
            8045                8050                8055

GAG GAG CTC TGG CCA TGG ATG GCC CAC GTG CTG CTG CCC TAC GTC CAC    11416
Glu Glu Leu Trp Pro Trp Met Ala His Val Leu Leu Pro Tyr Val His
        8060                8065                8070

GGG AAC CAG TCC AGC CCA GAG CTG GGG CCC CCA CGG CTG CGG CAG GTG    11464
Gly Asn Gln Ser Ser Pro Glu Leu Gly Pro Pro Arg Leu Arg Gln Val
8075                8080                8085                8090

CGG CTG CAG GAA GCA CTC TAC CCA GAC CCT CCC GGC CCC AGG GTC CAC    11512
```

```
                                                                -continued

Arg Leu Gln Glu Ala Leu Tyr Pro Asp Pro Gly Pro Arg Val His
            8095                8100                8105

ACG TGC TCG GCC GCA GGA GGC TTC AGC ACC AGC GAT TAC GAC GTT GGC         11560
Thr Cys Ser Ala Ala Gly Gly Phe Ser Thr Ser Asp Tyr Asp Val Gly
                8110                8115                8120

TGG GAG AGT CCT CAC AAT GGC TCG GGG ACG TGG GCC TAT TCA GCG CCG         11608
Trp Glu Ser Pro His Asn Gly Ser Gly Thr Trp Ala Tyr Ser Ala Pro
        8125                8130                8135

GAT CTG CTG GGG GCA TGG TCC TGG GGC TCC TGT GCC GTG TAT GAC AGC         11656
Asp Leu Leu Gly Ala Trp Ser Trp Gly Ser Cys Ala Val Tyr Asp Ser
    8140                8145                8150

GGG GGC TAC GTG CAG GAG CTG GGC CTG AGC CTG GAG GAG AGC CGC GAC         11704
Gly Gly Tyr Val Gln Glu Leu Gly Leu Ser Leu Glu Glu Ser Arg Asp
8155                8160                8165                8170

CGG CTG CGC TTC CTG CAG CTG CAC AAC TGG CTG GAC AAC AGG AGC CGC         11752
Arg Leu Arg Phe Leu Gln Leu His Asn Trp Leu Asp Asn Arg Ser Arg
            8175                8180                8185

GCT GTG TTC CTG GAG CTC ACG CGC TAC AGC CCG GCC GTG GGG CTG CAC         11800
Ala Val Phe Leu Glu Leu Thr Arg Tyr Ser Pro Ala Val Gly Leu His
        8190                8195                8200

GCC GCC GTC ACG CTG CGC CTC GAG TTC CCG GCG GCC GGC CGC GCC CTG         11848
Ala Ala Val Thr Leu Arg Leu Glu Phe Pro Ala Ala Gly Arg Ala Leu
    8205                8210                8215

GCC GCC CTC AGC GTC CGC CCC TTT GCG CTG CGC CGC CTC AGC GCG GGC         11896
Ala Ala Leu Ser Val Arg Pro Phe Ala Leu Arg Arg Leu Ser Ala Gly
8220                8225                8230

CTC TCG CTG CCT CTG CTC ACC TCG GTG TGC CTG CTG CTG TTC GCC GTG         11944
Leu Ser Leu Pro Leu Leu Thr Ser Val Cys Leu Leu Leu Phe Ala Val
8235                8240                8245                8250

CAC TTC GCC GTG GCC GAG GCC CGT ACT TGG CAC AGG GAA GGG CGC TGG         11992
His Phe Ala Val Ala Glu Ala Arg Thr Trp His Arg Glu Gly Arg Trp
            8255                8260                8265

CGC GTG CTG CGG CTC GGA GCC TGG GCG CGG TGG CTG CTG GTG GCG CTG         12040
Arg Val Leu Arg Leu Gly Ala Trp Ala Arg Trp Leu Leu Val Ala Leu
        8270                8275                8280

ACG GCG GCC ACG GCA CTG GTA CGC CTC GCC CAG CTG GGT GCC GCT GAC         12088
Thr Ala Ala Thr Ala Leu Val Arg Leu Ala Gln Leu Gly Ala Ala Asp
    8285                8290                8295

CGC CAG TGG ACC CGT TTC GTG CGC GGC CGC CCG CGC CGC TTC ACT AGC         12136
Arg Gln Trp Thr Arg Phe Val Arg Gly Arg Pro Arg Arg Phe Thr Ser
8300                8305                8310

TTC GAC CAG GTG GCG CAC GTG AGC TCC GCA GCC CGT GGC CTG GCG GCC         12184
Phe Asp Gln Val Ala His Val Ser Ser Ala Ala Arg Gly Leu Ala Ala
8315                8320                8325                8330

TCG CTG CTC TTC CTG CTT TTG GTC AAG GCT GCC CAG CAC GTA CGC TTC         12232
Ser Leu Leu Phe Leu Leu Leu Val Lys Ala Ala Gln His Val Arg Phe
            8335                8340                8345

GTG CGC CAG TGG TCC GTC TTT GGC AAG ACA TTA TGC CGA GCT CTG CCA         12280
Val Arg Gln Trp Ser Val Phe Gly Lys Thr Leu Cys Arg Ala Leu Pro
        8350                8355                8360

GAG CTC CTG GGG GTC ACC TTG GGC CTG GTG GTG CTC GGG GTA GCC TAC         12328
Glu Leu Leu Gly Val Thr Leu Gly Leu Val Val Leu Gly Val Ala Tyr
    8365                8370                8375

GCC CAG CTG GCC ATC CTG CTC GTG TCT TCC TGT GTG GAC TCC CTC TGG         12376
Ala Gln Leu Ala Ile Leu Leu Val Ser Ser Cys Val Asp Ser Leu Trp
8380                8385                8390

AGC GTG GCC CAG GCC CTG TTG GTG CTG TGC CCT GGG ACT GGG CTC TCT         12424
Ser Val Ala Gln Ala Leu Leu Val Leu Cys Pro Gly Thr Gly Leu Ser
8395                8400                8405                8410
```

| | |
|---|---|
| ACC CTG TGT CCT GCC GAG TCC TGG CAC CTG TCA CCC CTG CTG TGT GTG<br>Thr Leu Cys Pro Ala Glu Ser Trp His Leu Ser Pro Leu Leu Cys Val<br>                8415                          8420                          8425 | 12472 |
| GGG CTC TGG GCA CTG CGG CTG TGG GGC GCC CTA CGG CTG GGG GCT GTT<br>Gly Leu Trp Ala Leu Arg Leu Trp Gly Ala Leu Arg Leu Gly Ala Val<br>                8430                          8435                          8440 | 12520 |
| ATT CTC CGC TGG CGC TAC CAC GCC TTG CGT GGA GAG CTG TAC CGG CCG<br>Ile Leu Arg Trp Arg Tyr His Ala Leu Arg Gly Glu Leu Tyr Arg Pro<br>                8445                          8450                          8455 | 12568 |
| GCC TGG GAG CCC CAG GAC TAC GAG ATG GTG GAG TTG TTC CTG CGC AGG<br>Ala Trp Glu Pro Gln Asp Tyr Glu Met Val Glu Leu Phe Leu Arg Arg<br>                8460                          8465                          8470 | 12616 |
| CTG CGC CTC TGG ATG GGC CTC AGC AAG GTC AAG GAG TTC CGC CAC AAA<br>Leu Arg Leu Trp Met Gly Leu Ser Lys Val Lys Glu Phe Arg His Lys<br>8475                        8480                          8485                          8490 | 12664 |
| GTC CGC TTT GAA GGG ATG GAG CCG CTG CCC TCT CGC TCC TCC AGG GGC<br>Val Arg Phe Glu Gly Met Glu Pro Leu Pro Ser Arg Ser Ser Arg Gly<br>                        8495                          8500                          8505 | 12712 |
| TCC AAG GTA TCC CCG GAT GTG CCC CCA CCC AGC GCT GGC TCC GAT GCC<br>Ser Lys Val Ser Pro Asp Val Pro Pro Pro Ser Ala Gly Ser Asp Ala<br>                8510                          8515                          8520 | 12760 |
| TCG CAC CCC TCC ACC TCC TCC AGC CAG CTG GAT GGG CTG AGC GTG AGC<br>Ser His Pro Ser Thr Ser Ser Ser Gln Leu Asp Gly Leu Ser Val Ser<br>                8525                          8530                          8535 | 12808 |
| CTG GGC CGG CTG GGG ACA AGG TGT GAG CCT GAG CCC TCC CGC CTC CAA<br>Leu Gly Arg Leu Gly Thr Arg Cys Glu Pro Glu Pro Ser Arg Leu Gln<br>                8540                          8545                          8550 | 12856 |
| GCC GTG TTC GAG GCC CTG CTC ACC CAG TTT GAC CGA CTC AAC CAG GCC<br>Ala Val Phe Glu Ala Leu Leu Thr Gln Phe Asp Arg Leu Asn Gln Ala<br>8555                        8560                          8565                          8570 | 12904 |
| ACA GAG GAC GTC TAC CAG CTG GAG CAG CAG CTG CAC AGC CTG CAA GGC<br>Thr Glu Asp Val Tyr Gln Leu Glu Gln Gln Leu His Ser Leu Gln Gly<br>                8575                          8580                          8585 | 12952 |
| CGC AGG AGC AGC CGG GCG CCC GCC GGA TCT TCC CGT GGC CCA TCC CCG<br>Arg Arg Ser Ser Arg Ala Pro Ala Gly Ser Ser Arg Gly Pro Ser Pro<br>                8590                          8595                          8600 | 13000 |
| GGC CTG CGG CCA GCA CTG CCC AGC CGC CTT GCC CGG GCC AGT CGG GGT<br>Gly Leu Arg Pro Ala Leu Pro Ser Arg Leu Ala Arg Ala Ser Arg Gly<br>                8605                          8610                          8615 | 13048 |
| GTG GAC CTG GCC ACT GGC CCC AGC AGG ACA CCC CTT CGG GCC AAG AAC<br>Val Asp Leu Ala Thr Gly Pro Ser Arg Thr Pro Leu Arg Ala Lys Asn<br>8620                        8625                          8630 | 13096 |
| AAG GTC CAC CCC AGC AGC ACT TAGTCCTCCT TCCTGGCGGG GGTGGGCCGT<br>Lys Val His Pro Ser Ser Thr<br>8635                        8640 | 13147 |
| GGAGTCGGAG TGGACACCGC TCAGTATTAC TTTCTGCCGC TGTCAAGGCC GAGGGCCAGG | 13207 |
| CAGAATGGCT GCACGTAGGT TCCCCAGAGA GCAGGCAGGG GCATCTGTCT GTCTGTGGGC | 13267 |
| TTCAGCACTT TAAAGAGGCT GTGTGGCCAA CCAGGACCCA GGGTCCCCTC CCCAGCTCCC | 13327 |
| TTGGGAAGGA CACAGCAGTA TTGGACGGTT CTAGCCTCT GAGATGCTAA TTTATTTCCC | 13387 |
| CGAGTCCTCA GGTACAGCGG GCTGTGCCCG GCCCCACCCC CTGGGCAGAT GTCCCCCACT | 13447 |
| GCTAAGGCTG CTGGCTTCAG GGAGGGTTAG CCTGCACCGC CGCCACCCTG CCCCTAAGTT | 13507 |
| ATTACCTCTC CAGTTCCTAC CGTACTCCCT GCACCGTCTC ACTGTGTGTC TCGTGTCAGT | 13567 |
| AATTTATATG GTGTTAAAAT GTGTATATTT TTGTATGTCA CTATTTTCAC TAGGGCTGAG | 13627 |
| GGGCCTGCGC CCAGAGCTGG CCTCCCCCAA CACCTGCTGC GCTTGGTAGG TGTGGTGGCG | 13687 |
| TTATGGCAGC CCGGCTGCTG CTTGGATGCG AGCTTGGCCT TGGGCCGGTG CTGGGGGCAC | 13747 |

```
AGCTGTCTGC CAGGCACTCT CATCACCCCA GAGGCCTTGT CATCCTCCCT TGCCCCAGGC    13807

CAGGTAGCAA GAGAGCAGCG CCCAGGCCTG CTGGCATCAG GTCTGGGCAA GTAGCAGGAC    13867

TAGGCATGTC AGAGGACCCC AGGGTGGTTA GAGGAAAAGA CTCCTCCTGG GGGCTGGCTC    13927

CCAGGGTGGA GGAAGGTGAC TGTGTGTGTG TGTGTGTGCG CGCGCGACGC GCGAGTGTGC    13987

TGTATGGCCC AGGCAGCCTC AAGGCCCTCG GAGCTGGCTG TGCCTGCTTC TGTGTACCAC    14047

TTCTGTGGGC ATGGCCGCTT CTAGAGCCTC GACACCCCCC CAACCCCCGC ACCAAGCAGA    14107

CAAAGTCAAT AAAAGAGCTG TCTGACTGCA AAAAAAAAA A                         14148

(2) INFORMATION FOR SEQ ID NO: 8:

(i) SEQUENCE CHARACTERISTICS:
        (A) LENGTH: 4302 amino acids
        (B) TYPE: amino acid
        (D) TOPOLOGY: linear (ii) MOLECULE TYPE: protein (xi) SEQUENCE DESCRIPTION: SEQ ID NO: 8:

Met Pro Pro Ala Ala Pro Ala Arg Leu Ala Leu Ala Leu Gly Leu Gly
  1               5                  10                  15

Leu Trp Leu Gly Ala Leu Ala Gly Gly Pro Gly Arg Gly Cys Gly Pro
             20                  25                  30

Cys Glu Pro Pro Cys Leu Cys Gly Pro Ala Pro Gly Ala Ala Cys Arg
         35                  40                  45

Val Asn Cys Ser Gly Arg Gly Leu Arg Thr Leu Gly Pro Ala Leu Arg
     50                  55                  60

Ile Pro Ala Asp Ala Thr Ala Leu Asp Val Ser His Asn Leu Leu Arg
 65                  70                  75                  80

Ala Leu Asp Val Gly Leu Leu Ala Asn Leu Ser Ala Leu Ala Glu Leu
                 85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Arg Trp Ala Glu Glu Gln Gln
    130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Pro Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
```

-continued

```
                275                 280                 285
Leu Ala Ala Phe His Ile Ala Ala Pro Leu Pro Val Thr Ala Thr Arg
    290                 295                 300
Trp Asp Phe Gly Asp Gly Ser Ala Glu Val Asp Ala Ala Gly Pro Ala
305                 310                 315                 320
Ala Ser His Arg Tyr Val Leu Pro Gly Arg Tyr His Val Thr Ala Val
                325                 330                 335
Leu Ala Leu Gly Ala Gly Ser Ala Leu Leu Gly Thr Asp Val Gln Val
                340                 345                 350
Glu Ala Ala Pro Ala Ala Leu Glu Leu Val Cys Pro Ser Ser Val Gln
                355                 360                 365
Ser Asp Glu Ser Leu Asp Leu Ser Ile Gln Asn Arg Gly Gly Ser Gly
                370                 375                 380
Leu Glu Ala Ala Tyr Ser Ile Val Ala Leu Gly Glu Glu Pro Ala Arg
385                 390                 395                 400
Ala Val His Pro Leu Cys Pro Ser Asp Thr Glu Ile Phe Pro Gly Asn
                405                 410                 415
Gly His Cys Tyr Arg Leu Val Val Glu Lys Ala Ala Trp Leu Gln Ala
                420                 425                 430
Gln Glu Gln Cys Gln Ala Trp Ala Gly Ala Ala Leu Ala Met Val Asp
                435                 440                 445
Ser Pro Ala Val Gln Arg Phe Leu Val Ser Arg Val Thr Arg Ser Leu
                450                 455                 460
Asp Val Trp Ile Gly Phe Ser Thr Val Gln Gly Val Glu Val Gly Pro
465                 470                 475                 480
Ala Pro Gln Gly Glu Ala Phe Ser Leu Glu Ser Cys Gln Asn Trp Leu
                485                 490                 495
Pro Gly Glu Pro His Pro Ala Thr Ala Glu His Cys Val Arg Leu Gly
                500                 505                 510
Pro Thr Gly Trp Cys Asn Thr Asp Leu Cys Ser Ala Pro His Ser Tyr
                515                 520                 525
Val Cys Glu Leu Gln Pro Gly Gly Pro Val Gln Asp Ala Glu Asn Leu
                530                 535                 540
Leu Val Gly Ala Pro Ser Gly Asp Leu Gln Gly Pro Leu Thr Pro Leu
545                 550                 555                 560
Ala Gln Gln Asp Gly Leu Ser Ala Pro His Glu Pro Val Glu Val Met
                565                 570                 575
Val Phe Pro Gly Leu Arg Leu Ser Arg Glu Ala Phe Leu Thr Thr Ala
                580                 585                 590
Glu Phe Gly Thr Gln Glu Leu Arg Arg Pro Ala Gln Leu Arg Leu Gln
                595                 600                 605
Val Tyr Arg Leu Leu Ser Thr Ala Gly Thr Pro Glu Asn Gly Ser Glu
                610                 615                 620
Pro Glu Ser Arg Ser Pro Asp Asn Arg Thr Gln Leu Ala Pro Ala Cys
625                 630                 635                 640
Met Pro Gly Gly Arg Trp Cys Pro Gly Ala Asn Ile Cys Leu Pro Leu
                645                 650                 655
Asp Ala Ser Cys His Pro Gln Ala Cys Ala Asn Gly Cys Thr Ser Gly
                660                 665                 670
Pro Gly Leu Pro Gly Ala Pro Tyr Ala Leu Trp Arg Glu Phe Leu Phe
                675                 680                 685
Ser Val Ala Ala Gly Pro Pro Ala Gln Tyr Ser Val Thr Leu His Gly
                690                 695                 700
```

-continued

```
Gln Asp Val Leu Met Leu Pro Gly Asp Leu Val Gly Leu Gln His Asp
705                 710                 715                 720

Ala Gly Pro Gly Ala Leu Leu His Cys Ser Pro Ala Pro Gly His Pro
            725                 730                 735

Gly Pro Gln Ala Pro Tyr Leu Ser Ala Asn Ala Ser Ser Trp Leu Pro
        740                 745                 750

His Leu Pro Ala Gln Leu Glu Gly Thr Trp Ala Cys Pro Ala Cys Ala
    755                 760                 765

Leu Arg Leu Leu Ala Ala Thr Glu Gln Leu Thr Val Leu Leu Gly Leu
770                 775                 780

Arg Pro Asn Pro Gly Leu Arg Met Pro Gly Arg Tyr Glu Val Arg Ala
785                 790                 795                 800

Glu Val Gly Asn Gly Val Ser Arg His Asn Leu Ser Cys Ser Phe Asp
                805                 810                 815

Val Val Ser Pro Val Ala Gly Leu Arg Val Ile Tyr Pro Ala Pro Arg
            820                 825                 830

Asp Gly Arg Leu Tyr Val Pro Thr Asn Gly Ser Ala Leu Val Leu Gln
        835                 840                 845

Val Asp Ser Gly Ala Asn Ala Thr Ala Thr Ala Arg Trp Pro Gly Gly
850                 855                 860

Ser Val Ser Ala Arg Phe Glu Asn Val Cys Pro Ala Leu Val Ala Thr
865                 870                 875                 880

Phe Val Pro Gly Cys Pro Trp Glu Thr Asn Asp Thr Leu Phe Ser Val
                885                 890                 895

Val Ala Leu Pro Trp Leu Ser Glu Gly Glu His Val Val Asp Val Val
            900                 905                 910

Val Glu Asn Ser Ala Ser Arg Ala Asn Leu Ser Leu Arg Val Thr Ala
        915                 920                 925

Glu Glu Pro Ile Cys Gly Leu Arg Ala Thr Pro Ser Pro Glu Ala Arg
    930                 935                 940

Val Leu Gln Gly Val Leu Val Arg Tyr Ser Pro Val Val Glu Ala Gly
945                 950                 955                 960

Ser Asp Met Val Phe Arg Trp Thr Ile Asn Asp Lys Gln Ser Leu Thr
                965                 970                 975

Phe Gln Asn Val Val Phe Asn Val Ile Tyr Gln Ser Ala Ala Val Phe
            980                 985                 990

Lys Leu Ser Leu Thr Ala Ser Asn His Val Ser Asn Val Thr Val Asn
        995                 1000                1005

Tyr Asn Val Thr Val Glu Arg Met Asn Arg Met Gln Gly Leu Gln Val
    1010                1015                1020

Ser Thr Val Pro Ala Val Leu Ser Pro Asn Ala Thr Leu Val Leu Thr
1025                1030                1035                1040

Gly Gly Val Leu Val Asp Ser Ala Val Glu Val Ala Phe Leu Trp Asn
                1045                1050                1055

Phe Gly Asp Gly Glu Gln Ala Leu His Gln Phe Gln Pro Pro Tyr Asn
            1060                1065                1070

Glu Ser Phe Pro Val Pro Asp Pro Ser Val Ala Gln Val Leu Val Glu
        1075                1080                1085

His Asn Val Met His Thr Tyr Ala Ala Pro Gly Glu Tyr Leu Leu Thr
    1090                1095                1100

Val Leu Ala Ser Asn Ala Phe Glu Asn Leu Thr Gln Gln Val Pro Val
1105                1110                1115                1120
```

-continued

```
Ser Val Arg Ala Ser Leu Pro Ser Val Ala Val Gly Val Ser Asp Gly
            1125                1130                1135

Val Leu Val Ala Gly Arg Pro Val Thr Phe Tyr Pro His Pro Leu Pro
        1140                1145                1150

Ser Pro Gly Gly Val Leu Tyr Thr Trp Asp Phe Gly Asp Gly Ser Pro
            1155                1160                1165

Val Leu Thr Gln Ser Gln Pro Ala Ala Asn His Thr Tyr Ala Ser Arg
        1170                1175                1180

Gly Thr Tyr His Val Arg Leu Glu Val Asn Asn Thr Val Ser Gly Ala
1185                1190                1195                1200

Ala Ala Gln Ala Asp Val Arg Val Phe Glu Glu Leu Arg Gly Leu Ser
            1205                1210                1215

Val Asp Met Ser Leu Ala Val Glu Gln Gly Ala Pro Val Val Val Ser
        1220                1225                1230

Ala Ala Val Gln Thr Gly Asp Asn Ile Thr Trp Thr Phe Asp Met Gly
            1235                1240                1245

Asp Gly Thr Val Leu Ser Gly Pro Glu Ala Thr Val Glu His Val Tyr
        1250                1255                1260

Leu Arg Ala Gln Asn Cys Thr Val Thr Val Gly Ala Ala Ser Pro Ala
1265                1270                1275                1280

Gly His Leu Ala Arg Ser Leu His Val Leu Val Phe Val Leu Glu Val
            1285                1290                1295

Leu Arg Val Glu Pro Ala Ala Cys Ile Pro Thr Gln Pro Asp Ala Arg
        1300                1305                1310

Leu Thr Ala Tyr Val Thr Gly Asn Pro Ala His Tyr Leu Phe Asp Trp
        1315                1320                1325

Thr Phe Gly Asp Gly Ser Ser Asn Thr Thr Val Arg Gly Cys Pro Thr
        1330                1335                1340

Val Thr His Asn Phe Thr Arg Ser Gly Thr Phe Pro Leu Ala Leu Val
1345                1350                1355                1360

Leu Ser Ser Arg Val Asn Arg Ala His Tyr Phe Thr Ser Ile Cys Val
            1365                1370                1375

Glu Pro Glu Val Gly Asn Val Thr Leu Gln Pro Glu Arg Gln Phe Val
        1380                1385                1390

Gln Leu Gly Asp Glu Ala Trp Leu Val Ala Cys Ala Trp Pro Pro Phe
        1395                1400                1405

Pro Tyr Arg Tyr Thr Trp Asp Phe Gly Thr Glu Glu Ala Ala Pro Thr
        1410                1415                1420

Arg Ala Arg Gly Pro Glu Val Thr Phe Ile Tyr Arg Asp Pro Gly Ser
1425                1430                1435                1440

Tyr Leu Val Thr Val Thr Ala Ser Asn Asn Ile Ser Ala Ala Asn Asp
            1445                1450                1455

Ser Ala Leu Val Glu Val Gln Glu Pro Val Leu Val Thr Ser Ile Lys
        1460                1465                1470

Val Asn Gly Ser Leu Gly Leu Glu Leu Gln Gln Pro Tyr Leu Phe Ser
        1475                1480                1485

Ala Val Gly Arg Gly Arg Pro Ala Ser Tyr Leu Trp Asp Leu Gly Asp
        1490                1495                1500

Gly Gly Trp Leu Glu Gly Pro Glu Val Thr His Ala Tyr Asn Ser Thr
1505                1510                1515                1520

Gly Asp Phe Thr Val Arg Val Ala Gly Trp Asn Glu Val Ser Arg Ser
            1525                1530                1535

Glu Ala Trp Leu Asn Val Thr Val Lys Arg Arg Val Arg Gly Leu Val
```

-continued

```
               1540              1545              1550
Val Asn Ala Ser Arg Thr Val Pro Leu Asn Gly Ser Val Ser Phe
        1555              1560              1565
Ser Thr Ser Leu Glu Ala Gly Ser Asp Val Arg Tyr Ser Trp Val Leu
    1570              1575              1580
Cys Asp Arg Cys Thr Pro Ile Pro Gly Gly Pro Thr Ile Ser Tyr Thr
1585              1590              1595              1600
Phe Arg Ser Val Gly Thr Phe Asn Ile Ile Val Thr Ala Glu Asn Glu
            1605              1610              1615
Val Gly Ser Ala Gln Asp Ser Ile Phe Val Tyr Val Leu Gln Leu Ile
            1620              1625              1630
Glu Gly Leu Gln Val Val Gly Gly Arg Tyr Phe Pro Thr Asn His
        1635              1640              1645
Thr Val Gln Leu Gln Ala Val Val Arg Asp Gly Thr Asn Val Ser Tyr
    1650              1655              1660
Ser Trp Thr Ala Trp Arg Asp Arg Gly Pro Ala Leu Ala Gly Ser Gly
1665              1670              1675              1680
Lys Gly Phe Ser Leu Thr Val Leu Glu Ala Gly Thr Tyr His Val Gln
            1685              1690              1695
Leu Arg Ala Thr Asn Met Leu Gly Ser Ala Trp Ala Asp Cys Thr Met
                1700              1705              1710
Asp Phe Val Glu Pro Val Gly Trp Leu Met Val Thr Ala Ser Pro Asn
            1715              1720              1725
Pro Ala Ala Val Asn Thr Ser Val Thr Leu Ser Ala Glu Leu Ala Gly
        1730              1735              1740
Gly Ser Gly Val Val Tyr Thr Trp Ser Leu Glu Glu Gly Leu Ser Trp
1745              1750              1755              1760
Glu Thr Ser Glu Pro Phe Thr Thr His Ser Phe Pro Thr Pro Gly Leu
            1765              1770              1775
His Leu Val Thr Met Thr Ala Gly Asn Pro Leu Gly Ser Ala Asn Ala
            1780              1785              1790
Thr Val Glu Val Asp Val Gln Val Pro Val Ser Gly Leu Ser Ile Arg
        1795              1800              1805
Ala Ser Glu Pro Gly Gly Ser Phe Val Ala Ala Gly Ser Ser Val Pro
    1810              1815              1820
Phe Trp Gly Gln Leu Ala Thr Gly Thr Asn Val Ser Trp Cys Trp Ala
1825              1830              1835              1840
Val Pro Gly Gly Ser Ser Lys Arg Gly Pro His Val Thr Met Val Phe
            1845              1850              1855
Pro Asp Ala Gly Thr Phe Ser Ile Arg Leu Asn Ala Ser Asn Ala Val
            1860              1865              1870
Ser Trp Val Ser Ala Thr Tyr Asn Leu Thr Ala Glu Glu Pro Ile Val
        1875              1880              1885
Gly Leu Val Leu Trp Ala Ser Ser Lys Val Val Ala Pro Gly Gln Leu
    1890              1895              1900
Val His Phe Gln Ile Leu Leu Ala Ala Gly Ser Ala Val Thr Phe Arg
1905              1910              1915              1920
Leu Gln Val Gly Gly Ala Asn Pro Glu Val Leu Pro Gly Pro Arg Phe
            1925              1930              1935
Ser His Ser Phe Pro Arg Val Gly Asp His Val Val Ser Val Arg Gly
            1940              1945              1950
Lys Asn His Val Ser Trp Ala Gln Ala Gln Val Arg Ile Val Val Leu
        1955              1960              1965
```

-continued

```
Glu Ala Val Ser Gly Leu Gln Met Pro Asn Cys Cys Glu Pro Gly Ile
            1970                1975                1980
Ala Thr Gly Thr Glu Arg Asn Phe Thr Ala Arg Val Gln Arg Gly Ser
1985                1990                1995                2000
Arg Val Ala Tyr Ala Trp Tyr Phe Ser Leu Gln Lys Val Gln Gly Asp
                2005                2010                2015
Ser Leu Val Ile Leu Ser Gly Arg Asp Val Thr Tyr Thr Pro Val Ala
            2020                2025                2030
Ala Gly Leu Leu Glu Ile Gln Val Arg Ala Phe Asn Ala Leu Gly Ser
            2035                2040                2045
Glu Asn Arg Thr Leu Val Leu Glu Val Gln Asp Ala Val Gln Tyr Val
            2050                2055                2060
Ala Leu Gln Ser Gly Pro Cys Phe Thr Asn Arg Ser Ala Gln Phe Glu
2065                2070                2075                2080
Ala Ala Thr Ser Pro Ser Pro Arg Val Ala Tyr His Trp Asp Phe
                2085                2090                2095
Gly Asp Gly Ser Pro Gly Gln Asp Thr Asp Glu Pro Arg Ala Glu His
            2100                2105                2110
Ser Tyr Leu Arg Pro Gly Asp Tyr Arg Val Gln Val Asn Ala Ser Asn
            2115                2120                2125
Leu Val Ser Phe Phe Val Ala Gln Ala Thr Val Thr Val Gln Val Leu
            2130                2135                2140
Ala Cys Arg Glu Pro Glu Val Asp Val Val Leu Pro Leu Gln Val Leu
2145                2150                2155                2160
Met Arg Arg Ser Gln Arg Asn Tyr Leu Glu Ala His Val Asp Leu Arg
            2165                2170                2175
Asp Cys Val Thr Tyr Gln Thr Glu Tyr Arg Trp Glu Val Tyr Arg Thr
            2180                2185                2190
Ala Ser Cys Gln Arg Pro Gly Arg Pro Ala Arg Val Ala Leu Pro Gly
            2195                2200                2205
Val Asp Val Ser Arg Pro Arg Leu Val Leu Pro Arg Leu Ala Leu Pro
            2210                2215                2220
Val Gly His Tyr Cys Phe Val Phe Val Val Ser Phe Gly Asp Thr Pro
2225                2230                2235                2240
Leu Thr Gln Ser Ile Gln Ala Asn Val Thr Val Ala Pro Glu Arg Leu
                2245                2250                2255
Val Pro Ile Ile Glu Gly Gly Ser Tyr Arg Val Trp Ser Asp Thr Arg
            2260                2265                2270
Asp Leu Val Leu Asp Gly Ser Glu Ser Tyr Asp Pro Asn Leu Glu Asp
            2275                2280                2285
Gly Asp Gln Thr Pro Leu Ser Phe His Trp Ala Cys Val Ala Ser Thr
            2290                2295                2300
Gln Arg Glu Ala Gly Gly Cys Ala Leu Asn Phe Gly Pro Arg Gly Ser
2305                2310                2315                2320
Ser Thr Val Thr Ile Pro Arg Gly Arg Leu Ala Ala Gly Val Glu Tyr
                2325                2330                2335
Thr Phe Ser Leu Thr Val Trp Lys Ala Gly Arg Lys Glu Glu Ala Thr
                2340                2345                2350
Asn Gln Thr Val Leu Ile Arg Ser Gly Arg Val Pro Ile Val Ser Leu
            2355                2360                2365
Glu Cys Val Ser Cys Lys Ala Gln Ala Val Tyr Glu Val Ser Arg Ser
            2370                2375                2380
```

-continued

```
Ser Tyr Val Tyr Leu Glu Gly Arg Cys Leu Asn Cys Ser Ser Gly Ser
2385                2390                2395                2400

Lys Arg Gly Arg Trp Ala Ala Arg Thr Phe Ser Asn Lys Thr Leu Val
                2405                2410                2415

Leu Asp Glu Thr Thr Thr Ser Thr Gly Ser Ala Gly Met Arg Leu Val
                2420                2425                2430

Leu Arg Arg Gly Val Leu Arg Asp Gly Glu Gly Tyr Thr Phe Thr Leu
                2435                2440                2445

Thr Val Leu Gly Arg Ser Gly Glu Glu Glu Gly Cys Ala Ser Ile Arg
                2450                2455                2460

Leu Ser Pro Asn Arg Pro Leu Gly Gly Ser Cys Arg Leu Phe Pro
2465                2470                2475                2480

Leu Gly Ala Val His Ala Leu Thr Thr Lys Val His Phe Glu Cys Thr
                2485                2490                2495

Gly Trp His Asp Ala Glu Asp Ala Gly Ala Pro Leu Val Tyr Ala Leu
                2500                2505                2510

Leu Leu Arg Arg Cys Arg Gln Gly His Cys Glu Glu Phe Cys Val Tyr
                2515                2520                2525

Lys Gly Ser Leu Ser Ser Tyr Gly Ala Val Leu Pro Pro Gly Phe Arg
                2530                2535                2540

Pro His Phe Glu Val Gly Leu Ala Val Val Val Gln Asp Gln Leu Gly
2545                2550                2555                2560

Ala Ala Val Val Ala Leu Asn Arg Ser Leu Ala Ile Thr Leu Pro Glu
                2565                2570                2575

Pro Asn Gly Ser Ala Thr Gly Leu Thr Val Trp Leu His Gly Leu Thr
                2580                2585                2590

Ala Ser Val Leu Pro Gly Leu Leu Arg Gln Ala Asp Pro Gln His Val
                2595                2600                2605

Ile Glu Tyr Ser Leu Ala Leu Val Thr Val Leu Asn Glu Tyr Glu Arg
                2610                2615                2620

Ala Leu Asp Val Ala Ala Glu Pro Lys His Glu Arg Gln His Arg Ala
2625                2630                2635                2640

Gln Ile Arg Lys Asn Ile Thr Glu Thr Leu Val Ser Leu Arg Val His
                2645                2650                2655

Thr Val Asp Asp Ile Gln Gln Ile Ala Ala Ala Leu Ala Gln Cys Met
                2660                2665                2670

Gly Pro Ser Arg Glu Leu Val Cys Arg Ser Cys Leu Lys Gln Thr Leu
                2675                2680                2685

His Lys Leu Glu Ala Met Met Leu Ile Leu Gln Ala Glu Thr Thr Ala
                2690                2695                2700

Gly Thr Val Thr Pro Thr Ala Ile Gly Asp Ser Ile Leu Asn Ile Thr
2705                2710                2715                2720

Gly Asp Leu Ile His Leu Ala Ser Ser Asp Val Arg Ala Pro Gln Pro
                2725                2730                2735

Ser Glu Leu Gly Ala Glu Ser Pro Ser Arg Met Val Ala Ser Gln Ala
                2740                2745                2750

Tyr Asn Leu Thr Ser Ala Leu Met Arg Ile Leu Met Arg Ser Arg Val
                2755                2760                2765

Leu Asn Glu Glu Pro Leu Thr Leu Ala Gly Glu Glu Ile Val Ala Gln
                2770                2775                2780

Gly Lys Arg Ser Asp Pro Arg Ser Leu Leu Cys Tyr Gly Gly Ala Pro
2785                2790                2795                2800

Gly Pro Gly Cys His Phe Ser Ile Pro Glu Ala Phe Ser Gly Ala Leu
```

-continued

```
                2805                2810                2815
Ala Asn Leu Ser Asp Val Val Gln Leu Ile Phe Leu Val Asp Ser Asn
            2820                2825                2830
Pro Phe Pro Phe Gly Tyr Ile Ser Asn Tyr Thr Val Ser Thr Lys Val
            2835                2840                2845
Ala Ser Met Ala Phe Gln Thr Gln Ala Gly Ala Gln Ile Pro Ile Glu
            2850                2855                2860
Arg Leu Ala Ser Glu Arg Ala Ile Thr Val Lys Val Pro Asn Asn Ser
2865                2870                2875                2880
Asp Trp Ala Ala Arg Gly His Arg Ser Ser Ala Asn Ser Ala Asn Ser
                2885                2890                2895
Val Val Val Gln Pro Gln Ala Ser Val Gly Ala Val Val Thr Leu Asp
                2900                2905                2910
Ser Ser Asn Pro Ala Ala Gly Leu His Leu Gln Leu Asn Tyr Thr Leu
            2915                2920                2925
Leu Asp Gly His Tyr Leu Ser Glu Glu Pro Glu Pro Tyr Leu Ala Val
            2930                2935                2940
Tyr Leu His Ser Glu Pro Arg Pro Asn Glu His Asn Cys Ser Ala Ser
2945                2950                2955                2960
Arg Arg Ile Arg Pro Glu Ser Leu Gln Gly Ala Asp His Arg Pro Tyr
                2965                2970                2975
Thr Phe Phe Ile Ser Pro Gly Ser Arg Asp Pro Ala Gly Ser Tyr His
            2980                2985                2990
Leu Asn Leu Ser Ser His Phe Arg Trp Ser Ala Leu Gln Val Ser Val
            2995                3000                3005
Gly Leu Tyr Thr Ser Leu Cys Gln Tyr Phe Ser Glu Glu Asp Met Val
            3010                3015                3020
Trp Arg Thr Glu Gly Leu Leu Pro Leu Glu Glu Thr Ser Pro Arg Gln
3025                3030                3035                3040
Ala Val Cys Leu Thr Arg His Leu Thr Ala Phe Gly Ala Ser Leu Phe
                3045                3050                3055
Val Pro Pro Ser His Val Arg Phe Val Phe Pro Glu Pro Thr Ala Asp
                3060                3065                3070
Val Asn Tyr Ile Val Met Leu Thr Cys Ala Val Cys Leu Val Thr Tyr
            3075                3080                3085
Met Val Met Ala Ala Ile Leu His Lys Leu Asp Gln Leu Asp Ala Ser
        3090                3095                3100
Arg Gly Arg Ala Ile Pro Phe Cys Gly Gln Arg Gly Arg Phe Lys Tyr
3105                3110                3115                3120
Glu Ile Leu Val Lys Thr Gly Trp Gly Arg Gly Ser Gly Thr Thr Ala
                3125                3130                3135
His Val Gly Ile Met Leu Tyr Gly Val Asp Ser Arg Ser Gly His Arg
            3140                3145                3150
His Leu Asp Gly Asp Arg Ala Phe His Arg Asn Ser Leu Asp Ile Phe
            3155                3160                3165
Arg Ile Ala Thr Pro His Ser Leu Gly Ser Val Trp Lys Ile Arg Val
            3170                3175                3180
Trp His Asp Asn Lys Gly Leu Ser Pro Ala Trp Phe Leu Gln His Val
3185                3190                3195                3200
Ile Val Arg Asp Leu Gln Thr Ala Arg Ser Ala Phe Phe Leu Val Asn
                3205                3210                3215
Asp Trp Leu Ser Val Glu Thr Glu Ala Asn Gly Gly Leu Val Glu Lys
                3220                3225                3230
```

-continued

```
Glu Val Leu Ala Ala Ser Asp Ala Leu Leu Arg Phe Arg Arg Leu
            3235                3240                3245
Leu Val Ala Glu Leu Gln Arg Gly Phe Phe Asp Lys His Ile Trp Leu
            3250                3255                3260
Ser Ile Trp Asp Arg Pro Arg Ser Arg Phe Thr Arg Ile Gln Arg
3265                3270                3275                3280
Ala Thr Cys Cys Val Leu Leu Ile Cys Leu Phe Leu Gly Ala Asn Ala
            3285                3290                3295
Val Trp Tyr Gly Ala Val Gly Asp Ser Ala Tyr Ser Thr Gly His Val
            3300                3305                3310
Ser Arg Leu Ser Pro Leu Ser Val Asp Thr Val Ala Val Gly Leu Val
            3315                3320                3325
Ser Ser Val Val Val Tyr Pro Val Tyr Leu Ala Ile Leu Phe Leu Phe
            3330                3335                3340
Arg Met Ser Arg Ser Lys Val Ala Gly Ser Pro Ser Pro Thr Pro Ala
3345                3350                3355                3360
Gly Gln Gln Val Leu Asp Ile Asp Ser Cys Leu Asp Ser Ser Val Leu
            3365                3370                3375
Asp Ser Ser Phe Leu Thr Phe Ser Gly Leu His Ala Glu Ala Phe Val
            3380                3385                3390
Gly Gln Met Lys Ser Asp Leu Phe Leu Asp Asp Ser Lys Ser Leu Val
            3395                3400                3405
Cys Trp Pro Ser Gly Glu Gly Thr Leu Ser Trp Pro Asp Leu Leu Ser
            3410                3415                3420
Asp Pro Ser Ile Val Gly Ser Asn Leu Arg Gln Leu Ala Arg Gly Gln
3425                3430                3435                3440
Ala Gly His Gly Leu Gly Pro Glu Glu Asp Gly Phe Ser Leu Ala Ser
            3445                3450                3455
Pro Tyr Ser Pro Ala Lys Ser Phe Ser Ala Ser Asp Glu Asp Leu Ile
            3460                3465                3470
Gln Gln Val Leu Ala Glu Gly Val Ser Ser Pro Ala Pro Thr Gln Asp
            3475                3480                3485
Thr His Met Glu Thr Asp Leu Leu Ser Ser Leu Ser Ser Thr Pro Gly
            3490                3495                3500
Glu Lys Thr Glu Thr Leu Ala Leu Gln Arg Leu Gly Glu Leu Gly Pro
3505                3510                3515                3520
Pro Ser Pro Gly Leu Asn Trp Glu Gln Pro Gln Ala Ala Arg Leu Ser
            3525                3530                3535
Arg Thr Gly Leu Val Glu Gly Leu Arg Lys Arg Leu Leu Pro Ala Trp
            3540                3545                3550
Cys Ala Ser Leu Ala His Gly Leu Ser Leu Leu Leu Val Ala Val Ala
            3555                3560                3565
Val Ala Val Ser Gly Trp Val Gly Ala Ser Phe Pro Pro Gly Val Ser
            3570                3575                3580
Val Ala Trp Leu Leu Ser Ser Ser Ala Ser Phe Leu Ala Ser Phe Leu
3585                3590                3595                3600
Gly Trp Glu Pro Leu Lys Val Leu Leu Glu Ala Leu Tyr Phe Ser Leu
            3605                3610                3615
Val Ala Lys Arg Leu His Pro Asp Glu Asp Thr Leu Val Glu Ser
            3620                3625                3630
Pro Ala Val Thr Pro Val Ser Ala Arg Val Pro Arg Val Arg Pro Pro
            3635                3640                3645
```

```
His Gly Phe Ala Leu Phe Leu Ala Lys Glu Glu Ala Arg Lys Val Lys
3650                3655                3660

Arg Leu His Gly Met Leu Arg Ser Leu Leu Val Tyr Met Leu Phe Leu
3665                3670                3675                3680

Leu Val Thr Leu Leu Ala Ser Tyr Gly Asp Ala Ser Cys His Gly His
                3685                3690                3695

Ala Tyr Arg Leu Gln Ser Ala Ile Lys Gln Glu Leu His Ser Arg Ala
                3700                3705                3710

Phe Leu Ala Ile Thr Arg Ser Glu Glu Leu Trp Pro Trp Met Ala His
                3715                3720                3725

Val Leu Leu Pro Tyr Val His Gly Asn Gln Ser Ser Pro Glu Leu Gly
                3730                3735                3740

Pro Pro Arg Leu Arg Gln Val Arg Leu Gln Glu Ala Leu Tyr Pro Asp
3745                3750                3755                3760

Pro Pro Gly Pro Arg Val His Thr Cys Ser Ala Ala Gly Gly Phe Ser
                3765                3770                3775

Thr Ser Asp Tyr Asp Val Gly Trp Glu Ser Pro His Asn Gly Ser Gly
                3780                3785                3790

Thr Trp Ala Tyr Ser Ala Pro Asp Leu Leu Gly Ala Trp Ser Trp Gly
                3795                3800                3805

Ser Cys Ala Val Tyr Asp Ser Gly Gly Tyr Val Gln Glu Leu Gly Leu
                3810                3815                3820

Ser Leu Glu Glu Ser Arg Asp Arg Leu Arg Phe Leu Gln Leu His Asn
3825                3830                3835                3840

Trp Leu Asp Asn Arg Ser Arg Ala Val Phe Leu Glu Leu Thr Arg Tyr
                3845                3850                3855

Ser Pro Ala Val Gly Leu His Ala Ala Val Thr Leu Arg Leu Glu Phe
                3860                3865                3870

Pro Ala Ala Gly Arg Ala Leu Ala Leu Ser Val Arg Pro Phe Ala
                3875                3880                3885

Leu Arg Arg Leu Ser Ala Gly Leu Ser Leu Pro Leu Leu Thr Ser Val
                3890                3895                3900

Cys Leu Leu Leu Phe Ala Val His Phe Ala Val Ala Glu Ala Arg Thr
3905                3910                3915                3920

Trp His Arg Glu Gly Arg Trp Arg Val Leu Arg Leu Gly Ala Trp Ala
                3925                3930                3935

Arg Trp Leu Leu Val Ala Leu Thr Ala Ala Thr Ala Leu Val Arg Leu
                3940                3945                3950

Ala Gln Leu Gly Ala Ala Asp Arg Gln Trp Thr Arg Phe Val Arg Gly
                3955                3960                3965

Arg Pro Arg Arg Phe Thr Ser Phe Asp Gln Val Ala His Val Ser Ser
                3970                3975                3980

Ala Ala Arg Gly Leu Ala Ala Ser Leu Leu Phe Leu Leu Leu Val Lys
3985                3990                3995                4000

Ala Ala Gln His Val Arg Phe Val Arg Gln Trp Ser Val Phe Gly Lys
                4005                4010                4015

Thr Leu Cys Arg Ala Leu Pro Glu Leu Leu Gly Val Thr Leu Gly Leu
                4020                4025                4030

Val Val Leu Gly Val Ala Tyr Ala Gln Leu Ala Ile Leu Leu Val Ser
                4035                4040                4045

Ser Cys Val Asp Ser Leu Trp Ser Val Ala Gln Ala Leu Leu Val Leu
                4050                4055                4060

Cys Pro Gly Thr Gly Leu Ser Thr Leu Cys Pro Ala Glu Ser Trp His
```

```
                4065                4070                4075                4080
Leu Ser Pro Leu Leu Cys Val Gly Leu Trp Ala Leu Arg Leu Trp Gly
                    4085                4090                4095
Ala Leu Arg Leu Gly Ala Val Ile Leu Arg Trp Arg Tyr His Ala Leu
            4100                4105                4110
Arg Gly Glu Leu Tyr Arg Pro Ala Trp Glu Pro Gln Asp Tyr Glu Met
        4115                4120                4125
Val Glu Leu Phe Leu Arg Arg Leu Arg Leu Trp Met Gly Leu Ser Lys
    4130                4135                4140
Val Lys Glu Phe Arg His Lys Val Arg Phe Glu Gly Met Glu Pro Leu
4145                4150                4155                4160
Pro Ser Arg Ser Ser Arg Gly Ser Lys Val Ser Pro Asp Val Pro Pro
                4165                4170                4175
Pro Ser Ala Gly Ser Asp Ala Ser His Pro Ser Thr Ser Ser Ser Gln
            4180                4185                4190
Leu Asp Gly Leu Ser Val Ser Leu Gly Arg Leu Gly Thr Arg Cys Glu
        4195                4200                4205
Pro Glu Pro Ser Arg Leu Gln Ala Val Phe Glu Ala Leu Leu Thr Gln
    4210                4215                4220
Phe Asp Arg Leu Asn Gln Ala Thr Glu Asp Val Tyr Gln Leu Glu Gln
4225                4230                4235                4240
Gln Leu His Ser Leu Gln Gly Arg Arg Ser Ser Arg Ala Pro Ala Gly
                4245                4250                4255
Ser Ser Arg Gly Pro Ser Pro Gly Leu Arg Pro Ala Leu Pro Ser Arg
            4260                4265                4270
Leu Ala Arg Ala Ser Arg Gly Val Asp Leu Ala Thr Gly Pro Ser Arg
        4275                4280                4285
Thr Pro Leu Arg Ala Lys Asn Lys Val His Pro Ser Ser Thr
    4290                4295                4300

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..23
        (D) OTHER INFORMATION:/function= "AH3 F9 primer"

(xi) SEQUENCE DESCRIPTION: SEQ ID NO: 9:

TTTGACAAGC ACATCTGGCT CTC                                                      23

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA (vi) ORIGINAL SOURCE:
```

```
            (A) ORGANISM: Homo sapiens (ix) FEATURE:
            (A) NAME/KEY: misc_feature
            (B) LOCATION:1..20
            (D) OTHER INFORMATION:/function= "AH3 B7 primer"

(xi) SEQUENCE DESCRIPTION: SEQ ID NO: 10:

TACACCAGGA GGCTCCGCAG                                                    20

(2) INFORMATION FOR SEQ ID NO: 11:

(i) SEQUENCE CHARACTERISTICS:
            (A) LENGTH: 21 base pairs
            (B) TYPE: nucleic acid
            (C) STRANDEDNESS: single
            (D) TOPOLOGY: unknown (ii) MOLECULE TYPE: cDNA (vi) ORIGINAL SOURCE:
            (A) ORGANISM: Homo sapiens (ix) FEATURE:
            (A) NAME/KEY: misc_feature
            (B) LOCATION:1..21
            (D) OTHER INFORMATION:/function= "3A3 C1 primer"

(xi) SEQUENCE DESCRIPTION: SEQ ID NO: 11:

CGCCGCTTCA CTAGCTTCGA C                                                  21

(2) INFORMATION FOR SEQ ID NO: 12:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (ii) MOLECULE TYPE: cDNA (vi) ORIGINAL SOURCE:
            (A) ORGANISM: Homo sapiens (ix) FEATURE:
            (A) NAME/KEY: misc_feature
            (B) LOCATION:1..20
            (D) OTHER INFORMATION:/function= "3A3 C2 primer"

(xi) SEQUENCE DESCRIPTION: SEQ ID NO: 12:

ACGCTCCAGA GGGAGTCCAC                                                    20

(2) INFORMATION FOR SEQ ID NO: 13:

(i) SEQUENCE CHARACTERISTICS:
            (A) LENGTH: 20 base pairs
            (B) TYPE: nucleic acid
            (C) STRANDEDNESS: single
            (D) TOPOLOGY: unknown (ii) MOLECULE TYPE: cDNA (vi) ORIGINAL SOURCE:
            (A) ORGANISM: Homo sapiens (ix) FEATURE:
            (A) NAME/KEY: misc_feature
            (B) LOCATION:1..20
            (D) OTHER INFORMATION:/function= "AH4F2 primer"

(xi) SEQUENCE DESCRIPTION: SEQ ID NO: 13:

GGGCAAGGGA GGATGACAAG                                                    20
```

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION:1..21
        (D) OTHER INFORMATION:/function= "JH14B3 primer"

(xi) SEQUENCE DESCRIPTION: SEQ ID NO: 14:

GGGTTTATCA GCAGCAAGCG G                                            21

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..30
        (D) OTHER INFORMATION:/function= "N2765 primer"

(xi) SEQUENCE DESCRIPTION: SEQ ID NO: 15:

GGCGCGGCGG GCGGCATCGT TAGGGCAGCG                            30

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..30
        (D) OTHER INFORMATION:/function= "N5496 primer"

(xi) SEQUENCE DESCRIPTION: SEQ ID NO: 16:

GGCGGGCGGC ATCGTTAGGG CAGCGCGCGC                            30

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown

```
    (ii) MOLECULE TYPE: cDNA (vi) ORIGINAL SOURCE:
         (A) ORGANISM: Homo sapiens (ix) FEATURE:
         (A) NAME/KEY: misc_feature
         (B) LOCATION:1..30
         (D) OTHER INFORMATION:/function= "N5495 primer"

(xi) SEQUENCE DESCRIPTION: SEQ ID NO: 17:

ACCTGCTGCT GAGCGACGCC CGCTCGGGGC                                        30

(2) INFORMATION FOR SEQ ID NO: 18:

(i) SEQUENCE CHARACTERISTICS:
        (A) LENGTH: 54 base pairs
        (B) TYPE: nucleic acid
        (C) STRANDEDNESS: unknown
        (D) TOPOLOGY: unknown (ii) MOLECULE TYPE: genomic DNA (vi) ORIGINAL SOURCE:
         (A) ORGANISM: Homo sapiens (xi) SEQUENCE DESCRIPTION: SEQ ID NO: 18:

TTTTGGTCAA GGTGAGGGCT GGGCCGGTGG GCGCGGGGCT GGGCGCACAC CCCA             54

(2) INFORMATION FOR SEQ ID NO: 19:

(i) SEQUENCE CHARACTERISTICS:
        (A) LENGTH: 554 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
         (A) ORGANISM: Homo sapiens (ix) FEATURE:
         (A) NAME/KEY: misc_feature
         (D) OTHER INFORMATION:/function= "1A1H0.6 probe"

(xi) SEQUENCE DESCRIPTION: SEQ ID NO: 19:

AAGCTTGGCA CCATCAAGGG CCAGTTCAAC TTTGTCCACG TGATCGTCAC CCCGCTGGAC        60

TACGAGTGCA ACCTGGTGTC CCTGCAGTGC AGGAAAGACA TGGAGGGCCT TGTGGACACC       120

AGCGTGGCCA AGATCGTGTC TGACCGCAAC CTGCCCTTCG TGGCCCGCCA GATGGCCCTG       180

CACGCAAATA TGGCCTCACA GGTGCATCAT AGCCGCTCCA ACCCCACCGA TATCTACCCC       240

TCCAAGTGGA TTGCCCGGCT CCGCCACATC AAGCGGCTCC GCCAGCGGAT CTGCGAGGAA       300

GCCGCCTACT CCAACCCCAG CCTACCTCTG GTGCACCCTC CGTCCCATAG CAAAGCCCCT       360

GCACAGACTC CAGCCGAGCC CACACCTGGC TATGAGGTGG CCAGCGGAA GCGCCTCATC       420

TCCTCGGTGG AGGACTTCAC CGAGTTTGTG TGAGGCCGGG GCCCTCCCTC CTGCACTGGC       480

CTTGGACGGT ATTGCCTGTC AGTGAAATAA ATAAAGTCCT GACCCCAGTG CACAGACATA       540

GAGGCACAGA TTGC                                                        554

(2) INFORMATION FOR SEQ ID NO: 20:

(i) SEQUENCE CHARACTERISTICS:
        (A) LENGTH: 192 base pairs
        (B) TYPE: nucleic acid
        (C) STRANDEDNESS: unknown
```

(D) TOPOLOGY: unknown (ii) MOLECULE TYPE: other nucleic acid (vi) ORIGINAL SOURCE:
        (A) ORGANISM: Homo sapiens (ix) FEATURE:
        (A) NAME/KEY: misc_feature
        (D) OTHER INFORMATION:/function= "CW10F probe"

(xi) SEQUENCE DESCRIPTION: SEQ ID NO: 20:

GTCCGCGGTC GCACGTACGC TTCTGGTGTG TGTGAGACGT GCGGGGCTGG GAAGTGTTGG      60

CAGACGGCGA GTACGTCCTC ACTCCTTTTG TTCTTTTGAC CTAAGCTGGC GAGTGGCACT     120

GCTGAGTTCC GCTCAGTGCC CGCCCTGATG TGCGACCCCC GTGCATTCTT GCTGTTAGGT     180

GGTGGCGGTG TG                                                         192

(2) INFORMATION FOR SEQ ID NO: 21:

(i) SEQUENCE CHARACTERISTICS:
        (A) LENGTH: 41 base pairs
        (B) TYPE: nucleic acid
        (C) STRANDEDNESS: unknown
        (D) TOPOLOGY: unknown (ii) MOLECULE TYPE: other nucleic acid (vi) ORIGINAL SOURCE:
        (A) ORGANISM: Homo sapiens (ix) FEATURE:
        (A) NAME/KEY: misc_feature
        (D) OTHER INFORMATION:/function= "CW10R probe"

(xi) SEQUENCE DESCRIPTION: SEQ ID NO: 21:

AGGCAGGTCT CCCCCACGAC CAGGGGAGAG GCACCCAAGG T                          41

(2) INFORMATION FOR SEQ ID NO: 22:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: other nucleic acid (vi) ORIGINAL SOURCE:
        (A) ORGANISM: Homo sapiens (xi) SEQUENCE DESCRIPTION: SEQ ID NO: 22:

AGTCAGTAAT TTATATGGTG TTAAAATGTG A                                     31

(2) INFORMATION FOR SEQ ID NO: 23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein

```
        (vi) ORIGINAL SOURCE:
              (A) ORGANISM: Homo sapiens (xi) SEQUENCE DESCRIPTION: SEQ ID NO: 23:

Trp Asp Phe Gly Asp Ser
1                   5
```

What is claimed is:

1. An isolated polypeptide comprising a polycystic kidney disease-1 protein having the amino acid sequence of SEQ ID NO: 8.

2. An isolated polypeptide comprising a PKD1 protein fragment having the amino acid sequence of SEQ ID NO: 2.

3. An isolated polypeptide comprising a PKD1 protein fragment having the amino acid of SEQ ID NO: 6.

4. An isolated polypeptide comprising a PKD1 protein fragment having the amino acid sequence encoded by a nucleic acid probe selected from the group consisting of:
   (a) (OX114) a nucleic acid comprising 446 base pairs between nucleotides 1746–2192 as defined in SEQ ID NO:1;
   (b) (OX32) a nucleic acid comprising 135 base pairs between nucleotides 3696–3831 as defined in SEQ ID NO:1;
   (c) (OX875) a nucleic acid comprising about 5.5 Kb flanked by the two XbaI sites shown in FIG. 3a and encompassing the EcoRI site separating the CW10 (41 Kb) and JH1 (18 Kb) fragment, and further separating CW21 and JH14 fragments; and
   (d) (WS-219) a nucleic acid comprising about 27 Kb encompassing a portion of the PKD1 gene, wherein said portion is flanked by the EcoRI site separating the CW20 and JH1 fragments and the BamH1 site separating the JH6 and JH8 fragments, and wherein said nucleic acid extends 3' of the PKD1 gene within fragment JH1 and into the PKD1 gene to within fragment JH6 as shown in FIG. 12.

5. An isolated mutant polypeptide encoded by a nucleic acid molecule comprising a deletion mutant of SEQ ID NO:1 wherein said deletion in SEQ ID NO:1 is selected from the group consisting of:
   (a) (OX 114) a nucleic acid comprising 446 base pairs between nucleotides 1746–2192 as defined in SEQ ID NO:1;
   (b) (OX32) a nucleic acid comprising 135 base pairs between nucleotides 3696–3831 as defined in SEQ ID NO:1;
   (c) (OX875) a nucleic acid comprising about 5.5 Kb flanked by the two XbaI sites shown in FIG. 3a and encompassing the EcoRI site separating the CW10 (41 Kb) and JH1 (18 Kb) fragment, and further separating the CW21 and JH14 fragments; and
   (d) (WS-219) a nucleic acid comprising about 27 Kb encompassing a portion of the PKD 1 gene, wherein said portion is flanked by the EcoRI site separating the CW20 and JH1 fragments and the BamH1 site separating the JH6 and JH8 fragments, and wherein said nucleic acid extends 3' of the PKD1 gene within fragment JH1 and into the PKD1 gene to within fragment JH6 as shown in FIG. 12.

\* \* \* \* \*